United States Patent
Ren et al.

(10) Patent No.: US 9,828,378 B2
(45) Date of Patent: *Nov. 28, 2017

(54) KINASE INHIBITORS AND METHODS OF USE

(71) Applicant: Intellikine LLC, La Jolla, CA (US)

(72) Inventors: Pingda Ren, San Diego, CA (US); Yi Liu, San Diego, CA (US); Liansheng Li, San Diego, CA (US); Katrina Chan, San Diego, CA (US); Troy Edward Wilson, San Marino, CA (US)

(73) Assignee: Intellikine LLC, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,296

(22) Filed: Jul. 7, 2015

(65) Prior Publication Data

US 2016/0024099 A1  Jan. 28, 2016

Related U.S. Application Data

(62) Division of application No. 13/002,438, filed as application No. PCT/US2009/049983 on Jul. 8, 2009, now Pat. No. 9,096,611.

(60) Provisional application No. 61/079,127, filed on Jul. 8, 2008.

(51) Int. Cl.
| | |
|---|---|
| *C07D 487/04* | (2006.01) |
| *C07D 519/00* | (2006.01) |
| *A61K 31/519* | (2006.01) |
| *C07D 471/04* | (2006.01) |
| *A61K 45/06* | (2006.01) |
| *A61K 31/52* | (2006.01) |
| *A61K 31/505* | (2006.01) |

(52) U.S. Cl.
CPC .......... *C07D 487/04* (2013.01); *A61K 31/505* (2013.01); *A61K 31/519* (2013.01); *A61K 31/52* (2013.01); *A61K 45/06* (2013.01); *C07D 471/04* (2013.01); *C07D 519/00* (2013.01)

(58) Field of Classification Search
CPC ... C07D 487/04; C07D 519/00; A61K 31/519
USPC ........................................ 544/262; 514/262.1
See application file for complete search history.

(56) References Cited

U.S. PATENT DOCUMENTS

| | | | |
|---|---|---|---|
| 4,704,381 A | 11/1987 | Schaumann et al. |
| 5,240,941 A | 8/1993 | Bruneau |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,214,834 B1 | 4/2001 | Jadhav et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,319,660 B1 | 11/2001 | Allway et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

U.S. Appl. No. 14/106,479, filed Dec. 13, 2013, Knight et al.

(Continued)

*Primary Examiner* — Susanna Moore
(74) *Attorney, Agent, or Firm* — Honigman Miller Schwartz and Cohn LLP; Lucy X. Yang; Jonathan P. O'Brien

(57) ABSTRACT

The present invention provides chemical entities or compounds and pharmaceutical compositions thereof that are capable of modulating certain protein kinases such as mTor, tyrosine kinases, and/or lipid kinases such as PI3 kinase. Also provided in the present invention are methods of using these compositions to modulate activities of one or more of these kinases, especially for therapeutic applications.

18 Claims, 1 Drawing Sheet

(56) References Cited

U.S. PATENT DOCUMENTS

| | | |
|---|---|---|
| 6,387,894 B1 | 5/2002 | Fossa |
| 6,390,821 B1 | 5/2002 | Shokat |
| 6,417,194 B1 | 7/2002 | Fox et al. |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanu et al. |
| 6,562,819 B2 | 5/2003 | Carson et al. |
| 6,583,161 B1 | 6/2003 | Medina |
| 6,613,798 B1 | 9/2003 | Porter et al. |
| 6,624,119 B1 | 9/2003 | Reinhard et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,474 B2 | 3/2004 | Hirst et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,800,633 B2 | 10/2004 | Castelhano et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,228 B2 | 12/2006 | Kasibhatla et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,241,890 B2 | 7/2007 | Kasibhatla et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,271,262 B2 | 9/2007 | La Greca et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 2001/0024833 A1 | 9/2001 | Laborde et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0212113 A1 | 11/2003 | Dyatkina et al. |
| 2003/0225098 A1 | 12/2003 | Hirst et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Bhat et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |

(56) References Cited

U.S. PATENT DOCUMENTS

| | | |
|---|---|---|
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187230 A1 | 8/2005 | Ding et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0222177 A1 | 10/2005 | Sim et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0166997 A1 | 7/2006 | Zhang et al. |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0246551 A1 | 11/2006 | Stack et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0112005 A1 | 5/2007 | Chen et al. |
| 2007/0142405 A1 | 6/2007 | Dong et al. |
| 2007/0149521 A1 | 6/2007 | Crew et al. |
| 2007/0203143 A1 | 8/2007 | Sheppard et al. |
| 2007/0213355 A1 | 9/2007 | Capraro et al. |
| 2007/0224672 A1 | 9/2007 | Leban et al. |
| 2007/0249598 A1 | 10/2007 | Wang et al. |
| 2007/0254883 A1 | 11/2007 | Crew et al. |
| 2007/0270452 A1 | 11/2007 | Blagg et al. |
| 2007/0293489 A1 | 12/2007 | Adams et al. |
| 2007/0293516 A1 | 12/2007 | Knight et al. |
| 2008/0003254 A1 | 1/2008 | Mack et al. |
| 2008/0032960 A1 | 2/2008 | Knight et al. |
| 2008/0039491 A1 | 2/2008 | Ronan et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0184760 A1 | 7/2010 | Ren et al. |
| 2010/0190749 A1 | 7/2010 | Ren et al. |
| 2010/0273776 A1 | 10/2010 | Lindquist et al. |
| 2011/0046165 A1 | 2/2011 | Ren et al. |
| 2011/0077268 A1 | 3/2011 | Liu et al. |
| 2011/0124641 A1 | 5/2011 | Ren et al. |
| 2011/0144134 A1 | 6/2011 | Shokat et al. |
| 2011/0160232 A1 | 6/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0294930 A1 | 11/2012 | Ren et al. |
| 2014/0030256 A1 | 1/2014 | Ren et al. |
| 2014/0128599 A1 | 5/2014 | Ren et al. |

FOREIGN PATENT DOCUMENTS

| | | |
|---|---|---|
| DE | 2004713 A1 | 8/1971 |
| EP | 0773023 A1 | 5/1997 |
| EP | 1020445 B1 | 8/2008 |
| GB | 812366 | 4/1959 |
| GB | 937725 | 9/1963 |
| GB | 1291417 A | 10/1972 |
| JP | 61109797 | 5/1986 |
| JP | 5256693 A | 10/1993 |
| JP | 8295667 A | 11/1996 |
| JP | 9143163 A | 6/1997 |
| JP | 10206995 A | 8/1998 |
| JP | 2000072773 A | 3/2000 |
| JP | 2002-037787 | 2/2002 |
| JP | 2002131859 A | 5/2002 |
| JP | 2003073357 A | 3/2003 |
| JP | 2004161716 A | 6/2004 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/22443 A1 | 11/1993 |
| WO | WO 94/13677 A1 | 6/1994 |
| WO | WO 94/17803 A1 | 8/1994 |
| WO | WO 95/12588 A1 | 5/1995 |
| WO | WO 95/29673 A1 | 11/1995 |
| WO | WO 95/32984 A1 | 12/1995 |
| WO | WO 96/31510 A1 | 10/1996 |
| WO | WO 96/40706 A1 | 12/1996 |
| WO | WO 97/28133 A1 | 8/1997 |
| WO | WO 97/28161 A1 | 8/1997 |
| WO | WO 98/14450 A1 | 4/1998 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 00/42042 A2 | 7/2000 |
| WO | WO 00/42042 A3 | 11/2000 |
| WO | WO 01/02369 A2 | 1/2001 |
| WO | WO 01/16114 A2 | 3/2001 |

(56) References Cited

FOREIGN PATENT DOCUMENTS

| | | |
|---|---|---|
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/000688 A1 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 02/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/085248 A1 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/114180 A1 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/023115 A2 | 3/2007 |
| WO | WO 2007/025090 A2 | 3/2007 |
| WO | WO 2007/023115 A3 | 4/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/095223 A2 | 8/2007 |
| WO | WO 2007/075554 A3 | 9/2007 |
| WO | WO 2007/103308 A2 | 9/2007 |
| WO | WO 2007/106503 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124405 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/031594 A1 | 3/2008 |
| WO | WO 2008/037477 A1 | 4/2008 |
| WO | WO 2008/047821 A1 | 4/2008 |
| WO | WO 2007/106503 A3 | 5/2008 |
| WO | WO 2008/063625 A2 | 5/2008 |
| WO | WO 2008/064018 A1 | 5/2008 |
| WO | WO 2007/121453 A3 | 7/2008 |
| WO | WO 2007/135380 A3 | 7/2008 |
| WO | WO 2008/063625 A3 | 7/2008 |
| WO | WO 2008/079028 A1 | 7/2008 |
| WO | WO 2008/082487 A2 | 7/2008 |
| WO | WO 2008/083070 A1 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2007/124405 A3 | 12/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |

(56) References Cited

FOREIGN PATENT DOCUMENTS

| WO | WO 2009/021990 A1 | 2/2009 |
|---|---|---|
| WO | WO 2009/023718 A2 | 2/2009 |
| WO | WO 2008/094737 A3 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/059304 A2 | 5/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/059304 A3 | 8/2009 |
| WO | WO 2009/100406 A2 | 8/2009 |
| WO | WO 2007/079164 A3 | 9/2009 |
| WO | WO 2009/114874 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2009/114874 A3 | 12/2009 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/051043 A1 | 5/2010 |
| WO | WO 2010/039534 A3 | 8/2010 |
| WO | WO 2010/088050 A2 | 8/2010 |
| WO | WO 2010/099139 A2 | 9/2010 |
| WO | WO 2010/099139 A3 | 10/2010 |
| WO | WO 2010/118367 A2 | 10/2010 |
| WO | WO 2010/088050 A3 | 11/2010 |
| WO | WO 2010/129816 A2 | 11/2010 |
| WO | WO 2010/118367 A3 | 3/2011 |

OTHER PUBLICATIONS

U.S. Appl. No. 14/139,723, filed Dec. 23, 2013, Ren et al.
U.S. Appl. No. 14/186,486, filed Feb. 21, 2014, Tanaka et al.
Office action dated Mar. 26, 2014 for U.S. Appl. No. 11/719,722.
Office action dated May 6, 2014 for U.S. Appl. No. 13/003,562.
Office action dated Dec. 2, 2013 for U.S. Appl. No. 12/920,966.
Sam, et al. Benzoxazoles: Potent Skeletal Muscle Relaxants. J Pharm Sci. May 1964;53:538-44.
West, et al. Activation of the PI3K/Akt pathway and chemotherapeutic resistance. Drug Resist Updat. Dec. 2002;5(6):234-48.
Bogert, et al. "Researches on quinazolines (Fifteenth paper), on a 3-aminoquinazoline, and the corresponding 3.3'-diquinazolyl, from 6-nitroacetanthranil and hydrazine hydrate" Journal of the American Chemical Society, (1906), 28(7), 884-893.
Elslager, et al. "Synthetic schistosomicides. VII. 6-Alkoxy-8-(aminoalkyl)amino-5-azoquinolines" Journal of Medicinal Chemisty (1964), 7(5) 663-4.
Hansch, et al. "Quantitative structure-activity relation of antimalarial and dihydrofolate reductase inhibition by quinazolines and 5-substituted benzyl-2,4-diaminopyrimidines" Journal of Medicinal Chemistry (1977), 20(1), 96-102.
Office action dated Jul. 8, 2013 for U.S. Appl. No. 12/677,098.
Richter, et al. "Inhibition of mammalian dihydrofolate reductase by selected 2,4-diaminoquinazolines and related compounds" Journal of Medicinal Chemistry (1974), 17(9), 943-7.
Vopicka, et al. "Quinazolines. III. Interaction of aniline with 2-chloro-4-alkoxyquinazolines and 2-chloro-4-ketodihydroquinazoline" Journal of the American Chemical Society (1932), 54, 1068-1070.
European search report dated Jan. 4, 2013 for EP Application No. 12175019.4.
McMahon, et al. VEGF receptor signaling in tumor angiogenesis. The Oncologist. 2000; 5(suppl 1)3-10.
Office action dated Feb. 8, 2013 for U.S. Appl. No. 12/509,281.
Office action dated Feb. 11, 2013 for U.S. Appl. No. 13/003,562.
Office action dated Feb. 27, 2013 for U.S. Appl. No. 12/920,970.
Office action dated Mar. 14, 2007 for U.S. Appl. No. 10/871,732.
Office action dated Mar. 23, 2006 for U.S. Appl. No. 10/871,732.
Office action dated May 10, 2012 for U.S. Appl. No. 12/586,241.
Office action dated May 10, 2012 for U.S. Appl. No. 12/586,309.
Office action dated May 29, 2012 for U.S. Appl. No. 12/509,281.
Office action dated Jun. 3, 2009 for U.S. Appl. No. 11/732,856.
Office action dated Jun. 20, 2012 for U.S. Appl. No. 11/719,722.
Office action dated Oct. 11, 2011 for U.S. Appl. No. 11/719,722.
Office action dated Oct. 25, 2012 for U.S. Appl. No. 12/586,241.
Office action dated Oct. 25, 2012 for U.S. Appl. No. 12/586,309.
Office action dated Oct. 30, 2006 for U.S. Appl. No. 10/871,732.
Office action dated Nov. 20, 2007 for U.S. Appl. No. 10/871,732.
Office action dated Dec. 24, 2008 for U.S. Appl. No. 11/732,856.
Pinedo, et al. Translational research: the role of VEGF in tumor angiogenesis. The Oncologist. 2000; 5(suppl 1):1-2.
Tseng, et al. Synergistic interactions between imatinib mesylate and the novel phosphoinositide-dependent kinase-1 inhibitor OSU-03012 in overcoming imatinib mesylate resistance. Blood. May 15, 2005;105(10):4021-7. Epub Jan. 21, 2005.
U.S. Appl. No. 13/112,611, filed May 20, 2011, Ren et al.
U.S. Appl. No. 13/289,540, filed Nov. 4, 2011, Ren et al.
Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan., 14:1390-1395 (1975).
Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011.
Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.
Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.
Chaisuparat, et al. Dual Inhibition of PI3K(alpha) and mTOR as an Alternative Treatment for Kaposi's Sarcoma. Cancer Research. 2008;68:8361.
Chappelow, et al. Neovascular Age-Related Macular Degeneration: Potential Therapies. Drugs. 2008;68(8):1029-1036.
Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.
Dijksman, et al. 271. 1 : 2-Dihydro-2-tbianaphthalene derivatives. Part I. Preparation and reactions of 1 : 2-dihydro-1-keto-2-thianaphthalenes. J. Chem. Soc. 1951:1213-18.
Donati. Emerging Therapies for Neovascular Age-Related Macular Degeneration: State of the Art. Ophthalmologica. 2007;221:366-377.
European search report and search opinion dated Oct. 26, 2011 for Application No. 9700424.6.
European Search Report dated Mar. 1, 2010 for EP Application No. 07873406.8.
Extended European Search Report from corresponding European Application No. 09700784.3 dated Oct. 28, 2011.
Farag, et al. Synthesis and reactivity of 2-(benzothiazol-2-y1)-1-bromo-1,2-ethanedione-1-arylhydrazones. Heteroatom Chemistry. 1997; 8(1):45-50.
Graupera, et al. Angiogenesis selectively requires the p110 isoform of PI3K to control endothelial cell migration. Nature. 2008;453:662-666.
Hellwinkel, et al. Heterocyclensynthesen mit MF/A12O3-Basensystemen: 2-Arylbenzofurane and 2,3-Diarylisochinolin-1(2H)-one. Synthesis. 1995;1995(9):1135-41.
International Preliminary Report on Patentability from International Application No. PCT/US2009/000042 dated Jul. 6, 2010.

(56) References Cited

OTHER PUBLICATIONS

International search report and written opinion dated Aug. 22, 2011 for PCT/US2011/037412.
International search report and written opinion dated Nov. 20, 2009 for PCT/US2009/005380.
International search report dated Nov. 2, 2010 for PCT Application No. US10/02020.
International search report dated Mar. 11, 2009 for PCT Application No. US2009/00038.
International search report dated Mar. 23, 2009 for PCT Application No. US2009/00042.
Kajita, et al. Nickel-catalyzed decarbonylative addition of phthalimides to alkynes. J Am Chem Soc. May 14, 2008;130(19):6058-9.
Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Lee, et al. All roads lead to mTOR: integrating inflammation and tumor angiogenesis. . . Cell Cycle. 2007;6(24):3011-3014.
Majumder, et al. mTOR inhibition reverses Ala-dependent prostate intraepithelial neoplasia through regulation of apoptotic and HIF-1-dependent pathways. Nature Medicine. 2004;10:594-601.
Mellinghoff, et al. TORward AKTually useful mouse models. Nature Medicine. 2004;10:579-580.
Modi, et at. Isoquinolones: Part IV—Synthesis of 3-Methyl, 3-Formyl & Other 3-Substituted N-Arylisoquinolones, Indian J. Chem. 1979; 18B:304-306.
Nemazanyi, et al. 3-Amino-4-aryl-1(2H)-isoquinolones. Chemistry of Heterocyclic Compounds. Mar. 1991;27(3):307-8.
Oda, et al. PIK3CA Cooperates with Other Phosphatidylinositol 3'-Kinase Pathway Mutations to Effect Oncogenic Transformation. Cancer Research. 2008;68:8127.
Ozaki, et al. Studies on 4 (1H)-Quinamlinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Stanoeva et al. Homophthalic anhydrides and their application to the synthesis of heterocyclic compounds (review). Chemistry of Heterocyclic Compounds. Dec. 1984;20(12);1305-15.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).
Wu, et al. One-pot two-step microwave-assisted reaction in constructing 4,5-disubstituted pyrazolopyrimidines. Org Lett. Oct. 2, 2003;5(20):3587-90.
Yaguchi, et al. Antitumor activity of ZSTK474, a new phosphatidylinositol 3-kinase inhibitor. J. Natl. Cancer. Inst. 2006; 98(8): 545-556. Abstract only.

European extended search report and search opinion dated Jan. 31, 2012 for EP Application No. 09795147.9.
U.S. Appl. No. 13/016,957, filed Jan. 28, 2011, Tanaka et al.
Abdel-Mohsen. Synthesis, Reactions and Antimicrobial Activity of 2-Amino-4-(8-quinolinol-5-yl)-1-(p-tolyl)-pyrrole-3-carbonitrile. Bull. Korean Chem. Soc. 2005;26(5);719-728.
Andrews, R.C., et al. "Effects of the 11β-Hydroxysteroid Dehydrogenase Inhibitor Carbenoxolone on Insulin Sensitivity in Men with Type 2 Diabetes", J. Clin. Endocrinol. Metab. (2003) 88(1):285-291.
Arnold, et al. "Pyrrolo[2,3-d]pyrimidines containing an extended 5-substituent as potent and selective inhibitors of lck I", Bioorg. & Med. Chem. Lett (2000) 10:2167-70.
Banker, G.S., et al. Modern Pharmaceutics, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", J. Med. Chem. (2002) 45(18):3813-3815.
Barnes, P.J., et al. "Efficacy and Safety of Inhaled Corticosteroids in Asthma", Am. Rev. Respir. Dis. (1993) 148:S1-26.
Beeram, et al. Akt-induced endocrine therapy resistance is reversed by inhibition of mTOR signaling. Ann Oncol. Aug. 2007;18(8):1323-8.
Bell, G., et al. "Glucokinase Mutations Insulin Secretion, and Diabetes Mellitus", Anne. Rev. Physiol., (1996) 58:171-186.
Bhat, et al. Pyrazolopyrimidine nucleosides. 12. Synthesis and biological activity of certain pyrazolo[3,4-d]pyrimidine nucleosides related to adenosine. J Med Chem. Oct. 1981;24(10):1165-72.
Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.
Bohren, K.M., et al. "Expression, Crystallization and Preliminary Crystallographic Analysis of Human Carbonyl Reductase", J. Mol. Biol. (1994) 224:659-664.
Cox, B., et al. "Human Colorectal Cancer Cells Efficiently Conjugate the Cyclopentenone Prostaglandin, Prostaglandin J2 to Glutathione", Biochim. Biophys. Acta (2002) 1584:37-45.
Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", Eur. J. Endocrinol. (2000) 142:200-207.
Ding, S., et al. "A Combinatorial Scaffold Approach Toward Kinase-Directed Heterocycle Libraries", J. Am. Chem. Soc. (2002) 124(8):1594-1596.
Ding, S., et al. "A Concise and Traceless Linker Strategy Toward Combinatorial Libraries of 2,6,9-Substituted Purines", J. Org. Chem. (2001) 66:8273-8276.
Ding, S., et al. "Resin-Capture and Release Strategy Toward Combinatorial Libraries of 2,6,9-Substituted Purines", J. Comb. Chem.(2002) 4:183-186.
European Examination Report dated Sep. 14, 2011 for EP Application No. 07873406.8, 4 pages.
European search report dated Feb. 4, 2011 for EP Application No. 05857011.0.
European search report dated Feb. 24, 2010 for EP Application No. 07754845.1.
Examination report dated Oct. 27, 2010 for GB Application No. GB0819947.3.
Fajans, S., et al."Maturity Onset Diabetes of the Young (MODY)", Diabet. Med. (1996) 13:S90-S95.
Fan, et al. A dual phosphoinositide-3-kinase alpha/mTOR inhibitor cooperates with blockade of epidermal growth factor receptor in PTEN-mutant glioma. Cancer Res. Sep. 1, 2007;67(17):7960-5.
Feinstein, M.B., et al. "Regulation of the Action of Hydrocotisone in Airway Epithelial Cells by 11β-Hydroxysteroid Dehydrogenase", Am. J. Respir. Cell. Mol. Biol. (1999) 21:403-408.
Feldman, et al. Active-site inhibitors of mTOR target rapamycin-resistant outputs of mTORC1 and mTORC2. PLoS Biol. Feb. 10, 2009;7(2):371-383.
Fingl, E., et al. "General Principles", The Pharmacological Basis of Therapeutics, Fifth Edition (1975), Ch. 1, 1-46.

(56) References Cited

OTHER PUBLICATIONS

Forrest, G.L., et al. "Carbonyl Reductase", Chem. Biol. Interact. (2000) 129:21-40.
Forrest, G.L., et al. "Induction of a Human Carbonyl Reductase Gene Located on Chromosome 21", Biochim. Biophys. Acta. (1990) 1048:149-155.
Franzen, R. "The Suzuki, the Heck, and the Stille reaction—three versative methods for the introduction of new C—C bonds on solid support", Can J. Chem. (2000) 78:957-962.
Funder, J.W., et al. "Mineralocorticoid Action: Target Tissue Specificity Is Enzyme, Not Receptor, Mediated", Science (1998) 242:583-585.
Garber, M.E., et al. "Diversity of Gene Expression in Adenocarcinoma of the Lung", Proc. Nat. Acad. Sci. USA (2001) 98(24):13784-13789.
Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.
Haase, A.,et al. "Detection of Viral Nucleic Acids by in Situ Hybridization", Methods in Virology (1984) VII:189-226.
Hanefeld, U., et al. "One-pot Synthesis of Tetrasubstituted Pyrazoles Proof of Regiochemistry", J. Chem. Soc. Perkin Trans. (1996) 1:1545-1552.
International Preliminary Report on Patentability and Written Opinion dated Apr. 19, 2011 for International Application No. PCT/US2009/060985, 6 pages.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International search report and written opinion dated Jan. 15, 2010 for PCT/US2009/064717.
International search report and written opinion dated Jul. 22, 2005 for PCT/US2004/019782.
International search report and written opinion dated Dec. 11, 2008 for PCT Application No. US08/78990.
International search report and written opinion dated Mar. 15, 2010 for PCT Application No. US2009/049969.
International search report dated Apr. 5, 2006 for PCT/FR2005/051073.
International search report dated Aug. 27, 2008 for PCT/US2007/008395.
International search report dated Sep. 25, 2008 for PCT/US2007/008355.
International search report dated Jan. 11, 2010 for PCT Application No. US2009/05959.
International search report dated Jan. 12, 2010 for PCT Application No. US2009/05958.
International search report dated Oct. 2, 2006 for PCT/US2005/042524.
International search report dated Dec. 24, 2009 for PCT Application No. US09/37313.
International search report dated Aug. 13, 2010 for PCT Applilcation No. US09/37324.
International Search Report dated Jun. 28, 2010 for International Application No. PCT/US2009/060985, 5 pages.
Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.
Kallberg, et al. Short-Chain Dehydrogenase/Reductase (SDR) Relationships: a Large Family with Eight Clusters Common to Human, Animal, and Plant Genomes. Protein Sci. (2002) 11:636-641.
Kallberg, et al. Short-Chain Dehydrogenases/Reductases (SDRs). Eur. J. Biochem. (2002) 269:4409-4417.
Kim, et al. Activation and function of the mTORC1 pathway in mast cells. J Immunol. Apr. 1, 2008;180(7):4586-95.
Knight, et al. "A Pharmacological Map of the P13-K Family Defines a Role for p110α in Insulin Signaling", Cell (2006) 125:733-747.
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, et al. 5-Substituierte 4-Aminopyrimidine durch Aminomethinylierung von Acetonitrilen. Liebigs Ann. Chem. 1977:537-544.
Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.
Mayer, T.U., et al. "Small Molecule Inhibitor of Mitotic Spindle Bipolarity Identified in a Pheontype-Based Screen", Science (1999) 286:971-974.
Miyaura, N., et al., "Palladium-Catalyzed Cross-Coupling Reactions of Organoboron Compounds," Chem. Rev. (1995) 95(7):2457-2483.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Naicanishi, M., et al. "Cloning and Sequence Analysis of a cDNA Encoding Tetrameric Carbonyl Reductase of Pig Lung", Biochem. Biophys. Acta (1993) 194(3):1311-1316.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.
Oppermann, U.C., et al. "Forms and Functions of Human SDR Enzymes", Chem. Biol. Interact. (2001) 130-132(1-3):699-705.
Persson, C.G. "Glucocorticoids for Asthma—Early Contributions", Pulm. Pharmacol. (1989) 2:163-166.
Petrie, et al. A novel biotinylated adenylate analogue derived from pyrazolo[3,4-d]pyrimirline for labeling DNA probes. Bioconjug Chem. Nov.-Dec. 1991;2(6):441-6.
Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", J. Med. Chem. (1990) 33:1984-1992.
Report of the Expert Committee on the Diagnosis and Classification of Diabetes Mellitus, Diabetes Care (1992) 2(Suppl 1):S5-S19.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 11β—hydroxysteroid Dehydrogenase Type-2", J. Steroid Biochm. Mol. Biol. (2000) 72:231-237.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.
Supplementary European Examination Report dated Sep. 20, 2011 for EP Application No. 07754845.1, 4 pages.

(56) References Cited

OTHER PUBLICATIONS

Takeuchi, et al. Synergistic augmentation of rapamycin-induced autophagy in malignant glioma cells by phosphatidylinositol 3-kinase/protein kinase B inhibitors. Cancer Res. Apr. 15, 2005;65(8):3336-46.
Tanaka, M., et al. "An Unbiased Cell Morphology-Based Screen for New, Biologically Active Small Molecules", PLoS Biology (2005) 3(5):0764-0776.
Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.
White, P.C., et al. "11β—Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-d]pyrimidines-Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Apsel, et al. Targeted polypharmacology: discovery of dual inhibitors of tyrosine and phosphoinositide kinases. Nat Chem Biol. Nov. 2008;4(11):691-9.
International search report dated Feb. 17, 2010 for PCT Application No. US2009/049983.

Figure 1: PI3K/Akt/mTOR Signaling Pathway
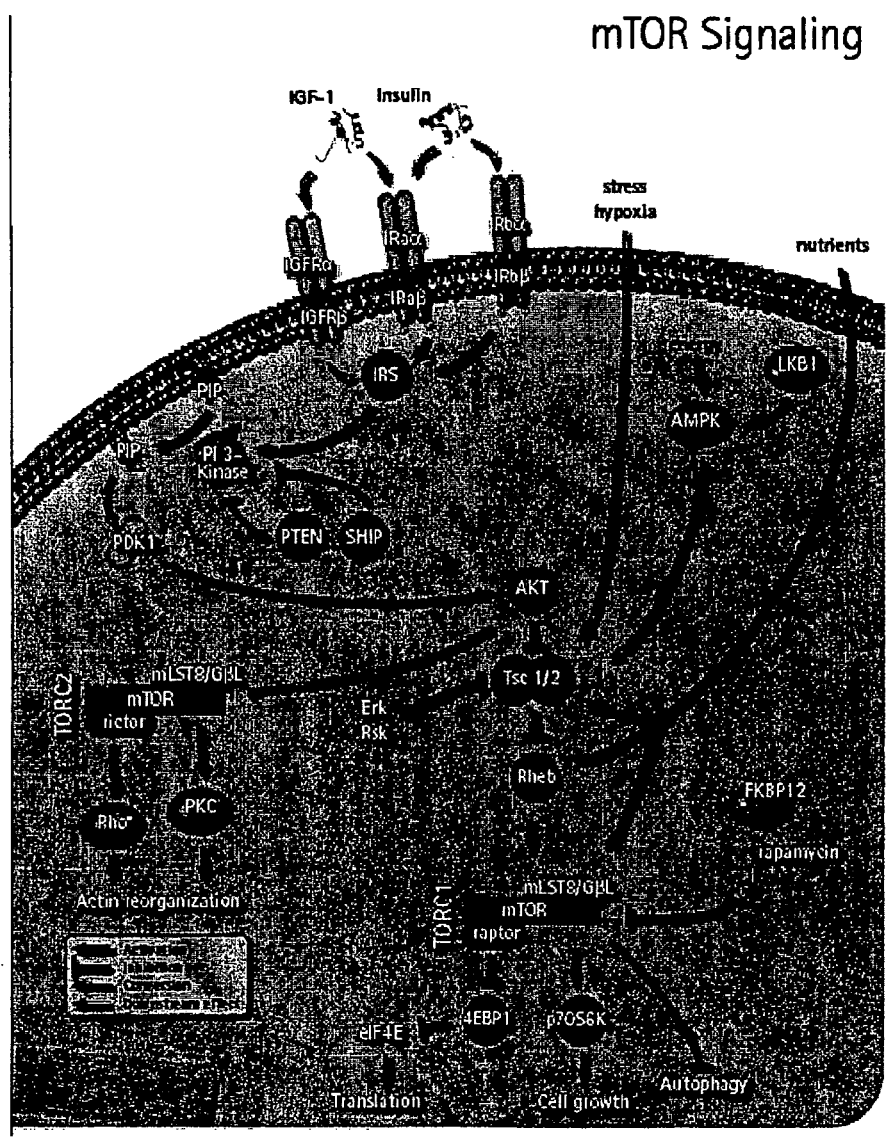

KINASE INHIBITORS AND METHODS OF USE

PRIORITY CLAIM

This application is a divisional of U.S. patent application Ser. No. 13/002,438 filed Mar. 25, 2011, which is the United States National Phase filing of PCT/US2009/049983 filed Jul. 8, 2009. This application also claims priority under 35 U.S.C. §119(e) to U.S. Provisional Patent Application No. 61/079,127 filed Jul. 8, 2008. The entire contents of the aforementioned applications are herein incorporated by reference.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as the Akt/PDK1 pathway, mTOR, the Tec family kinases, and the Rho family GTPases. The class II and III PI3-Ks play a key role in intracellular trafficking through the synthesis of PI(3)P and PI(3,4)P2.

The production of phosphatidylinositol-3,4,5-trisphosphate initiates potent growth and survival signals. In some epithelial cancers the PI3K pathway is activated by direct genetic mutation. Additionally, the PI3K signaling pathway appears to be a crucial survival and growth signal in a broad spectrum of cancers. As PI3K signaling pathway plays a pivotal role in cell proliferation and differentiation, inhibition of this pathway is believed to be beneficial in hyperproliferative diseases.

Downstream mediators of the PI3K signal transduction pathway include Akt and mammalian target of rapamycin (mTOR). Akt possesses a pleckstrin homology (PH) domain that binds PIP3, leading to Akt kinase activation. Akt phosphorylates many substrates and is a central downstream effector of PI3K for diverse cellular responses. Full activation of Akt typically requires phosphorylation of T308 in the activation loop and S473 in a hydrophobic motif. One important function of Akt is to augment the activity of mTOR, through phosphorylation of TSC2 and other mechanisms.

mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitrochondrial function.

mTOR exists in two complexes, mTORC1 and mTORC2. mTORC1 contains the raptor subunit and mTORC2 contains rictor. These complexes are differentially regulated, and have distinct substrate specificities and rapamycin sensitivity. For example, mTORC1 phosphorylates S6 kinase (S6K) and 4EBP1, promoting increased translation and ribosome biogenesis to facilitate cell growth and cell cycle progression. S6K also acts in a feedback pathway to attenuate PI3K/Akt activation. mTORC2 is generally insensitive to rapamycin. mTORC2 is though to modulate growth factor signaling by phosphorylating the C-terminal hydrophobic motif of some AGC kinases such as Akt. In many cellular contexts, mTORC2 is required for phosphorylation of the S473 site of Akt.

Dysregulation of signaling pathways mediated by many other kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

As such, kinases particularly protein kinases such as mTor and lipid kinases such as PI3Ks are prime targets for drug development. The present invention addresses a need in the art by providing a new class of kinase inhibitors and various treatment methods.

SUMMARY OF THE INVENTION

In one aspect, the invention provides a compound of Formula I or a pharmaceutically acceptable salt thereof:

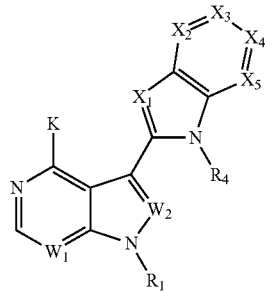

Formula I wherein K is $NR^{31}R^{32}$, $CH_3$, $CH_2G$, $CHGG$, $CGGG$, $G$, or H, wherein G is Cl, Br, or F;

$W_1$ and $W_2$ are independently CH, $CR_5$, or N;

$X_1, X_2, X_3, X_4,$ and $X_5$ are independently N or $CR_2$, wherein no more than two adjacent ring atoms are N and the total number of $X_1, X_2, X_3, X_4,$ and $X_3$ which are N is no more than 4;

$R_1$ is H, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl- heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —C(=O)O—, —C(=O)$NR^{31}$—, —S(O)—, —S—, —S(O)$_2$—, —S(O)$_2NR^{31}$—, or —$NR^{31}$—;

each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S (O)$_{0-2}R^{32}$, —$NR^{31}$C(=$NR^{32}$)$NR^{33}R^{32}$, —$NR^{31}$C (=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S (O)$_{0-2}R^{32}$, —$NR^{31}$C(=$NR^{32}$)$NR^{33}R^{32}$, —$NR^{31}$C (=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)$R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

each instance of $R_5$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S (O)$_{0-2}R^{32}$, —$NR^{31}$C(=$NR^{32}$)$NR^{33}R^{32}$, —$NR^{31}$C (=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R^{31}$, $R^{32}$, and $R^{33}$, in each instance, is independently H, $C_{1-10}$alkyl, —$C_{3-8}$cycloalkyl, aryl, hetaryl, or heterocycloalkyl; and wherein when $X_1, X_2, X_3, X_4,$ and $X_5$ are CH, K is $NH_2$, $R_4$ is H, and $W_1$ is N and $W_2$ is N, then $R_1$ is not -cyclo$C_4H_7$.

In one embodiment, K is $NH_2$, and $W_1$ and $W_2$ are N.

In another aspect, the invention provides a method of treating a disease or of inhibiting cell proliferation with a compound of Formula:

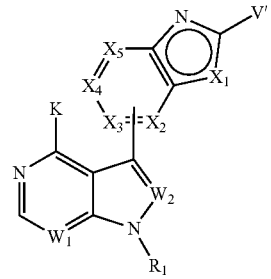

wherein K is $NR^{31}R^{32}$, $CH_3$, $CH_2F$, $CHF_2$, $CF_3$, F, or H;

V' is -(L')$_k$-$R_1$;

$W_1$ and $W_2$ are independently CH, $CR_5$, or N;

$X_1$ is N, O or S;

$X_2, X_3, X_4,$ and $X_5$ are independently N or $CR_2$, wherein no more than two adjacent ring atoms are N and the total number of $X_2, X_3, X_4,$ and $X_5$ which are N is no more than 3;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{1-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —C(=O)O—, —C(=O)$NR^{31}$—, —S(O)—, —S—, —S(O)$_2$—, —S(O)$_2NR^{31}$—, or —$NR^{31}$—;

L' is —O—, —$NR^{31}$—, —S(O)$_{0-2}$—, —C(O)—, —C(O)N ($R^{31}$)—, —N($R^{31}$)C(O)—, —N($R^{31}$)S(O)—, —N($R^{31}$)S (O)$_2$—, —C(O)O—, —CH($R^{31}$)N(C(O)$OR^{32}$)—, —CH ($R^{31}$)N(C(O)$R^{32}$)—, —CH($R^{31}$)N(SOR$^{32}$)—, —CH ($R^{31}$)N($R^{32}$)—, —CH($R^{32}$)C(O)N($R^{32}$)—, —CH($R^{31}$)N ($R^{32}$)C(O)—, —CH($R^{31}$)N($R^{32}$)S(O)—, or —CH($R^{31}$)N ($R^{32}$)S(O)$_2$—;

k, in each instance, is 0 or 1;

each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{33}$, —OC(=O)OR$^{33}$, —OC(=O)NR$^{31}$R$^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —R$^{31}$, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^2$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{33}$, —OC(=O)OR$^{33}$, —OC(=O)NR$^{31}$R$^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)R$^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

each instance of $R_5$ is independently hydrogen, halo, —OH, —R$^{31}$, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{33}$, —OC(=O)OR$^{33}$, —OC(=O)NR$^{31}$R$^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

R$^{31}$, R$^{32}$, and R$^{33}$, in each instance, is independently H, $C_{1-10}$alkyl, —$C_{3-8}$cycloalkyl, aryl, hetaryl, or heterocycloalkyl; and wherein the compound inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ.

In another aspect, the invention additionally provides a compound of Formula:

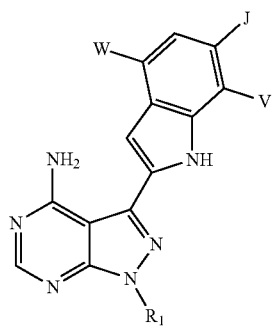

wherein $R_1$ is $C_{1-10}$alkyl, unsubstituted or substituted by one or more independent $R_3$ substituents;

each instance of $R_3$ is independently hydrogen, halo, —OH, —R$^{31}$, —CF$_3$, —OCF$_3$, —OR$^{31}$, —NR$^{31}$R$^{32}$, —C(O)R$^{31}$, —CO$_2$R$^{31}$, —C(O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{33}$, —OC(=O)OR$^{33}$, —OC(=O)NR$^{31}$R$^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)R$^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

J, V, and W are independently hydrogen, halo, —OH, —CF$_3$, —OCF$_3$, —OR$^{31}$, —NR$^{31}$R$^{32}$, —C(O)R$^{31}$, —C$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)N$^{33}$R$^{32}$, —NR$^{31}$C(=NR$^{32}$)OR$^{33}$, —OC(=O)OR$^{33}$, —OC(=O)NR$^{31}$R$^{32}$, —OP(O)(OR$^{31}$)$_2$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl and $R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{1-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents, and wherein at least one of J, V, and W is not hydrogen;

R$^{31}$, R$^{32}$, and R$^{33}$, in each instance, is independently H, $C_{1-10}$alkyl, —$C_{3-8}$cycloalkyl, aryl, hetaryl, or heterocycloalkyl; wherein $R_1$ is not -cycloC$_4$H$_7$.

In a further aspect, the invention provides a compound of Formula:

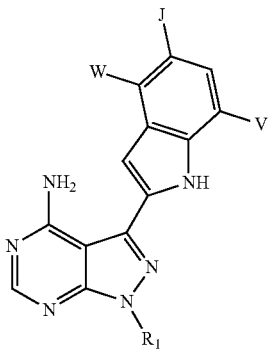

wherein $R_1$ is $C_{1-10}$alkyl, unsubstituted or substituted by one or more independent $R_3$ substituents;

each instance of $R_3$ is independently hydrogen, halo, —OH, —R$^{31}$, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{33}$, —OC(=O)OR$^{33}$, —OC(=O)NR$^{31}$R$^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl; $R_4$ is hydrogen, —C(O)R$^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

J, V, and W are independently hydrogen, halo, —OH, —CF$_3$, —OCF$_3$, —OR$^{31}$, —NR$^{31}$R$^{32}$, —C(O)R$^{31}$, —C$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —NR$^{31}$C(=NR$^{32}$)NR$^{33}$R$^{32}$, —NR$^{31}$C(=NR$^{32}$)OR$^{31}$, —OC(=O)OR$^{33}$, —OC(=O)NR$^{33}$R$^{32}$, —OP(O)(OR$^{31}$)$_2$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl and $R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents and wherein at least two of J, V and W are not hydrogen;

$R^{31}$, $R^{32}$, and $R^{33}$, in each instance, is independently H, $C_{1-10}$alkyl, —$C_{3-8}$cycloalkyl, aryl, hetaryl, or heterocycloalkyl; and wherein $R_1$ is not -cyclo$C_4H_7$.

In various embodiments, J is hydrogen, fluoro, chloro, bromo, hydroxy, methoxy, cyano, or amido; V is hydrogen, hetaryl, trifluoromethyl, trifluoromethoxy, methyl, cycloalkyl, cyano, chloro, bromo, fluoro, amido, or sulfonate; and W is hydrogen, hydroxy, methoxy, trifluoromethoxy, fluoro, bromo, chloro, or amido.

In some embodiments, J, V, and W are independently H, OH, Cl, OMe, or F; and $R_1$ is $C_{1-10}$alkyl, $C_{3-8}$cycloalkyl, or heterocycloalkyl. In various embodiments, V is OH, OMe, or Cl. In various embodiments, $R_1$ is isopropyl. In other embodiments, $R_1$ is cyclopentyl. In yet other embodiments, $R_1$ is morpholino or substituted piperidinyl.

In various embodiments, K is amino, hydrogen or methyl.

In some embodiments, $W_1$ and $W_2$ are CH. In some embodiments, $W_1$ and $W_2$ are N. In some embodiments, $W_1$ is CH, and $W_2$ is N. In some embodiments, $W_1$ is N and $W_2$ is CH.

In various embodiments, $X_1$, $X_2$, $X_3$, $X_4$, and $X_5$ are $CR_2$; or $X_1$, is N, and $X_2$, $X_3$, $X_4$, and $X_5$ are $CR_2$; or $X_2$, is N, and $X_1$, $X_3$, $X_4$, and $X_5$ are $CR_2$; or $X_3$, is N, and $X_1$, $X_2$, $X_4$, and $X_3$ are $CR_2$; or $X_4$, is N, and $X_1$, $X_2$, $X_3$, and $X_5$ are $CR_2$; or $X_5$ is N, and $X_1$, $X_2$, $X_3$, and $X_4$ are $CR_2$; or $X_1$ and $X_2$ are N, and $X_3$, $X_4$, and $X_5$ are $CR_2$; or X, and $X_3$ are N, and $X_2$, $X_4$, and $X_5$ are $CR_2$; or X, and $X_4$ are N, and $X_2$, $X_3$, and $X_5$ are $CR_2$; or X, and X, are N, and $X_2$, $X_3$, and $X_4$ are $CR_2$; or $X_2$ and $X_4$ are N, and $X_1$, $X_3$, and $X_5$ are $CR_2$; or $X_3$ and $X_5$ are N, and $X_1$, $X_2$, and $X_4$ are $CR_2$; or $X_2$ and $X_4$ are N, and $X_1$, $X_3$, and $X_5$ are $CR_2$; or $X_1$, $X_2$, and $X_4$ are N, and $X_3$ and $X_5$ are $CR_2$; or $X_3$ and $X_5$ are N, and $X_2$ and $X_3$ are N, and $X_1$, $X_3$, and $X_4$ are $CR_2$; or $X_1$, $X_2$, and $X_5$ are N, and $X_4$ and $X_5$ are $CR_2$; or $X_3$ and X, are N, and $X_1$, $X_2$, and $X_4$ are $CR_2$; or $X_1$, $X_3$, and X, are N, and $X_2$ and $X_4$ are $CR_2$.

In various embodiments, each $R_2$ is independently hydrogen, halo, —OH, —$CF_3$, —$OCF_3$, —$OR^{31}$, —$NR^{31}R^{32}$, —C(O)$R^{31}$, —C(=O)$NR^{31}R^{32}$, —$NO_2$, —CN, —S(O)$_{0-2}$$R^{31}$, —$SO_2NR^{31}R^{32}$, $C_{1-10}$alkyl, heterocycloalkyl, aryl, or hetaryl.

In various embodiments, $R_4$ is -L-$C_{1-10}$alkyl, -L-$C_{3-8}$cycloalkyl, -L-heteroaryl, -L-heterocycloalkyl, -L-$C_{1-10}$alkyl-heterocylyl, -L-$C_{3-8}$cycloalkyl-heterocycloalkyl, or -L-$C_{1-10}$alkylhetaryl. In various embodiments, L is absent.

In various embodiments, $R_3$ is independently halo, —OH, —$NR^{31}R^{32}$, —C(O)$R^{31}$, —$CO_2R^{31}$, —C(=O)$NR^{31}R^{32}$, —$NR^{31}C(O)R^{32}$, —$NR^{31}C(O)OR^{32}$, —$NR^{31}S(O)_{0-2}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl.

In various embodiments, $R_4$ is hydrogen or $C_{1-10}$alkyl.

In a further aspect of the invention, a pharmaceutical composition is provided, comprising a compound of the invention and a pharmaceutically acceptable carrier.

In a further aspect of the invention, a method is provided of treating a subject suffering from a disease mediated by mTorC1 and/or mTorC2 comprising administering an effective amount of a compound of the invention to the subject.

In some embodiments of the methods of invention, the disease is bone disorder, inflammatory disease, immune disease, nervous system disease, metabolic disease, respiratory disease, cardiac disease or a neoplastic condition. In some embodiments, the disease is a neoplastic condition such as restenosis. In other embodiments, the neoplastic condition is cancer. In some embodiments, the cancer is selected from B cell lymphoma, T cell lymphoma, non small cell lung carcinoma, and leukemia. In other embodiments, the disease is an autoimmune disorder.

In some embodiments of the methods of the invention, the method further comprises administering a second therapeutic agent. In some embodiments, the compound substantially inhibits full activation of Akt in a cell and the second therapeutic agent is an anti-cancer agent, and further the efficacy of said treatment is enhanced through a synergistic effect of the compound and the anti-cancer agent. For example, the anti-cancer agent is selected from the group consisting of rapamycin, Gleevec, or derivative thereof that inhibits a mammalian target of rapamycin or Gleevec. In some embodiments, the compound or the second therapeutic agent is administered parenterally, orally, intraperitoneally, intravenously, intraarterially, transdermally, intramuscularly, liposomally, via local delivery by catheter or stent, subcutaneously, intraadiposally, or intrathecally.

In some embodiments, one or more of the subject compounds yield selective inhibition of mTor-mediated signal transduction without affecting upstream PI3K. In some other embodiments, the compounds provided herein can inhibit mTor-mediated activity more effectively than rapamycin, hence providing an alternative treatment for rapamycin-resistant conditions.

In some embodiments, one or more of the subject compound selectively inhibits both mTorC1 and mTorC2 activity relative to all type I phosphatidylinositol 3-kinases (PI3-kinase) consisting of PI3-kinase α, PI3-kinase β, PI3-kinase γ, and PI3-kinase δ.

In some embodiments, one or more of the subject compound selectively inhibits both mTor activity with an IC50 value of about 100 nM, 50 nM, 10 nM, 5 nM, 100 pM, 10 pM or even 1 pM, or less as ascertained in an in vitro kinase assay.

In some embodiments, one or more of the subject compound is substantially ineffective in inhibiting a type I PI3-kinase at a concentration of 100 nM, 200 nM, 500 nM, or 1uM, 5 uM or 10 uM, or higher in an in vitro kinase assay.

In some embodiments, one or more of the subject compound inhibits phosphorylation of Akt (S473) and Akt (T308) more effectively than rapamycin when tested at a comparable molar concentration in an in vitro kinase assay.

In some embodiments, one or more of the subject compound competes with ATP for binding to ATP-binding site on mTorC1 and/or mTorC2.

In some embodiments, one or more of the subject compound causes apoptosis of said cell or cell cycle arrest.

In another aspect, the invention provides a method for inhibiting cell proliferation comprising contacting a cell with a compound of the invention that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ. In some embodiments, the compound of the invention selectively inhibits both mTorC1 and mTorC2 activity, and simultaneously inhibits Akt phosphorylation at residues S473 and T308. In other embodiments, the compound selectively inhibits both mTorC1 and mTorC2 activity relative to all type I phosphatidylinositol 3-kinases (PI3-kinase) consisting of PI3-kinase α, PI3-kinase β, PI3-kinase γ, and PI3-kinase δ. In other embodiments, the compound of the invention inhibits phosphorylation of Akt (S473) and Akt (T308) more effectively than rapamycin when tested at a comparable molar concentration in an in vitro kinase assay.

In some embodiments, the inhibition of cell-proliferation is evidenced by an assay selected from the group consisting of an MTS cell proliferation assay, a resazurin assay, a colony formation assay, flow cytometry, a cell division tracker dye assay, immunoblotting, and a phosflow assay. In other embodiments, the inhibition takes place in vitro.

In some embodiments, the compound competes with ATP for binding to ATP-binding site on mTorC1 and/or mTorC2. In other embodiments, the compound inhibits phosphorylation of S473 of Akt more effectively than phosphorylation of T308 of Akt when tested at a comparable molar concentration. In yet other embodiments, the cell is a neoplastic cell and wherein the compound inhibits full activation of Akt in a cell and wherein the compound is an anti-cancer agent, wherein said inhibition of cell proliferation is enhanced through a synergistic effect of said compound and said anti-cancer agent. In some embodiments, the inhibition causes apoptosis of said cell or cell cycle arrest. In specific embodiments, the cell is rapamycin-resistant.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts cellular components in the PI3 kinase/Akt/mTor pathway.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The terms "treatment," "treating," "palliating," and "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" as applied to a biologically active agent refers to the agent's ability to selectively reduce the target signaling activity as compared to off-target signaling activity, via direct or interact interaction with the target.

"mTorC1 and/or mTorC2 activity" as applied to a biologically active agent refers to the agent's ability to modulate signal transduction mediated by mTorC1 and/or mTorC2. For example, modulation of mTorC1 and/or mTorC2 activity is evidenced by alteration in signaling output from the PI3K/Akt/mTor pathway.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionucleotides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures wherein hydrogen is replaced by deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") include those embodiments, for example, an embodiment of any composition of matter, composition, method, or process, or the like, that "consist of" or "consist essentially of" the described features.

The following abbreviations and terms have the indicated meanings throughout:

PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PIKK=Phosphoinositide Kinase Like Kinase; AIDS=Acquired Immuno Deficiency Syndrome; TLC=Thin Layer Chromatography; MeOH=Methanol; and CHCl$_3$=Chloroform.

"Acyl" refers to a —(C═O)R radical wherein "R" is alkyl, aryl, heteroaryl, heteroalkyl, or heterocycloalkyl, which are as described herein. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Alkoxy" refers to a (alkyl)O-radical, where alkyl is as described herein and contains 1 to 10 carbons (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. A alkoxy moiety may be substituted by one or more of the substituents described as suitable substituents for an alkyl radical.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e. vinyl), prop-1-enyl (i.e. allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to refers to an -(alkenyl) cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to refers to an -(alkynyl) cycloalkyl radical where alkynyl and cyclo alkyl are as disclosed herein and which are optionally substituted by one or more of the substituents described as suitable substituents for alkynyl and cycloalkyl respectively.

"Amino" or "amine" refers to a —N($R^a$)$_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon). In some embodiments it is a C$_1$-C$_4$ amido or amide radical, which includes the amide carbonyl in the total number of carbons in the radical. The R$_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (ie. C$_2$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a C$_3$-C$_8$ cycloalkyl radical. In some embodiments, it is a C$_3$-C$_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively "Ester" refers to a chemical radical of formula —COOR, where R is selected from the group consisting of alkyl, cycloalkyl, aryl, heteroaryl (bonded through a ring carbon) and heteroalicyclic (bonded through a ring carbon).

Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers "to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers "to an -(heteroalkyl)heteroaryl radical where heteroalkyl and heteroaryl are as disclosed herein and which are optionally substituted by one or more of the substituents described as suitable substituents for heteroalkyl and heteroaryl respectively "Heteroalkylheterocycloalkyl" refers "to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl respectively "Heteroalkylcycloalkyl" refers "to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively "Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quatemized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofuranzanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4.5]thieno[2,3-d]pyrimidinyl 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cycloepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" or "hetarylalkyl" refers to an (heteroaryl)alkyl-radical where heteroaryl and alkyl are as disclosed herein and which are optionally substituted by one or more of the substituents described as suitable substituents for aryl and alkyl respectively.

"Heterocycloalkyl" refers to a stable 3- to 18-membered non-aromatic ring (e.g., $C_3$-$C_{18}$ heterocycloalkyl) radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heteroaryl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyL thiazolidinyl, tetrahydrofuryL trithianyl, tetrahydropyranyL thiomorpholinyl, thiamorpholinyl, 1-oxo-thiomorpholinyl, and 1,1-dioxo-thiomorpholinyl. Unless stated otherwise specifically in the specification, a heterocylyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(Rah (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Heterocycloalkyloxy" refers to a (heterocycloalkyl)-O— moiety, where the heterocycloalkyl moiety is attached via a carbon atom to oxygen, wherein the oxygen functions as a linker to attach the moiety to a compound. The heterocycloalkyl is as described herein and is optionally substituted by one or more substituents described herein as suitable for heterocycloalkyl.

"Heteroalicyclic" refers to a cycloalkyl radical that includes at least one heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless stated otherwise specifically in the specification, a heteroalicyclic group is optionally substituted by one or more of substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Imino" refers to the —N—H radical.

"Isocyanato" refers to a —NCO radical.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)— or (S)—. The present chemical entities, pharmaceutical compositions and methods are meant to include all such possible isomers, including racemic mixtures, optically pure forms and intermediate mixtures. Optically active (R)— and (S)— isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined. When the compounds described herein contain olefinic double bonds or other centers of geometric asymmetry, and unless specified otherwise, it is intended that the compounds include both E and Z geometric isomers.

"Isothiocyanato" refers to a —NCS radical.

"Mercaptyl" refers to a (alkyl)S— or (H)S— radical.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Sulfinyl" refers to a —S(=O)—R radical, where R is selected from the group consisting of alkyl, cycloalkyl, aryl, heteroaryl (bonded through a ring carbon) and heteroalicyclic (bonded through a ring carbon).

"Sulfonyl" refers to a —S(=O)$_2$—R radical, where R is selected from the group consisting of alkyl, cycloalkyl, aryl, heteroaryl (bonded through a ring carbon) and heteroalicyclic (bonded through a ring carbon).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Thiocyanato" refers to a —CNS radical.

"Thioxo" refers to the =S radical.

"Substituted" means that the referenced group may be substituted with one or more additional group(s) individually and independently selected from acyl, alkyl, alkylaryl, cycloalkyl, aralkyl, aryl, carbohydrate, heteroaryl, heterocyclic, hydroxy, alkoxy, aryloxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamidyl, sulfoxyl, sulfonate, and amino, including mono- and di-substituted amino groups, and the protected derivatives thereof. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds of the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A compound of Formula I or a pharmaceutically acceptable salt thereof is provided in this invention,

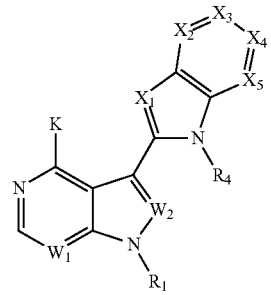

Formula I wherein K is $NR^{31}R^{32}$, $CH_3$, $CH_2G$, $CHGG$, $CGGG$, G, or H, wherein G is Cl, Br, or F;

$W_1$ and $W_2$ are independently CH, $CR_5$, or N;

$X_1$, $X_2$, $X_3$, $X_4$, and $X_5$ are independently N or $CR_2$, wherein no more than two adjacent ring atoms are N and the total number of $X_1$, $X_2$, $X_3$, $X_4$, and $X_3$ which are N is no more than 4;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylhetaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —C(=O)O—, —C(=O)$NR^{31}$—, —S—, —S(O)—, —S(O)$_2$—, —S(O)$_2NR^{31}$—, or —$NR^{31}$—, each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)$R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)R, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}C(=O)R^{32}$, —$NR^{31}C(=O)OR)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R^{31}$, $R^{32}$, and $R^{33}$, in each instance, is independently H, $C_{1-10}$alkyl, —$C_{3-8}$cycloalkyl, aryl, hetaryl or heterocycloalkyl; and wherein when K is $NH_2$, $X_1$, $X_2$, $X_3$, $X_4$ and $X_3$ are CH, $W_1$ and $W_2$ are N, then $R_1$ is not -cyclo$C_4H_7$.

In some embodiments, K is $NH_2$. In some embodiments, K is $NR^{31}R^{32}$. In some embodiments, K is $CH_3$. In one embodiment, K is $CH_2F$, $CHF_2$, or $CF_3$. In another embodiment, K is $CH_2F$. In another embodiment, K is $CHF_2$. In a further embodiment, K is $CF_3$. In another embodiment, K is $CH_2Cl$. In another embodiment, K is $CHCl_2$. In a further embodiment, K is $CCl_3$. In another embodiment, K is $CH_2Br$. In another embodiment, K is $CHBr_2$. In a further embodiment, K is $CBr_3$. In another embodiment, K is Br. In another embodiment, K is Cl. In another embodiment, K is F. In another embodiment, K is H. In some embodiments, $W_1$ is CH. In some embodiments, $W_1$ is $CR_5$. In other embodiments, $W_1$ is N. In some embodiments, $W_2$ is CH. In some embodiments, $W_2$ is $CR_5$. In some embodiments $W_2$ is N. In some embodiments, $W_1$ and $W_2$ are CH. In some embodiments, $W_1$ and $W_2$ are $CR_5$. In some embodiments, $W_1$ is CH and $W_2$ is $CR_5$. In some embodiments, $W_1$ is CR, and $W_2$ is CH. In some embodiments, $W_1$ and $W_2$ are N. In some embodiments, $W_1$ is CH and $W_2$ is N. In some embodiments, $W_1$ is CR, and $W_2$ is N. In some embodiments, $W_1$ is N and $W_2$ is CH. In some embodiments, $W_1$ is N and $W_2$ is $CR_5$.

In some embodiments, $X_1$, $X_2$, $X_3$, $X_4$, and $X_3$ are $CR_2$. In some embodiments, $X_1$ is N, and $X_2$, $X_3$, $X_4$, and $X_5$ are $CR_2$. In some embodiments, $X_2$ is N, and $X_1$, $X_3$, $X_4$, and $X_5$ are $CR_2$. In some embodiments, $X_3$ is N, and $X_1$, $X_2$, $X_4$, and $X_5$ are $CR_2$. In some embodiments, $X_4$ is N, and $X_1$, $X_2$, $X_3$, and $X_5$ are $CR_2$. In some embodiments, $X_5$ is N, and $X_1$, $X_2$, $X_3$, and $X_4$ are $CR_2$. In some embodiments, $X_1$ and $X_2$ are N, and $X_3$, $X_4$, and $X_5$ are $CR_2$. In some embodiments, $X_1$ and $X_3$ are N, and $X_2$, $X_4$, and $X_5$ are $CR_2$. In some embodiments, $X_1$ and $X_4$ are N, and $X_2$, $X_3$, and X, are $CR_2$. In some embodiments, $X_1$ and X, are N, and $X_2$, $X_3$, and $X_4$ are $CR_2$. In some embodiments, $X_3$ and X, are N, and $X_1$, $X_2$, and $X_4$ are $CR_2$. In some embodiments, $X_2$ and $X_4$ are N, and $X_1$, $X_3$, and $X_5$ are $CR_2$. In some embodiments, $X_1$, $X_2$, and $X_4$ are N, and $X_3$ and $X_5$ are $CR_2$. In some embodiments, $X_2$ and $X_5$ are N, and $X_1$, $X_3$, and $X_4$ are $CR_2$. In some embodiments, $X_1$, $X_2$, and $X_5$ are N, and $X_4$ and $X_5$ are $CR_2$. In some embodiments, $X_3$ and X, are N, and $X_1$, $X_2$, and $X_4$ are $CR_2$. In some embodiments, $X_1$, $X_3$, and $X_5$ are N, and $X_2$ and $X_4$ are $CR_2$.

A compound of Formula II or a pharmaceutically acceptable salt thereof is provided in this invention,

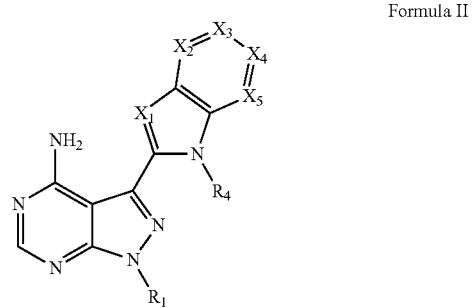

Formula II wherein $X_1$, $X_2$, $X_3$, $X_4$, and $X_5$ are independently N or $CR_2$, wherein no more than two adjacent ring atoms are N and the total number of $X_1$, $X_2$, $X_3$, $X_4$, and $X_5$ which are N is no more than 4;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —C(=O)O—, —C(=O)$NR^{31}$—, —S—, —S(O)—, —S(O)$_2$—, —S(O)$_2NR^{31}$—, or —$NR^{31}$;

each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}C(=O)R^{32}$, —$NR^{31}C(=O)OR^{32}$, —$NR^{31}C(O)NR^{32}R^{33}$, —$NR^{31}$S(O)$_{0-2}$ $R^{32}$, —$NR^{31}C(=NR^{32})NR^{33}R^{32}$, —$NR^{31}$C(=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$C_2R^{31}$, —C(=O)$NR^{31}R^{32}$, —$NO_2$, —CN, —S(O)$_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}$S(O)$_{0-2}R^{32}$, —$NR^{31}C(=NR^{32})NR^{33}R^{32}$, —$NR^{31}C(=NR^{32})$ $OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)$R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

$R^{31}$, $R^{32}$, and $R^{33}$, in each instance, is independently H, $C_{1-10}$alkyl, —$C_{3-8}$cycloalkyl, aryl, hetaryl or heterocycloalkyl; and wherein when $X_1$, $X_2$, $X_3$, $X_4$, and $X_5$ are CH, $R_1$ is not -cyclo$C_4H_7$.

In some embodiments, $X_1$, $X_2$, $X_3$, $X_4$, and $X_5$ are $CR_2$. In some embodiments, $X_1$ is N, and $X_2$, $X_3$, $X_4$, and $X_5$ are $CR_2$. In some embodiments, $X_2$ is N, and $X_1$, $X_3$, $X_4$, and $X_5$ are $CR_2$. In some embodiments, $X_3$ is N, and $X_1$, $X_2$, $X_4$, and $X_5$ are $CR_2$. In some embodiments, $X_4$ is N, and $X_1$, $X_2$, $X_3$, and $X_5$ are $CR_2$. In some embodiments, $X_5$ is N, and $X_1$, $X_2$, $X_3$, and $X_4$ are CR. In some embodiments, $X_1$ and $X_2$ are N, and $X_3$, $X_4$, and $X_5$ are CR. In some embodiments, $X_1$ and $X_3$ are N, and $X_2$, $X_4$, and $X_5$ are CR. In some embodiments, $X_1$ and $X_4$ are N, and $X_2$, $X_3$, and $X_5$ are CR. In some embodiments, $X_1$ and $X_5$ are N, and $X_2$, $X_3$, and $X_4$ are CR. In some embodiments, $X_2$ and $X_4$ are N, and $X_1$, $X_3$, and $X_5$ are CR. In some embodiments, $X_3$ and $X_5$ are N, and $X_1$, $X_2$, and $X_4$ are CR. In some embodiments, $X_2$ and $X_4$ are N, and $X_1$, $X_3$, and $X_5$ are CR. In some embodiments, $X_1$, $X_2$, and $X_4$ are N, and $X_3$ and $X_5$ are CR. In some embodiments, $X_2$ and $X_5$ are N, and $X_1$, $X_3$, and $X_4$ are CR. In some embodiments, $X_1$, $X_2$, and $X_5$ are N, and $X_4$ and $X_5$ are CR. In some embodiments, $X_3$ and $X_5$ are N, and $X_1$, $X_2$, and $X_4$ are $CR_2$. In some embodiments, $X_1$, $X_3$, and $X_5$ are N, and $X_2$ and $X_4$ are $CR_2$. In another aspect of the invention, compounds of Formula III and pharmaceutically acceptable salts thereof are provided:

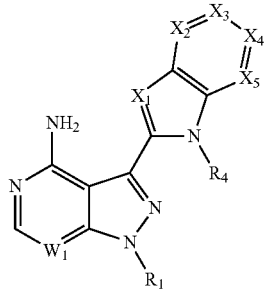

Formula III wherein $X_1$, $X_2$, $X_3$, $X_4$, and $X_5$ are independently N or $CR_2$, wherein no more than two adjacent ring atoms are N and the total number of $X_1$, $X_2$, $X_3$, $X_4$, and $X_5$ which are N is no more than 4;

$W_1$ is independently CH or $CR_5$;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl -heteroaryl, each of which is unsubstituted or substituted by one or more independent $R_3$ substituents;

L is absent, C=O, —C(=O)O—, —C(=O)$NR^{31}$—, —S—, —S(O)—, —S(O)$_2$—, —S(O)$_2NR^{31}$—, or —$NR^{31}$, each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$C_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$C_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —C(O)$R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

each instance of $R_5$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl; and $R^{31}$, $R^{32}$, and $R^{33}$, in each instance, is independently H, $C_{1-10}$alkyl, —$C_{3-8}$cycloalkyl, aryl, hetaryl or heterocycloalkyl.

In some embodiments, $X_1$, $X_2$, $X_3$, $X_4$, and $X_5$ are $CR_2$. In some embodiments, $X_1$ is N, and $X_2$, $X_3$, $X_4$, and $X_5$ are $CR_2$. In some embodiments, $X_2$ is N, and $X_1$, $X_3$, $X_4$, and $X_5$ are $CR_2$. In some embodiments, $X_3$ is N, and $X_1$, $X_2$, $X_4$, and $X_5$ are $CR_2$. In some embodiments, $X_4$ is N, and $X_1$, $X_2$, $X_3$, and $X_5$ are $CR_2$. In some embodiments, $X_5$ is N, and $X_1$, $X_2$, $X_3$, and $X_4$ are CR. In some embodiments, $X_1$ and $X_2$ are N, and $X_3$, $X_4$, and $X_5$ are CR. In some embodiments, $X_1$ and $X_3$ are N, and $X_2$, $X_4$, and $X_5$ are CR. In some embodiments, $X_1$ and $X_4$ are N, and $X_2$, $X_3$, and X, are CR. In some embodiments, $X_1$ and $X_5$ are N, and $X_2$, $X_3$, and $X_4$ are CR. In some embodiments, $X_2$ and $X_4$ are N, and $X_1$, $X_3$, and $X_5$ are CR. In some embodiments, $X_3$ and $X_5$ are N, and $X_1$, $X_2$, and $X_4$ are CR. In some embodiments, $X_2$ and $X_4$ are N, and $X_1$, $X_3$, and $X_5$ are CR. In some embodiments, $X_1$, $X_2$, and $X_4$ are N, and $X_3$ and $X_5$ are CR. In some embodiments, $X_2$ and $X_5$ are N, and $X_1$, $X_3$, and $X_4$ are CR. In some embodiments, $X_1$, $X_2$, and $X_5$ are N, and $X_4$ and $X_5$ are CR. In some embodiments, $X_3$ and $X_5$ are N, and $X_1$, $X_2$, and $X_4$ are $CR_2$. In some embodiments, $X_1$, $X_3$, and $X_5$ are N, and $X_2$ and $X_4$ are $CR_2$. In some embodiments, $W_1$ is CH. In some embodiments, $W_1$ is $CR_5$.

In another aspect of the invention, compounds of Formula IV and pharmaceutically acceptable salts thereof are provided:

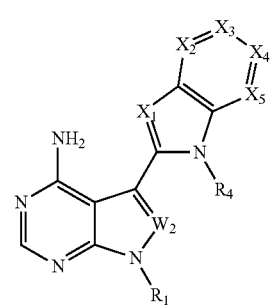

Formula IV wherein $X_1$, $X_2$, $X_3$, $X_4$, and $X_3$ are independently N or $CR_2$, wherein no more than two adjacent ring atoms are N and the total number of $X_1$, $X_2$, $X_3$, $X_4$, and $X_3$ which are N is no more than 4;

$W_2$ is CH or $CR_5$;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$ cycloalkyl-heteroaryl, each of which is unsubstituted or substituted by one or more independent $R_3$ substituents;

L is absent, C=O, —C(=O)O—, —C(=O)$NR^{31}$—, —S—, —S(O)—, —S(O)$_2$, —S(O)$_2NR^{31}$—, or —$NR^{31}$, each instance of $R_2$ is independently hydrogen, halo, —OH, —$R^{31}$, —$CF_3$, —$OCF_3$, —$OR^{31}$, —$NR^{31}R^{32}$, —C(O)R, —$CO_2R^{31}$, —C(=O)$NR^{31}R^{32}$, —$NO_2$, —CN, —S(O)$_2R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{32}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=O)$OR^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R^4$ is hydrogen, —$C(O)R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

each instance of $R_5$ is independently hydrogen, halo, —OH, —$R^{13}$, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{32}C(=NR^{32})OR^{33}$, —$OC(=O)OR^{33}$, —$OC(=O)NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl; and $R^{31}$, $R^{32}$, and $R^{33}$, in each instance, is independently H, $C_{1-10}$alkyl, —$C_{3-8}$cycloalkyl, aryl, hetaryl or heterocycloalkyl.

In some embodiments, $X_1$, $X_2$, $X_3$, $X_4$, and $X_5$ are $CR_2$. In some embodiments, $X_1$ is N, and $X_2$, $X_3$, $X_4$, and $X_5$ are $CR_2$. In some embodiments, $X_2$ is N, and $X_1$, $X_3$, $X_4$, and $X_5$ are $CR_2$. In some embodiments, $X_3$ is N, and $X_1$, $X_2$, $X_4$, and $X_5$ are $CR_2$. In some embodiments, $X_4$ is N, and $X_1$, $X_2$, and $X_5$ are $CR_2$. In some embodiments, X, is N, and $X_1$, $X_2$, $X_3$, and $X_4$ are CR. In some embodiments, X, and $X_2$ are N, and $X_3$, $X_4$, and $X_3$ are CR. In some embodiments, $X_1$ and $X_3$ are N, and $X_2$, $X_4$, and $X_5$ are CR. In some embodiments, X, and $X_4$ are N, and $X_2$, $X_3$, and $X_5$ are CR. In some embodiments, $X_1$ and $X_5$ are N, and $X_2$, $X_3$, and $X_4$ are CR. In some embodiments, $X_2$ and $X_4$ are N, and $X_1$, $X_3$, and $X_5$ are CR. In some embodiments, $X_3$ and $X_5$ are N, and $X_1$, $X_2$, and $X_4$ are CR. In some embodiments, $X_2$ and $X_4$ are N, and $X_1$, $X_3$, and $X_5$ are CR. In some embodiments, $X_1$, $X_2$, and $X_4$ are N, and $X_3$ and X, are CR. In some embodiments, $X_2$ and $X_3$ are N, and $X_1$, $X_3$, and $X_4$ are CR. In some embodiments, $X_1$, $X_2$, and $X_5$ are N, and $X_4$ and $X_5$ are CR. In some embodiments, $X_3$ and $X_5$ are N, and $X_1$, $X_2$, and $X_4$ are $CR_2$. In some embodiments, $X_1$, $X_3$, and $X_5$ are N, and $X_2$ and $X_4$ are $CR_2$. In some embodiments, $W_2$ is CH. In some embodiments, $W_2$ is $CR_5$.

In another aspect of the invention, compounds of Formula V and pharmaceutically acceptable salts thereof are provided:

Formula V wherein K is $CH_3$. $CH_2F$, $CHF_2$, $CF_3$, F, or H;

wherein $X_1$, $X_2$, $X_3$, $X_4$, and $X_5$ are independently N or $CR_2$, wherein no more than two adjacent ring atoms are N and the total number of $X_1$, $X_2$, $X_3$, $X_4$, and $X_3$ which are N is no more than 4;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —$C(=O)O$—, —$C(=O)NR^{31}$—, —S—, —S(O)—, —$S(O)_2$—, —$S(O)_2NR^{31}$—, or —$NR^{-1}$, each instance of $R_2$ is independently hydrogen, halo, —OH, —$R^{31}$, —$CF_3$, —$OCF_3$, —$OR^{31}$, —$NR^{31}R^{32}$, —$C(O)R^{31}$, —$C_2R^{31}$, —$C(=O)NR^{31}R^{32}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —$C(O)R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl; and $R^{31}$, $R^{32}$, and $R^{33}$, in each instance, is independently H, $C_{1-10}$alkyl, —$C_{3-8}$cycloalkyl, aryl, hetaryl or heterocycloalkyl.

In some embodiments, K is $CH_3$. In another embodiment, K is $CH_2F$. In another embodiment, K is $CHF_2$. In a further embodiment, K is $CF_3$. In another embodiment, K is $CH_2Cl$. In another embodiment, K is $CHCl_2$. In a further embodiment, K is $CCl_3$. In another embodiment, K is $CH_2Br$. In another embodiment, K is $CHBr_2$. In a further embodiment, K is $CBr_3$. In another embodiment, K is H. In another embodiment, K is Br. In another embodiment, K is Cl. In another embodiment, K is F. In some embodiments, $X_1$, $X_2$, $X_3$, $X_4$, and $X_5$ are $CR_2$. In some embodiments, $X_1$ is N, and $X_2$, $X_3$, $X_4$, and $X_5$ are $CR_2$. In some embodiments, $X_2$ is N, and $X_1$, $X_3$, $X_4$, and $X_5$ are $CR_2$. In some embodiments, $X_3$ is N, and $X_1$, $X_2$, $X_4$, and $X_5$ are $CR_2$. In some embodiments, $X_4$ is N, and $X_1$, $X_2$, $X_3$, and X, are $CR_2$. In some embodiments, X, is N, and $X_1$, $X_2$, $X_3$, and $X_4$ are CR. In some embodiments, $X_1$ and $X_2$ are N, and $X_3$, $X_4$, and $X_5$ are CR. In some embodiments, $X_1$ and $X_3$ are N, and $X_2$, $X_4$, and $X_5$ are CR. In some embodiments, $X_1$ and $X_4$ are N, and $X_2$, $X_3$, and $X_5$ are CR. In some embodiments, $X_1$ and $X_5$ are N, and $X_2$, $X_3$, and $X_4$ are CR. In some embodiments, $X_2$ and $X_4$ are N, and $X_1$, $X_3$, and $X_5$ are CR. In some embodiments, $X_3$ and $X_5$ are N, and $X_1$, $X_2$, and $X_4$ are CR. In some embodiments, $X_2$ and $X_4$ are N, and $X_1$, $X_3$, and $X_5$ are CR. In some embodiments, $X_1$, $X_2$, and $X_4$ are N, and $X_3$ and $X_5$ are CR. In some embodiments, $X_2$ and $X_5$ are N, and $X_1$, $X_3$, and $X_4$ are CR. In some embodiments, $X_1$, $X_2$, and $X_5$ are N, and $X_4$ and $X_5$ are CR. In some embodiments, $X_3$ and $X_5$ are N, and $X_1$, $X_2$, and $X_4$ are $CR_2$. In some embodiments, $X_1$, $X_3$, and $X_5$ are N, and $X_2$ and $X_4$ are $CR_2$.

In another aspect, the invention provides a method of treating a disease using a compound of Formula:

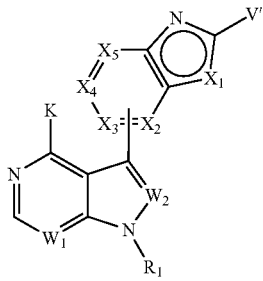

wherein K is $NR^{31}R^{32}$, $CH_3$, $CH_2F$, $CHF_2$, $CF_3$, F, or H;
V' is $-(L')_k-R_1$;
$W_1$ and $W_2$ are independently CH, $CR_5$, or N;
$X_1$ is N, O or S;
$X_2$, $X_3$, $X_4$, and $X_5$ are independently N or $CR_2$, wherein no more than two adjacent ring atoms are N and the total number of $X_2$, $X_3$, $X_4$, and $X_5$ which are N is no more than 3;
$R_1$ is H, -L-$C_{1-10}$alkyl, -L-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents; L is absent, C=O, —C(=O)O—, —C(=O)$NR^{31}$—, —S—, —S(O)—, —S(O)$_2$—, —S(O)$_2NR^{31}$—, or —$NR^{31}$—;
L' is —O—, —$NR^{31}$—, —S(O)$_{0-2}$—, —C(O)—, —C(O)N($R^{31}$)—, —N($R^{31}$)C(O)—, —N($R^{31}$)S(O)—, —N($R^{31}$)S(O)$_2$—, —C(O)O—, —CH($R^{31}$)N(C(O)O$R^{32}$)—, —CH($R^{31}$)N(C(O)$R^{32}$)—, —CH($R^{31}$)N(SO$_2R^{32}$)—, —CH($R^{31}$)N($R^{32}$)—, —CH($R^{31}$)C(O)N($R^{32}$)—, —CH($R^{31}$)N($R^{32}$)C(O)—, —CH($R^{31}$)N($R^{32}$)S(O)—, or —CH($R^{31}$)N($R^{32}$)S(O)$_2$—;
k, in each instance, is 0 or 1;
each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —CO$_2R^{31}$, —C(=O)$NR^{31}R^{32}$, —$NO_2$, —CN, —S(O)$_{0-2}R^{31}$, —SO$_2NR^{31}R^{32}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)O$R^{33}$, —OC(=O)O$R^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;
each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —CO$_2R^{31}$, —C(=O)$NR^{31}R^{32}$, —$NO_2$, —CN, —S(O)O$_2R^{31}$, —SO$_2NR^{31}R^{32}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)O$R^{33}$, —OC(=O)O$R^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;
$R_4$ is hydrogen, —C(O)$R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;
each instance of $R_5$ is independently hydrogen, halo, —OH, —$R^{31}$, —$CF_3$, —$OCF_3$, —$OR^{31}$, —$NR^{31}R^{32}$, —C(O)$R^{31}$, —CO$_2R^{31}$, —C(=O)$NR^{31}R^{32}$, —$NO_2$, —CN, —S(O)$_{0-2}R^{31}$, —SO$_2NR^{31}R^{32}$, —$NR^3$C(=O)$R^{32}$, —$NR^{31}$C(O)O$R^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)O$R^{33}$, —OC(=O)O$R^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;
$R^{31}$, $R^{32}$, and $R^{33}$, in each instance, is independently H, $C_{1-10}$alkyl, —$C_{3-8}$cycloalkyl, aryl, hetaryl, or heterocycloalkyl;
and wherein the compound inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ.

In one embodiment, the comn pound is:

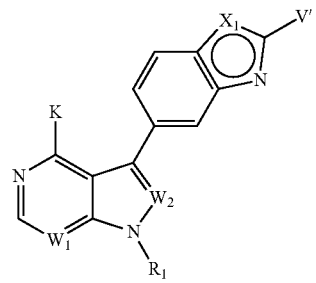

In another aspect, the invention additionally provides a compound of Formula:

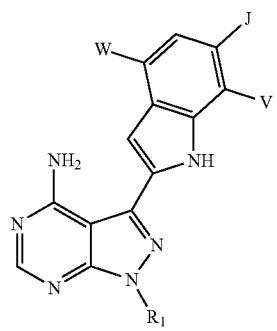

wherein $R_1$ is $C_{1-10}$alkyl, unsubstituted or substituted by one or more independent $R_3$ substituents; each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —CO$_2R^{31}$, —C(=O)$NR^{31}R^{32}$, —$NO_2$, —CN, —S(O)$_2R^{31}$, —SO$_2NR^{31}R^{32}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)O$R^{33}$, —OC(=O)O$R^{33}$, —OC(=O)$NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —$C(O)R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

J, V, and W are independently hydrogen, halo, —OH, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)_{0-2}R^{31}$, —$SO_2NR^{31}R^{32}$, —$NR^3C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, —$OP(O)(OR^{31})_2$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl and $R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents, wherein at least one of J, V, and W is not hydrogen;

$R^{31}$, $R^{32}$, and $R^{33}$, in each instance, is independently H, $C_{1-10}$alkyl, —$C_{3-8}$cycloalkyl, aryl, hetaryl, or heterocycloalkyl.

In a further aspect the invention provides a compound of Formula:

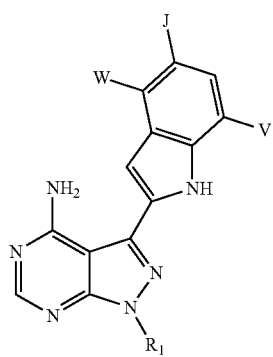

wherein $R_1$ is $C_{1-10}$alkyl, unsubstituted or substituted by one or more independent $R_3$ substituents;

each instance of $R_3$ is independently hydrogen, halo, —OH, —$R^{31}$, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)O_2R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl;

$R_4$ is hydrogen, —$C(O)R^{31}$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, or heteroalkyl;

J, V, and W are independently hydrogen, halo, —OH, —$CF_3$, —$OCF_3$, —$OR^{31}$, —$NR^{31}R^{32}$, —$C(O)R^{31}$, —$CO_2R^{31}$, —$C(=O)NR^{31}R^{32}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$NR^{31}C(=NR^{32})NR^{33}R^{32}$, —$NR^{31}C(=NR^{32})OR^{33}$, —$OC(=O)OR^{33}$, —$OC(=O)NR^{31}R^{32}$, —$OP(O)(OR^{31})_2$, $C_{1-10}$alkyl, $C_{3-8}$cycloalkyl, —$C_{2-10}$alkenyl-, —$C_{2-10}$alkynyl, —$C_{1-10}$alkoxy, -heterocycloalkyl, aryl, hetaryl, or heteroalkyl and $R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents and wherein at least two of J, V, and W are not hydrogen;

$R^{31}$, $R^{32}$, and $R^{33}$, in each instance, is independently H, $C_{1-10}$alkyl, —$C_{3-8}$cycloalkyl, aryl, hetaryl, or heterocycloalkyl.

The following embodiments illustrate various compounds of the invention.

In one embodiment, the compound of the invention is not compound 1 in Table 1.

In one embodiment, L' is —NH— and k is 1. In one embodiment, V' is $NH_2$. In another embodiment, V' is —NH—$R_1$ or —NHCO—$R_1$. In one embodiment, V' is —NH—$C_{1-10}$alkyl. In another embodiment, V' is —NHCO—$C_{1-10}$alkyl. Such $C_{1-10}$alkyl groups include methyl, propyl, isopropyl, and other such alkyl groups. In yet another embodiment, V' is -L'-$C_{3-8}$cycloalkyl. For example, V' is —NHCO—$C_{3-8}$cycloalkyl.

In one embodiment, L is absent. In another embodiment, L is C=O. In another embodiment, L is —C(=O)O—. In a further embodiment, L is —C(=O)NR$^{31}$—. In one embodiment, L is —S(O)—. In another embodiment, L is —S(O)$_2$—. In yet another embodiment, L is —S(O)$_2$NR$^{31}$. In another embodiment, L is —NR$^{31}$.

In one embodiment, L' is absent. In another embodiment, L' is —NR$^{31}$. In another embodiment, L' is C=O. In another embodiment, L' is —C(=O)O—. In a further embodiment, L' is —C(O)NR$^{31}$—. In one embodiment, L' is —S(O)—. In another embodiment, L' is —S(O)$_2$—. In yet another embodiment, L' is —S(O)$_2$NR$^{31}$—. In another embodiment, L' is —NR$^{31}$.

In various embodiments, $R_1$ is -L-$C_{1-10}$alkyl, which is unsubstituted. In another embodiment, $R_1$ is -L-$C_{1-10}$alkyl, which is substituted by one or more independent $R^3$ substituents. In yet another embodiment, $R_1$ is -L-unsubstituted $C_{1-10}$alkyl, where L is absent. In another embodiment, $R_1$ is -L-$C_{1-10}$alkyl, which is substituted by one or more independent $R^3$ substituents, and L is absent.

In various embodiments, $R_1$ is -L-$C_{3-8}$cycloalkyl, which is unsubstituted. In another embodiment, $R_1$ is L-$C_{3-8}$cycloalkyl, which is substituted by one or more independent $R^3$ substituents. In another embodiment, $R_1$ is -L-$C_{3-8}$cycloalkyl, which is unsubstituted, and L is absent. In a further embodiment, $R_1$ is -L-$C_{3-8}$cycloalkyl which is substituted by one or more independent $R^3$ substituents, and L is absent.

In one embodiment, $R_1$ is H.

In another embodiment, $R_1$ is -L-aryl, which is unsubstituted. In another embodiment, $R_1$ is -L-aryl, which is substituted by one or more independent $R^3$ substituents. In another embodiment, $R_1$ is -L-aryl which is unsubstituted, and L is absent. In yet another embodiment, $R_1$ is -L-aryl, which is substituted by one or more independent $R^3$ substituents, and L is absent.

In various embodiments, $R_1$ is -L-heteroaryl, which is unsubstituted. In another embodiment, $R_1$ is -L-heteroaryl, which is substituted by one or more independent $R^3$ substituents. In a further embodiment, $R_1$ is -L-heteroaryl which is unsubstituted and L is absent. In yet another embodiment, $R_1$ is -L-heteroaryl, which is substituted by one or more independent $R^3$ substituents, and L is absent.

In various embodiments, $R_1$ is -L-$C_{1-10}$alkylaryl, which is unsubstituted. In another embodiment, $R_1$ is -L-$C_{1-10}$alkylaryl, which is substituted by one or more independent $R^3$ substituents. In a further embodiment, $R_1$ is -L-$C_{1-10}$alkylaryl which is unsubstituted and L is absent. In yet another embodiment, $R_1$ is -L-$C_{1-10}$alkylaryl, which is substituted by one or more independent $R^3$ substituents, where L is absent.

In various embodiments, $R_1$ is -L-$C_{1-10}$alkylhetaryl, which is unsubstituted. In another embodiment, $R_1$ is -L-$C_{1-10}$alkylhetaryl, which is substituted by one or more independent $R^3$ substituents. In a further embodiment, $R_1$ is -L-$C_{1-10}$ alkylhetaryl which is unsubstituted and L is absent. In yet another embodiment, $R_1$ is -L-$C_{1-10}$alkylhetaryl, which is substituted by one or more independent $R^3$ substituents, where L is absent.

In various embodiments, $R_1$ is -L-$C_{1-10}$alkylheterocylyl, which is unsubstituted. In another embodiment, $R_1$ is -L-$C_{1-10}$alkylheterocylyl, which is substituted by one or more independent $R^3$ substituents. In a further embodiment, $R_1$ is -L-$C_{1-10}$alkylheterocylyl which is unsubstituted and L is absent. In yet another embodiment, $R_1$ is -L-$C_{1-10}$alkylheterocylyl, which is substituted by one or more independent $R^3$ substituents, where L is absent.

In various embodiments, $R_1$ is -L-$C_{2-10}$alkenyl, which is unsubstituted. In another embodiment, $R_1$ is -L-$C_{2-10}$alkenyl which is substituted by one or more independent $R^3$ substituents. In a further embodiment, $R_1$ is -L-$C_{2-10}$ alkenyl which is unsubstituted and L is absent. In yet another embodiment, $R_1$ is -L-$C_{2-10}$alkenyl, which is substituted by one or more independent $R^3$ substituents, where L is absent.

In various embodiments, $R_1$ is -L-$C_{2-10}$alkynyl, which is unsubstituted. In another embodiment, $R_1$ is -L-$C_{2-10}$alkynyl which is substituted by one or more independent $R^3$ substituents. In a further embodiment, $R_1$ is -L-$C_{2-10}$ alkynyl which is unsubstituted and L is absent. In yet another embodiment, $R_1$ is -L-$C_{2-10}$alkynyl, which is substituted by one or more independent $R^3$ substituents, where L is absent.

In various embodiments, $R_1$ is -L-$C_{2-10}$alkenyl-$C_{3-8}$cycloalkyl, which is unsubstituted. In another embodiment, $R_1$ is -L-$C_{2-10}$alkenyl-$C_{3-8}$cycloalkyl which is substituted by one or more independent $R^3$ substituents. In a further embodiment, $R_1$ is -L-$C_{2-10}$alkenyl-$C_{3-8}$cycloalkyl which is unsubstituted and L is absent. In yet another embodiment, $R_1$ is -L-$C_{2-10}$alkenyl-$C_{3-8}$cycloalkyl, which is substituted by one or more independent $R^3$ substituents, where L is absent.

In various embodiments, $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$ substituents. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$ substituents, where L is absent.

In various embodiments, $R_1$ is -L-heteroalkyl, which is unsubstituted. In another embodiment, $R_1$ is -L-heteroalkyl which is substituted by one or more independent $R^3$ substituents. In a further embodiment, $R_1$ is -L-heteroalkyl which is unsubstituted and L is absent. In yet another embodiment, $R_1$ is -L-heteroalkyl, which is substituted by one or more independent $R^3$ substituents, where L is absent.

In various embodiments, $R_1$ is -L-heteroalkylaryl, which is unsubstituted. In another embodiment, $R_1$ is -L-heteroalkylaryl which is substituted by one or more independent $R^3$ substituents. In a further embodiment, $R_1$ is -L-heteroalkylaryl which is unsubstituted and L is absent. In yet another embodiment, $R_1$ is -L-heteroalkylaryl, which is substituted by one or more independent $R^3$ substituents, where L is absent.

In various embodiments, $R_1$ is -L-heteroalkylheteroaryl, which is unsubstituted. In another embodiment, R, is -L-heteroalkylheteroaryl, which is substituted by one or more independent $R^3$ substituents. In a further embodiment, $R_1$ is -L-heteroalkylheteroaryl which is unsubstituted and L is absent. In yet another embodiment, $R_1$ is -L-heteroalkylheteroaryl, which is substituted by one or more independent $R^3$ substituents, where L is absent.

In various embodiments, $R_1$ is -L-heteroalkyl-heterocylyl, which is unsubstituted. In another embodiment, R, is -L-heteroalkyl-heterocylyl, which is substituted by one or more independent $R^3$ substituents. In a further embodiment, $R_1$ is -L-heteroalkyl-heterocylyl which is unsubstituted, and L is absent. In yet another embodiment, R, is -L-heteroalkyl-heterocylyl, which is substituted by one or more independent $R^3$ substituents, where L is absent.

In various embodiments, $R_1$ is -L-heteroalkyl-$C_{3-8}$cycloalkyl, which is unsubstituted. In another embodiment, $R_1$ is -L-heteroalkyl-$C_{3-8}$cycloalkyl, which is substituted by one or more independent $R^3$ substituents. In a further embodiment, $R_1$ is -L-heteroalkyl-$C_{3-8}$cycloalkyl which is unsubstituted and L is absent. In yet another embodiment, $R_1$ is -L-heteroalkyl-$C_{3-8}$cycloalkyl, which is substituted by one or more independent $R^3$ substituents, where L is absent.

In various embodiments, $R_1$ is -L-aralkyl, which is unsubstituted. In another embodiment, $R_1$ is -L-aralkyl, which is substituted by one or more independent $R^3$ substituents. In a further embodiment, $R_1$ is -L-aralkyl which is unsubstituted. In yet another embodiment, $R_1$ is -L-aralkyl, which is substituted by one or more independent $R^3$ substituents, where L is absent.

In various embodiments, $R_1$ is -L-heteroaralkyl, which is unsubstituted. In another embodiment, $R_1$ is -L-heteroaralkyl, which is substituted by one or more independent $R^3$ substituents. In a further embodiment, $R_1$ is -L-heteroaralkyl which is unsubstituted and L is absent. In yet another embodiment, $R_1$ is -L-heteroaralkyl, which is substituted by one or more independent $R^3$ substituents, where L is absent.

In various embodiments, $R_1$ is -L-heterocycloalkyl, which is unsubstituted. In another embodiment, $R_1$ is -L-heterocycloalkyl, which is substituted by one or more independent $R^3$ substituents. In a further embodiment, $R_1$ is -L-heterocycloalkyl which is unsubstituted and L is absent. In yet another embodiment, $R_1$ is -L-heterocycloalkyl, which is substituted by one or more independent $R^3$ substituents, where L is absent.

In various embodiments, $R_1$ is -L-$C_{3-8}$cycloalkyl-heterocycloalkyl, which is unsubstituted. In another embodiment, $R_1$ is -L-$C_{3-8}$cycloalkyl-heterocycloalkyl, which is substituted by one or more independent $R^3$ substituents. In yet another embodiment, $R_1$-L-$C_{3-8}$cycloalkyl-heterocycloalkyl, which is unsubstituted, and L is absent. In a further embodiment, $R_1$ is -L-$C_{3-8}$cycloalkyl-heterocycloalkyl which is substituted by one or more independent $R^3$ substituents, and L is absent.

In various embodiments, $R_1$ is -L-$C_{3-8}$cycloalkyl-heteroaryl, which is unsubstituted. In another embodiment, $R_1$ is -L-$C_{3-8}$cycloalkyl-heteroaryl, which is substituted by one or more independent R³ substituents. In yet another embodiment, R₁-L-C₃₋₈cycloalkyl-heteroaryl, which is unsubstituted, and L is absent. In a further embodiment, R₁ is -L-C₃₋₈cycloalkyl-heteroaryl which is substituted by one or more independent R³ substituents, and L is absent.
In various embodiments, R₁ is:
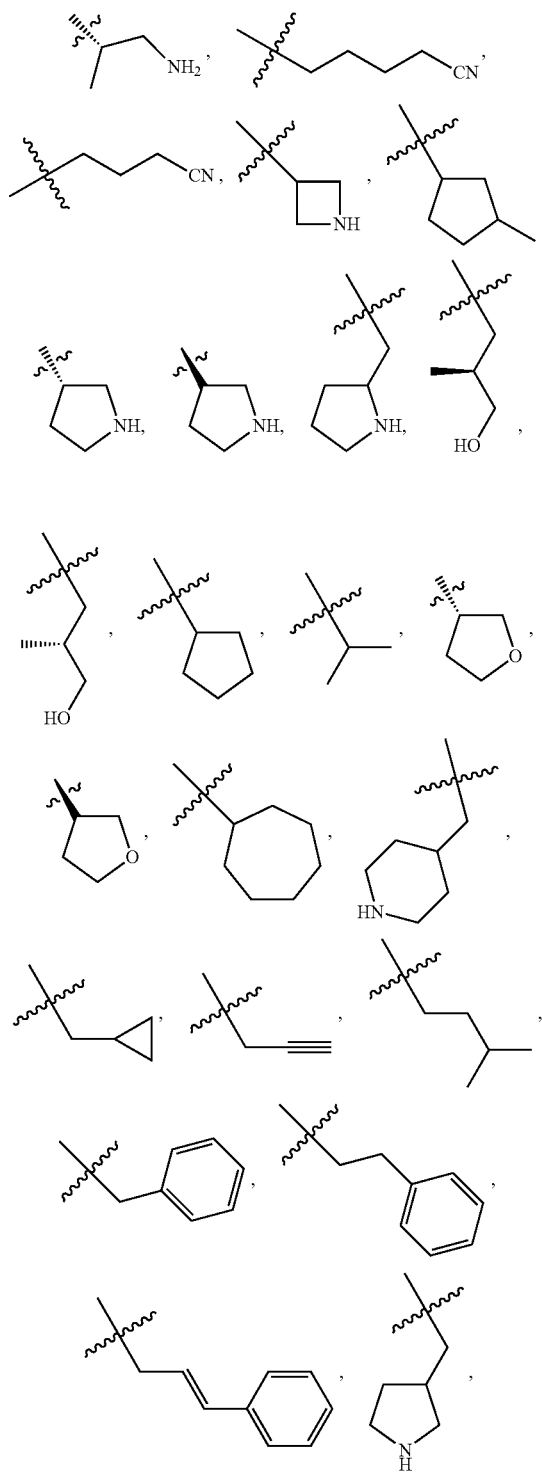
-continued
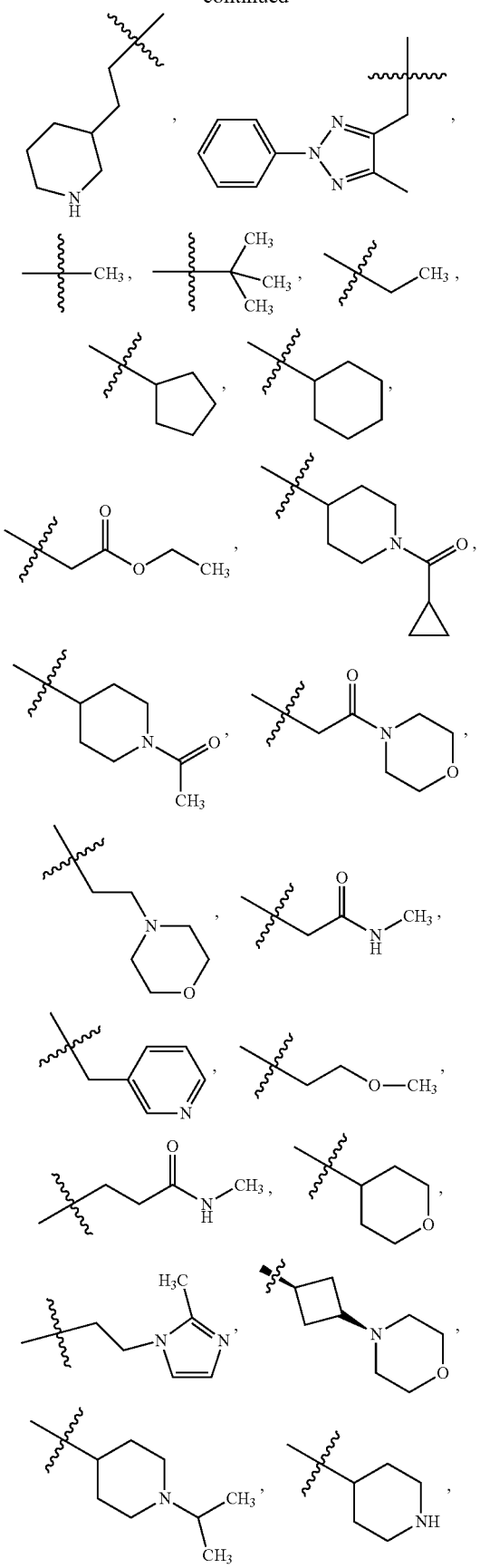

In various embodiments, $R_2$ is hydrogen. In various embodiments, $R_2$ is halo. In various embodiments, $R_2$ is —OH. In various embodiments, $R_2$ is —$R^{31}$. In various embodiments, $R_2$ is —$CF_3$. In various embodiments, $R_2$ is —$OCF_3$. In various embodiments, $R_2$ is —$OR^{31}$. In various embodiments, $R_2$ is —$NR^{31}R^{32}$. In various embodiments, $R_2$ is —$C(O)R^{31}$. In various embodiments, $R_2$ is —$CO_2R^{31}$. In various embodiments, $R_2$ is —$C(=O)NR^{31}R^{32}$. In various embodiments, $R_2$ is —$NO_2$. In various embodiments, $R_2$ is —CN. In various embodiments, $R_2$ is —$S(O)_{0-2}R^{31}$. In various embodiments, $R_2$ is —$SO_2NR^{31}R^{32}$. In various embodiments, $R_2$ is —$NR^{31}C(=O)R^{32}$. In various embodiments, $R_2$ is —$NR^{31}C(=O)OR^{32}$. In various embodiments, $R_2$ is —$NR^{31}C(=O)NR^{32}R^{33}$. In various embodiments, $R_2$ is —$NR^{31}S(O)_{0-2}R^{32}$. In various embodiments, $R_2$ is —$NR^{31}C(=NR^{32})NR^{33}R^{32}$, —$NR^{31}C(=NR^{32})OR^{33}$. In various embodiments, $R_2$ is —$OC(=O)OR^{33}$. In various embodiments, $R_2$ is —$OC(=O)NR^{31}R^{32}$. In various embodiments, $R_2$ is $C_{1-10}$alkyl. In various embodiments, $R_2$ is $C_{3-8}$cycloalkyl. In various embodiments, $R_2$ is —$C_{2-10}$alkenyl. In various embodiments, $R_2$ is —$C_{2-10}$alkynyl. In various embodiments, $R_2$ is —$C_{1-10}$alkoxy. In various embodiments, $R_2$ is -heterocycloalkyl. In various embodiments, $R_2$ is aryl. In various embodiments, $R_2$ is hetaryl. In various embodiments, $R_2$ is heteroalkyl.

In various embodiments, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is unsubstituted. In various embodiments, when $R_2$ is $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent halo. In another embodiment, when $R_2$ is $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —OH. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$R^{31}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$CF_3$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$OCF_3$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$OR^{31}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NR^{31}R^{32}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$C(O)R^{31}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$CO_2R^{31}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$C(=O)NR^{31}R^{32}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NO_2$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —CN. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$S(O)_{0-2}R^{31}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$SO_2NR^{31}R^{32}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NR^{31}C(=NR^{32})NR^{33}R^{32}$. In another embodiment, when $R_2$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$PO_3R^{31}R^{32}$.

In various embodiments, $R_3$ is hydrogen. In various embodiments, $R_3$ is halo. In various embodiments, $R_3$ is —OH. In various embodiments, $R_3$ is —$R^{31}$. In various embodiments, $R_3$ is —$CF_3$. In various embodiments, $R_3$ is —$OCF_3$. In various embodiments, $R_3$ is —$OR^{31}$. In various embodiments, $R_3$ is —$NR^{31}R^{32}$. In various embodiments, $R_3$ is —$C(O)R^{31}$. In various embodiments, $R_3$ is —$CO_2R^{31}$. In various embodiments, $R_3$ is —$C(=O)NR^{31}R^{32}$. In various embodiments, $R_3$ is —$NO_2$. In various embodiments, $R_3$ is —CN. In various embodiments, $R_3$ is —$S(O)_{0-2}R^{31}$. In various embodiments, $R_3$ is —$SO_2NR^{31}R^{32}$. In various embodiments, $R_3$ is —$NR^{31}C(=O)R^{32}$. In various embodiments, $R_3$ is —$NR^{31}C(=O)OR^{32}$. In various embodiments, $R_3$ is —$NR^{31}C(=O)NR^{32}R^{33}$. In various embodiments, $R_3$ is —$NR^{31}S(O)_{0-2}R^{32}$. In various embodiments, $R_3$ is —$NR^{31}C(=NR^{32})NR^{33}R^{32}$, —$NR^{31}C(=NR^{32})OR^{33}$. In various embodiments, $R_3$ is —$OC(=O)OR^3$. In various embodiments, $R_3$ is —$OC(=O)NR^{31}R^{32}$. In various embodiments, $R_3$ is $C_{1-10}$alkyl. In various embodiments, $R_2$ is $C_{3-8}$cycloalkyl. In various embodiments, $R_3$ is —$C_{2-10}$alkenyl. In various embodiments, $R_3$ is —$C_{2-10}$alkynyl. In various embodiments, $R_3$ is —$C_{1-10}$alkoxy. In various embodiments, $R_3$ is -heterocycloalkyl. In various embodiments, $R_3$ is aryl. In various embodiments, $R_3$ is hetaryl. In various embodiments, $R_3$ is heteroalkyl.

In various embodiments, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is unsubstituted. In various embodiments, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent halo. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —OH. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$R^{31}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$CF_3$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$OCF_3$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$OR^{31}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NR^{31}R^{32}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$C(O)R^{31}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$CO_2R^{31}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$C(=O)NR^{31}R^{32}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NO_2$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —CN. In another embodiment, when $R_3$ is $C_{1-10}$alkyl, $C_{3-8}$cycloalkyl, $C_{2-10}$alkynyl, $C_{2-10}$alkenyl. $C_{1-10}$alkoxy, heterocycloalkyl, aryl, heteroaryl, or heteroalkyl, it is substituted with one or more independent —$S(O)_{0-2}R^{31}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$SO_2NR^{31}R^{32}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$NR^{31}C(=NR^{32})NR^{31}R^{32}$. In another embodiment, when $R_3$ is $C_{1-10}$alkyl, $C_{3-8}$cycloalkyl, $C_{2-10}$alkynyl, $C_{2-10}$alkenyl, $C_{1-10}$alkoxy, heterocycloalkyl, aryl, heteroaryl, or heteroalkyl, it is substituted with one or more independent —$PO_3R^{31}R^{32}$.

In one embodiment, $R_4$ is hydrogen. In another embodiment, $R_4$ is —$C(O)R^{31}$. In another embodiment, $R_4$ is $C_{1-10}$alkyl. In another embodiment, $R_4$ is $C_{3-8}$cycloalkyl. In another embodiment, $R_4$ is —$C_{2-10}$alkenyl. In another embodiment, $R_4$ is —$C_{2-10}$alkynyl. In another embodiment, $R_4$ is —$C_{1-10}$alkoxy. In another embodiment, $R_4$ is heterocycloalkyl. In another embodiment, $R_4$ is heteroalkyl.

In various embodiments, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is unsubstituted. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent halo. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —OH. In another embodiment, when $R_4$ is —$C(O)R^{31}$, $C_{1-10}$alkyl, $C_{3-8}$cycloalkyl, $C_{2-10}$alkenyl $C_{2-10}$alkynyl, $C_{1-10}$alkoxy, heterocycloalkyl, or heteroalkyl, it is substituted with one or more independent —$R^{31}$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$CF_3$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$OCF_3$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$OR^{31}$. In another embodiment, when $R_4$ is —$C(O)R^{31}$, $C_{1-10}$alkyl, $C_{3-8}$cycloalkyl, $C_{2-10}$alkenyl $C_{2-10}$alkynyl, $C_{1-10}$alkoxy, heterocycloalkyl, or heteroalkyl, it is substituted with one or more independent —$NR^{31}R^{32}$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$C(O)R^{31}$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$CO_2R^{31}$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$C(=O)NR^{31}R^{32}$. In another embodiment, when $R_4$ is —$C(O)R^{31}$, $C_{1-10}$alkyl, $C_{3-8}$cycloalkyl, $C_{2-10}$alkenyl, $C_{2-10}$alkynyl, $C_{1-10}$alkoxy, heterocycloalkyl, or heteroalkyl, it is substituted with one or more independent —$NO_2$. In another embodiment, when $R_4$ is —C(O)R$^{31}$, C$_{1-10}$alkyl, C$_{3-8}$cycloalkyl, C$_{2-10}$alkenyl, C$_{2-10}$alkynyl C$_{1-10}$alkoxy, heterocycloalkyl, or heteroalkyl, it is substituted with one or more independent —CN. In another embodiment, when R$_4$ is —C(O)R$^{31}$, C$_{1-10}$alkyl, C$_{3-8}$cycloalkyl, C$_{2-10}$alkenyl, C$_{2-10}$alkynyl, C$_{1-10}$alkoxy, heterocycloalkyl, or heteroalkyl, it is substituted with one or more independent —S(O)$_{0-2}$R$^{31}$. In another embodiment, when R$_4$ is —C(O)R$^{31}$, C$_{1-10}$alkyl, C$_{3-8}$cycloalkyl, C$_{2-10}$alkenyl, C$_{2-10}$alkynyl, C$_{1-10}$alkoxy, heterocycloalkyl, or heteroalkyl, it is substituted with one or more independent —SO$_2$NR$^{31}$R$^{32}$. In another embodiment, when R$_4$ is —C(O)R$^{31}$, C$_{1-10}$alkyl, C$_{3-8}$cycloalkyl, C$_{2-10}$alkenyl, C$_{2-10}$alkynyl, C$_{1-10}$alkoxy, heterocycloalkyl, or heteroalkyl, it is substituted with one or more independent —NR$^{31}$C(=NR$^{32}$)NR$^{33}$R$^{32}$. In another embodiment, when R$_4$ is —C(O)R$^{31}$, C$_{1-10}$alkyl, C$_{3-8}$cycloalkyl, C$_{2-10}$alkenyl, C$_{2-10}$alkynyl, C$_{1-10}$alkoxy, heterocycloalkyl, or heteroalkyl, it is substituted with one or more independent —PO$_3$R$^{31}$R$^{32}$.

In various embodiments, R$_5$ is hydrogen. In various embodiments, R$_5$ is halo. In various embodiments, R$_5$ is —OH. In various embodiments, R$_5$ is —R$^{31}$. In various embodiments, R$_5$ is —CF$_3$. In various embodiments, R$_5$ is —OCF$_3$. In various embodiments, R$_5$ is —OR$^{31}$. In various embodiments, R$_5$ is —NR$^{31}$R$^{32}$. In various embodiments, R$_5$ is —C(O)R$^{31}$. In various embodiments, R$_5$ is —CO$_2$R$^{31}$. In various embodiments, R$_5$ is —C(=O)NR$^{31}$R$^{32}$. In various embodiments, R$_5$ is —NO$_2$. In various embodiments, R$_5$ is —CN. In various embodiments, R$_5$ is —S(O)$_{0-2}$R$^{31}$. In various embodiments, R$_5$ is —SO$_2$NR$^{31}$R$^{32}$. In various embodiments, R$_5$ is —NR$^{31}$C(=O)R$^{32}$. In various embodiments, R$_5$ is —NR$^{31}$C(=O)OR$^{32}$. In various embodiments, R$_5$ is —NR$^{31}$C(=O)NR$^{32}$R$^{33}$. In various embodiments, R$_5$ is —NR$^{31}$S(O)$_{0-2}$R$^{32}$. In various embodiments, R$_5$ is —NR$^{31}$C(=NR$^{32}$)NR$^{33}$R$^{32}$, —NR$^{31}$C(=NR$^{32}$)OR$^{33}$. In various embodiments, R$_5$ is —OC(=O)OR$^{33}$. In various embodiments, R$_5$ is —OC(=O)NR$^{31}$R$^{32}$. In various embodiments, R$_5$ is C$_{1-10}$alkyl. In various embodiments, R$_5$ is C$_{3-8}$cycloalkyl. In various embodiments, R$_5$ is —C$_{2-10}$alkenyl. In various embodiments, R$_5$ is —C$_{2-10}$alkynyl. In various embodiments, R$_5$ is —C$_{1-10}$alkoxy. In various embodiments, R$_5$ is -heterocycloalkyl. In various embodiments, R$_5$ is aryl. In various embodiments, R$_5$ is hetaryl. In various embodiments, R$_5$ is heteroalkyl.

In various embodiments, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is unsubstituted. In various embodiments, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent halo. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —OH. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —R$^{31}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —CF$_3$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —OCF$_3$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —OR$^{31}$. In another embodiment, when R$_3$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —NR$^{31}$R$^{32}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —C(O)R$^{31}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —CO$_2$R$^{31}$. In another embodiment, when R, is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —C(=O)NR$^{31}$R$^{32}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —NO$_2$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —CN. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —S(O)$_{0-2}$R$^{31}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —SO$_2$NR$^{31}$R$^{32}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —NR$^{31}$C(=NR$^{32}$)NR$^{31}$R$^{32}$. In another embodiment, when R$_5$ is C$_{1-10}$alkyl, C$_{3-8}$cycloalkyl, C$_{2-10}$alkynyl, C$_{2-10}$alkenyl, C$_{1-10}$alkoxy, heterocycloalkyl, aryl, heteroaryl, or heteroalkyl, it is substituted with one or more independent —PO$_3$R$^{31}$R$^{32}$.

In some embodiments, R$^{31}$ is H. In some embodiments, R$^{31}$ is C$_{1-10}$alkyl. In some embodiments, R$^{31}$ is —C$_{3-8}$cycloalkyl. In some embodiments, R$^{31}$ is aryl. In some embodiments, R$^{31}$ is hetaryl. In some embodiments, R$^{31}$ is heterocycloalkyl.

In various embodiments, when R$^{31}$ is C$_{1-10}$alkyl, C$_{3-8}$cycloalkyl, aryl, hetaryl, or heterocycloalkyl, it is unsubstituted. In another embodiment, when R$^{31}$ is C$_{1-10}$alkyl, C$_{3-8}$cycloalkyl, aryl, hetaryl, or heterocycloalkyl, it is substituted with one or more independent halo. In another embodiment, when R$^{31}$ is C$_{1-10}$alkyl, C$_{3-8}$cycloalkyl, aryl, hetaryl, or heterocycloalkyl, it is substituted with one or more independent —OH. In another embodiment, when R$^{31}$ is C$_{1-10}$alkyl, C$_{3-8}$cycloalkyl, aryl, hetaryl, or heterocycloalkyl, it is substituted with one or more independent-C$_{1-10}$alkyl. In another embodiment, when R$^{31}$ is C$_{1-10}$alkyl, C$_{3-8}$cycloalkyl, aryl, hetaryl, or heterocycloalkyl, it is substituted with one or more independent —CF$_3$. In another embodiment, when R$^{31}$ is C$_{1-10}$alkyl, C$_{3-8}$cycloalkyl, aryl, hetaryl, or heterocycloalkyl, it is substituted with one or more independent —OCF$_3$. In another embodiment, when R$^{31}$ is C$_{1-10}$alkyl, C$_{3-8}$cycloalkyl, aryl, hetaryl, or heterocycloalkyl, it is substituted with one or more independent —C$_{1-10}$alkoxy. In another embodiment, when R$^{31}$ is C$_{1-10}$alkyl, C$_{3-8}$cycloalkyl, aryl, hetaryl, or heterocycloalkyl, it is substituted with one or more independent —NH$_2$. In another embodiment, when R$^{31}$ is $C_{1-10}$alkyl, $C_{3-8}$cycloalkyl, aryl, hetaryl, or heterocycloalkyl, it is substituted with one or more independent —NH($C_{1-10}$alkyl). In another embodiment, when $R^{31}$ is $C_{1-10}$alkyl, $C_{3-8}$cycloalkyl, aryl, hetaryl, or heterocycloalkyl, it is substituted with one or more independent —N($C_{1-10}$alkyl)$_2$. In another embodiment, when $R^{31}$ is $C_{1-10}$alkyl, $C_{3-8}$cycloalkyl, aryl, hetaryl, or heterocycloalkyl, it is substituted with one or more independent —C(O) $C_{1-10}$alkyl. In another embodiment, when $R^{31}$ is $C_{1-10}$alkyl, $C_{3-8}$cycloalkyl, aryl, hetaryl, or heterocycloalkyl, it is substituted with one or more independent —CO$_2$$C_{1-10}$alkyl. In another embodiment, when $R^{31}$ is $C_{1-10}$alkyl, $C_{3-8}$cycloalkyl, aryl, hetaryl, or heterocycloalkyl, it is substituted with one or more independent —C(=O)NH$_2$. In another embodiment, when $R^{31}$ is $C_{1-10}$alkyl, $C_{3-8}$cycloalkyl, aryl, hetaryl, or heterocycloalkyl, it is substituted with one or more independent —C(=O)NH $C_{1-10}$alkyl. In another embodiment, when $R^{31}$ is $C_{1-10}$alkyl, $C_{3-8}$cycloalkyl, aryl, hetaryl, or heterocycloalkyl, it is substituted with one or more independent —C(=O)N($C_{1-10}$alkyl)$_2$. In another embodiment, when $R^{31}$ is $C_{1-10}$alkyl, $C_{3-8}$cycloalkyl, aryl, hetaryl, or heterocycloalkyl, it is substituted with one or more independent —NO$_2$. In another embodiment, when $R^{31}$ is $C_{1-10}$ alkyl, $C_{3-8}$cycloalkyl, aryl, hetaryl, or heterocycloalkyl, it is substituted with one or more independent —CN. In another embodiment, when $R^{31}$ is $C_{1-10}$alkyl, $C_{3-8}$cycloalkyl, aryl, hetaryl, or heterocycloalkyl, it is substituted with one or more independent —S(O)$_{0-2}$ $C_{1-10}$alkyl. In another embodiment, when $R^{31}$ is $C_{1-10}$alkyl, $C_{3-8}$cycloalkyl, aryl, hetaryl, or heterocycloalkyl, it is substituted with one or more independent —SO$_2$NH$_2$. In another embodiment, when $R^{31}$ is $C_{1-10}$alkyl, $C_{3-8}$cycloalkyl, aryl, hetaryl, or heterocycloalkyl, it is substituted with one or more independent —SO$_2$NH($C_{1-10}$alkyl). In another embodiment, when $R^{31}$ is $C_{1-10}$alkyl, $C_{3-8}$cycloalkyl, aryl, hetaryl, or heterocycloalkyl, it is substituted with one or more independent —SO$_2$N($C_{1-10}$alkyl)$_2$. In another embodiment, when $R^{31}$ is $C_{1-10}$alkyl, $C_{3-8}$cycloalkyl, aryl, hetaryl, or heterocycloalkyl, it is substituted with one or more independent —NHC(=NH)NH$_2$. In another embodiment, when $R^{31}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl). In another embodiment, when $R^{31}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl)$_2$. In another embodiment, when $R^{31}$ is $C_{1-10}$alkyl, $C_{3-8}$cycloalkyl, aryl, hetaryl, or heterocycloalkyl, it is substituted with one or more independent —PO$_3$H$_2$. In another embodiment, when $R^{31}$ is $C_{1-10}$alkyl, $C_{3-8}$cycloalkyl, aryl, hetaryl, or heterocycloalkyl, it is substituted with one or more independent —PO$_3$($C_{1-10}$alkyl)$_2$.

In some embodiments, $R^{32}$ is H. In some embodiments, $R^{32}$ is $C_{1-10}$alkyl. In some embodiments, $R^{32}$ is —$C_{3-8}$cycloalkyl. In some embodiments, $R^{32}$ is aryl. In some embodiments, $R^{32}$ is hetaryl. In some embodiments, $R^{32}$ is heterocycloalkyl.

In various embodiments, when $R^{32}$ is $C_{1-10}$alkyl, $C_{3-8}$cycloalkyl, aryl, hetaryl, or heterocycloalkyl, it is unsubstituted. In another embodiment, when $R^{32}$ is $C_{1-10}$alkyl $C_{3-8}$cycloalkyl, aryl, hetaryl, or heterocycloalkyl, it is substituted with one or more independent halo. In another embodiment, when $R^{32}$ is $C_{1-10}$alkyl, $C_{3-8}$cycloalkyl, aryl, hetaryl, or heterocycloalkyl, it is substituted with one or more independent —OH. In another embodiment, when $R^{32}$ is $C_{1-10}$alkyl, $C_{3-8}$cycloalkyl, aryl, hetaryl, or heterocycloalkyl, it is substituted with one or more independent-$C_{1-10}$alkyl. In another embodiment, when $R^{32}$ is $C_{1-10}$alkyl, $C_{3-8}$cycloalkyl, aryl, hetaryl, or heterocycloalkyl, it is substituted with one or more independent —CF$_3$. In another embodiment, when $R^{32}$ is $C_{1-10}$alkyl, $C_{3-8}$cycloalkyl, aryl, hetaryl, or heterocycloalkyl, it is substituted with one or more independent —OCF$_3$. In another embodiment, when $R^{32}$ is $C_{1-10}$alkyl, $C_{3-8}$cycloalkyl, aryl, hetaryl, or heterocycloalkyl, it is substituted with one or more independent —$C_{1-10}$alkoxy. In another embodiment, when $R^{32}$ is $C_{1-10}$alkyl, $C_{3-8}$cycloalkyl, aryl, hetaryl, or heterocycloalkyl, it is substituted with one or more independent —NH$_2$. In another embodiment, when $R^{32}$ is $C_{1-10}$alkyl, $C_{3-8}$cycloalkyl, aryl, hetaryl, or heterocycloalkyl, it is substituted with one or more independent —NH($C_{1-10}$alkyl). In another embodiment, when $R^{32}$ is $C_{1-10}$alkyl, $C_{3-8}$cycloalkyl, aryl, hetaryl, or heterocycloalkyl, it is substituted with one or more independent —N($C_{1-10}$alkyl)$_2$. In another embodiment, when $R^{32}$ is $C_{1-10}$alkyl, $C_{3-8}$cycloalkyl, aryl, hetaryl, or heterocycloalkyl, it is substituted with one or more independent —C(O) $C_{1-10}$alkyl. In another embodiment, when $R^{32}$ is $C_{1-10}$alkyl, $C_{3-8}$cycloalkyl, aryl, hetaryl, or heterocycloalkyl, it is substituted with one or more independent —CO$_2$$C_{1-10}$alkyl. In another embodiment, when $R^{32}$ is $C_{1-10}$alkyl, $C_{3-8}$cycloalkyl, aryl, hetaryl, or heterocycloalkyl, it is substituted with one or more independent —C(=O)NH$_2$. In another embodiment, when $R^{32}$ is $C_{1-10}$alkyl, $C_{3-8}$cycloalkyl, aryl, hetaryl, or heterocycloalkyl, it is substituted with one or more independent —C(=O)NH $C_{1-10}$alkyl. In another embodiment, when $R^{32}$ is $C_{1-10}$alkyl, $C_{3-8}$cycloalkyl, aryl, hetaryl, or heterocycloalkyl, it is substituted with one or more independent —C(=O)N($C_{1-10}$alkyl)$_2$. In another embodiment, when $R^{32}$ is $C_{1-10}$alkyl, $C_{3-8}$cycloalkyl, aryl, hetaryl, or heterocycloalkyl, it is substituted with one or more independent —NO$_2$. In another embodiment, when $R^{32}$ is $C_{1-10}$ alkyl, $C_{3-8}$cycloalkyl, aryl, hetaryl, or heterocycloalkyl, it is substituted with one or more independent —CN. In another embodiment, when $R^{32}$ is $C_{1-10}$alkyl, $C_{3-8}$cycloalkyl, aryl, hetaryl, or heterocycloalkyl, it is substituted with one or more independent —S(O)$_{0-2}$ $C_{1-10}$alkyl. In another embodiment, when $R^{32}$ is $C_{1-10}$alkyl, $C_{3-8}$cycloalkyl, aryl, hetaryl, or heterocycloalkyl, it is substituted with one or more independent —SO$_2$NH$_2$. In another embodiment, when $R^{32}$ is $C_{1-10}$alkyl, $C_{3-8}$cycloalkyl, aryl, hetaryl, or heterocycloalkyl, it is substituted with one or more independent —SO$_2$NH($C_{1-10}$alkyl). In another embodiment, when $R^{32}$ is $C_{1-10}$alkyl, $C_{3-8}$cycloalkyl, aryl, hetaryl, or heterocycloalkyl, it is substituted with one or more independent —SO$_2$N($C_{1-10}$alkyl)$_2$. In another embodiment, when $R^{32}$ is $C_{1-10}$alkyl, $C_{3-8}$cycloalkyl, aryl, hetaryl, or heterocycloalkyl, it is substituted with one or more independent —NHC(=NH)NH$_2$. In another embodiment, when $R^{32}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl). In another embodiment, when $R^{32}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl)$_2$. In another embodiment, when $R^{32}$ is $C_{1-10}$alkyl, $C_{3-8}$cycloalkyl, aryl, hetaryl, or heterocycloalkyl, it is substituted with one or more independent —PO$_3$H$_2$. In another embodiment, when $R^{32}$ is $C_{1-10}$alkyl, $C_{3-8}$cycloalkyl, aryl, hetaryl, or heterocycloalkyl, it is substituted with one or more independent —PO$_3$($C_{1-10}$alkyl)$_2$.

In some embodiments, $R^{33}$ is H. In some embodiments, $R^{33}$ is $C_{1-10}$alkyl. In some embodiments, $R^{33}$ is —$C_{3-8}$cycloalkyl. In some embodiments, $R^{33}$ is aryl. In some embodiments, $R^{33}$ is hetaryl. In some embodiments, $R^{33}$ is heterocycloalkyl.

In various embodiments, when $R^{33}$ is $C_{1-10}$alkyl, $C_{3-8}$cycloalkyl, aryl, hetaryl, or heterocycloalkyl, it is unsubstituted. In another embodiment, when $R^{33}$ is $C_{1-10}$alkyl, $C_{3-8}$cycloalkyl, aryl, hetaryl, or heterocycloalkyl, it is substituted with one or more independent halo. In another embodiment, when $R^{33}$ is $C_{1-10}$alkyl, $C_{3-8}$cycloalkyl, aryl, hetaryl, or heterocycloalkyl, it is substituted with one or more independent —OH. In another embodiment, when $R^{33}$ is $C_{1-10}$alkyl, $C_{3-8}$cycloalkyl, aryl, hetaryl, or heterocycloalkyl, it is substituted with one or more independent-$C_{1-10}$alkyl. In another embodiment, when $R^{33}$ is $C_{1-10}$alkyl, $C_{3-8}$cycloalkyl, aryl, hetaryl, or heterocycloalkyl, it is substituted with one or more independent —$CF_3$. In another embodiment, when $R^{33}$ is $C_{1-10}$alkyl, $C_{3-8}$cycloalkyl, aryl, hetaryl, or heterocycloalkyl, it is substituted with one or more independent —$OCF_3$. In another embodiment, when $R^{33}$ is $C_{1-10}$alkyl, $C_{3-8}$cycloalkyl, aryl, hetaryl, or heterocycloalkyl, it is substituted with one or more independent —$C_{1-10}$ alkoxy. In another embodiment, when $R^{33}$ is $C_{1-10}$alkyl, $C_{3-8}$cycloalkyl, aryl, hetaryl, or heterocycloalkyl, it is substituted with one or more independent —$NH_2$. In another embodiment, when $R^{33}$ is $C_{1-10}$alkyl, $C_{3-8}$cycloalkyl, aryl, hetaryl, or heterocycloalkyl, it is substituted with one or more independent —NH($C_{1-10}$alkyl). In another embodiment, when $R^{33}$ is $C_{1-10}$alkyl, $C_{3-8}$cycloalkyl, aryl, hetaryl, or heterocycloalkyl, it is substituted with one or more independent —N($C_{1-10}$alkyl)$_2$. In another embodiment, when $R^{33}$ is $C_{1-10}$alkyl, $C_{3-8}$cycloalkyl, aryl, hetaryl, or heterocycloalkyl, it is substituted with one or more independent —C(O)$C_{1-10}$alkyl. In another embodiment, when $R^{33}$ is $C_{1-10}$alkyl, $C_{3-8}$cycloalkyl, aryl, hetaryl, or heterocycloalkyl, it is substituted with one or more independent —$CO_2C_{1-10}$alkyl. In another embodiment, when $R^{33}$ is $C_{1-10}$alkyl, $C_{3-8}$cycloalkyl, aryl, hetaryl, or heterocycloalkyl, it is substituted with one or more independent —C(=O)$NH_2$. In another embodiment, when $R^{33}$ is $C_{1-10}$alkyl, $C_{3-8}$cycloalkyl, aryl, hetaryl, or heterocycloalkyl, it is substituted with one or more independent —C(=O)NH $C_{1-10}$alkyl. In another embodiment, when $R^{33}$ is $C_{1-10}$alkyl, $C_{3-8}$cycloalkyl, aryl, hetaryl, or heterocycloalkyl, it is substituted with one or more independent —C(=O)N($C_{1-10}$alkyl)$_2$. In another embodiment, when $R^{33}$ is $C_{1-10}$alkyl, $C_{3-8}$cycloalkyl, aryl, hetaryl, or heterocycloalkyl, it is substituted with one or more independent —$NO_2$. In another embodiment, when $R^{33}$ is $C_{1-10}$alkyl, $C_{3-8}$cycloalkyl, aryl, hetaryl, or heterocycloalkyl, it is substituted with one or more independent —CN. In another embodiment, when $R^{33}$ is $C_{1-10}$alkyl, $C_{3-8}$cycloalkyl, aryl, hetaryl, or heterocycloalkyl, it is substituted with one or more independent —S(O)$_{0-2}$ $C_{1-10}$alkyl. In another embodiment, when $R^{33}$ is $C_{1-10}$alkyl, $C_{3-8}$cycloalkyl, aryl, hetaryl, or heterocycloalkyl, it is substituted with one or more independent —$SO_2NH_2$. In another embodiment, when $R^{33}$ is $C_{1-10}$alkyl, $C_{3-8}$cycloalkyl, aryl, hetaryl, or heterocycloalkyl, it is substituted with one or more independent —$SO_2NH(C_{1-10}$alkyl). In another embodiment, when $R^{33}$ is $C_{1-10}$alkyl, $C_{3-8}$cycloalkyl, aryl, hetaryl, or heterocycloalkyl, it is substituted with one or more independent —$SO_2N(C_{1-10}$alkyl)$_2$. In another embodiment, when $R^{33}$ is $C_{1-10}$alkyl, $C_{3-8}$cycloalkyl, aryl, hetaryl, or heterocycloalkyl, it is substituted with one or more independent —NHC(=NH)$NH_2$. In another embodiment, when $R^{33}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl). In another embodiment, when $R^{33}$ is $C_{1-10}$alkyl, $C_{3-8}$cycloalkyl, aryl, hetaryl, or heterocycloalkyl, it is substituted with one or more independent —NHC(=NH)NH($C_{1-10}$alkyl)$_2$. In another embodiment, when $R^{33}$ is $C_{1-10}$alkyl, $C_{3-8}$cycloalkyl, aryl, hetaryl, or heterocycloalkyl, it is substituted with one or more independent —$PO_3H_2$. In another embodiment, when $R^{33}$ is $C_{1-10}$alkyl, $C_{3-8}$cycloalkyl, aryl, hetaryl, or heterocycloalkyl, it is substituted with one or more independent —$PO_3(C_{1-10}$alkyl)$_2$.

In some embodiments, the $R^{31}$ and $R^{32}$ in —$NR^{31}R^{32}$, —C(=O)$NR^{31}R^{32}$, or —$SO_2NR^{31}R^{32}$, are taken together with the nitrogen atom to which they are attached to form:

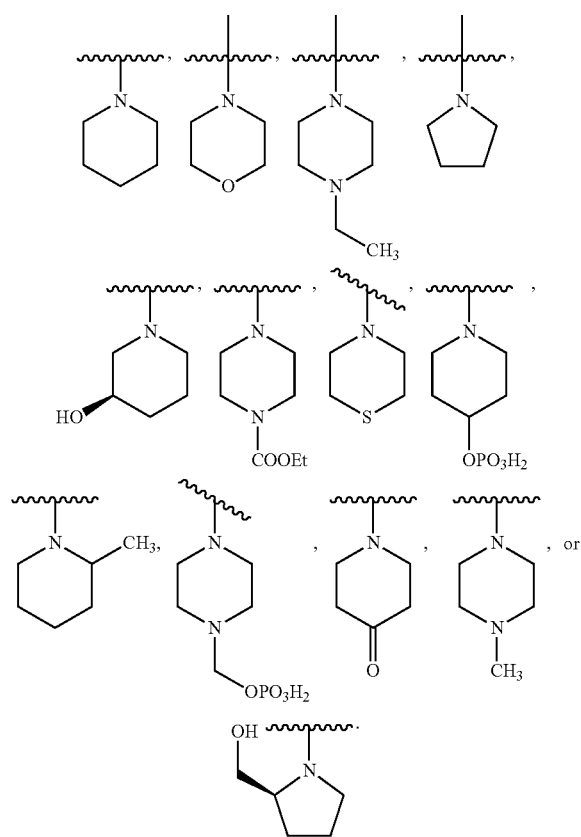

In some embodiments, when K is $NR^{31}R^{32}$, it is $NHCH_3$. In other embodiments, when K is $NR^{31}R^{32}$, it is $N(CH_3)_2$. In other embodiments, when K is $NR^{31}R^{32}$, it is $NHCH_2CH_3$. In other embodiments, when K is $NR^{31}R^{32}$, it is $N(CH_2CH_3)_2$. In other embodiments, when K is $NR^{31}R^{32}$, it is NH $CH_2CH_2CH_3$. In other embodiments, when K is $NR^{31}R^{32}$, it is $N(CH_2CH_2CH_3)_2$. In other embodiments, when K is $NR^{31}R^{32}$, it is $NHCH(CH_3)_2$. In other embodiments, when K is $NR^{31}R^{32}$, it is $N(CH(CH_3)_2)_2$. In other embodiments, when K is $NR^{31}R^{32}$, it is NH $CH_2CH_2CH_2CH_3$. In other embodiments, when K is $NR^{31}R^{32}$, it is $N(CH_2CH_2CH_2CH_3)_2$. In other embodiments, when K is $NR^{31}R^{32}$, it is $NHCH_2CH(CH_3)_2$. In other embodiments, when K is $NR^{31}R^{32}$, it is $N(CH_2CH(CH_3)_2)_2$. In other embodiments, when K is $NR^{31}R^{32}$, it is $NHCH(CH_3)CH_2CH_3$. In other embodiments, when K is $NR^{31}R^{32}$, it is $N(CH(CH_3)CH_2CH_3)_2$. In other embodiments, when K is $NR^{31}R^{32}$, it is NH $CH_2CH_2CH_2CH_2CH_3$. In other embodiments, when K is $NR^{31}R^{32}$, it is $N(CH_2CH_2CH_2CH_2CH_3)_2$.

In other embodiments, when K is $NR^{31}R^{32}$, it is $NHCH_2CH_2CH(CH_3)_2$. In other embodiments, when K is $NR^{31}R^{32}$, it is $N(CH_2CH_2CH(CH_3)_2)_2$. In other embodiments, when K is $NR^{31}R^{32}$, it is $NH\ CH_2CH(CH_3)CH_2CH_3$. In other embodiments, when K is $NR^{31}R^{32}$, it is $N(CH_2CH(CH_3)CH_2CH_3)_2$. In other embodiments, when K is $NR^{31}R^{32}$, it is $NHCH(CH_3)\ CH_2CH_2CH_3$. In other embodiments, when K is $NR^{31}R^{32}$, it is $N(CH(CH_3)\ CH_2CH_2CH_3)_2$. In other embodiments, when K is $NR^{31}R^{32}$, it is $NCH_3(CH_2CH_3)$. In other embodiments, when K is $NR^{31}R^{32}$, it is $NCH_3(CH(CH_3)_2)$. In other embodiments, when K is $NR^{31}R^{32}$, it is $NCH_3(CH_2CH_2CH_3)$. In other embodiments, when K is $NR^{31}R^{32}$, it is $NCH_2CH_3(CH(CH_3)_2)$.

In a particular embodiment of the invention, K in a compound of Formula I is $CH_2F$, $CHF_2$, or $CF_3$.

Some illustrative compounds of the invention are described in the following tables. The compounds of the invention are not limited in any way to the compounds illustrated herein.

Illustrative compounds of Formulae 1-A to 1-BP include each embodiment wherein $R_1$ is any one of $R_1$ as described in Table A, G is any one of G as described in Table B, and wherein W, V, and J are as described below.

Formula 1-A

Formula 1-B

Formula 1-C

-continued

Formula 1-D

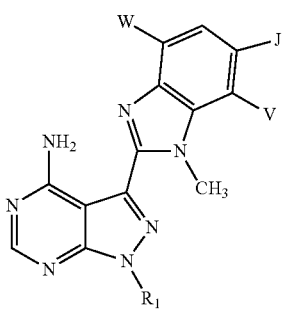

Formula 1-E

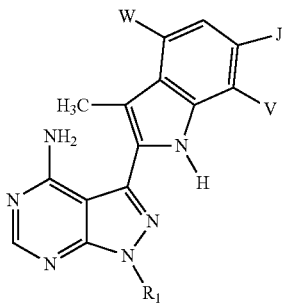

Formula 1-F

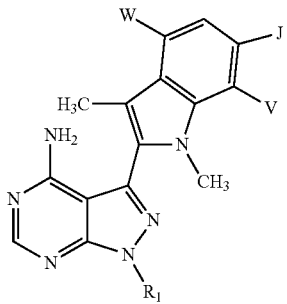

Formula 1-G

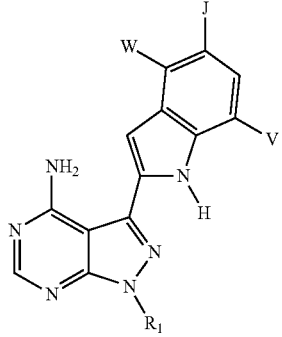

Formula 1-H

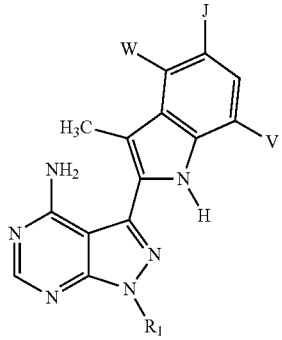

-continued
Formula 1-I
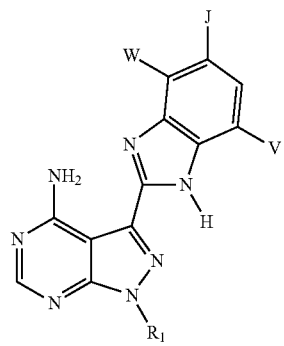
Formula 1-J
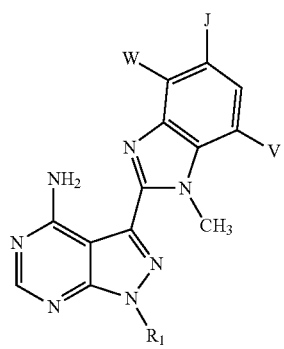
Formula 1-K
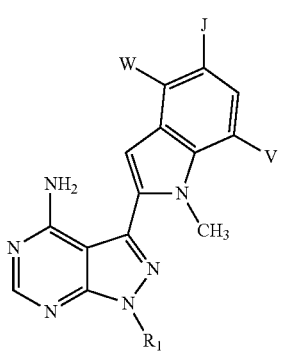
Formula 1-L
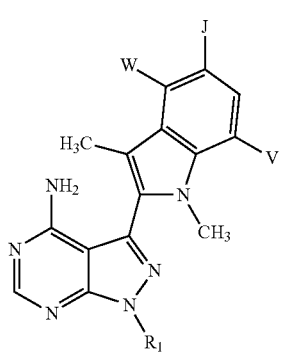
Formula 1-M
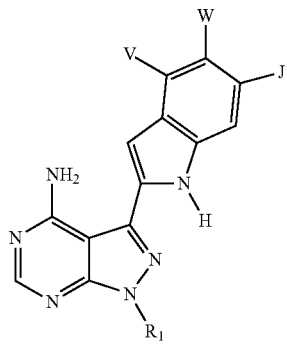
Formula 1-N
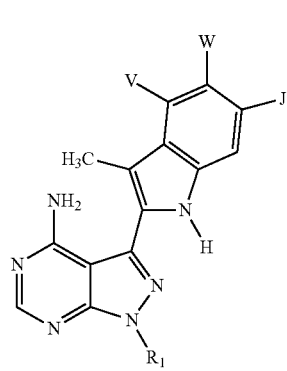
Formula 1-O
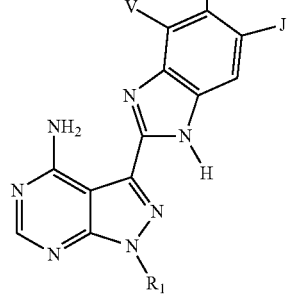
Formula 1-P
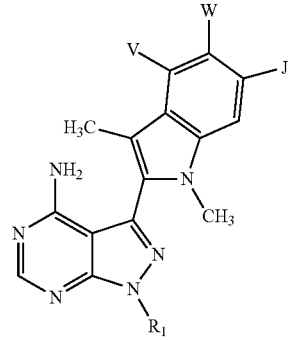

Formula 1-Q
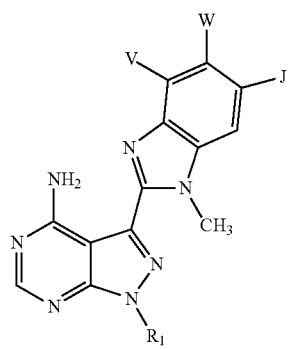
Formula 1-R
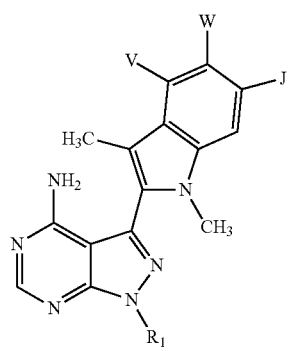
Formula 1-S
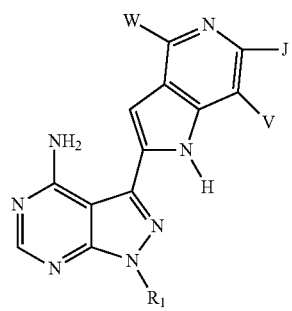
Formula 1-T
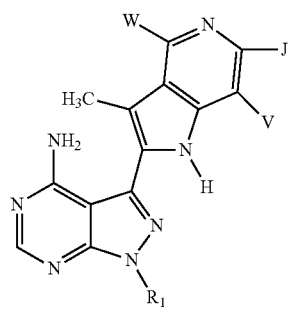
Formula 1-U
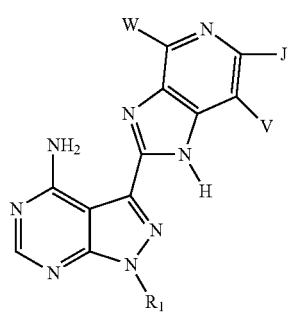
Formula 1-V
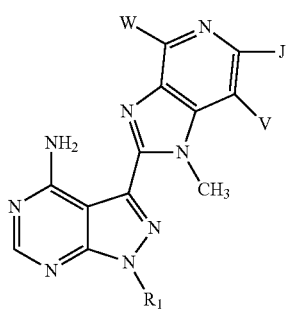
Formula 1-W
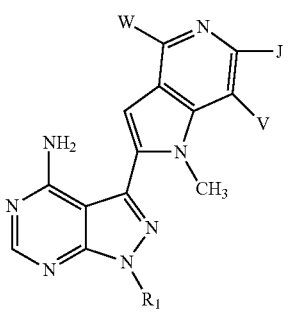
Formula 1-X
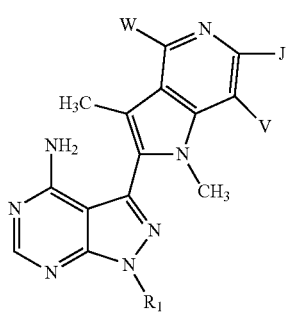
Formula 1-Y
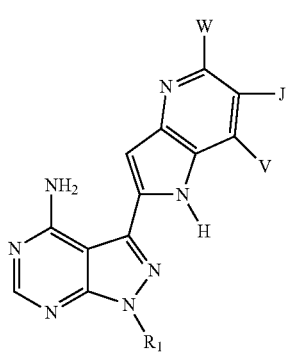
Formula 1-Z
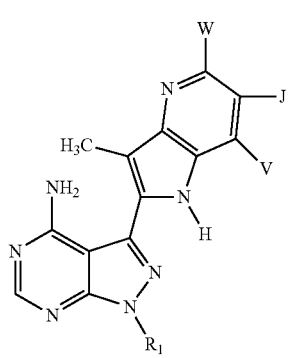

Formula 1-BA
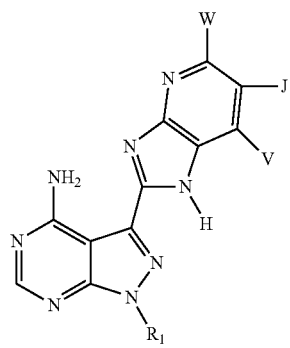
Formula 1-BB
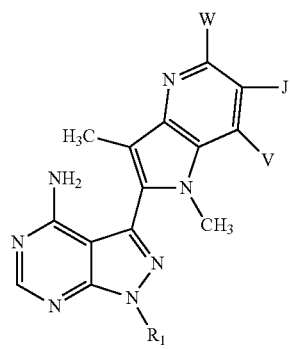
Formula 1-BC
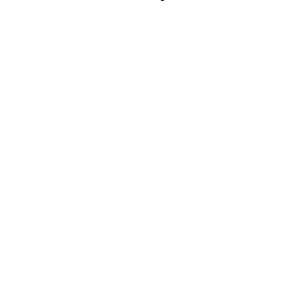
Formula 1-BD
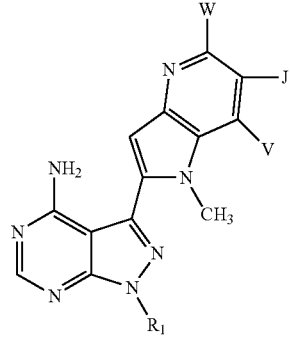
Formula 1-BA
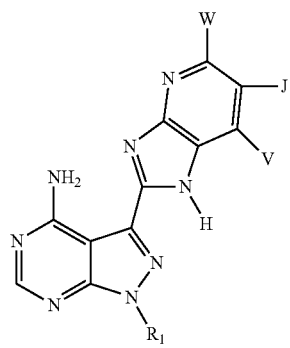
Formula 1-BB
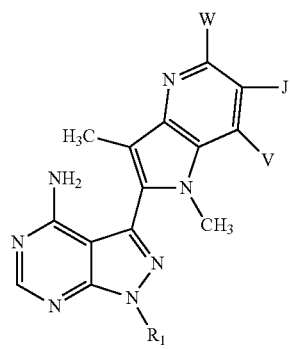
Formula 1-BC
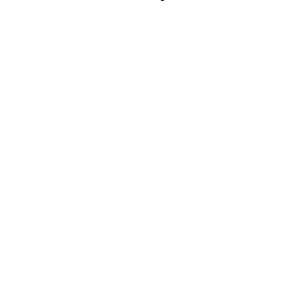
Formula 1-BD
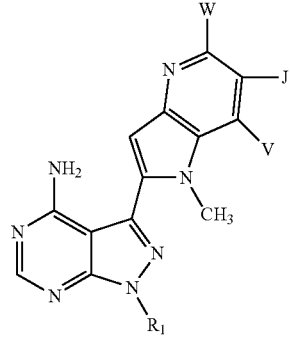
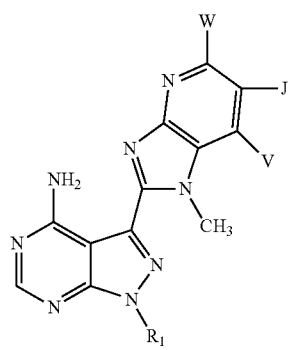
Formula 1-BE
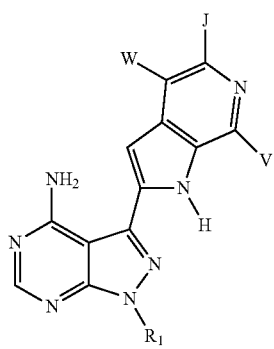
Formula 1-BF
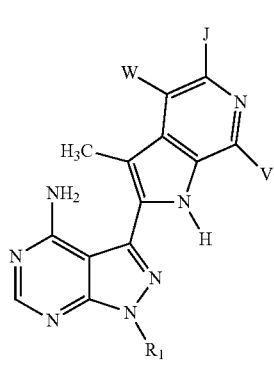
Formula 1-BG
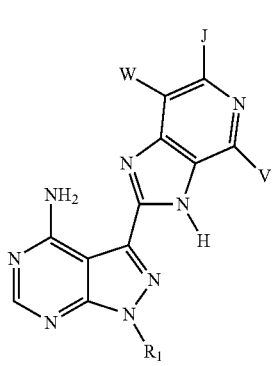
Formula 1-BH
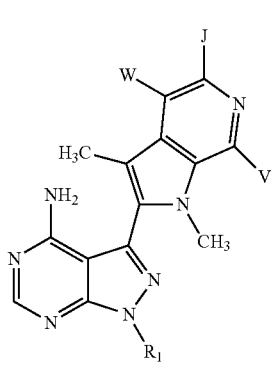

Formula 1-BI
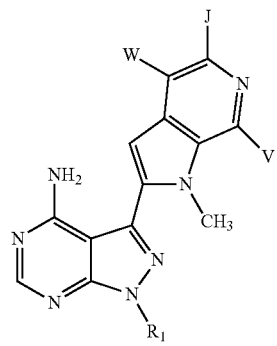
Formula 1-BJ
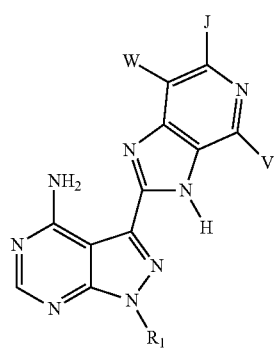
Formula 1-BK
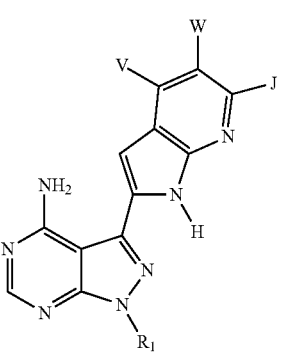
Formula 1-BL
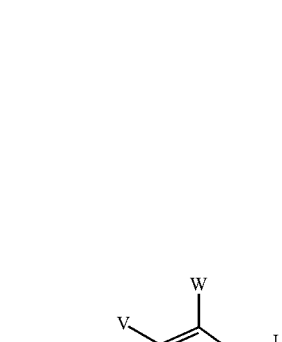
Formula 1-BM
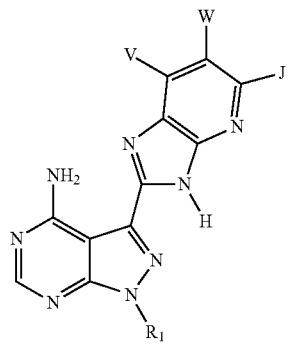
Formula 1-BN
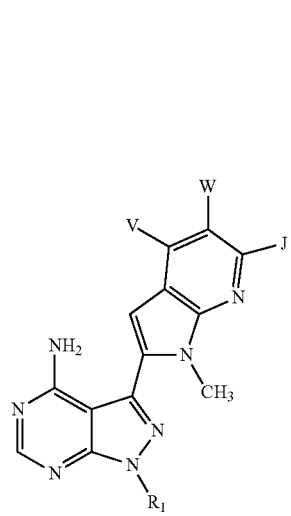
Formula 1-BO
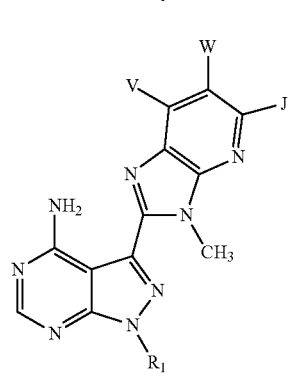
Formula 1-BP
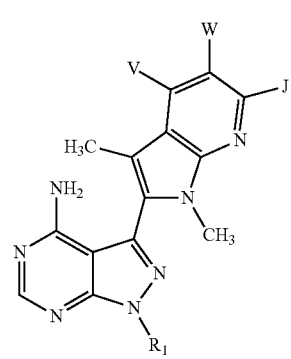

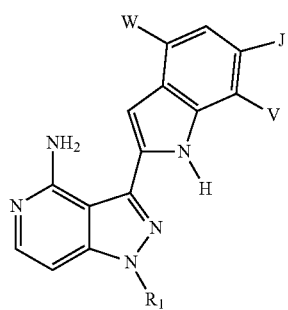
Formula 1-BR
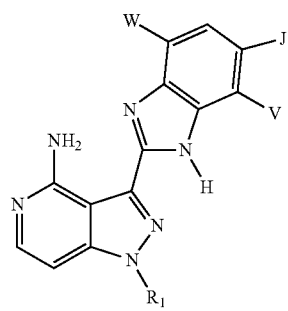
Formula 1-BS
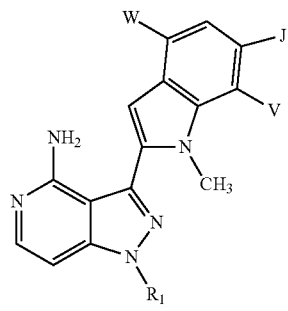
Formula 1-BT
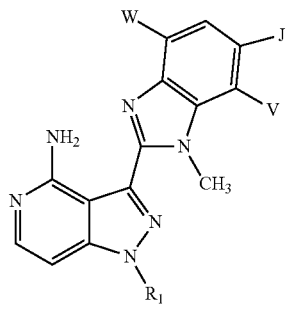
Formula 1-BU
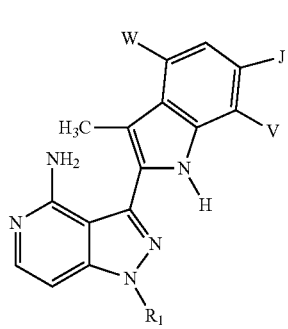
Formula 1-BV
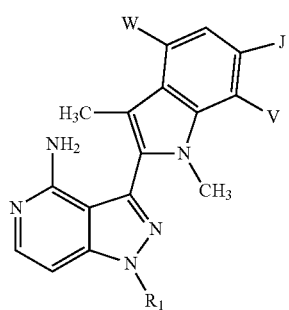
Formula 1-BW
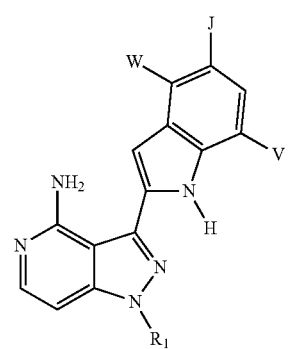
Formula 1-BX
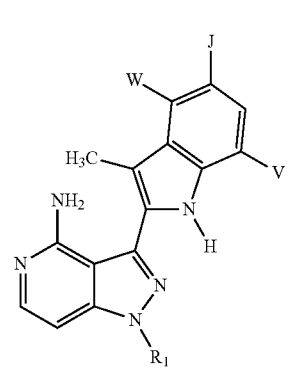
Formula 1-BY
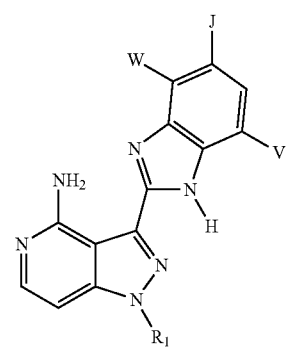
Formula 1-BZ Formula 1-CA
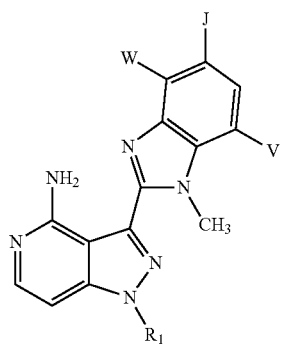
Formula 1-CB
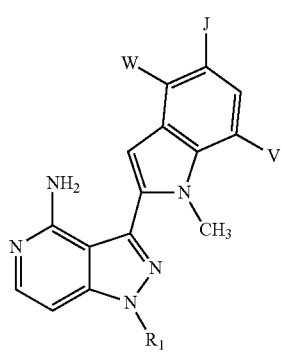
Formula 1-CC
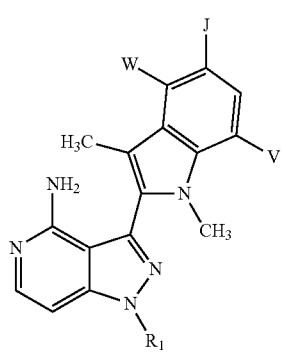
Formula 1-CD
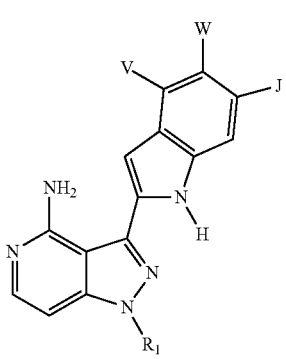
Formula 1-CE
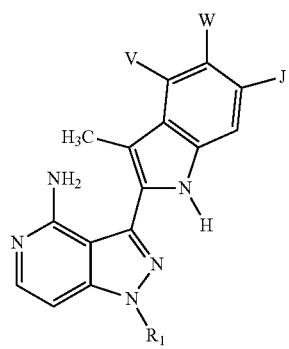
Formula 1-CF
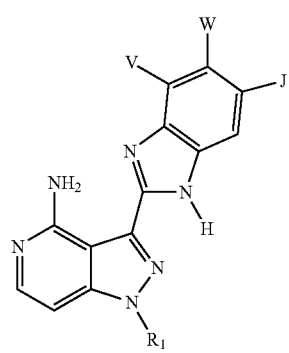
Formula 1-CG
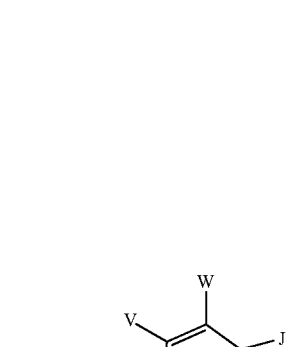
Formula 1-CH
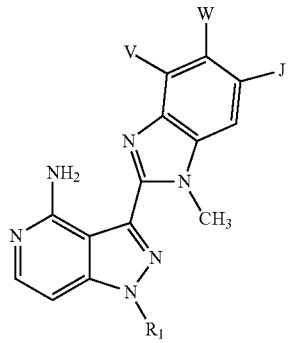

Formula 1-CI
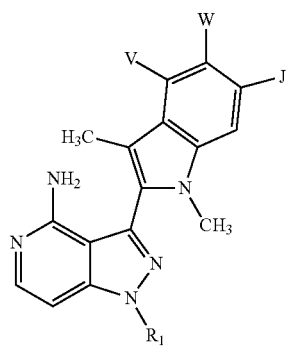
Formula 1-CJ
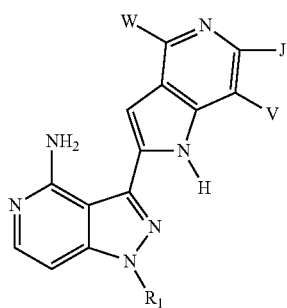
Formula 1-CK
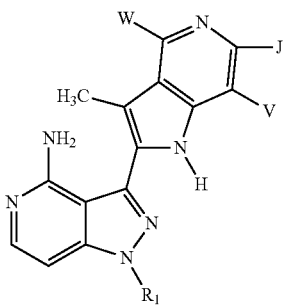
Formula 1-CL
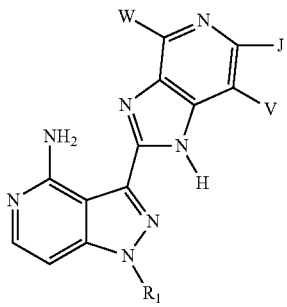
Formula 1-CM
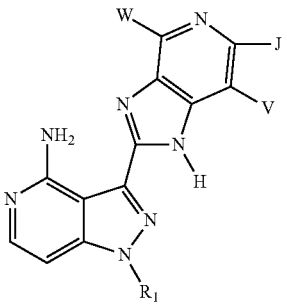
Formula 1-CN
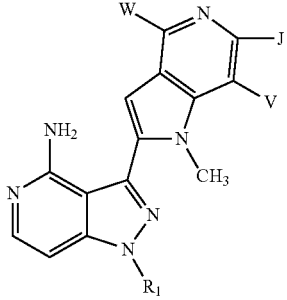
Formula 1-CO
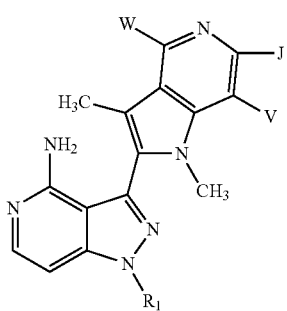
Formula 1-CP
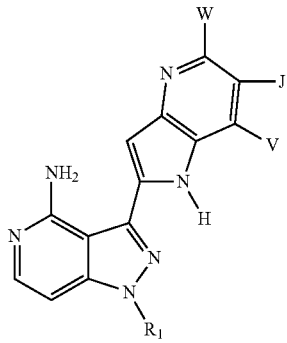
Formula 1-CQ
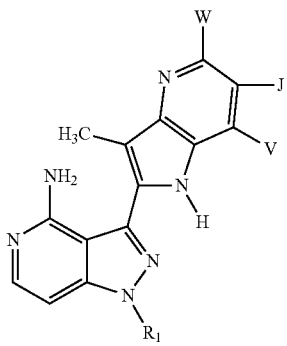
Formula 1-CR
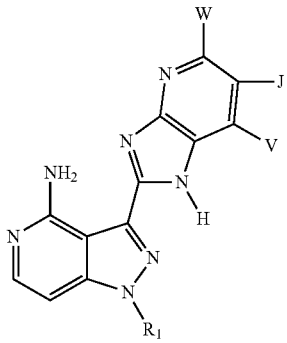

Formula 1-CS
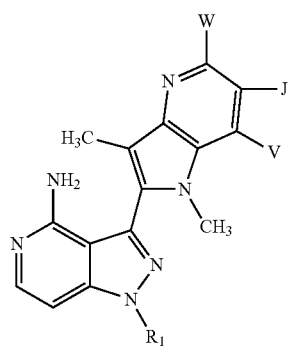
Formula 1-CT
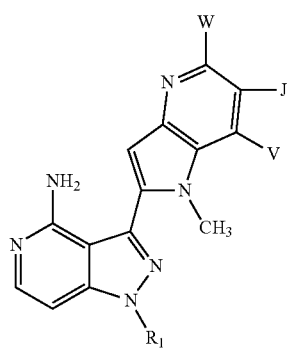
Formula 1-CU
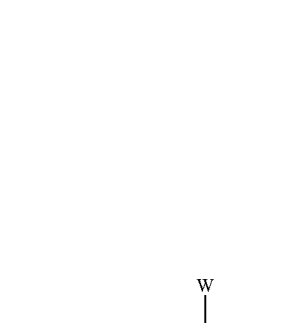
Formula 1-CV
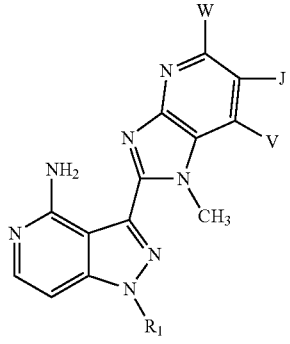
Formula 1-CW
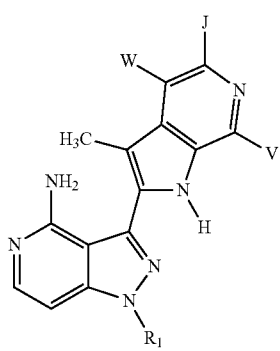
Formula 1-CX
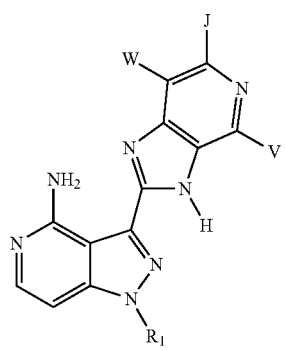
Formula 1-CY
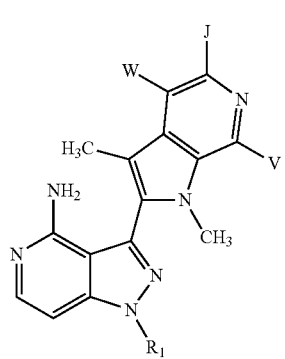
Formula 1-CZ
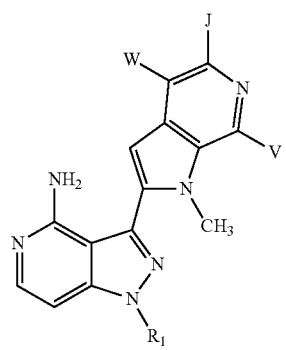

Formula 1-DA
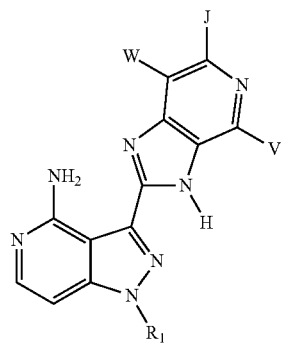
Formula 1-DB
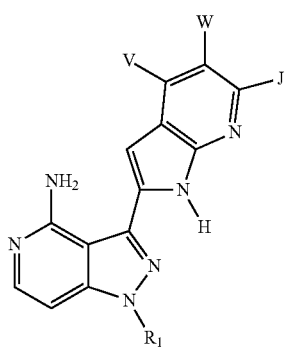
Formula 1-DC
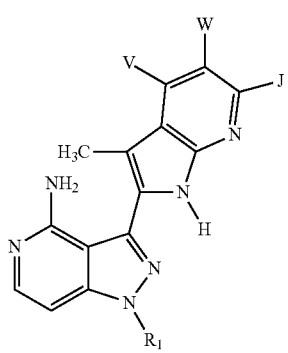
Formula 1-DE
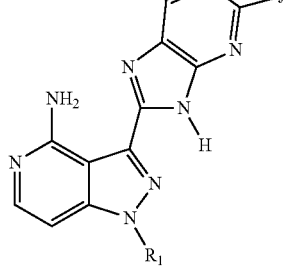
Formula 1-DF
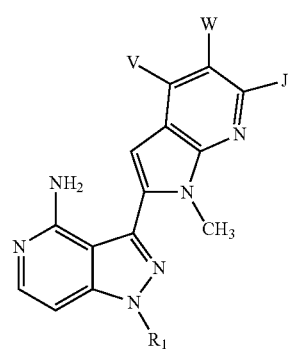
Formula 1-DG
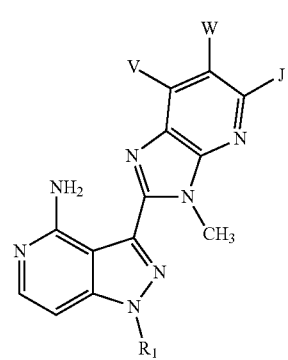
Formula 1-DH
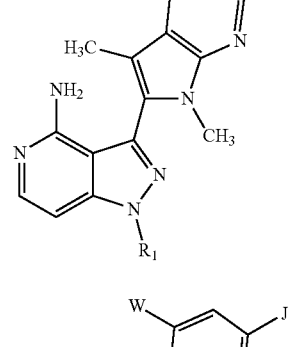
Formula 1-DI
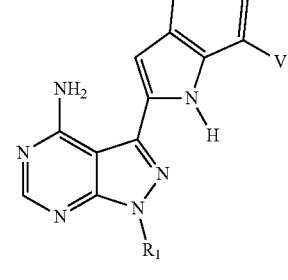

Formula 1-DJ
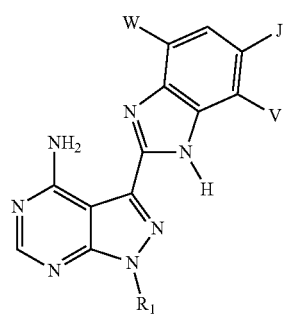
Formula 1-DK
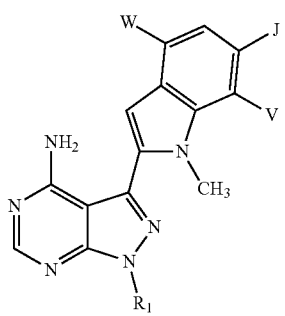
Formula 1-DL
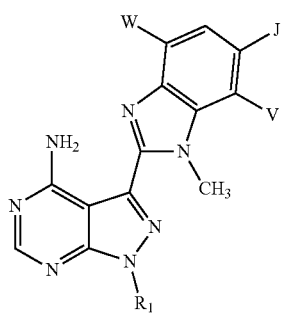
Formula 1-DM
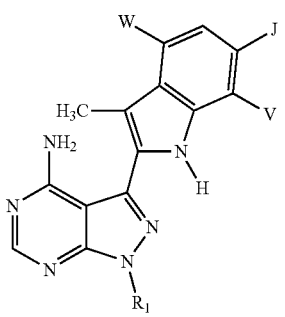
Formula 1-DN
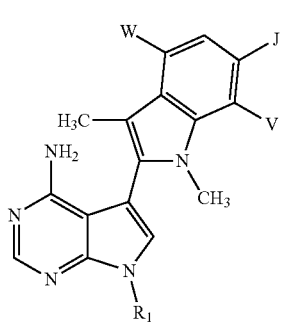
Formula 1-DO
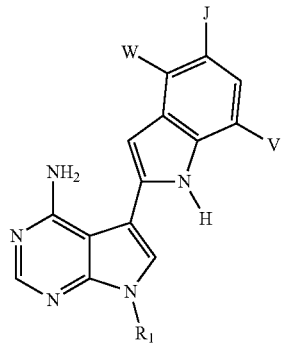
Formula 1-DP
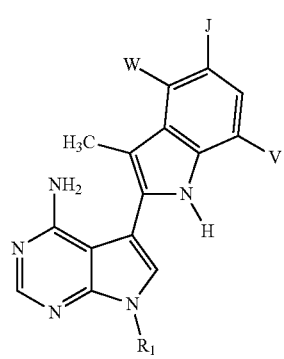
Formula 1-DQ
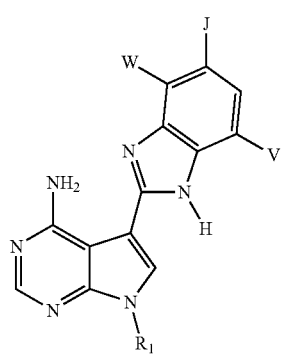
Formula 1-DR
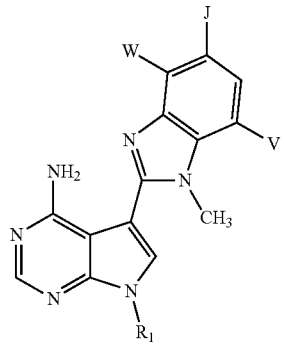

-continued
Formula 1-DS
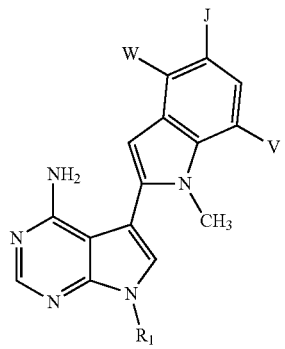
Formula 1-DT
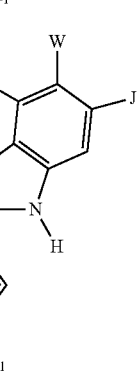
Formula 1-DU
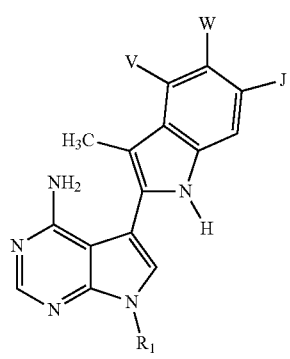
Formula 1-DV
-continued
Formula 1-DW
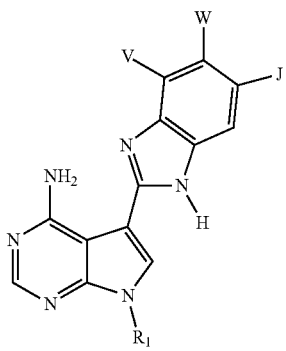
Formula 1-DX
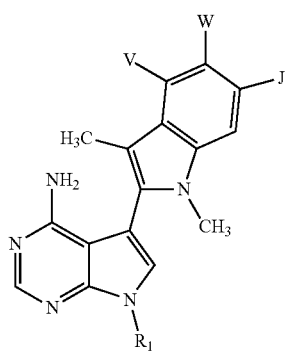
Formula 1-DY
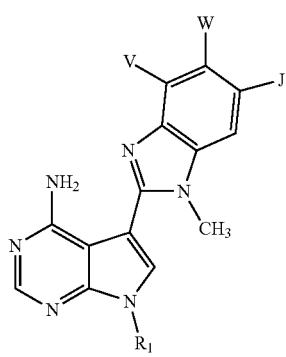
Formula 1-DZ
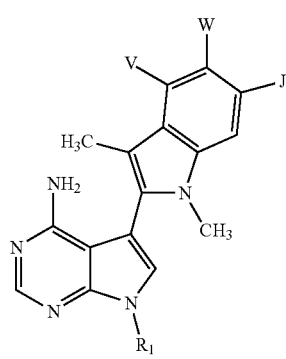

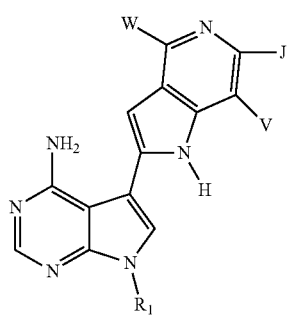
Formula 1-EA
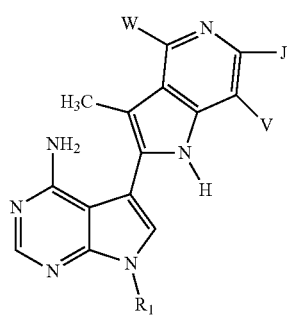
Formula 1-EB
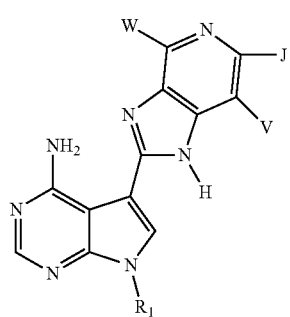
Formula 1-EC
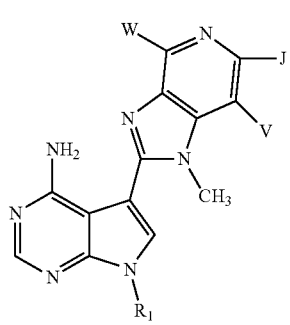
Formula 1-ED
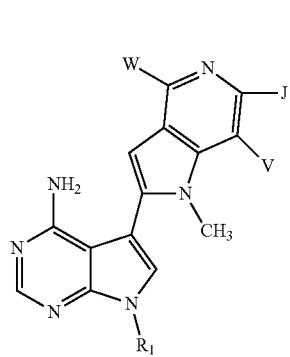
Formula 1-EF
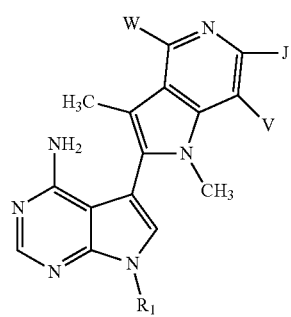
Formula 1-EG
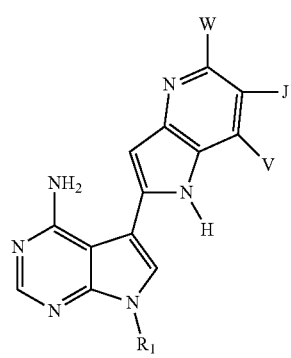
Formula 1-EH
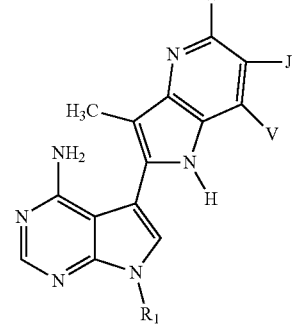
Formula 1-EI
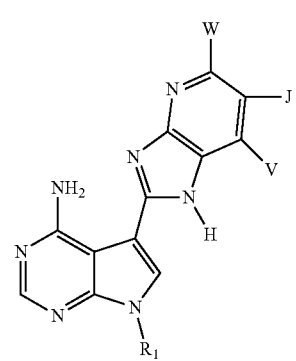
Formula 1-EJ Formula 1-EK
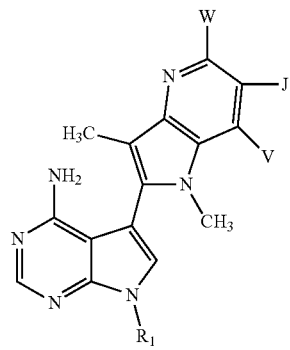
Formula 1-EL
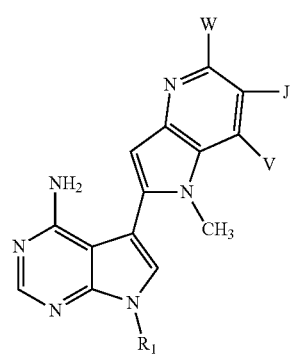
Formula 1-EM
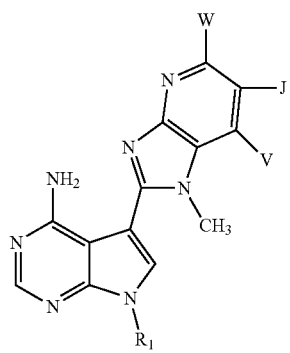
Formula 1-EN
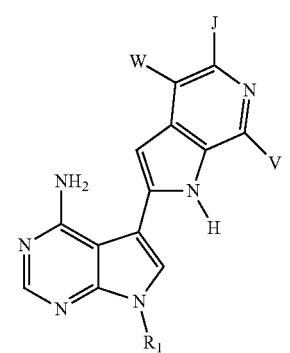
Formula 1-EO
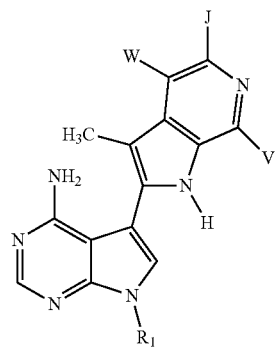
Formula 1-EP
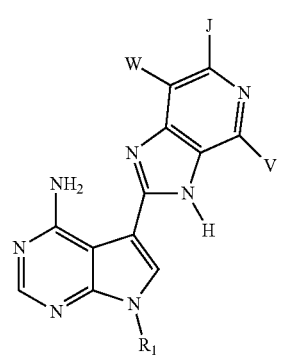
Formula 1-EQ
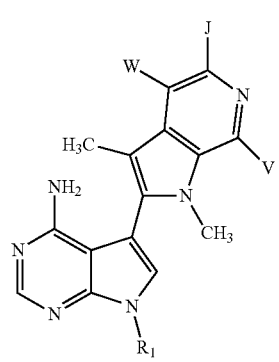
Formula 1-ER
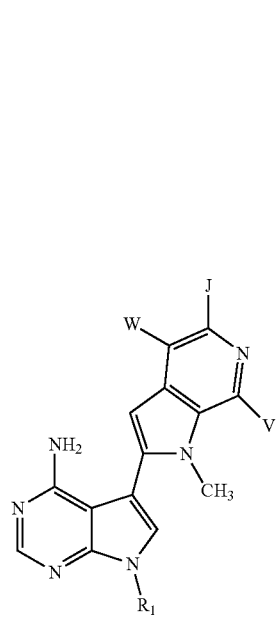

Formula 1-ES
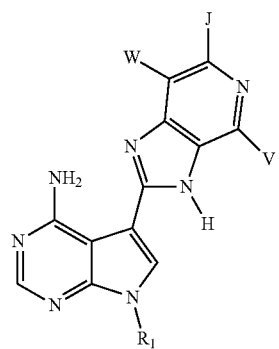
Formula 1-ET
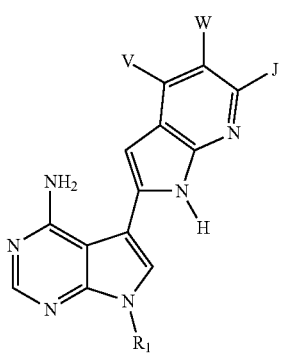
Formula 1-EU
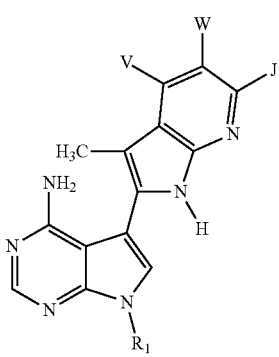
Formula 1-EV
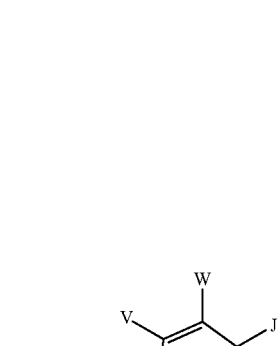
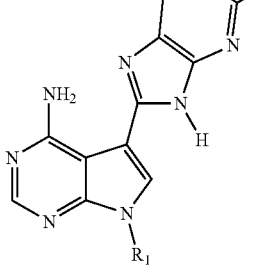
Formula 1-EW
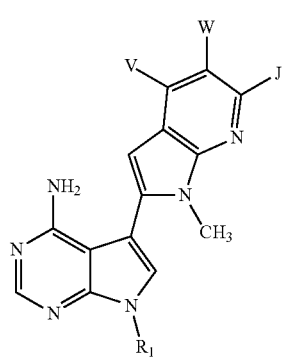
Formula 1-EX
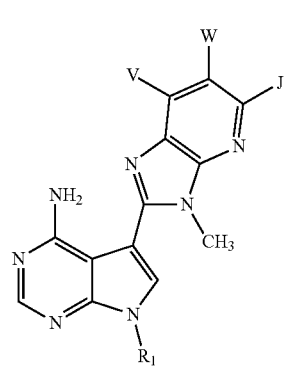
Formula 1-EY
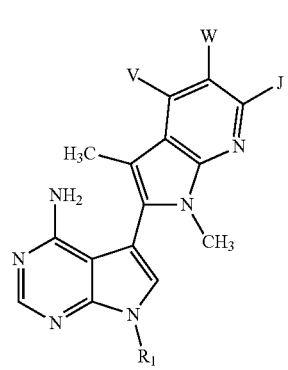
Formula 1-EZ
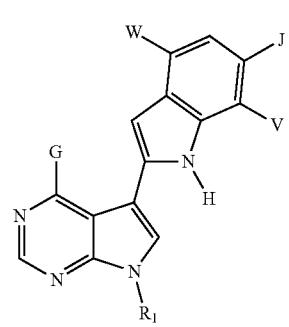

Formula 1-FA
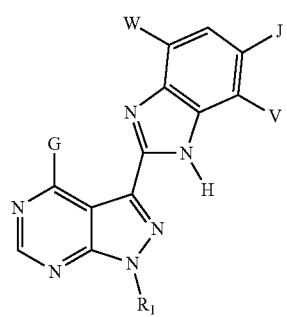
Formula 1-FB
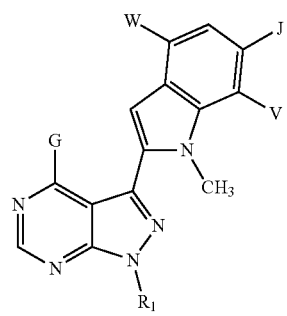
Formula 1-FC
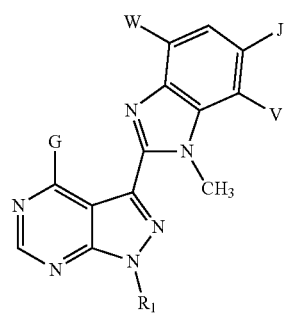
Formula 1-FD
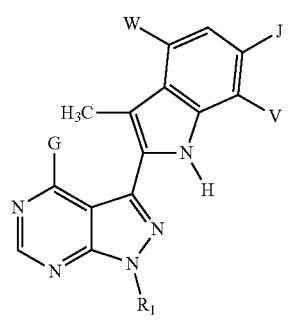
Formula 1-FE
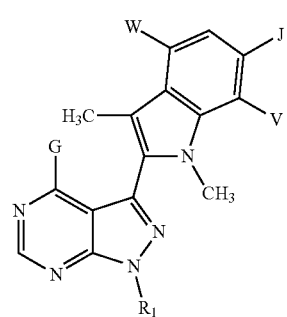
Formula 1-FF
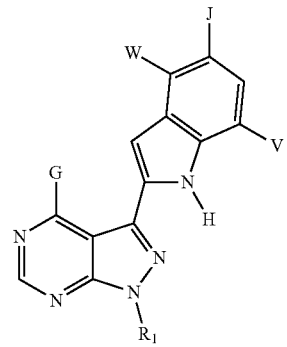
Formula 1-FG
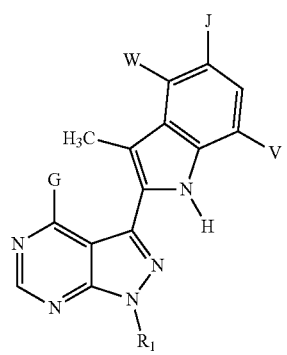
Formula 1-FH
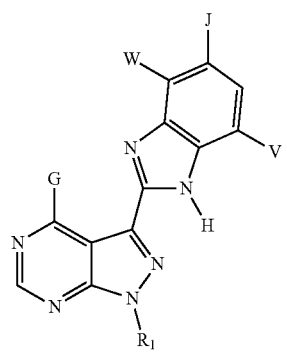
Formula 1-FI
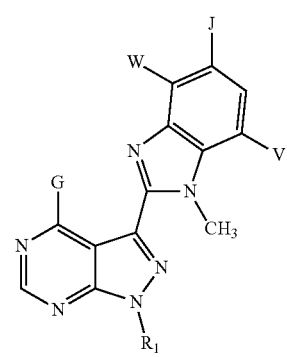

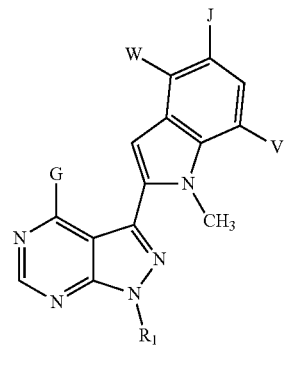 Formula 1-FJ
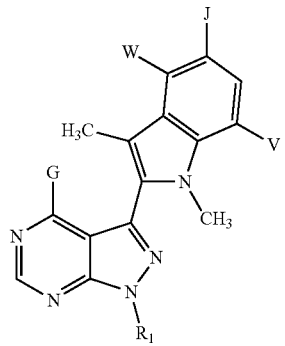 Formula 1-FK
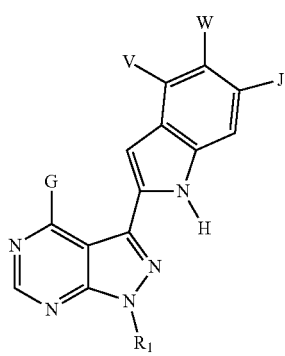 Formula 1-FL
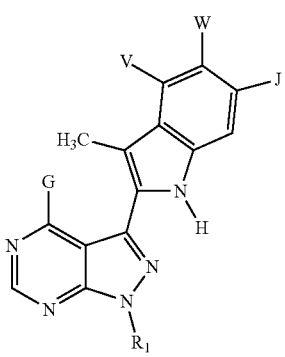 Formula 1-FM
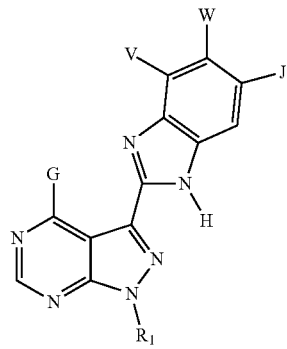 Formula 1-FN
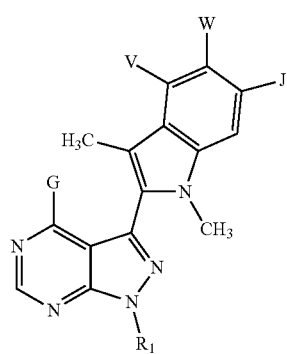 Formula 1-FO
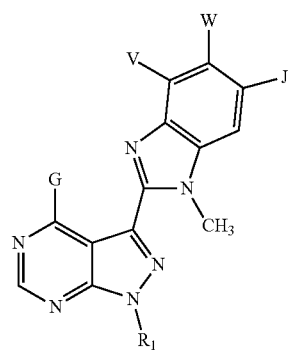 Formula 1-FP
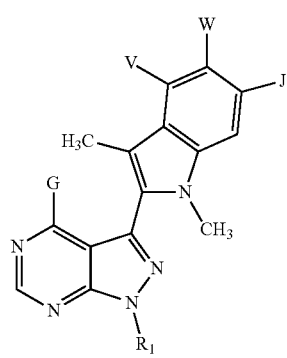 Formula 1-FQ 85
-continued
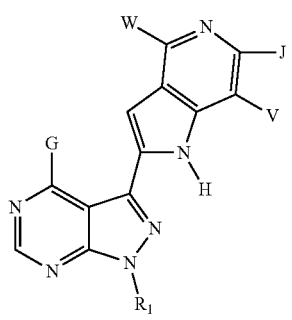
Formula 1-FR
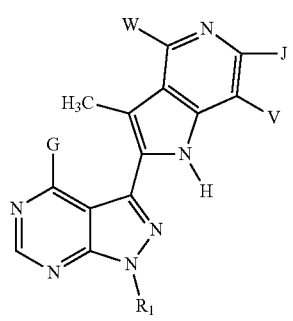
Formula 1-FS
Formula 1-FT
Formula 1-FU
Formula 1-FV
86
-continued
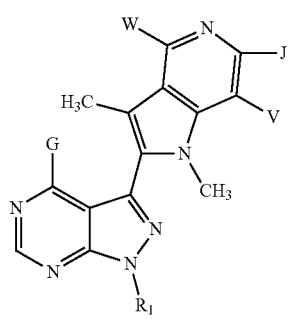
Formula 1-FW
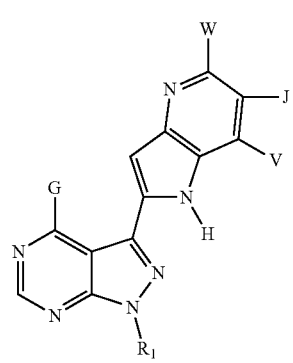
Formula 1-FX
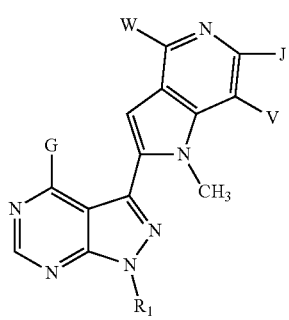
Formula 1-FY
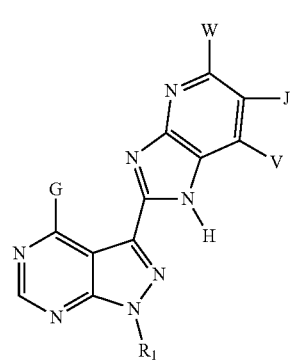
Formula 1-FZ Formula 1-GA
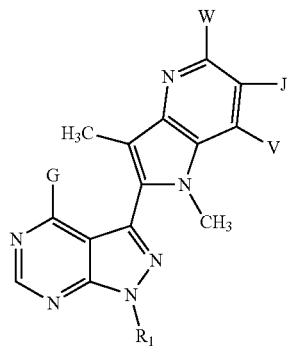
Formula 1-GB
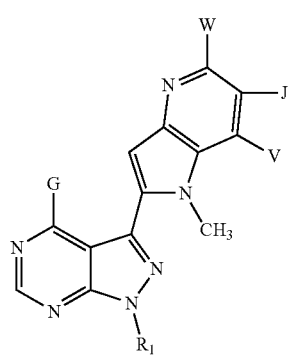
Formula 1-GC
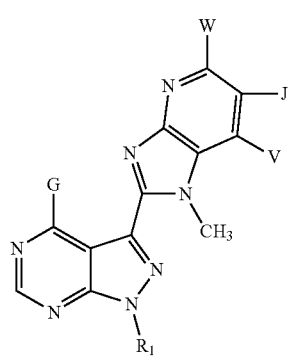
Formula 1-GC
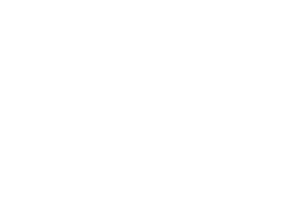
Formula 1-GE
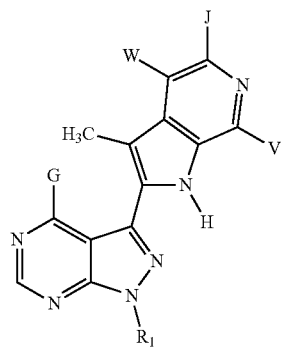
Formula 1-GF
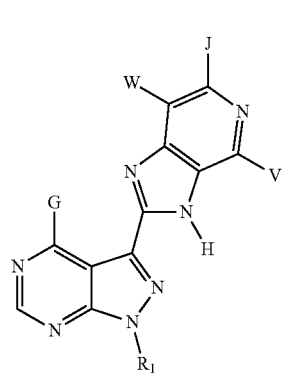
Formula 1-GG
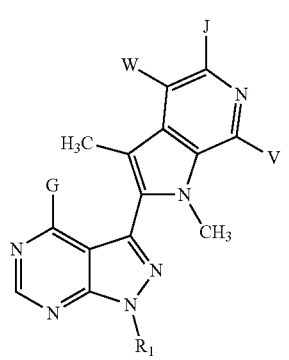
Formula 1-GH
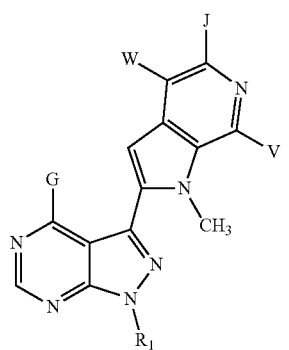
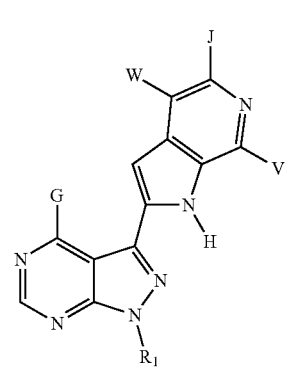

Formula 1-GI
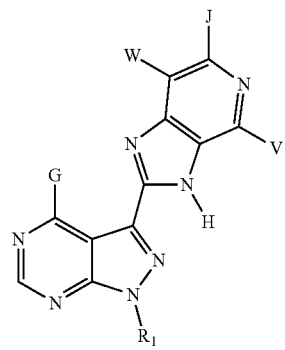
Formula 1-GJ
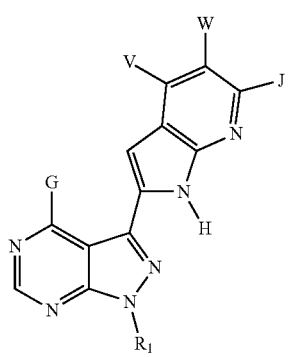
Formula 1-GK
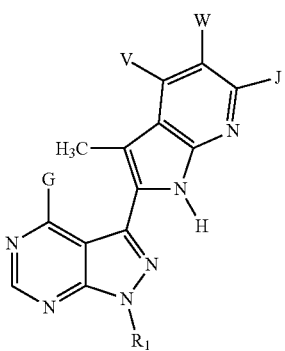
Formula 1-GL
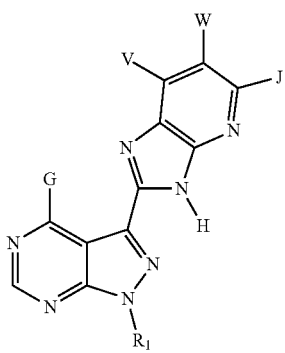
Formula 1-GM
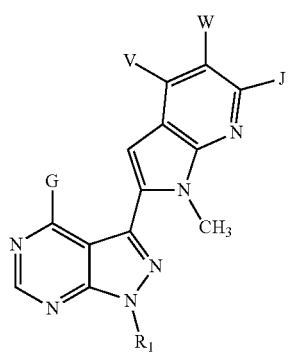
Formula 1-GN
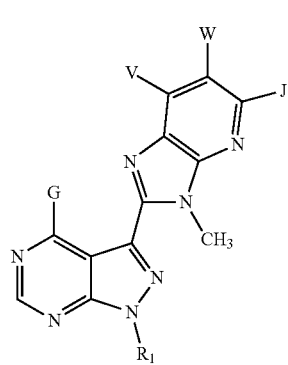
Formula 1-GO
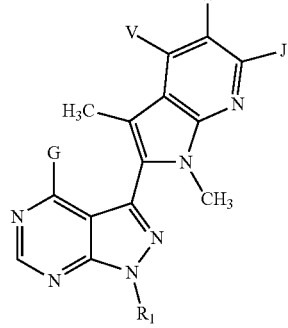
Formula 1-GP
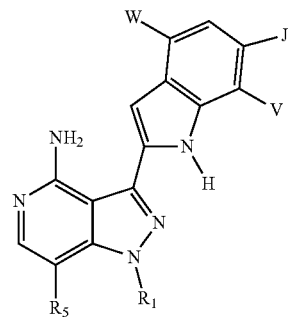

Formula 1-GQ
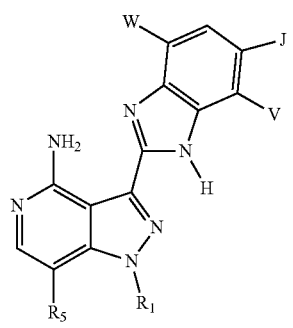
Formula 1-GR
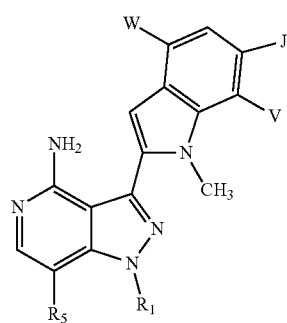
Formula 1-GS
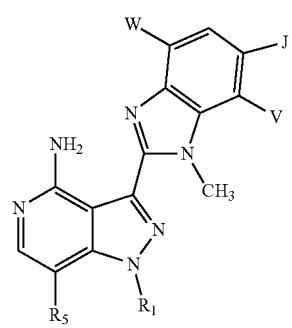
Formula 1-GT
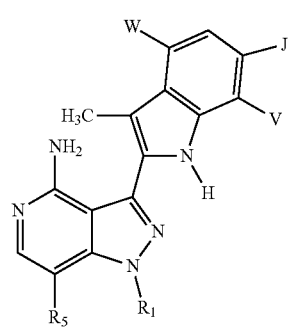
Formula 1-GU
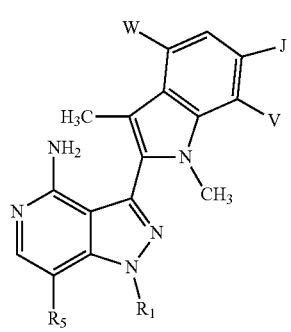
Formula 1-GV
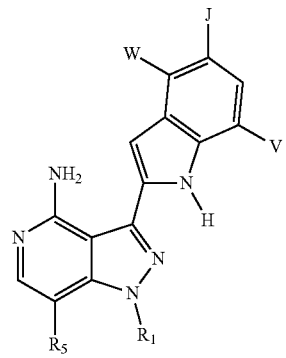
Formula 1-GW
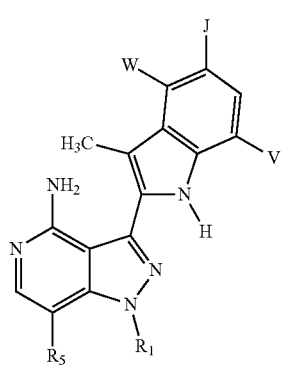
Formula 1-GX
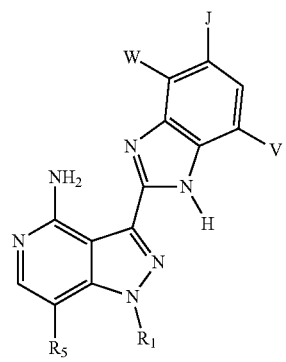
Formula 1-GY
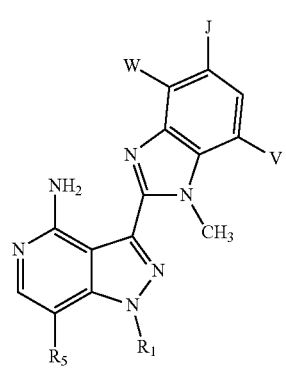

Formula 1-GZ
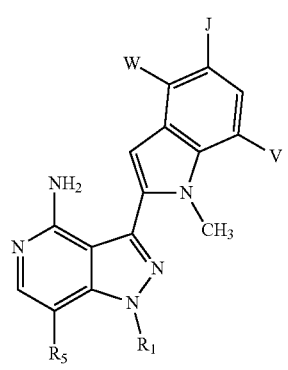
Formula 1-HA
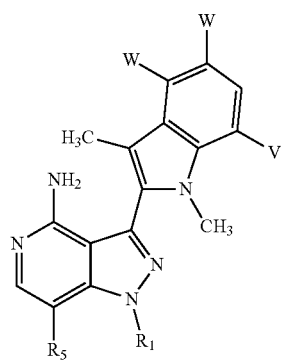
Formula 1-HB
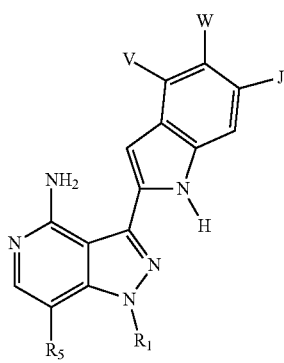
Formula 1-HC
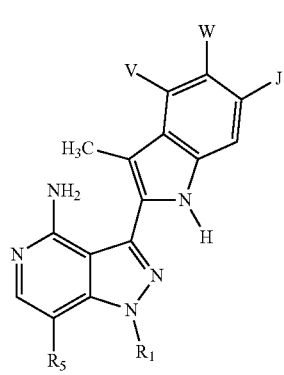
Formula 1-HD
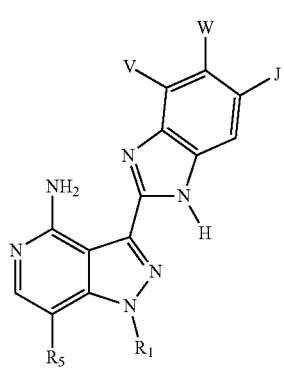
Formula 1-HE
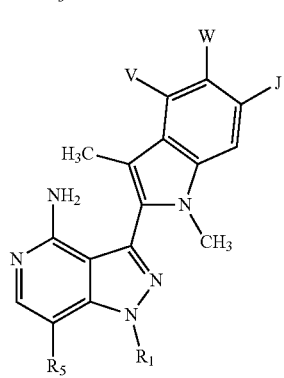
Formula 1-HF
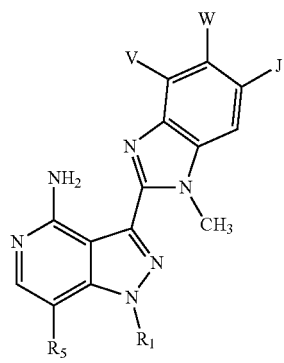
Formula 1-HG
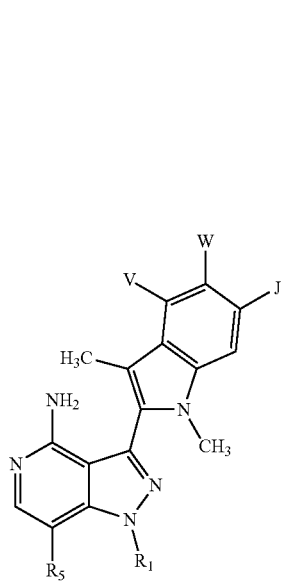

Formula 1-HH
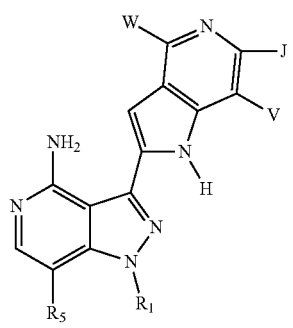
Formula 1-HI
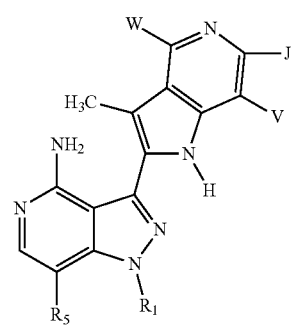
Formula 1-HJ
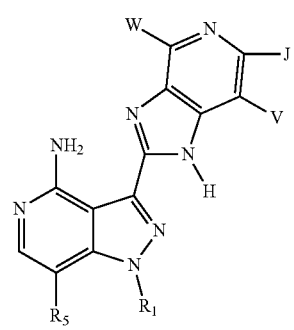
Formula 1-HK
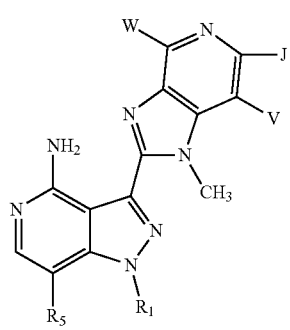
Formula 1-HL
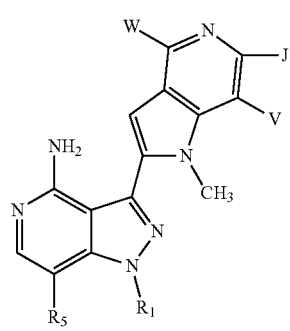
Formula 1-HM
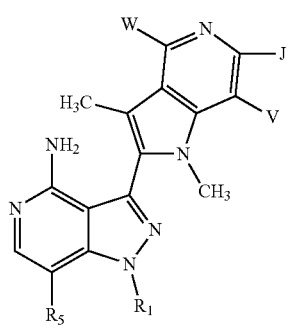
Formula 1-HN
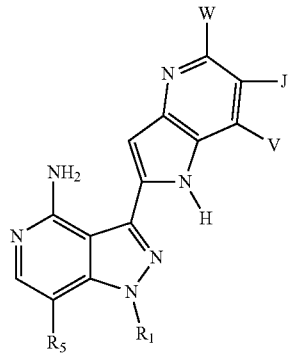
Formula 1-HO
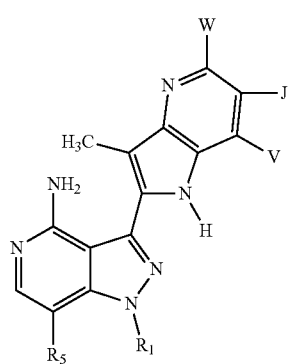
Formula 1-HP
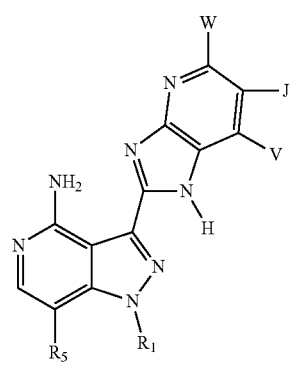

Formula 1-HQ
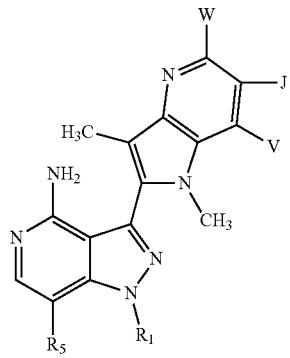
Formula 1-HR
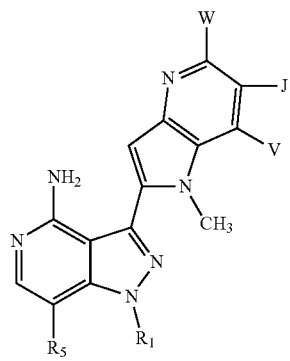
Formula 1-HS
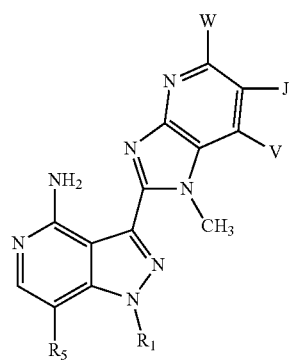
Formula 1-HT
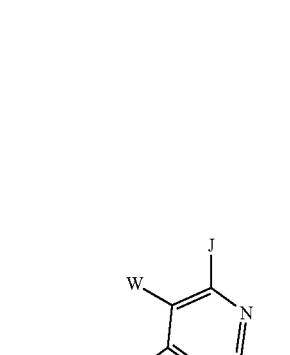
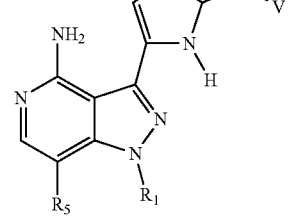
Formula 1-HU
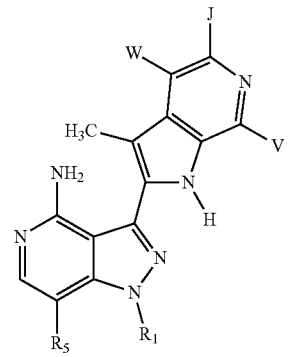
Formula 1-HV
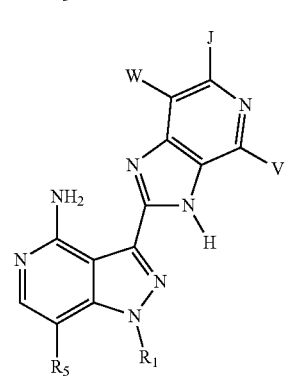
Formula 1-HW
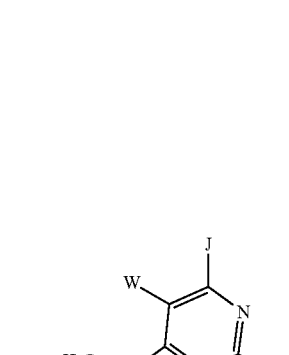
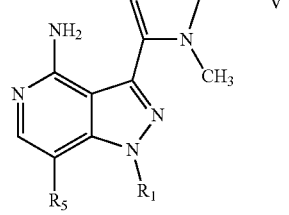
Formula 1-HX
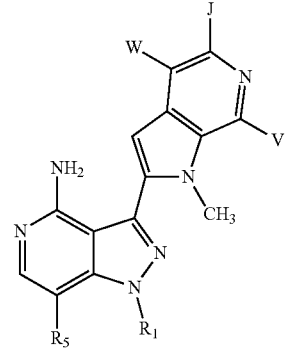

Formula 1-HY
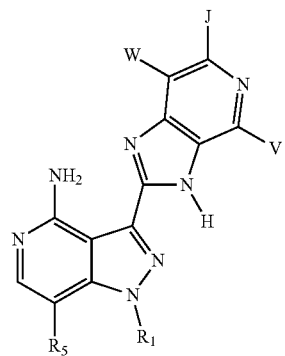
Formula 1-HZ
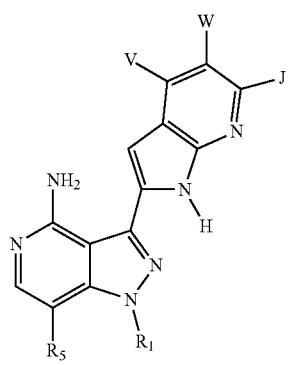
Formula 1-IA
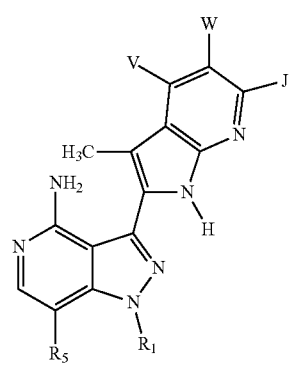
Formula 1-IB
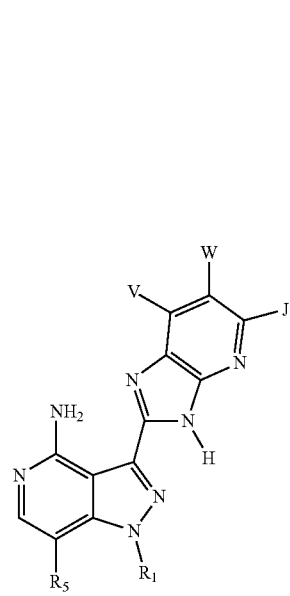
Formula 1-IC
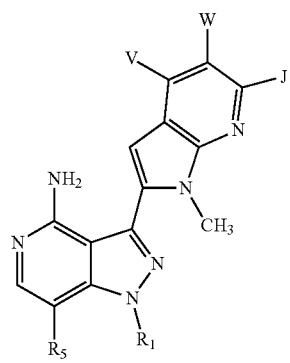
Formula 1-ID
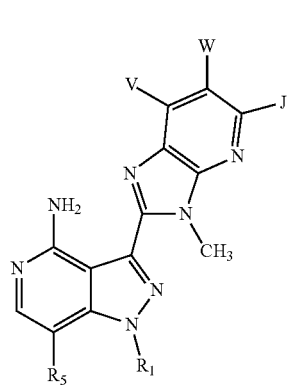
Formula 1-E
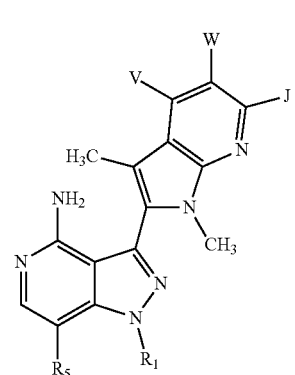
Formula 1-IF
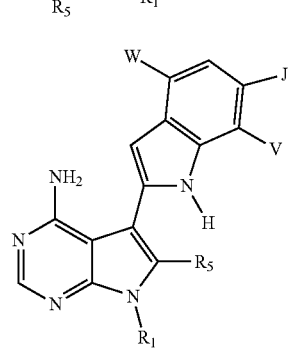

Formula 1-IG
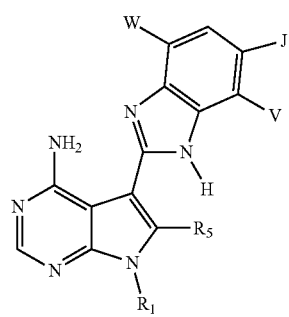
Formula 1-IH
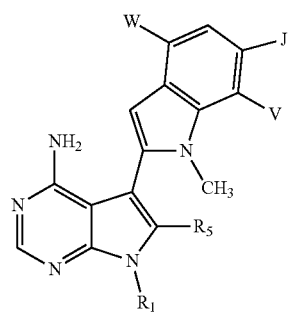
Formula 1-II
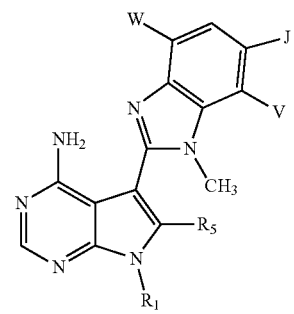
Formula 1-IJ
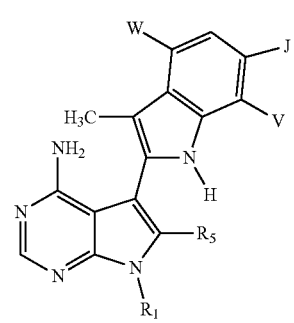
Formula 1-IK
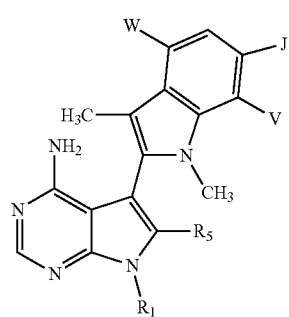
Formula 1-IL
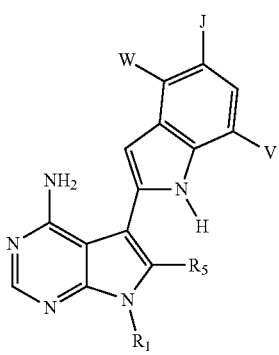
Formula 1-IM
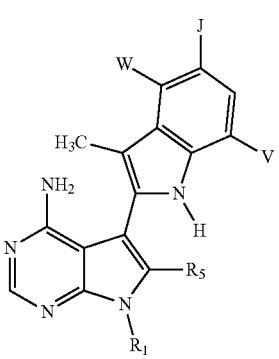
Formula 1-IN
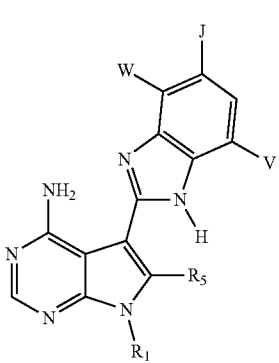
Formula 1-IO
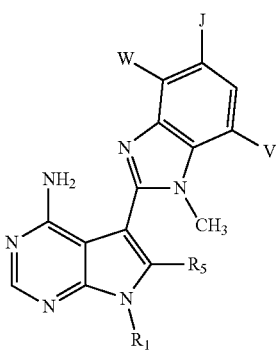

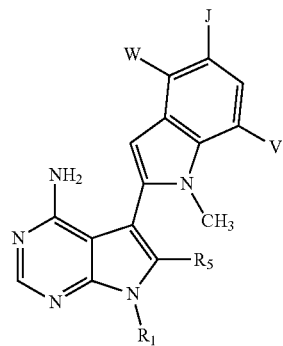
Formula 1-IP
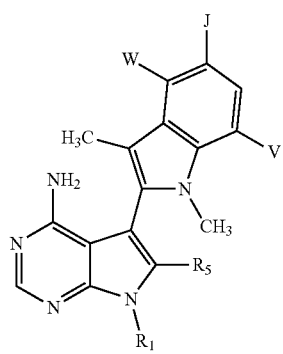
Formula 1-IQ
Formula 1-IR
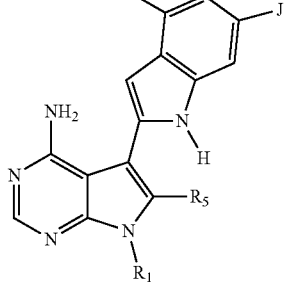
Formula 1-IS
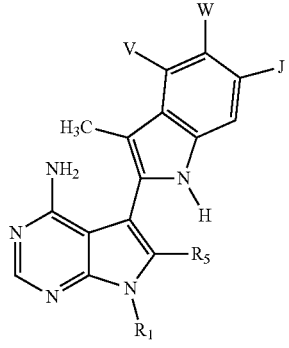
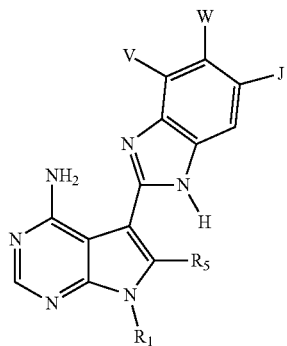
Formula 1-IT
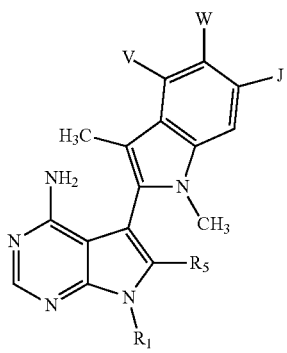
Formula 1-IU
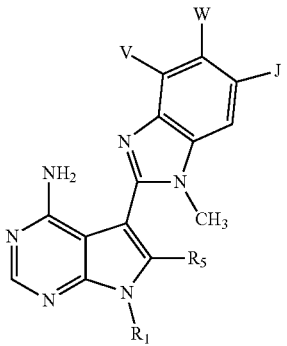
Formula 1-IW
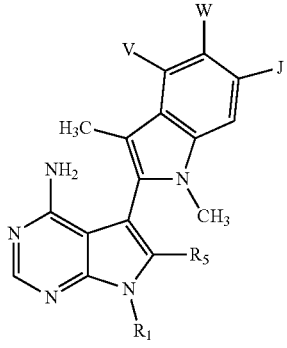
Formula 1-IX

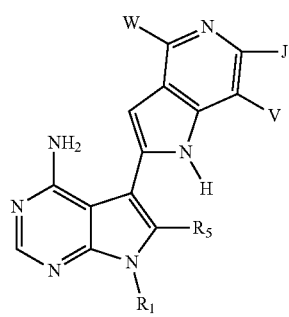
Formula 1-IY
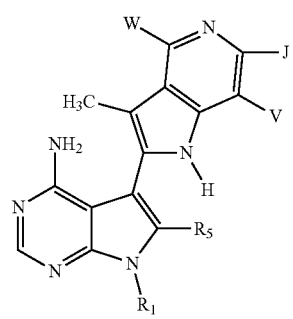
Formula 1-IZ
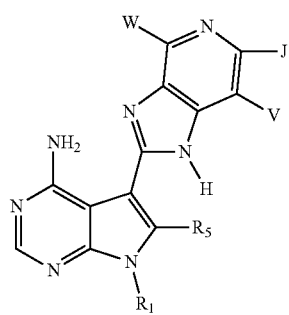
Formula 1-JA
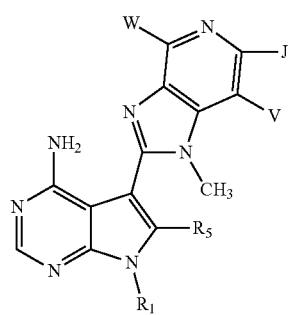
Formula 1-JB
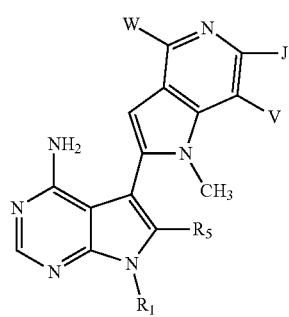
Formula 1-JC
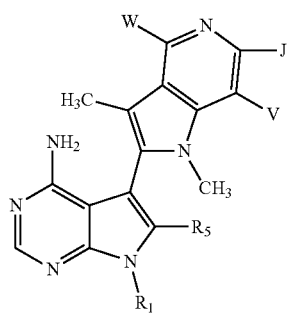
Formula 1-JD
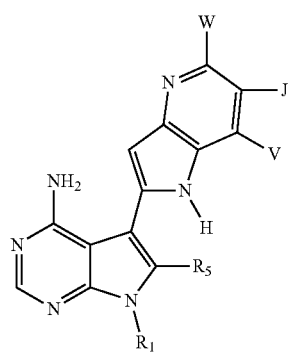
Formula 1-JE
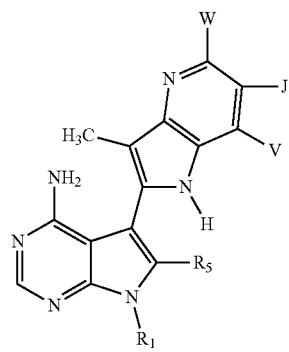
Formula 1-JF
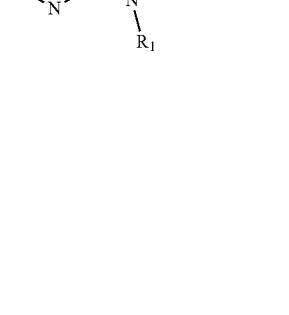
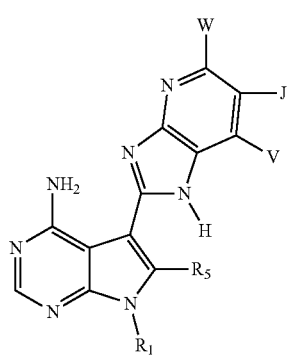
Formula 1-JG Formula 1-JH
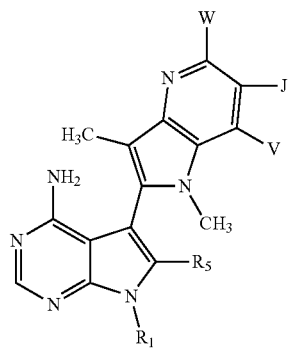
Formula 1-JI
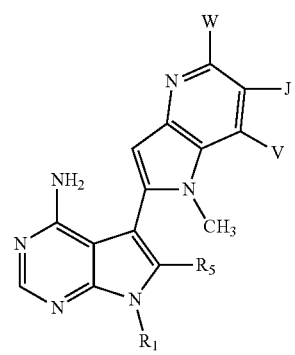
Formula 1-JK
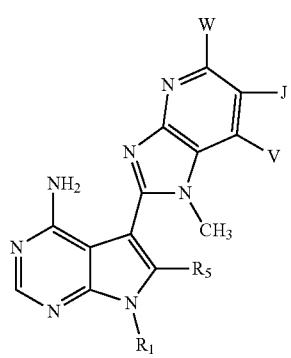
Formula 1-JL
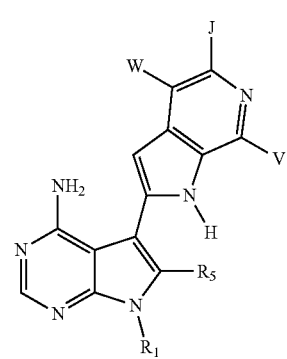
Formula 1-JM
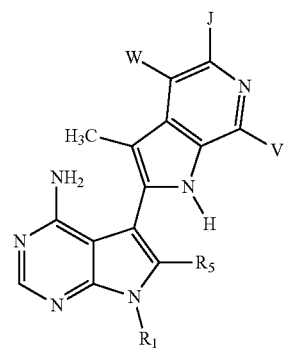
Formula 1-JN
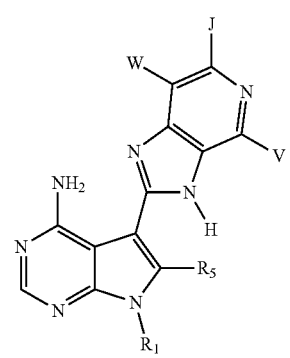
Formula 1-JO
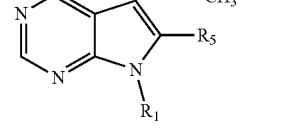
Formula 1-JO
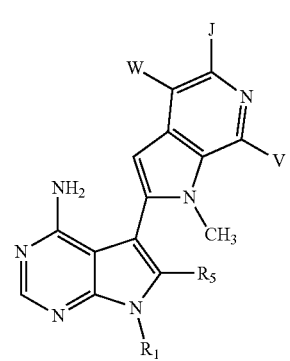

-continued

Formula 1-JQ

Formula 1-JR

Formula 1-JS

Formula 1-JT

-continued

Formula 1-JU

Formula 1-JV

Formula 1-JW

TABLE A

Compounds of the above Formulas 1-A to 1-JW with substituents of J, V, and W, as described below, are provided where $R_1$ is:

| Subclass # | $R_1$ |
|---|---|
| A-1 | (cyclobutyl) |
| A-2 | (tert-butyl) |

TABLE A-continued
Compounds of the above Formulas 1-A to 1-JW with substituents of J, V, and W, as described below, are provided where R₁ is:
| Subclass # | R₁ |
|---|---|
| A-3 | 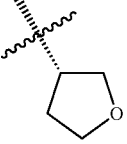 |
| A-4 | 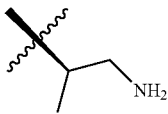 |
| A-5 | 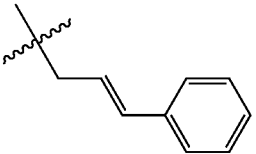 [SMILES: *C/C=C/c1ccccc1] |
| A-6 | 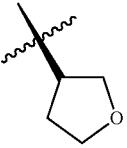 |
| A-7 | 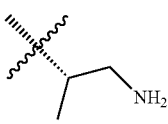 |
| A-8 |  |
| A-9 | 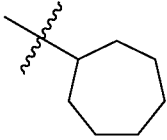 [SMILES: *C1CCCCCC1] |
| A-10 | 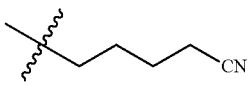 [SMILES: *CCCCC#N] |
| A-11 | 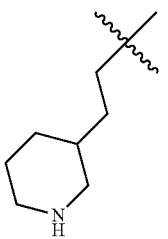 [SMILES: *CCC1CCCNC1] |
| A-12 | 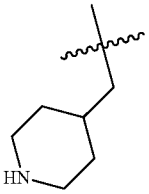 [SMILES: *CC1CCNCC1] |
| A-13 | 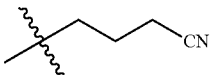 |
| A-14 | 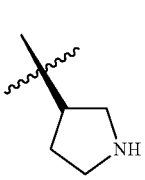 |
| A-15 | 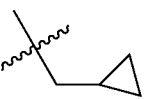 [SMILES: *CC1CC1] |
| A-16 | 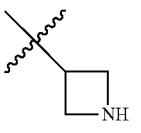 |
| A-17 | 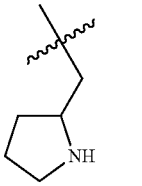 [SMILES: *CC1CCCN1] |
| A-18 |  |
| A-19 | 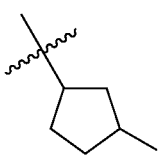 [SMILES: *C1CCC(C)C1] |
| A-20 |  |

TABLE A-continued
Compounds of the above Formulas 1-A to 1-JW with substituents of J, V, and W, as described below, are provided where R₁ is:
| Subclass # | R₁ |
|---|---|
| A-21 | 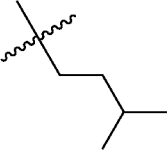 [SMILES: *CCC(C)C] |
| A-22 | 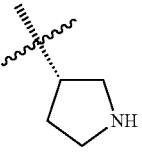 |
| A-23 |  |
| A-24 | 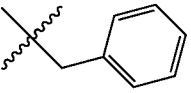 [SMILES: *Cc1ccccc1] |
| A-25 | 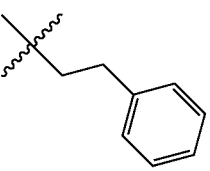 [SMILES: *CCc1ccccc1] |
| A-26 | 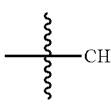 |
| A-27 | 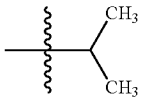 |
| A-28 | 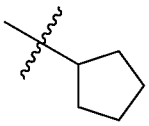 |
| A-29 | 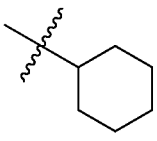 [SMILES: *C1CCCCC1] |
| A-30 | 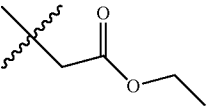 [SMILES: *CC(=O)OCC] |
| A-31 | 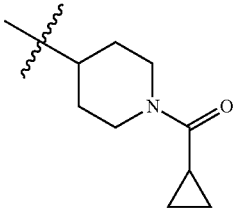 [SMILES: *C1CCN(C(=O)C2CC2)CC1] |
| A-32 | 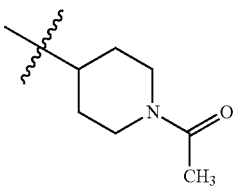 |
| A-33 | 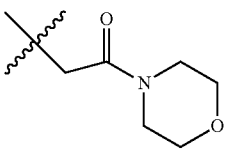 [SMILES: *CC(=O)N1CCOCC1] |
| A-34 | 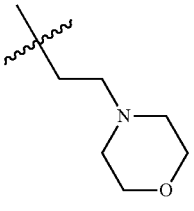 [SMILES: *CCN1CCOCC1] |
| A-35 | 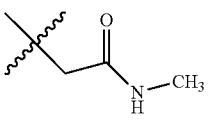 |
| A-36 | 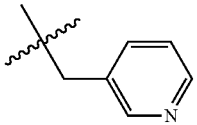 [SMILES: *Cc1cccnc1] |
| A-37 | 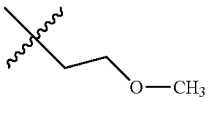 |
| A-38 | 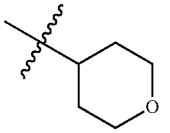 [SMILES: *C1CCOCC1] |
| A-39 | 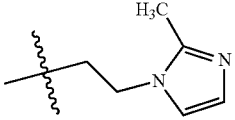 |

TABLE A-continued

Compounds of the above Formulas 1-A to 1-JW with substituents of J, V, and W, as described below, are provided where $R_1$ is:

| Subclass # | $R_1$ |
|---|---|
| A-40 | *trans*-cyclobutyl-morpholine |
| A-41 | cyclohexyl-OH |
| A-42 | piperidine (NH) |
| A-43 | N-isopropyl piperidine |
| A-44 | N-acetyl piperidine |
| A-45 | cyclobutyl-NHC(O)CH₃ |
| A-46 | *cis*-cyclobutyl-morpholine |
| A-47 | cyclobutyl-(N-methylpiperazine) |
| A-48 | cyclobutyl-C(O)NHCH₃ |
| A-49 | *trans*-cyclobutyl-OH |
| A-50 | *cis*-cyclobutyl-OH |
| A-51 | *trans*-cyclohexyl-morpholine |
| A-52 | *trans*-cyclohexyl-(N-methylpiperazine) |

TABLE B

Compounds of the above Formulae 1-EZ to 1-GO with substituents of J, V, and W, as described in below, are provided where G is:

| Subclass # | |
|---|---|
| B-1 | $CH_3$ |
| B-2 | $CH_2Cl$ |
| B-3 | $CHCl_2$ |
| B-4 | $CCl_3$ |
| B-5 | $CH_2Br$ |
| B-6 | $CHBr_2$ |
| B-7 | $CBr_3$ |
| B-8 | $CH_2F$ |
| B-9 | $CHF_2$ |
| B-10 | $CF_3$ |
| B-11 | H |
| B-12 | Cl |
| B-13 | Br |
| B-14 | F |
| B-15 | $NHCH_3$ |
| B-16 | $N(CH_3)_2$ |
| B-17 | 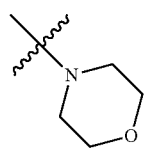 [SMILES: *N1CCOCC1] |
| B-18 | 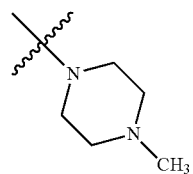 [SMILES: *N1CCN(C)CC1] |

TABLE C

Compounds of the above Formulae 1-GP to 1-JW with substituents of J, V, and W, as described below, are provided where $R_5$ is:

Subclass #

C-1

C-2

C-3

C-4

TABLE C-continued

Compounds of the above Formulae 1-GP to 1-JW with substituents of J, V, and W, as described below, are provided where $R_5$ is:

Subclass #

C-5

C-6

C-7

C-8

C-9

C-10

C-11

C-12

C-13

TABLE C-continued
Compounds of the above Formulae 1-GP to 1-JW with substituents of J, V, and W, as described below, are provided where $R_5$ is:
Subclass #
C-14 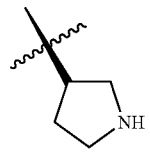
C-15 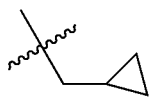 [SMILES: *CC1CC1]
A-16 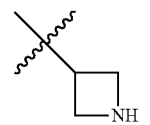 [SMILES: *C1CNC1]
A-17 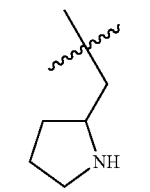 [SMILES: *CC1CCCN1]
A-18 
C-19 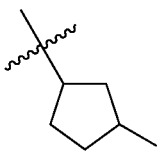 [SMILES: *C1CCC(C)C1]
C-20 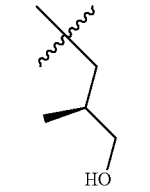 [SMILES: *C[C@H](C)CO]
C-21 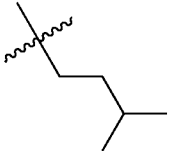 [SMILES: *CCC(C)C]
C-22 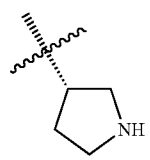
TABLE C-continued
Compounds of the above Formulae 1-GP to 1-JW with substituents of J, V, and W, as described below, are provided where $R_5$ is:
Subclass #
C-23 
C-24 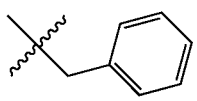
C-25 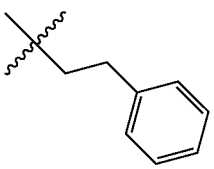 [SMILES: *CCc1ccccc1]
C 26 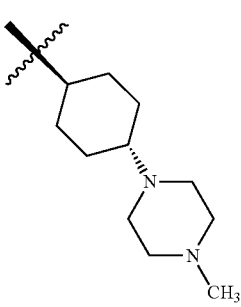
C-27 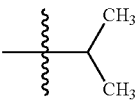
C-28 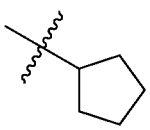
C-29 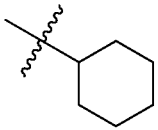 [SMILES: *C1CCCCC1]
C-30 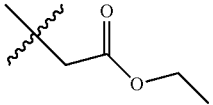 [SMILES: *CC(=O)OCC]
C-31 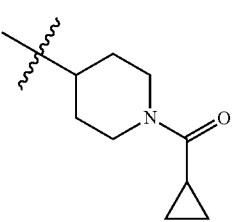 [SMILES: *C1CCN(C(=O)C2CC2)CC1]

TABLE C-continued
Compounds of the above Formulae 1-GP to 1-JW with substituents of J, V, and W, as described below, are provided where $R_5$ is:
Subclass #
C-32 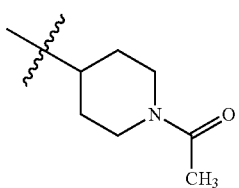 [SMILES: *C1CCN(C(C)=O)CC1]
C-33 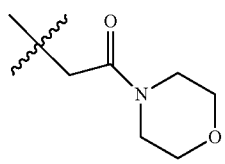 [SMILES: *CC(=O)N1CCOCC1]
C-34 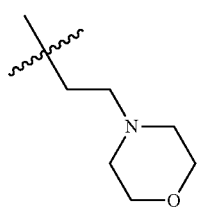 [SMILES: *CCN1CCOCC1]
C-35 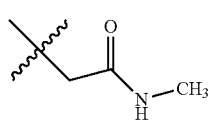
C-36 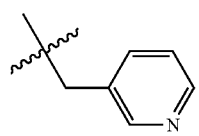 [SMILES: *Cc1cccnc1]
C-37 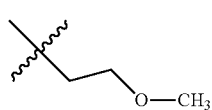 [SMILES: *CCOC]
C-38 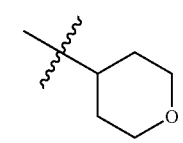 [SMILES: *C1CCOCC1]
C-39 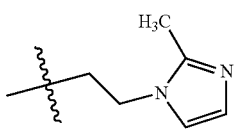 [SMILES: *CCn1ccnc1C]
C-40 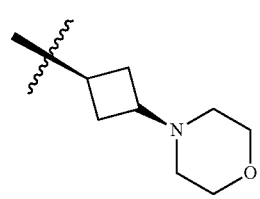
TABLE C-continued
Compounds of the above Formulae 1-GP to 1-JW with substituents of J, V, and W, as described below, are provided where $R_5$ is:
Subclass #
C-41 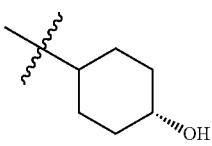
C-42 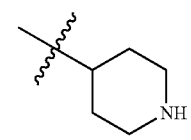
C-43 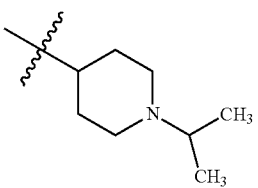 [SMILES: *C1CCN(C(C)C)CC1]
C-44 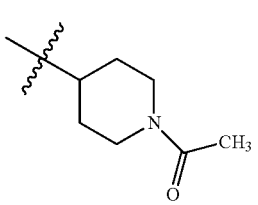 [SMILES: *C1CCN(C(C)=O)CC1]
C-45 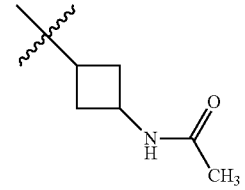 [SMILES: *C1CC(NC(C)=O)C1]
C-46 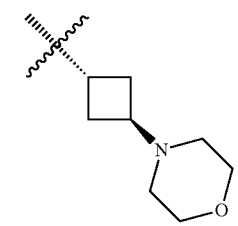
C-47 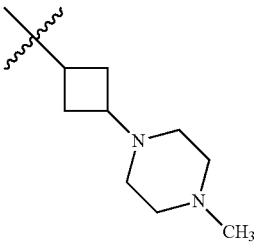 [SMILES: *C1CC(N2CCN(C)CC2)C1]

TABLE C-continued

Compounds of the above Formulae 1-GP to 1-JW with substituents of J, V, and W, as described below, are provided where $R_5$ is:

| Subclass # | |
|---|---|
| C-48 | (cyclobutyl with C(O)NHCH₃) |
| C-49 | (cyclobutyl with OH, trans) |
| C-50 | (cyclobutyl with OH, cis) |
| C-51 | (cyclohexyl with morpholino) |
| C-52 | —C(CH₃)— (tert-butyl-like) |
| C-53 | —CN |
| C-54 | —Cl |
| C-55 | —Br |
| C-56 | —F |
| C-57 | —OH |
| C-58 | —OCF₃ |
| C-59 | —CF₃ |
| C-60 | —NH₂ |
| C-61 | —NMe₂ |
| C-62 | —NO₂ |
| C-63 | —C(O)CH3 |
| C-64 | —SO₂Me |
| C-65 | —SO₂NH₂ |

Particular embodiments of J, V, and W of illustrative compounds of Formulae 1-A to 1-GO are described as follows, where Am=C(O)NH₂, Cy=cyclopropyl,

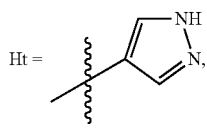

and So=-SO₂CH₃. In some embodiments, when J is H and V is H, W is H, Cl, Br, F, OH, OMe, or Am. In other embodiments, when J is H and V is Cl, W is H, Cl, Br, F, OH, OMe, or Am. In other embodiments, when J is H and V is Br, W is H, Cl, Br, F, OH, OMe, or Am. In other embodiments, when J is H and V is F, W is H, Cl, Br, F, OH, OMe, or Am. In other embodiments, when J is H and V is CH₃, W is H, Cl, Br, F, OH, OMe, or Am. In other embodiments, when J is H and V is OH, W is H, Cl, Br, F, OH, OMe, or Am. In other embodiments, when J is H and V is OMe, W is H, Cl, Br, F, OH, OMe, or Am. In other embodiments, when J is H and V is CF₃, W is H, Cl, Br, F, OH, OMe, or Am. In other embodiments, when J is H and V is So, W is H, Cl, Br, F, OH, OMe, or Am. In other embodiments, when J is H and V is Cy, W is H, Cl, Br, F, OH, OMe, or Am. In other embodiments, when J is H and V is CN, W is H, Cl, Br, F, OH, OMe, or Am. In other embodiments, when J is H and V is Me, W is H, Cl, Br, F, OH, OMe, or Am. In other embodiments, when J is H and V is Ht, W is H, Cl, Br, F, OH, OMe, or Am. In some embodiments, when J is Cl and V is H, W is H, Cl, Br, F, OH, OMe, or Am. In other embodiments, when J is Cl and V is Cl, W is H, Cl, Br, F, OH, OMe, or Am. In other embodiments, when J is Cl and V is Br, W is H. Cl, Br, F. OH, OMe, or Am. In other embodiments, when J is Cl and V is F, W is H, Cl, Br, F, OH, OMe, or Am. In other embodiments, when J is Cl and V is CH₃, W is H, Cl, Br, F, OH, OMe, or Am. In other embodiments, when J is Cl and V is OH, W is H, Cl, Br, F, OH, OMe, or Am. In other embodiments, when J is Cl and V is OMe, W is H, Cl, Br, F, OH, OMe, or Am. In other embodiments, when J is Cl and V is CF₃, W is H, Cl, Br, F, OH, OMe, or Am. In other embodiments, when J is Cl and V is So, W is H, Cl, Br, F, OH, OMe, or Am. In other embodiments, when J is Cl and V is Cy, W is H, Cl, Br, F, OH, OMe, or Am. In other embodiments, when J is Cl and V is CN, W is H, Cl, Br, F, OH, OMe, or Am. In other embodiments, when J is Cl and V is Me, W is H, Cl, Br, F, OH, OMe, or Am. In other embodiments, when J is Cl and V is Ht, W is H, Cl, Br, F, OH, OMe, or Am. In some embodiments, when J is Br and V is H, W is H, Cl, Br, F, OH, OMe, or Am. In other embodiments, when J is Br and V is Cl, W is H, Cl, Br, F, OH, OMe, or Am. In other embodiments, when J is Br and V is Br, W is H, Cl, Br, F, OH, OMe, or Am. In other embodiments, when J is Br and V is F, W is H, Cl, Br, F, OH, OMe, or Am. In other embodiments, when J is Br and V is CH₃, W is H, Cl, Br, F, OH, OMe, or Am. In other embodiments, when J is Br and V is OH, W is H, Cl, Br, F, OH, OMe, or Am. In other embodiments, when J is Br and V is OMe, W is H, Cl, Br, F, OH, OMe, or Am. In other embodiments, when J is Br and V is CF₃, W is H, Cl, Br, F, OH, OMe, or Am. In other embodiments, when J is Br and V is So, W is H, Cl, Br, F, OH, OMe, or Am. In other embodiments, when J is Br and V is Cy, W is H, Cl, Br, F, OH, OMe, or Am. In other embodiments, when J is Br and V is CN, W is H, Cl, Br, F, OH, OMe, or Am. In other embodiments, when J is Br and V is Me, W is H, Cl, Br, F, OH, OMe, or Am. In other embodiments, when J is Br and V is Ht, W is H, Cl, Br, F, OH, OMe, or Am. In some embodiments, when J is F and V is H, W is H, Cl, Br, F, OH, OMe, or Am. In other embodiments, when J is F and V is Cl, W is H, Cl, Br, F, OH, OMe, or Am. In other embodiments, when J is F and V is Br, W is H, Cl, Br, F, OH, OMe, or Am. In other embodiments, when J is F and V is F, W is H, Cl, Br, F, OH, OMe, or Am. In other embodiments, when J is F and V is CH₃, W is H, Cl, Br, F, OH, OMe, or Am. In other embodiments, when J is F and V is OH, W is H, Cl, Br, F, OH, OMe, or Am. In other embodiments, when J is F and V is OMe, W is H, Cl, Br, F, OH, OMe, or Am. In other embodiments, when J is F and V is CF₃, W is H, Cl, Br, F, OH, OMe, or Am. In other embodiments, when J is F and V is So, W is H, Cl, Br, F, OH, OMe, or Am. In other embodiments, when J is F and V is Cy, W is H, Cl, Br, F, OH, OMe, or Am. In other embodiments, when J is F and V is CN, W is H, Cl, Br, F, OH, OMe, or Am. In other embodiments, when J is F and V is Me, W is H, Cl, Br, F, OH, OMe, or Am. In other embodiments, when J is F and V is Ht, W is H, Cl, Br, F, OH, OMe, or Am. In some embodiments, when J is OH and V is H, W is H, Cl, Br, F, OH, OMe, or Am. In other embodiments, when J is OH and V is Cl, W is H, Cl, Br, F, OH, OMe, or Am. In other embodiments, when J is OH and V is Br, W is H, Cl, Br, F, OH, OMe, or Am. In other embodiments, when J is OH and V is F, W is H, Cl, Br, F, OH, OMe, or Am. In other embodiments, when J is OH and V is $CH_3$, W is H, Cl, Br, F, OH, OMe, or Am. In other embodiments, when J is OH and V is OH, W is H, Cl, Br, F, OH, OMe, or Am. In other embodiments, when J is OH and V is OMe, W is H, Cl, Br, F, OH, OMe, or Am. In other embodiments, when J is OH and V is $CF_3$, W is H, Cl, Br, F, OH, OMe, or Am. In other embodiments, when J is OH and V is So, W is H, Cl, Br, F, OH, OMe, or Am. In other embodiments, when J is OH and V is Cy, W is H, Cl, Br, F, OH, OMe, or Am. In other embodiments, when J is OH and V is CN, W is H, Cl, Br, F, OH, OMe, or Am. In other embodiments, when J is OH and V is Me, W is H, Cl, Br, F, OH, OMe, or Am. In other embodiments, when J is OH and V is Ht, W is H, Cl, Br, F, OH, OMe, or Am. In some embodiments, when J is OMe and V is H, W is H, Cl, Br, F, OH, OMe, or Am. In other embodiments, when J is OMe and V is Cl, W is H, Cl, Br, F, OH, OMe, or Am. In other embodiments, when J is OMe and V is Br, W is H, Cl, Br, F, OH, OMe, or Am. In other embodiments, when J is OMe and V is F, W is H, Cl, Br, F, OH, OMe, or Am. In other embodiments, when J is OMe and V is $CH_3$, W is H, Cl, Br, F, OH, OMe, or Am. In other embodiments, when J is OMe and V is OH, W is H, Cl, Br, F, OH, OMe, or Am. In other embodiments, when J is OMe and V is OMe, W is H, Cl, Br, F, OH, OMe, or Am. In other embodiments, when J is OMe and V is $CF_3$, W is H, Cl, Br, F, OH, OMe, or Am. In other embodiments, when J is OMe and V is So, W is H, Cl, Br, F, OH, OMe, or Am. In other embodiments, when J is OMe and V is Cy, W is H, Cl, Br, F, OH, OMe, or Am. In other embodiments, when J is OMe and V is CN, W is H, C, Br, F, OH, OMe, or Am. In other embodiments, when J is OMe and V is Me, W is H, Cl, Br, F, OH, OMe, or Am. In other embodiments, when J is OMe and V is Ht, W is H, Cl, Br, F, OH, OMe, or Am. In some embodiments, when J is Am and V is H, W is H, C, Br, F, OH, OMe, or Am. In other embodiments, when J is Am and V is Cl, W is H, Cl, Br, F, OH, OMe, or Am. In other embodiments, when J is Am and V is Br, W is H, Cl, Br, F, OH, OMe, or Am. In other embodiments, when J is Am and V is F, W is H, Cl, Br, F, OH, OMe, or Am. In other embodiments, when J is Am and V is $CH_3$, W is H, C, Br, F, OH, OMe, or Am. In other embodiments, when J is Am and V is OH, W is H, Cl, Br, F, OH, OMe, or Am. In other embodiments, when J is Am and V is OMe, W is H, C, Br, F, OH, OMe, or Am. In other embodiments, when J is Am and V is $CF_3$, W is H, Cl, Br, F, OH, OMe, or Am. In other embodiments, when J is Am and V is So, W is H, Cl, Br, F, OH, OMe, or Am. In other embodiments, when J is Am and V is Cy, W is H, Cl, Br, F, OH, OMe, or Am. In other embodiments, when J is Am and V is CN, W is H, Cl, Br, F, OH, OMe, or Am. In other embodiments, when J is Am and V is Me, W is H, Cl, Br, F, OH, OMe, or Am. In other embodiments, when J is Am and V is Ht, W is H, Cl, Br, F, OH, OMe, or Am.

The invention further provides illustrative compounds of Formulae 2-A to 2-R, which includes each embodiment wherein $R_1$ is any one of $R_1$ as described in Table A, and wherein W, V, and J are as described below.

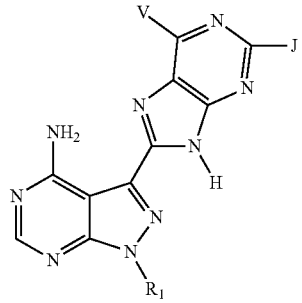

Formula 2-A

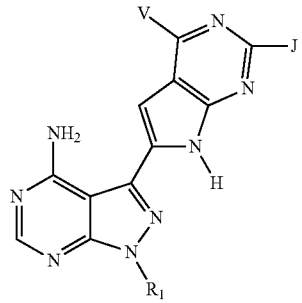

Formula 2-B

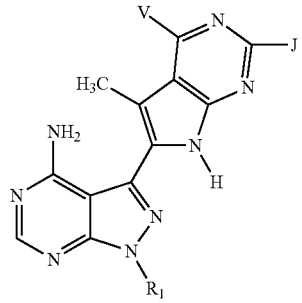

Formula 2-C

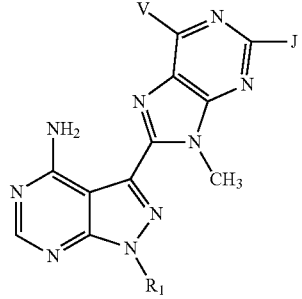

Formula 2-D

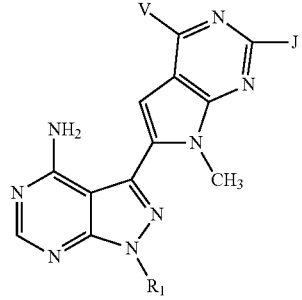

Formula 2-E

Formula 2-F
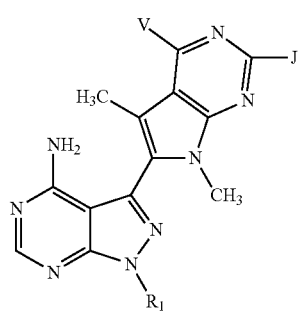
Formula 2-G
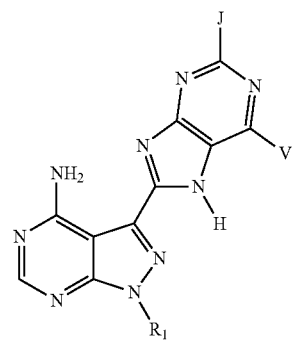
Formula 2-H
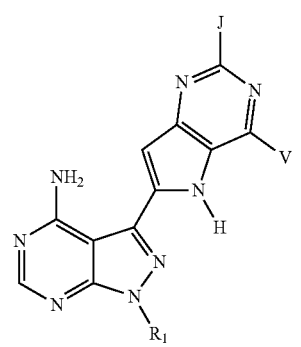
Formula 2-I
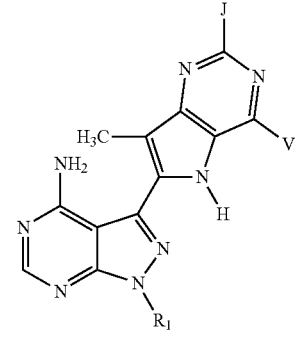
Formula 2-J
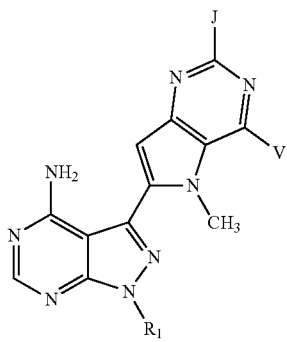
Formula 2-K
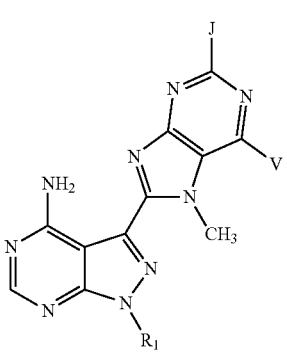
Formula 2-L
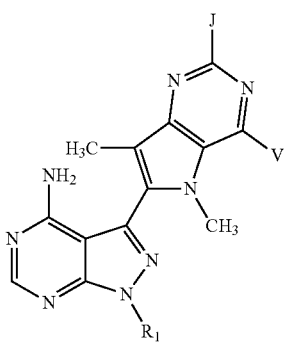
Formula 2-M
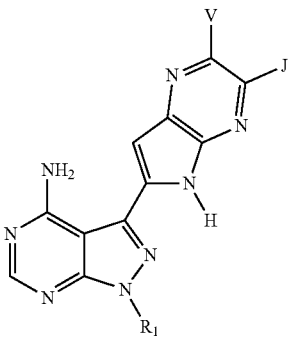

Formula 2-N
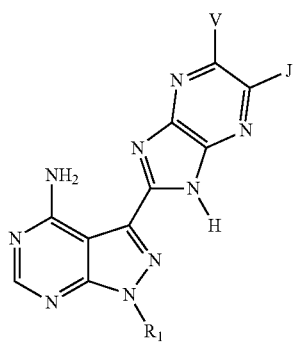
Formula 2-O
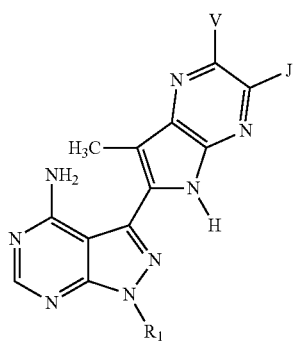
Formula 2-P
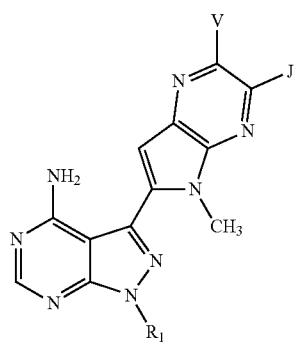
Formula 2-Q
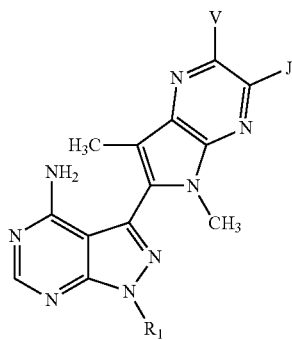
Formula 2-R
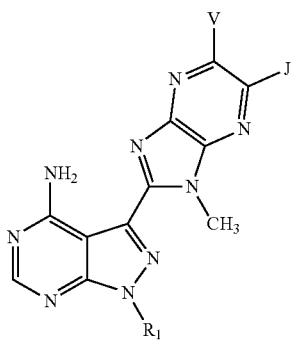
Formula 2-S
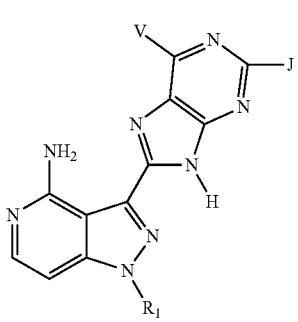
Formula 2-T
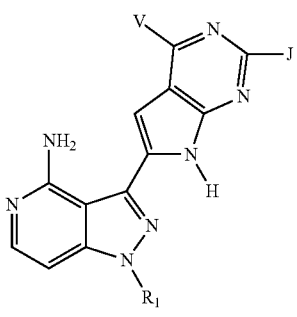
Formula 2-U
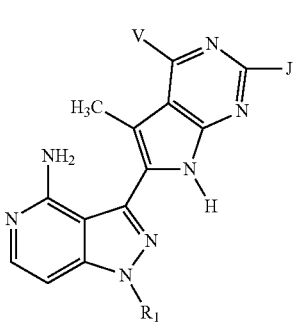
Formula 2-V
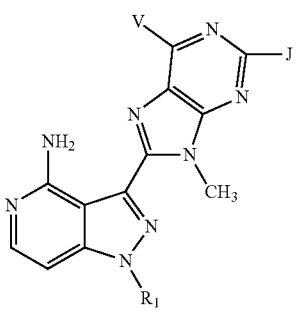

-continued
Formula 2-W
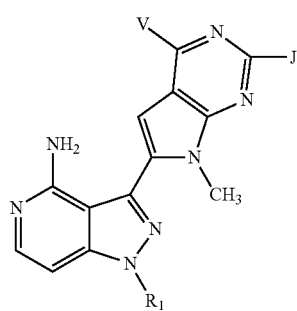
Formula 2-X
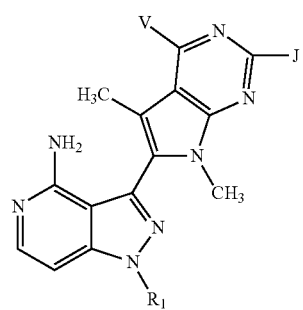
Formula 2-Y
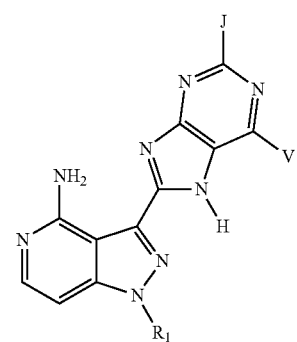
Formula 2-Z
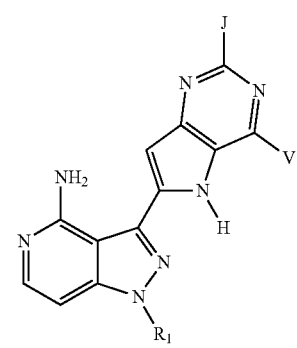
Formula 2-AA
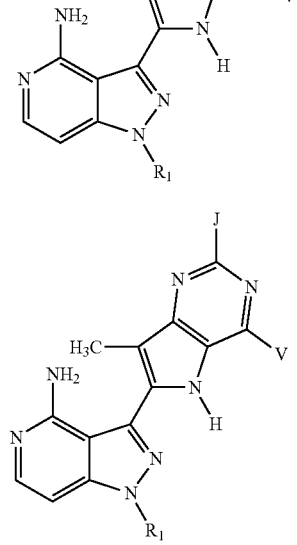
-continued
Formula 2-AB
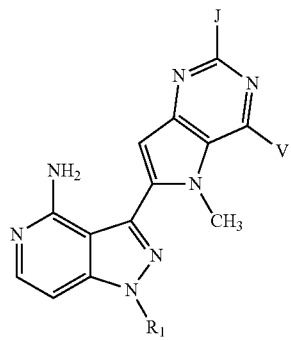
Formula 2-AC
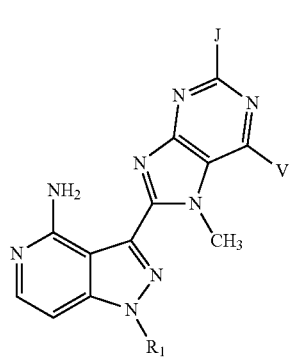
Formula 2-AD
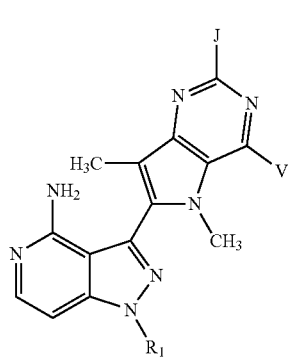
Formula 2-AE
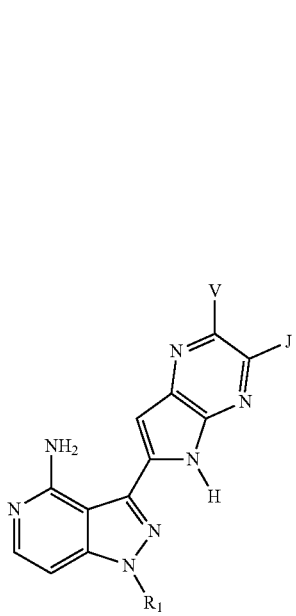

Formula 2-AF
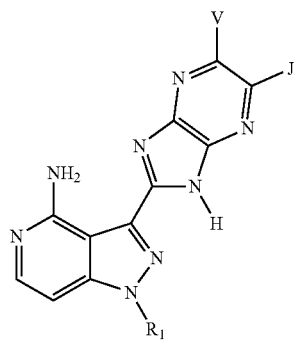
Formula 2-AG
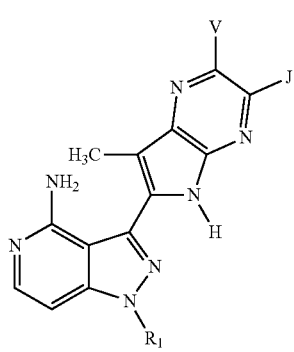
Formula 2-AH
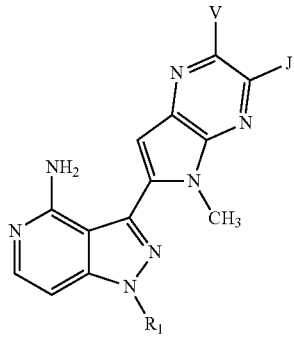
Formula 2-AI
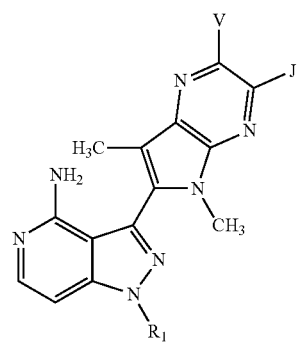
Formula 2-AJ
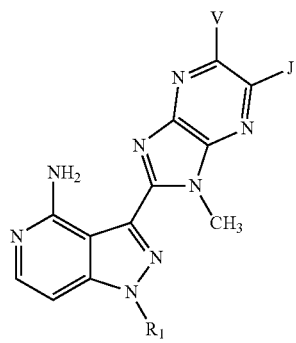
Formula 2-AK
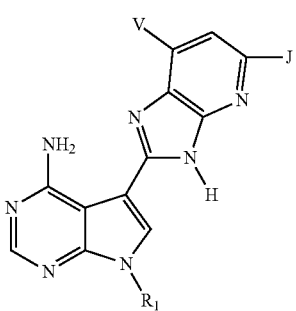
Formula 2-AL
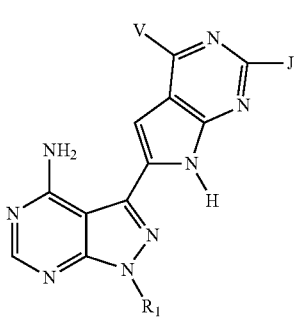
Formula 2-AM
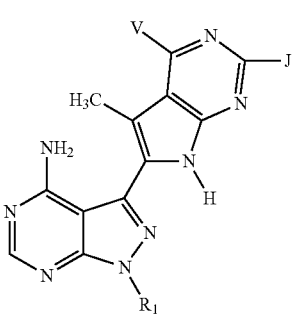
Formula 2-AN
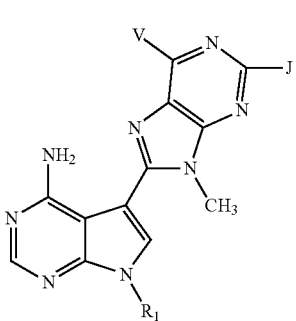

Formula 2-AO
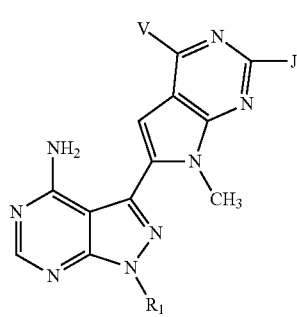
Formula 2-AP
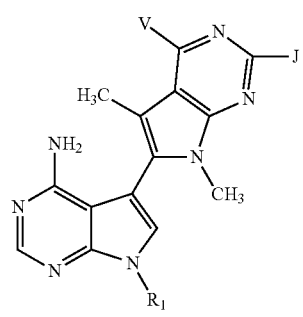
Formula 2-AQ
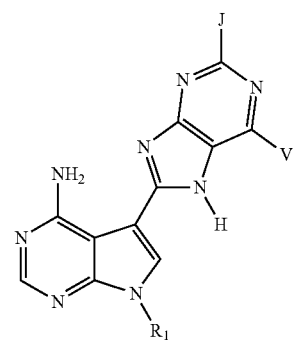
Formula 2-AR
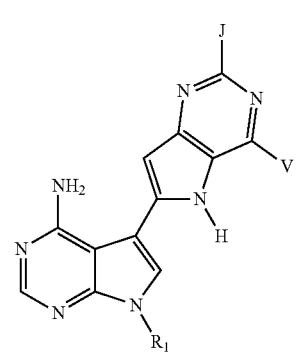
Formula 2-AS
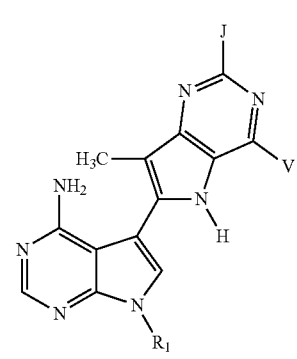
Formula 2-AT
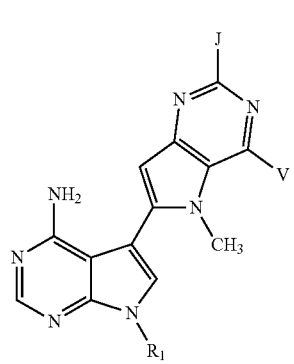
Formula 2-AU
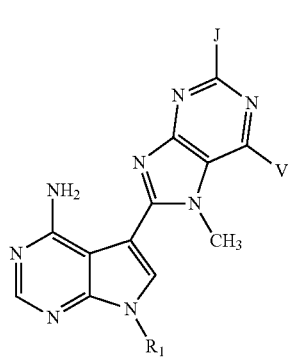
Formula 2-AV
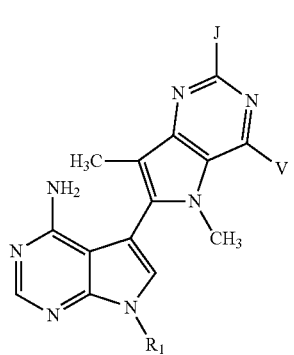
Formula 2-AW
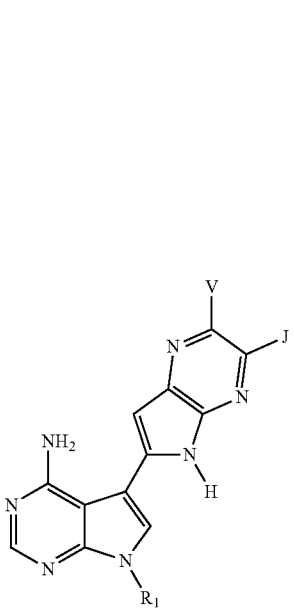

Formula 2-AX
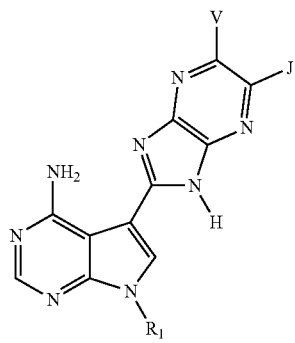
Formula 2-AY
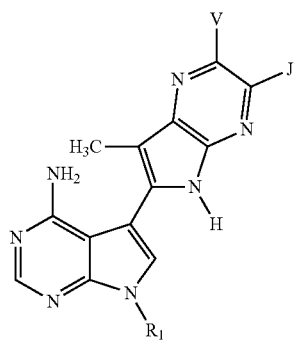
Formula 2-AZ
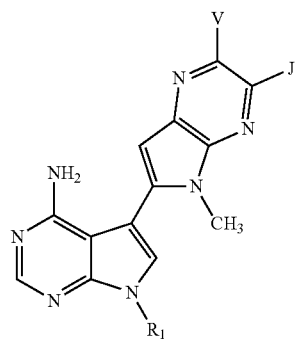
Formula 2-BA
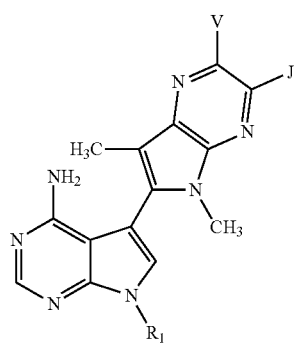
Formula 2-BB
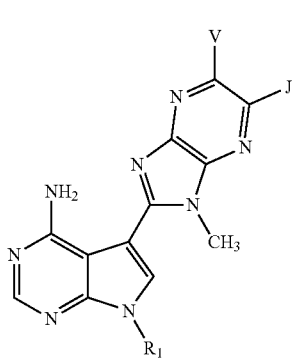
Formula 2-BC
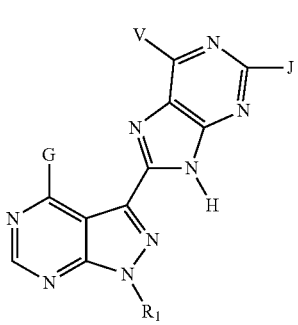
Formula 2-BD
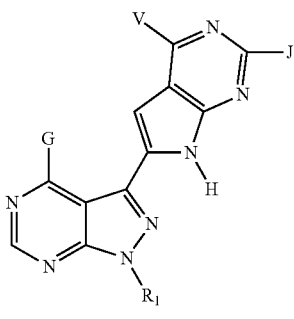
Formula 2-BE
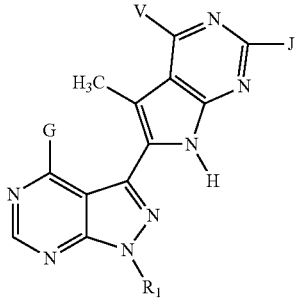
Formula 2-BF
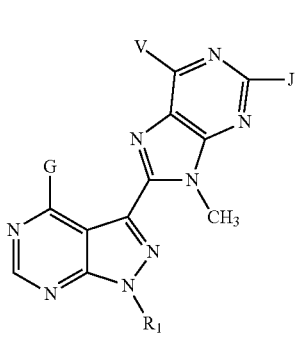

Formula 2-BG
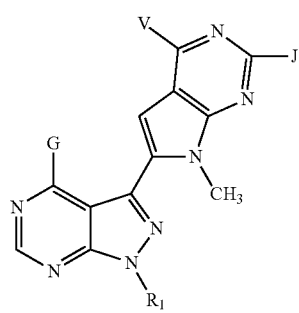
Formula 2-BH
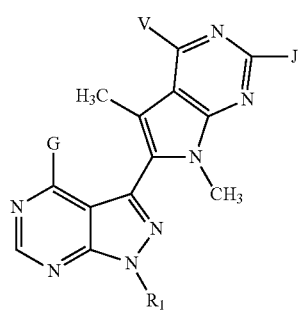
Formula 2-BI
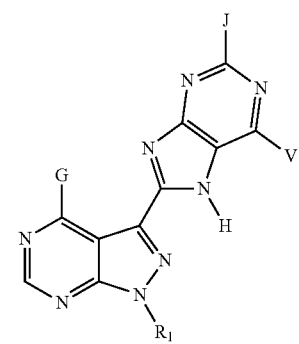
Formula 2-BJ
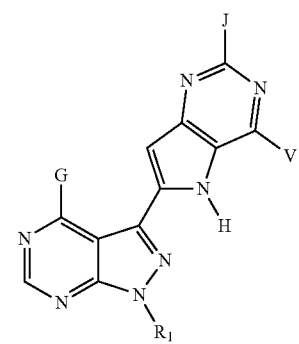
Formula 2-BI
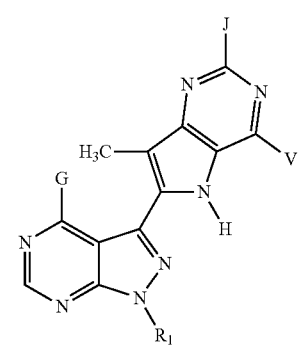
Formula 2-BJ
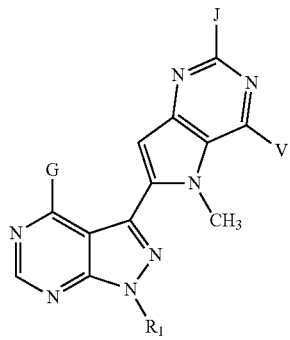
Formula 2-BK
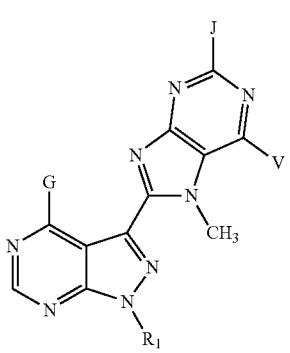
Formula 2-BL
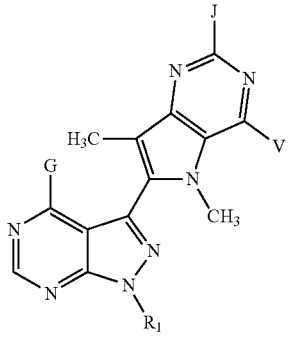
Formula 2-BM
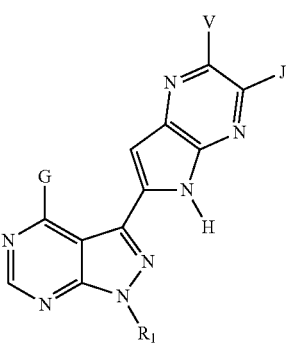

Formula 2-BN
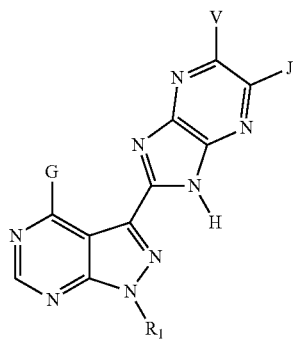
Formula 2-BO
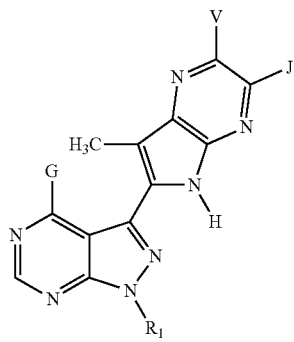
Formula 2-BP
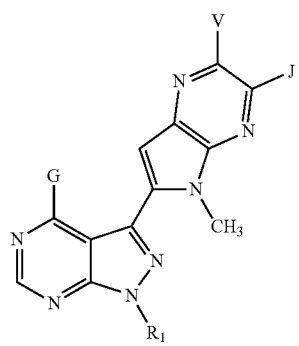
Formula 2-BQ
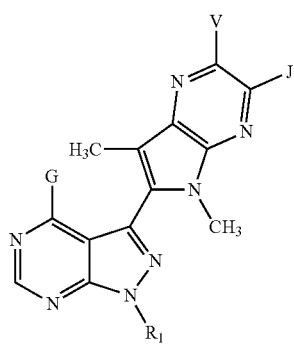
Formula 2-BR
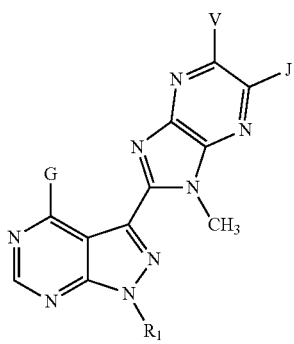
Formula 2-BS
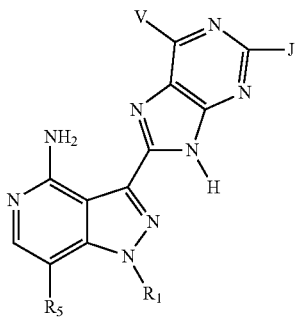
Formula 2-BT
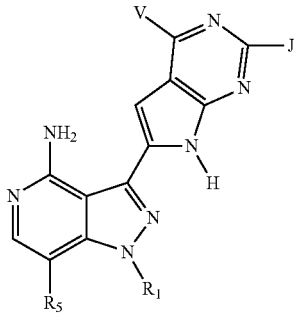
Formula 2-BU
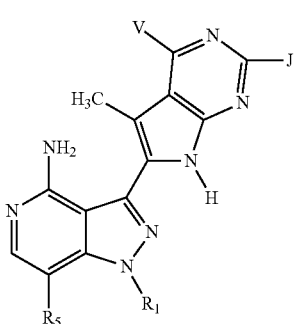
Formula 2-BV
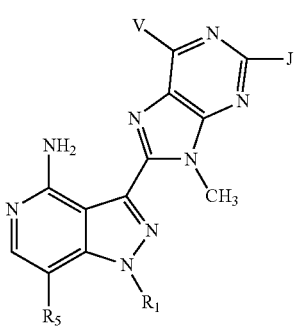

-continued
Formula 2-BW
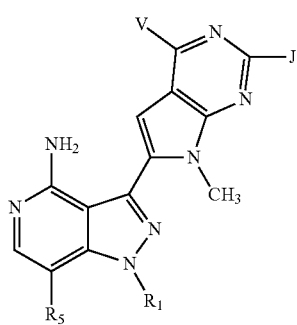
Formula 2-BX
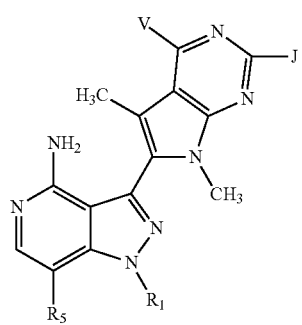
Formula 2-BY
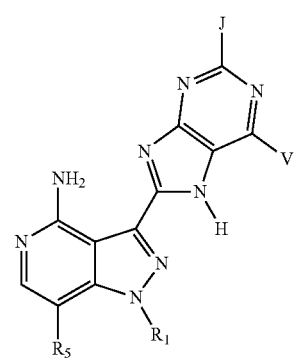
Formula 2-BZ
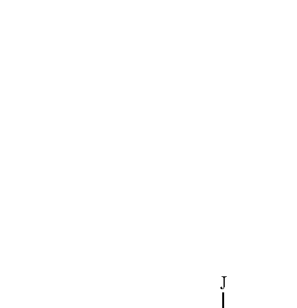
Formula 2-CA
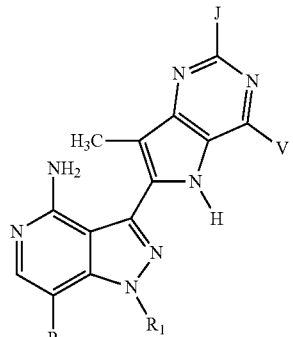
Formula 2-CB
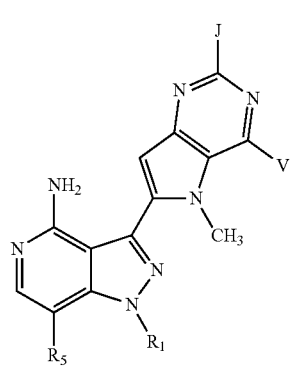
Formula 2-CC
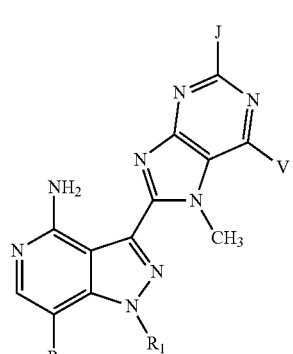
Formula 2-CD
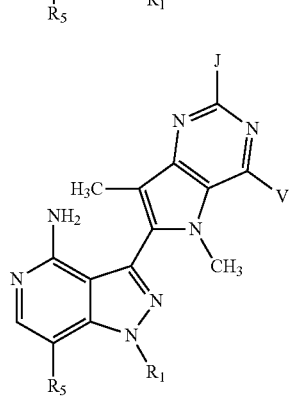

Formula 2-CE
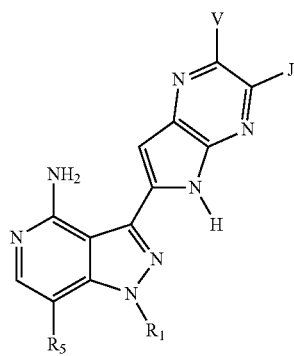
Formula 2-CF
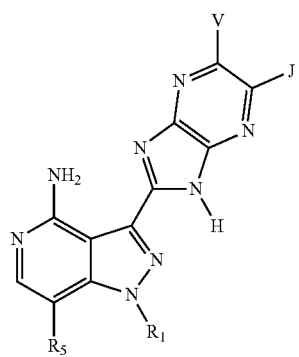
Formula 2-CG
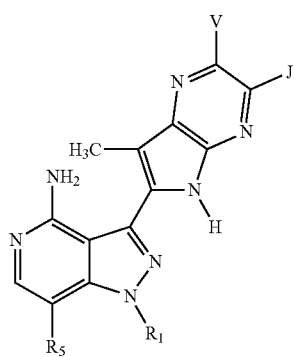
Formula 2-CH
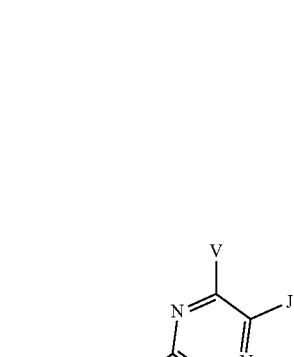
Formula 2-CI
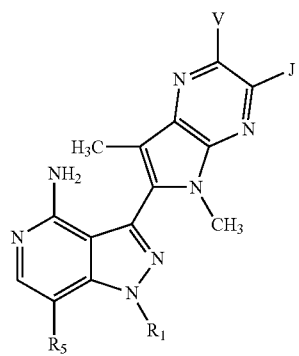
Formula 2-CJ
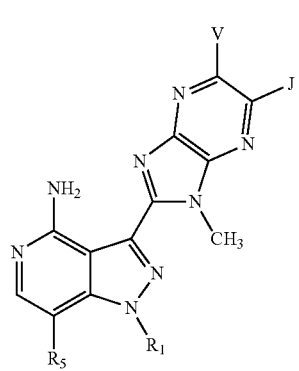
Formula 2-CK
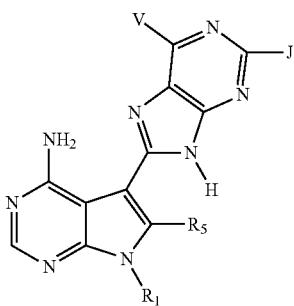
Formula 2-CL
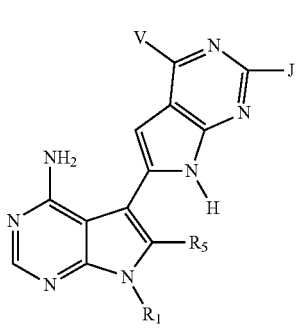
Formula 2-CM
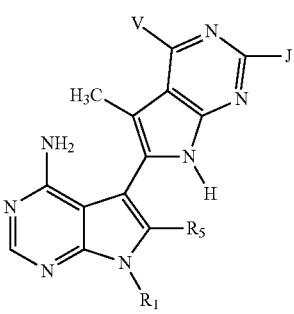

Formula 2-CN
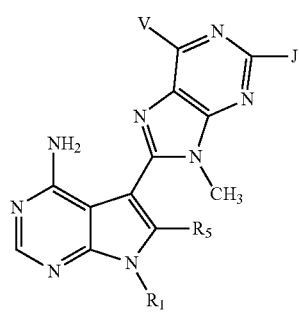
Formula 2-CO
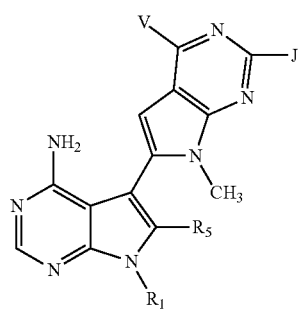
Formula 2-CP
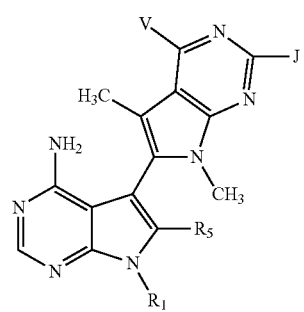
Formula 2-CQ
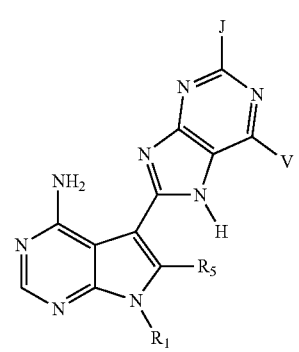
Formula 2-CR
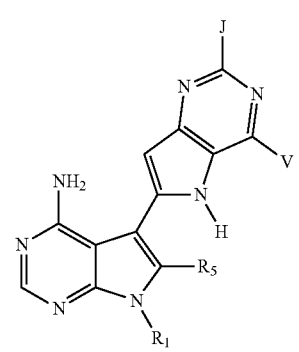
Formula 2-CS
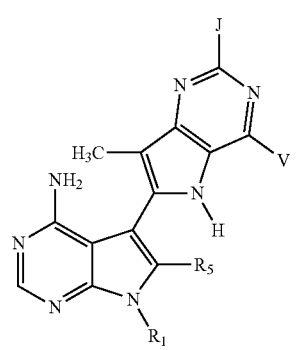
Formula 2-CT
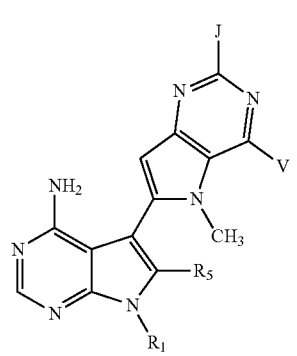
Formula 2-CU
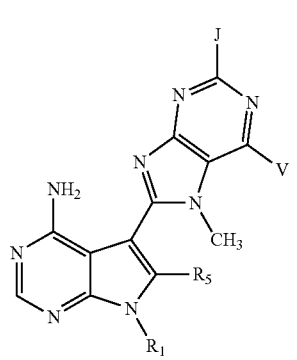
Formula 2-CV
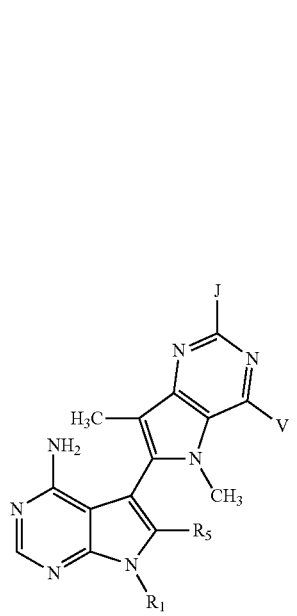

Formula 2-CW
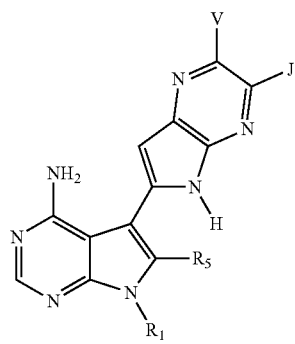
Formula 2-CX
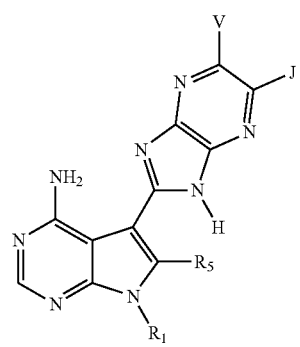
Formula 2-CY
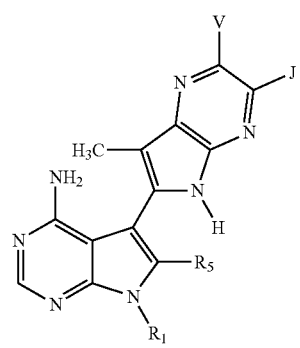
Formula 2-CZ
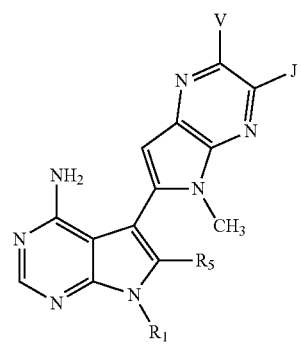
Formula 2-DA
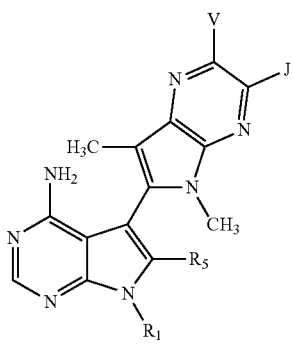
Formula 2-DB
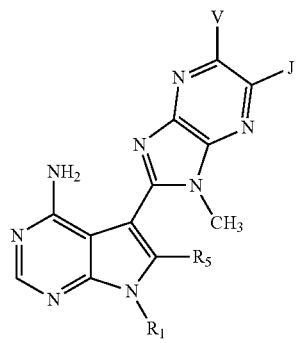
TABLE A
Compounds of the above Formulas 2-A to 2-DB with substituents of J, V, and W, as described below, are provided where $R_1$ is:
| Subclass # | $R_1$ |
|---|---|
| A-1 | 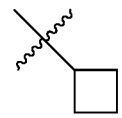 |
| A-2 | 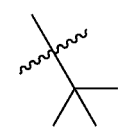 |
| A-3 | 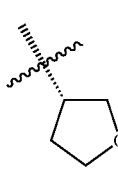 |
| A-4 |  |
| A-5 | 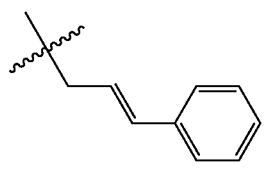 [SMILES: *C/C=C/c1ccccc1] |

TABLE A-continued

Compounds of the above Formulas 2-A to 2-DB with substituents of J, V, and W, as described below, are provided where $R_1$ is:

| Subclass # | $R_1$ |
| --- | --- |
| A-6 | 3-tetrahydrofuranyl |
| A-7 | (S)-1-methyl-2-aminoethyl |
| A-8 | (pyrrolidin-3-yl)methyl |
| A-9 | cycloheptyl |
| A-10 | 4-cyanobutyl |
| A-11 | (piperidin-3-yl)methyl |
| A-12 | (piperidin-4-yl)methyl |
| A-13 | 3-cyanopropyl |
| A-14 | (3S)-pyrrolidin-3-yl |
| A-15 | cyclopropylmethyl |
| A-16 | azetidin-3-yl |
| A-17 | (pyrrolidin-2-yl)methyl |
| A-18 | prop-2-ynyl |
| A-19 | (3-methylcyclopentyl)methyl |
| A-20 | (S)-2-methyl-3-hydroxypropyl |
| A-21 | 3-methylbutyl |
| A-22 | (3R)-pyrrolidin-3-yl |
| A-23 | (S)-3-hydroxy-2-methylpropyl (alt) |

TABLE A-continued
Compounds of the above Formulas 2-A to 2-DB with substituents of J, V, and W, as described below, are provided where $R_1$ is:
| Subclass # | $R_1$ |
|---|---|
| A-24 | 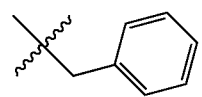 [SMILES: *Cc1ccccc1] |
| A-25 | 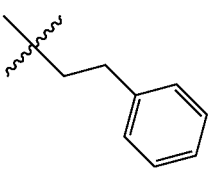 [SMILES: *CCc1ccccc1] |
| A-26 | 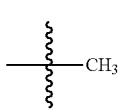 |
| A-27 | 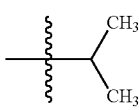 |
| A-28 | 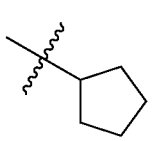 [SMILES: *C1CCCC1] |
| A-29 | 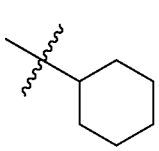 [SMILES: *C1CCCCC1] |
| A-30 | 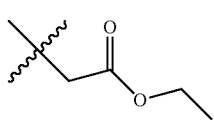 [SMILES: *CC(=O)OCC] |
| A-31 | 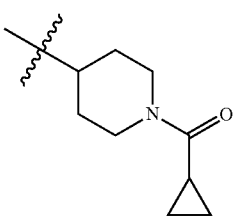 [SMILES: *C1CCN(C(=O)C2CC2)CC1] |
| A-32 | 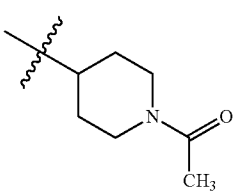 [SMILES: *C1CCN(C(C)=O)CC1] |
| A-33 | 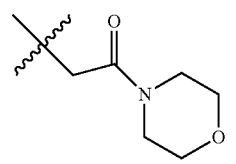 [SMILES: *CC(=O)N1CCOCC1] |
TABLE A-continued
Compounds of the above Formulas 2-A to 2-DB with substituents of J, V, and W, as described below, are provided where $R_1$ is:
| Subclass # | $R_1$ |
|---|---|
| A-34 | 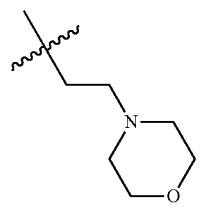 [SMILES: *CCN1CCOCC1] |
| A-35 | 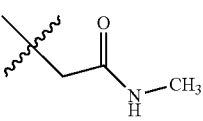 |
| A-36 | 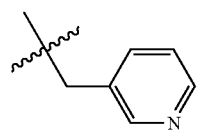 |
| A-37 | 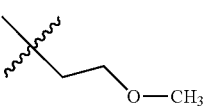 |
| A-38 | 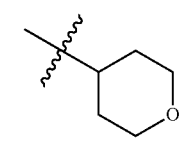 [SMILES: *C1CCOCC1] |
| A-39 | 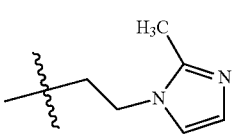 [SMILES: *CCn1ccnc1C] |
| A-40 | 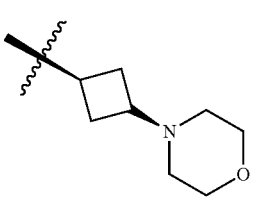 |
| A-41 | 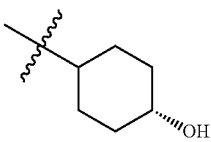 |
| A-42 | 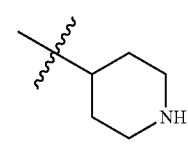 |

TABLE A-continued

Compounds of the above Formulas 2-A to 2-DB with substituents of J, V, and W, as described below, are provided where $R_1$ is:

| Subclass # | $R_1$ |
|---|---|
| A-43 | 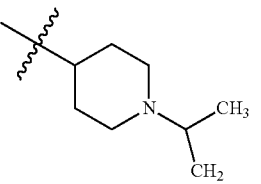 |
| A-44 | 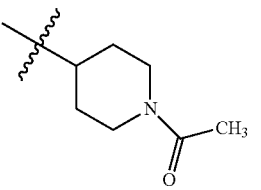 [SMILES: *C1CCN(C(C)=O)CC1] |
| A-45 | 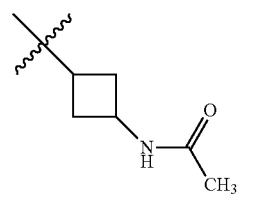 [SMILES: *C1CC(NC(C)=O)C1] |
| A-46 | 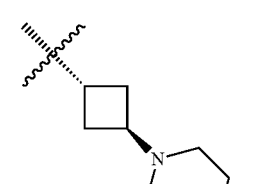 |
| A-47 | 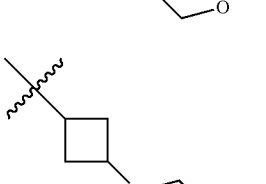 |
| A-48 | 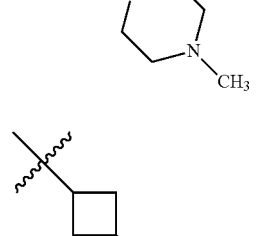 |
| A-49 | 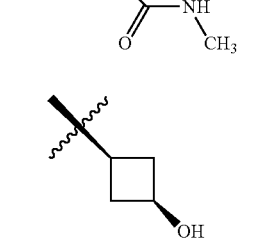 |
| A-50 | 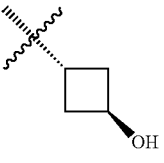 |
| A-51 | 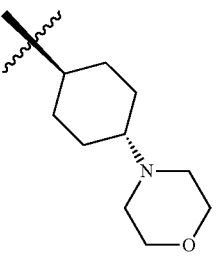 |
| A-52 | 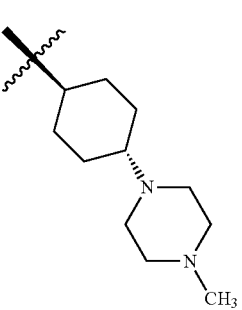 |

TABLE B

Compounds of the above Formulae 2-BC to 2-BR with substituents of J, V, and W, as described below, are provided where G is:

| Subclass # | |
|---|---|
| B-1 | $CH_3$ |
| B-2 | $CH_2Cl$ |
| B-3 | $CHCl_2$ |
| B-4 | $CCl_3$ |
| B-5 | $CH_2Br$ |
| B-6 | $CHBr_2$ |
| B-7 | $CBr_3$ |
| B-8 | $CH_2F$ |
| B-9 | $CHF_2$ |
| B-10 | $CF_3$ |
| B-11 | H |
| B-12 | Cl |
| B-13 | Br |
| B-14 | F |
| B-15 | $NHCH_3$ |
| B-16 | $N(CH_3)_2$ |
| B-17 | 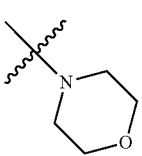 [SMILES: *N1CCOCC1] |

TABLE B-continued

Compounds of the above Formulae 2-BC to 2-BR with substituents of J, V, and W, as described below, are provided where G is:

Subclass #

B-18
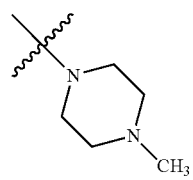 [SMILES: *N1CCN(C)CC1]

TABLE C

Compounds of the above Formulae 2-BS to 1-DB with substituents of J, V, and W, as described below, are provided where $R_5$ is:

Subclass #

C-1

C-2

C-3
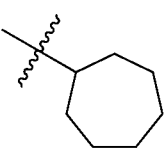

C-4
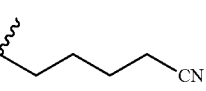

C-5

C-6
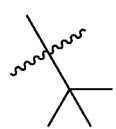 [SMILES: *C(C)(C)C]

C-7

TABLE C-continued

Compounds of the above Formulae 2-BS to 1-DB with substituents of J, V, and W, as described below, are provided where $R_5$ is:

Subclass #

C-8
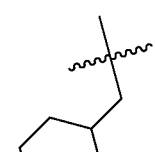

C-9
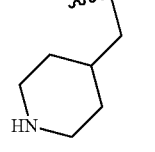

C-10
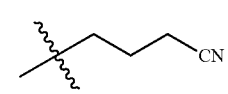 [SMILES: *CCCC#N]

C-11
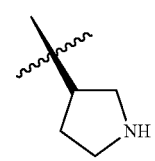

C-12
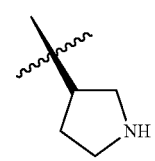

C-13
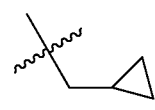 [SMILES: *CC1CC1]

C-14
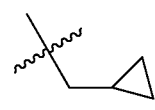 [SMILES: *CC1CC1]

C-15
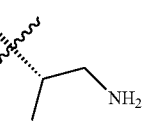

A-16
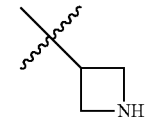 [SMILES: *C1CNC1]

TABLE C-continued
Compounds of the above Formulae 2-BS to 1-DB with substituents of J, V, and W, as described below, are provided where $R_5$ is:
Subclass #
A-17 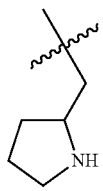 [SMILES: *CC1CCCN1]
A-18 
C-19 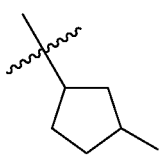 [SMILES: *C1CCC(C)C1]
C-20 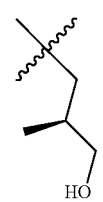 [SMILES: *C[C@H](C)CO]
C-21 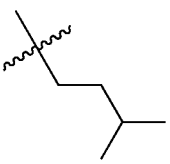
C-22 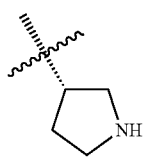
C-23 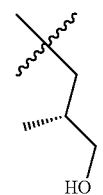
C-24 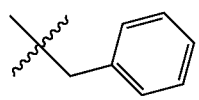 [SMILES: *Cc1ccccc1]
C-25 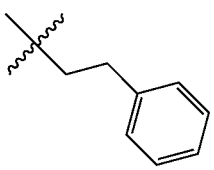 [SMILES: *CCc1ccccc1]
C 26 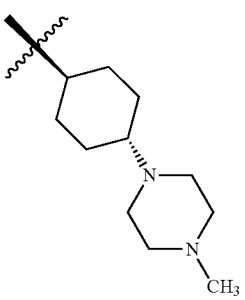
C-27 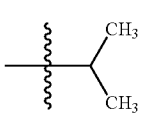
C-28 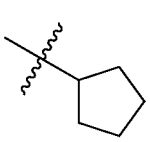 [SMILES: *C1CCCC1]
C-29 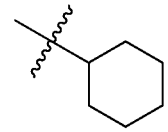 [SMILES: *C1CCCCC1]
C-30 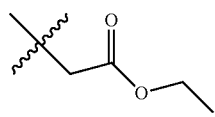 [SMILES: *CC(=O)OCC]
C-31 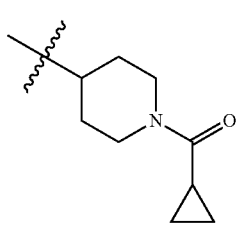 [SMILES: *C1CCN(C(=O)C2CC2)CC1]
C-32 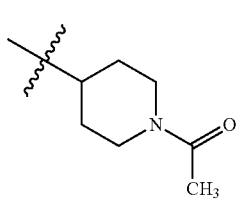
C-33 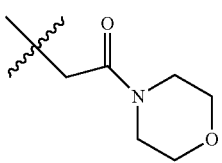 [SMILES: *CC(=O)N1CCOCC1]

TABLE C-continued
Compounds of the above Formulae 2-BS to 1-DB with substituents of J, V, and W, as described below, are provided where $R_5$ is:
Subclass #
C-34 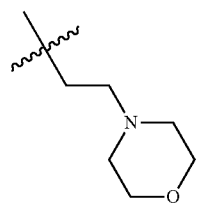 [SMILES: *CCN1CCOCC1]
C-35 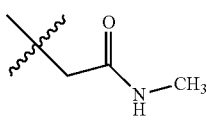 [SMILES: *CC(=O)NC]
C-36 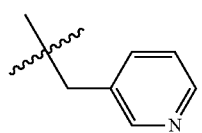
C-37 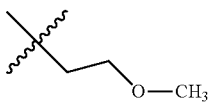
C-38 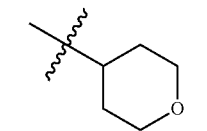
C-39 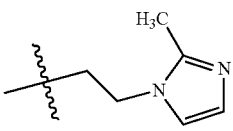 [SMILES: *CCn1ccnc1C]
C-40 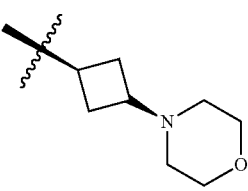
C-41 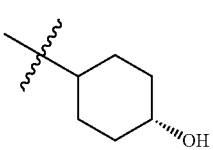
C-42 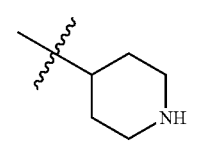 [SMILES: *C1CCNCC1]
TABLE C-continued
Compounds of the above Formulae 2-BS to 1-DB with substituents of J, V, and W, as described below, are provided where $R_5$ is:
Subclass #
C-43 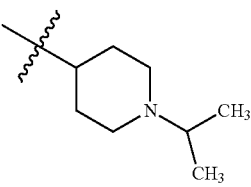 [SMILES: *C1CCN(C(C)C)CC1]
C-44 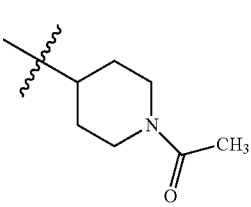
C-45 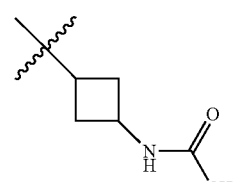
C-46 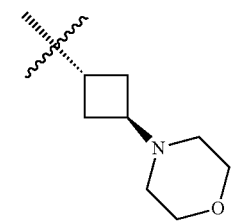
C-47 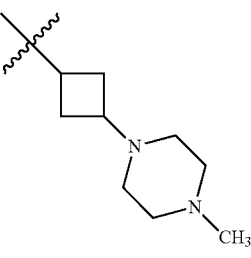 [SMILES: *C1CC(N2CCN(C)CC2)C1]
C-48 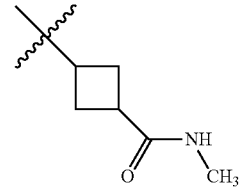 [SMILES: *C1CC(C(=O)NC)C1]
C-49 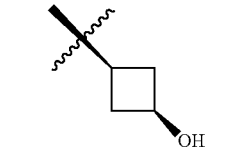

TABLE C-continued

Compounds of the above Formulae 2-BS to 1-DB with substituents of J, V, and W, as described below, are provided where R$_5$ is:

| Subclass # | |
|---|---|
| C-50 | 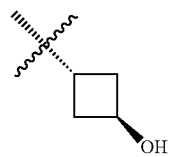 |
| C-51 | 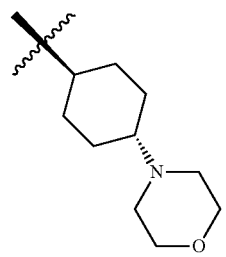 |
| C-52 | 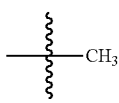 |
| C-53 | —CN |
| C-54 | —Cl |
| C-55 | —Br |
| C-56 | —F |
| C-57 | —OH |
| C-58 | —OCF$_3$ |
| C-59 | —CF$_3$ |
| C-60 | —NH$_2$ |
| C-61 | —NMe$_2$ |
| C-62 | —NO$_2$ |
| C-63 | —C(O)CH3 |
| C-64 | —SO$_2$Me |
| C-65 | —SO$_2$NH$_2$ |

Particular embodiments of J, V, and W of illustrative compounds of Formulae 2-A to 2-DB are described as follows, where Am=C(O)NH$_2$, Cy=cyclopropyl,

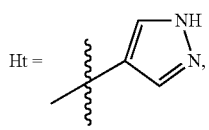

and So=-SO$_2$CH$_3$. In some embodiments, when V is H, J is H, Cl, Br, F, OH, or OMe. In other embodiments, when V is Cl, J is H, Cl, Br, F, OH, or OMe. In other embodiments, when V is Br, J is H, Cl, Br, F, OH, or OMe. In other embodiments, when V is F, J is H, Cl, Br, F, OH, or OMe. In other embodiments, when V is CH$_3$, J is H, Cl, Br, F, OH, or OMe. In other embodiments, when V is OH, J is H, Cl, Br, F, OH, or OMe. In other embodiments, when V is OMe, J is H, Cl, Br, F, OH, or OMe. In other embodiments, when V is CF$_3$, J is H, Cl, Br, F, OH, or OMe. In other embodiments, when V is So, J is H, Cl, Br, F, OH, or OMe. In other embodiments, when V is Cy, J is H, Cl, Br, F, OH, or OMe. In other embodiments, when V is CN, J is H, Cl, Br, F, OH, or OMe. In other embodiments, when V is Me, J is H, Cl, Br, F, OH, or OMe. In other embodiments, when V is Ht, J is H, Cl, Br, F, OH, or OMe.

The compounds disclosed herein may be prepared by the routes described below. Materials used herein are either commercially available or prepared by synthetic methods generally known in the art. These schemes are not limited to the compounds listed or by any particular substituents employed for illustrative purposes, but are useful generally for the compounds of the invention. Numbering does not necessarily correspond to that of claims or other tables.

I. General Route of Synthesis

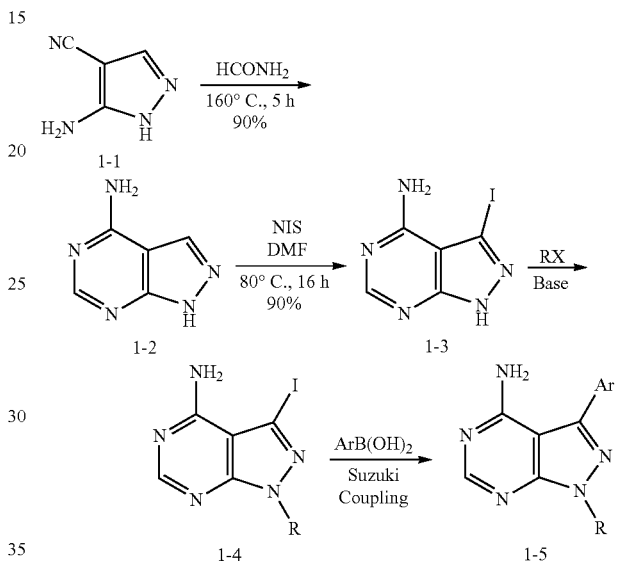

Scheme 1. Synthesis of 2-(4-amino-1H-pyrazolo[3,4-d]pyrimidin-3-yl) iodide (Cpd. 1-3), and general synthesis of compounds of the invention.

Scheme 1 depicts the synthesis of 2-(4-amino-1H-pyrazolo[3,4-d]pyrimidin-3-yl) iodide (Cpd. 1-3), an intermediate in the synthesis of the compounds of the invention and its further reactions to obtain final inhibitor analogs. Cyano substituted aminopyrazole 1-1 is heated with formamide at 160° C. for 5 hours to yield 2-(4-amino-1H-pyrazolo[3,4-d]pyrimidine (compound 1-2) in 90% yield. This intermediate is reacted with N-iodosuccinimide in dimethylformamide at 80° C. for 16 hours, to produce 2-(4-amino-1H-pyrazolo[3,4-d]pyrimidin-3-yl) iodide (Cpd. 1-3) in 90% yield.

The pyrazolopyrimidinyl iodide, Cpd. 1-3, is reacted with a species RX in the presence of a base, where X is a good leaving group such as for example, a halide, including bromo, chloro or iodide, or a tosylate, or another moiety which will act as a leaving group under the reaction conditions. The "R" portion of the moiety is alkyl, heterocycloalkyl, alkylaryl, alkylheteroaryl, alkenyl, alkynyl, or cycloalkyl. The base is, for example, potassium carbonate, cesium carbonate, sodium hydride, potassium tert-butoxide, and the like. The product, compound 1-4, incorporates a "R" moiety coupled to nitrogen, as shown. This intermediate is subjected to a Suzuki coupling, i.e. palladium catalyzed coupling between and iodide bearing compounds and a boronic acid, depicted as ArB(OH)$_2$ to produce a compound of the invention, Cpd. 1-5, after deprotection. Many boronic acid analogs of formula ArB(OH)$_2$ are commercially available, or may be synthesized as is known in the art, and may include heteroaromatic as well as carbocyclic aromatic moieties.

II. Illustrative Syntheses of Compounds with 1-Isopropyl Substitution

Example 1

Synthesis of 2-(4-amino-1-isopropyl-1H-pyrazolo[3,4-d]pyrimidin-3-yl)-1H-indol-5-ol (Compound 2-4)

Compound 2-4 is synthesized as shown in Scheme 2. Compound 1-3 is reacted with isopropyl bromide in dimethylformamide with potassium carbonate at 80° C., to provide the 1-isopropyl pyrazolopyrimidine 2-1. This intermediate with the protected indolyl boronic acid species 2-2, using tetrakistriphenylphosphine palladium catalysis in DME-water solvent at 80° C. for 4-5 hours, to produce the Suzuki coupling product, compound 2-3. Removal of the protecting groups with acid in dioxane yields the product, 2-(4-amino-1H-pyrazolo[3,4-d]pyrimidin-3-yl iodide (Cpd. 2-4).

Scheme 2. Synthesis of 2-(4-amino-1-isopropyl)-1H-pyrazolo[3,4-d]pyrimidin-3-yl)-1H-indol-5-ol (Compound 2-4).

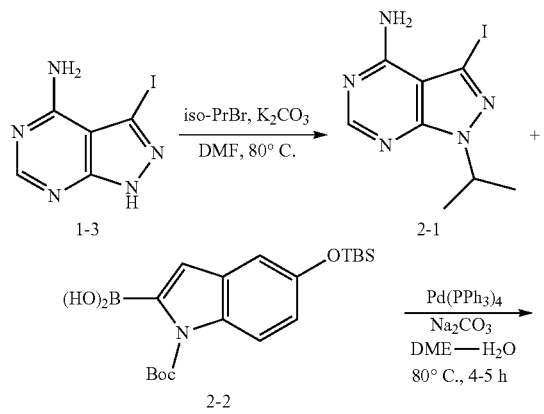

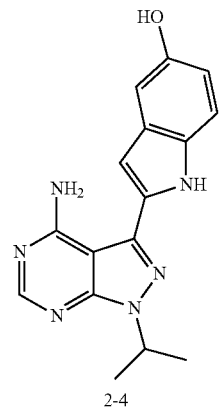

An alternative route to perform the Suzuki coupling is shown in Scheme 2-B. In this approach, methyl ether protection is used for the 5-hydroxy on the indolyl boronic acid. Palladium acetate and triphenylphosphine catalyze the coupling in the presence of sodium carbonate base to provide intermediate 2-6. Along with the desired product, some amount of partially de-protected product is also formed. The crude mixture is taken into the next step for complete Boc deprotection reaction with concentrated aqueous HCl in ethanol solution, and compound 2-7 is isolated as the HCl salt. The reaction is brought to approximately pH 8 with aqueous sodium carbonate to obtain the free base. Deprotection with borontribromide affords the final product, 2-(4-amino-1-isopropyl-1H-pyrazolo[3,4-d]pyrimidin-3-yl)-1H-indol-5-ol (Compound 2-4). This sequence can be generalized for other compounds of the invention.

Scheme 2-B. An alternative coupling strategy to yield 2-(4-amino-1-isopropyl-1H-pyrazolo[3,4-d]pyrimidin-3-yl)-1H-indol-5-ol (Compound 2-4).

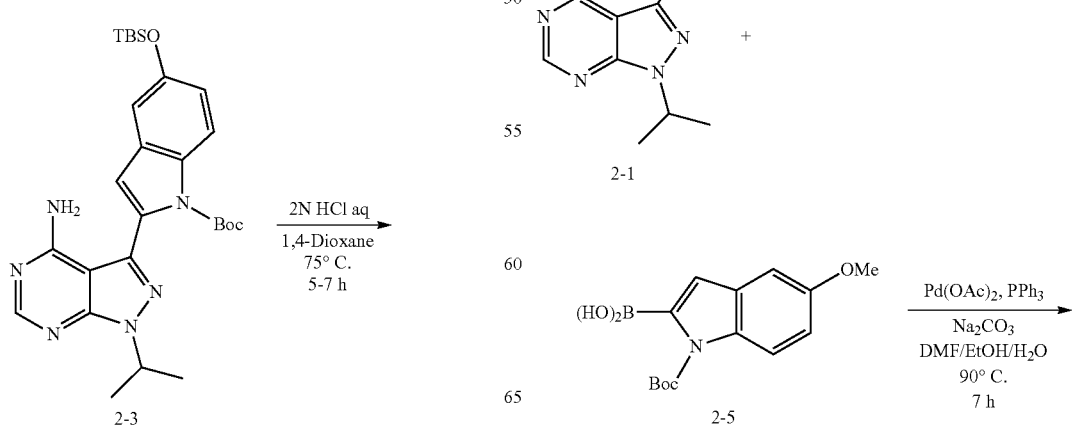

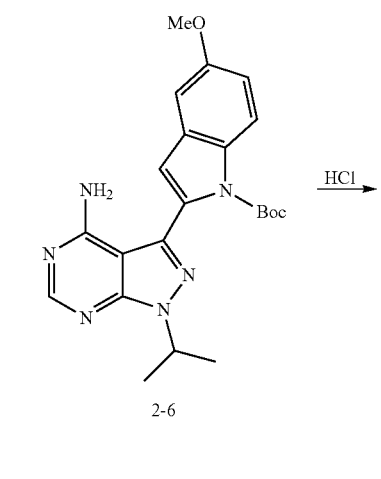

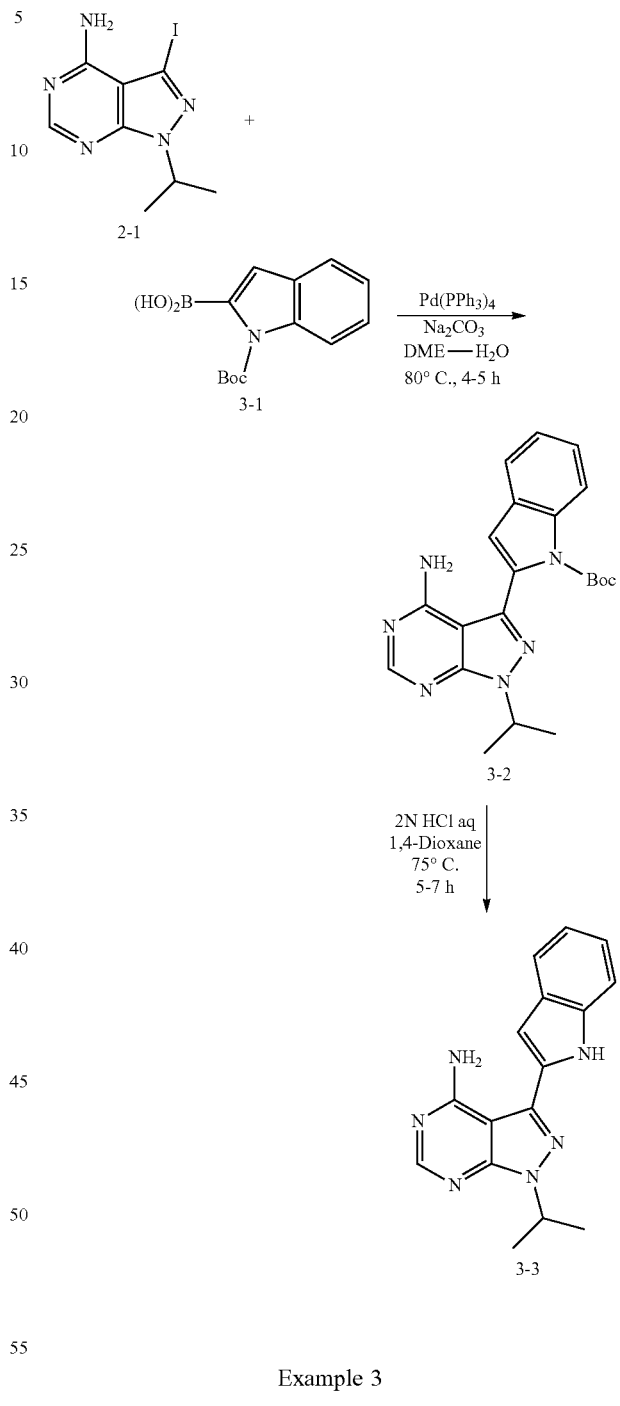

Scheme 3. Synthesis of 2-(4-amino-1-isopropyl-1H-pyrazolo[3,4-d]pyrimidin-3-yl)-1H-indole (Compound 3-3).

Example 2

2-(4-amino-1-isopropyl-1H-pyrazolo[3,4-d]pyrimidin-3-yl)-1H-indole (Compound 3-3) Synthesis of 2-(4-amino-1-isopropyl-1H-pyrazolo[3,4-d]pyrimidin-3-yl)-1H-indole (Compound 3-3) is accomplished via the same reactions as shown in Scheme 2, except that boronic acid 3-1 is used, as shown in Scheme 3.

Example 3

The synthesis of 2-(4-amino-1-isopropyl-1H-pyrazolo[3,4-d]pyrimidin-3-yl)-1H-indol-7-ol (Compound 3-4) is accomplished via the same reactions as in Schemes 1 and 2-B, using a 7-methoxy indolyl boronic acid instead of the 5-methoxy indolyl species illustrated in Scheme 2-B. Alternatively, Compound 3-4 is synthesized via the reactions as in Schemes 1 and 2, using a 7-tert-butyldimethylsilyloxy (TBS) indolyl boronic acid instead of the 5-TBSO-indolyl species illustrated in Scheme 2.

Compound 3-4

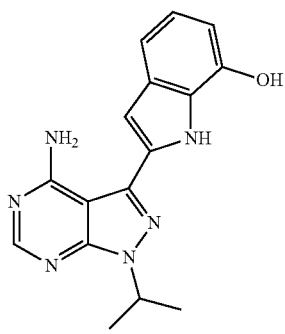

Example 4

The synthesis of 2-(4-amino-1-isopropyl-1H-pyrazolo[3,4-d]pyrimidin-3-yl)-1H-indol-6-ol (Compound 3-5) is accomplished via the same reactions as in Schemes 1 and 2-B, using a 6-methoxy indolyl boronic acid instead of the 5-methoxy indolyl species illustrated in Scheme 2-B. Alternatively, Compound 3-5 is synthesized via the reactions as in Schemes 1 and 2, using a 6-tert-butyldimethylsilyloxy (TBS) indolyl boronic acid instead of the 5-TBSO-indolyl species illustrated in Scheme 2.

Compound 3-5

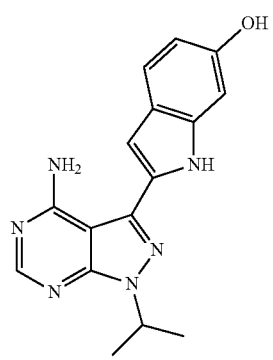

III. Illustrative Syntheses of Various Substituted Indolyl Boronic Acids

Example 5

Synthesis of 1-(tert-butoxycarbonyl)-7 chloro-5 methoxy-1H-indol-2-yl boronic acid is shown in Scheme 4. Meta-chlorophenol is nitrated with fuming nitric acid in acetic acid to yield 4-nitro-3-chlorophenol, compound 4-2. The phenol is methylated with dimethylsulfate and potassium carbonate in ethanol, producing compound 4-3, which is treated with vinyl Grignard reagent and cyclized to form the indole, compound 4-4. Compound 4-4 is protected with Boc and then treated with lithium diisopropylamide and triisopropylborate to produce the protected substituted boronic acid 4-6.

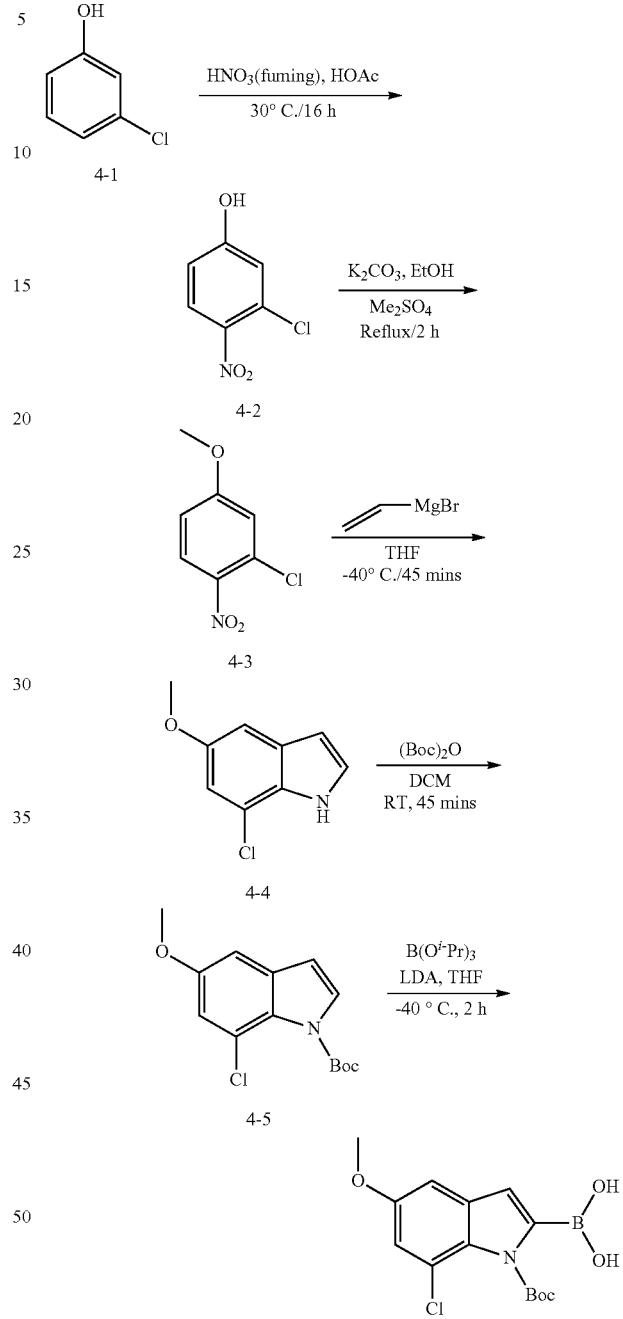

Scheme 4. The synthesis of 1-(tert-butoxycarbonyl)-7-chloro-5 methoxy-1H-indol-2-yl boronic acid (Cpd. 4-6 is shown.

Example 6

Synthesis of 1-(tert-butoxycarbonyl)-7-chloro-5-methoxy-1H-indol-2-yl boronic acid (Cpd. 5-4) is shown in Scheme 5. Compound 4-2 is protected as the TBS ether, treated with vinyl Grignard reagent, and cyclized to yield compound 5-2. Boc protection is carried out, and introduction of the boronic acid is performed as described above, yielding compound 5-4.

Scheme 5. Synthesis of 1-(tert-butoxycarbonyl)-7-chloro-5-methoxy-1H-indol-2-yl boronic acid (Cpd. 5-4).

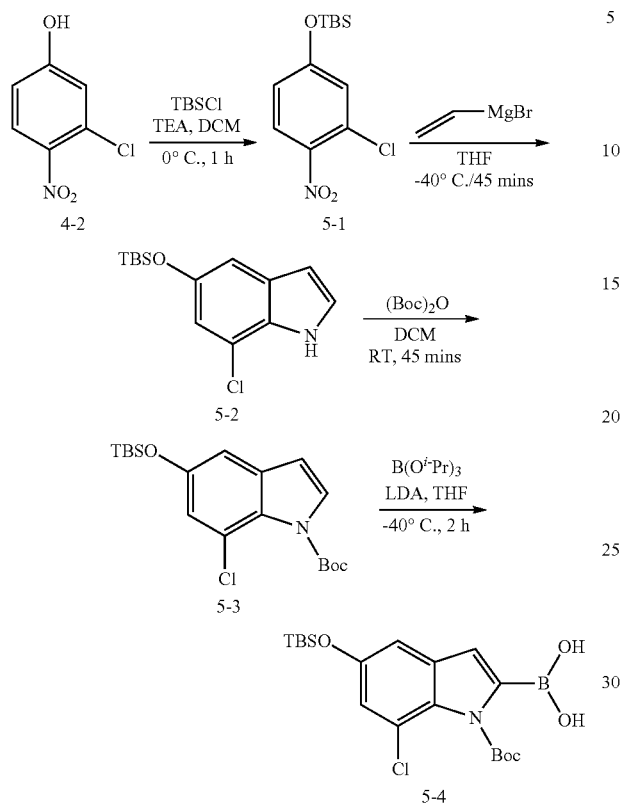

Example 7

Synthesis of 1-(tert-butoxycarbonyl)-6-chloro-5-methoxy-1H-indol-2yl boronic acid (Cpd. 6-7) is shown in Scheme 6. 3-Methyl-5-chlorophenol is nitrated using sodium nitrate/nitric acid in an acetic acid/sulfuric acid mixture. The resulting 4-nitro phenol (Cpd. 6-2) is converted to the methyl protected species, compound 6-3, using dimethylsulfate in aqueous dioxane. Compound 6-3 is elaborated to form the vinylogous pyrrolidinyl intermediate, compound 6-4, via condensation with dimethyl acetal and pyrrolidine. Reduction of the nitro substituent with hydrazine and Raney nickel results in cyclization to indolyl analog 6-5. Boc protection and introduction of the boronic acid species as described above affords boronic acid 6-7.

Scheme 6. Synthesis of 1-(tert-butoxycarbonyl)-6-chloro-5-methoxy-1H-indol-2yl boronic acid (Cpd. 6-7).

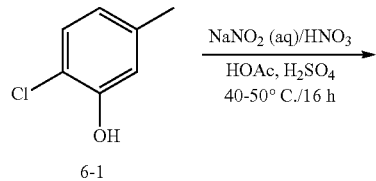

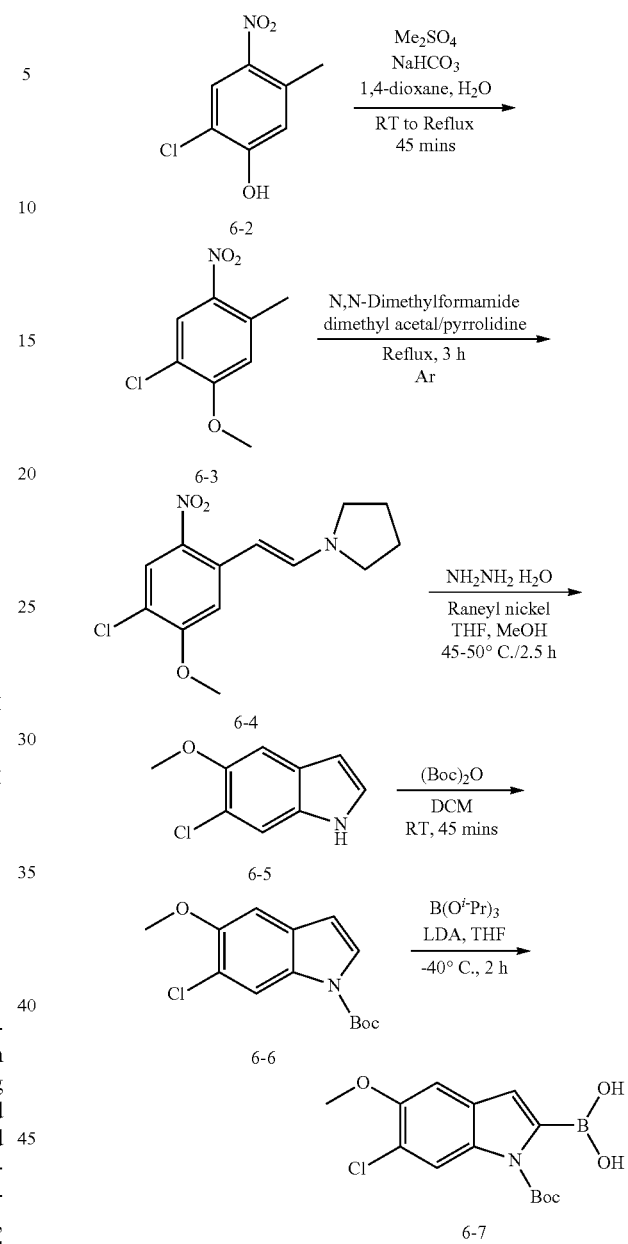

Example 8

The synthesis of 1-(tert-butoxycarbonyl)-5-(tert-butyldimethylsiloxy)-4-chloro-1H-indol-2-yl boronic acid (Compound 7-7) is shown in Scheme 7. 4-Nitro-2-chlorophenol (cpd. 4-1) is protected as the benzyl ether, and converted to the mixture of compounds 7-2 and 7-3. Treatment with palladium on carbon under a hydrogen atmosphere reduces the nitro functionality, cyclizes the indole heterocyclic ring and removes the O-benzyl protection, to obtain compound 7-4. The hydroxyl is reprotected as the tert-butyldimethylsilyl ether 7-5, the indole nitrogen is protected with Boc (Cpd. 7-6), and subsequently treated with treated with lithium diisopropylamide and triisopropylborate to produce the protected substituted boronic acid 7-7.

173

Scheme 7. Synthesis of 1-(tert-butoxycarbonyl)-5-(tert-butyldimethylsiloxy)-4-chloro-1H-indol-2-yl boronic acid (Cpd. 7-7).

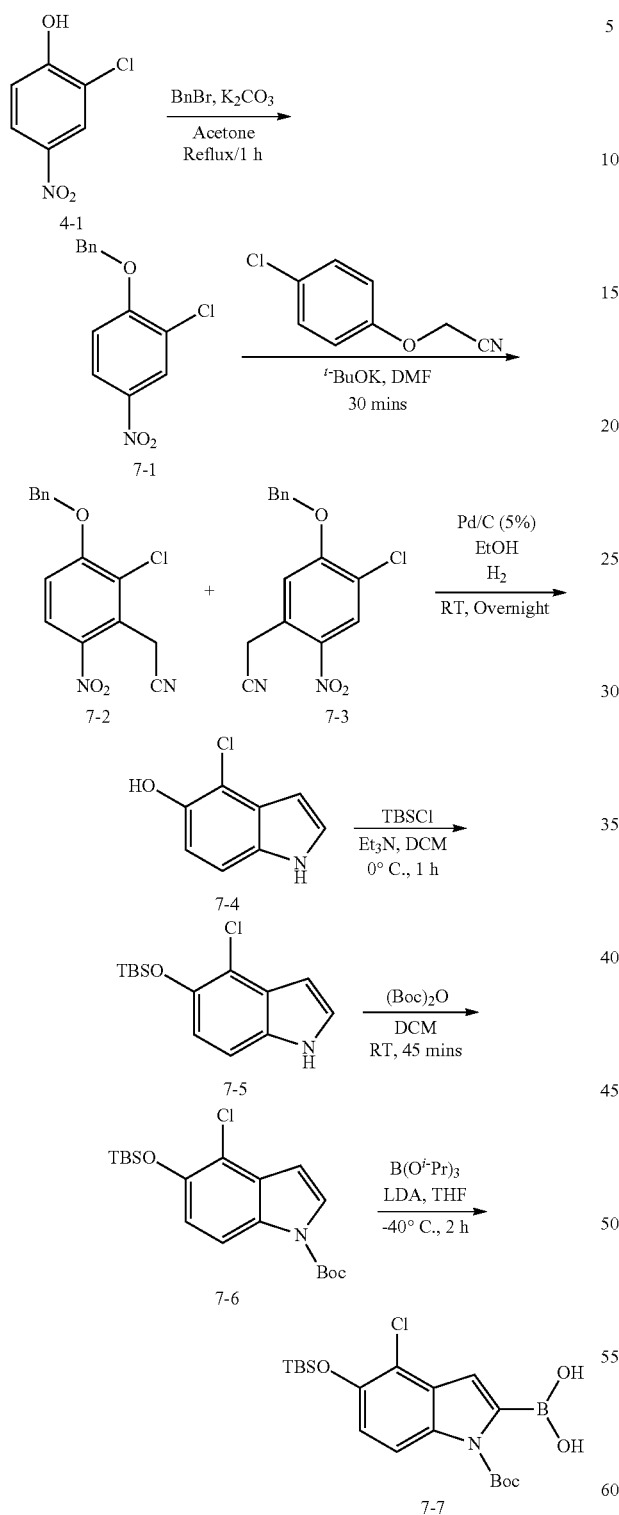

Example 9

Synthesis of 1-(tert-butoxycarbonyl)-4-chloro-7-methoxy-1H-indol-2-yl boronic acid (Compound 8-5) is shown in Scheme 8. 4-Chloro-2 nitrophenol is methylated with dimethylsulfate in ethanol and in the presence of potassium carbonate. Vinyl Grignard reagent adds to the resulting methoxy compound, compound 8-2, which then cyclizes to obtain the indole of compound 8-3. Boc protection of the basic nitrogen and treatment with triisopropyl boronate produces boronic acid 8-5.

Scheme 8. Synthesis of 1-(tert-butoxycarbonyl)-4-chloro-7-methoxy-1H-indol-2-yl boronic acid (Compound 8-5).

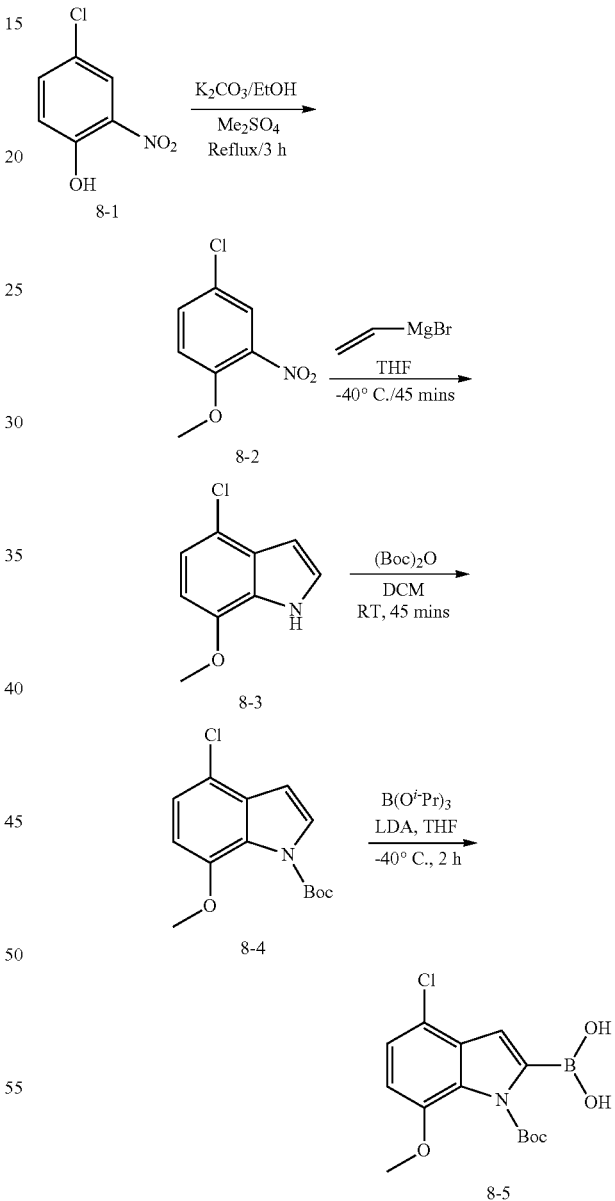

The boronic acids illustrated herein, compounds, compounds 4-6, 5-4, 6-7, 7-7 and 8-5 are illustrative, but not limiting examples of the intermediates of use in the syntheses of compounds of the invention. Many other variants are made, using variants of the syntheses shown above.

IV. Illustrative Syntheses of Other Compounds of the Invention

The following syntheses are illustrated with a 5-hydroxy indolyl moiety, but the invention encompasses all manner of substitutions as illustrated by the boronic acid syntheses above.

Example 10

The synthesis of 2-(4-amino-1-(4-N-acetyl-piperidin-1-yl)-1H-pyrazolo[3,4-d]pyrimidin-3-yl)-1H-indol-4-ol (Compound 9-6) is accomplished as illustrated in Scheme 9. Acetic anhydride is used to protect the nitrogen of 4-hydroxy piperidine to obtain compound 9-2. Tosyl chloride, with triethylamine and dimethylaminopyridine (DMAP) in methylene chloride is used to produce the tosylate 9-3. The iodopyrazolopyrimidine intermediate (compound 1-3) is reacted with tosylate 9-3 in dimethylformamide in the presence of cesium carbonate at 80° C. to couple the piperidinyl moiety to the pyrazolopyrimidine molecule, yielding intermediate 9-4. Compound 9-4 is transformed via a Suzuki coupling with boronic acid 2-2 using dichloro[1,1'-bis(diphenylphosphino)ferrocene]palladium II (PdCl₂(dppf)) in aqueous DME, to obtain compound 9-5, which is deprotected under acidic conditions to yield compound 9-6.

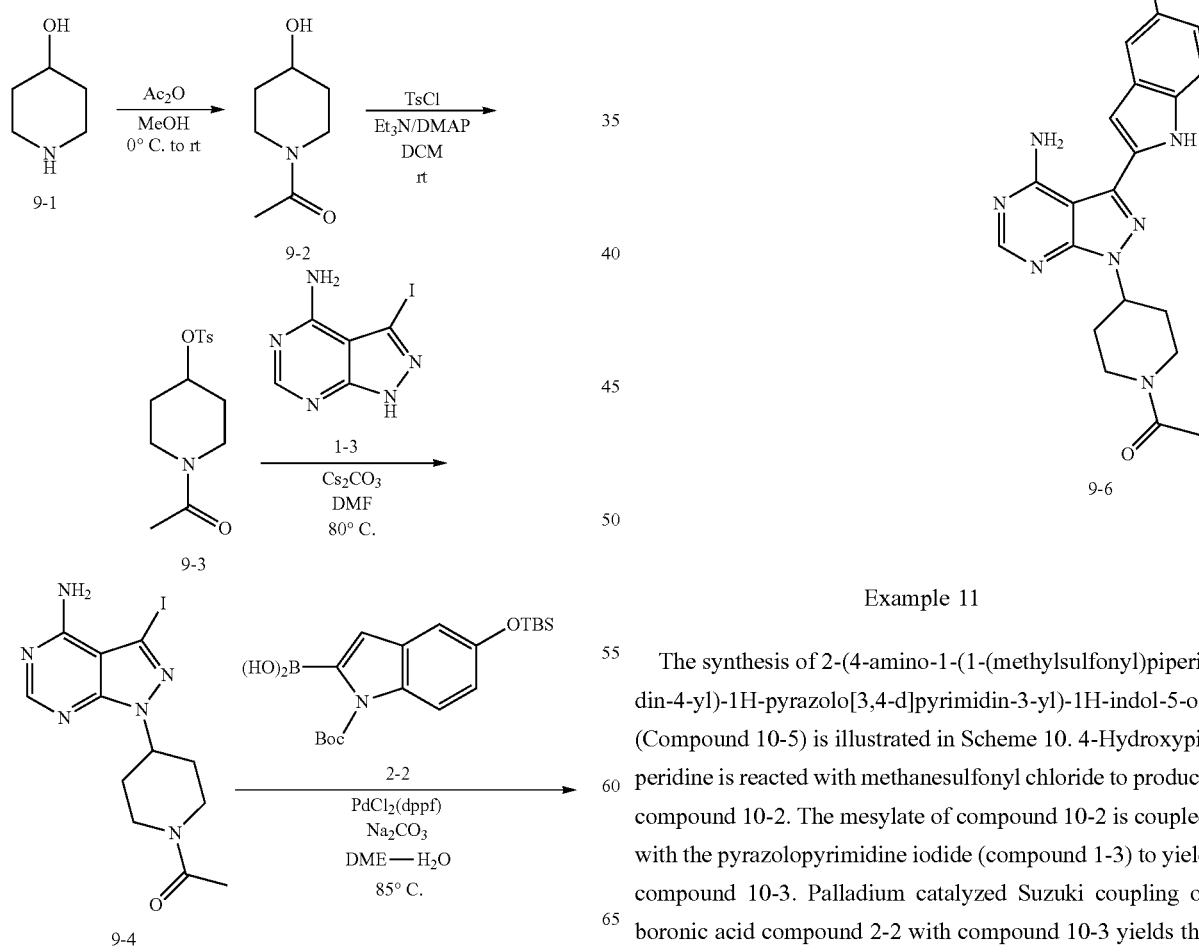

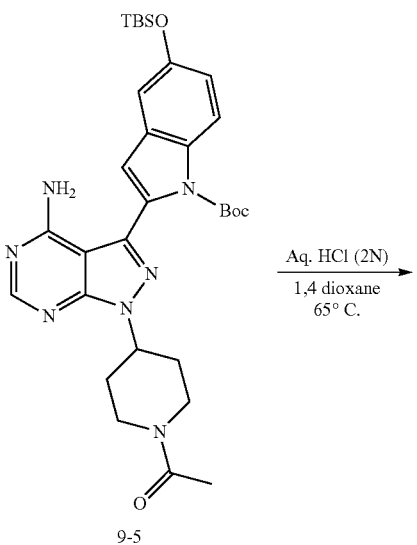

Example 11

The synthesis of 2-(4-amino-1-(1-(methylsulfonyl)piperidin-4-yl)-1H-pyrazolo[3,4-d]pyrimidin-3-yl)-1H-indol-5-ol (Compound 10-5) is illustrated in Scheme 10. 4-Hydroxypiperidine is reacted with methanesulfonyl chloride to produce compound 10-2. The mesylate of compound 10-2 is coupled with the pyrazolopyrimidine iodide (compound 1-3) to yield compound 10-3. Palladium catalyzed Suzuki coupling of boronic acid compound 2-2 with compound 10-3 yields the title compound (compound 10-5) after deprotection.

Scheme 10. Synthesis of 2-(4-amino-1-(1-(methylsulfonyl)piperidin-4-yl)-1H-pyrazolo[3,4-d]pyrimidin-3-yl)-1H-indol-5-ol (Compound 10-5).

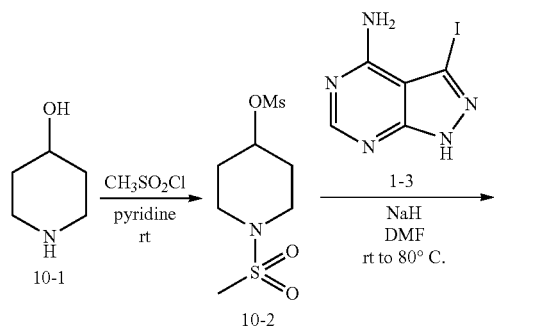

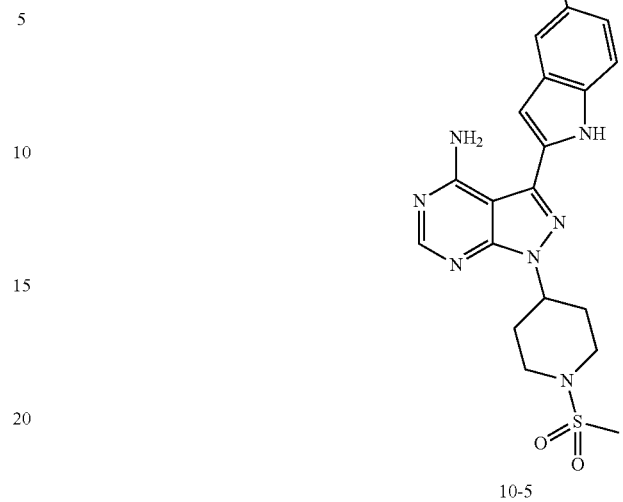

Example 12

The synthesis of 2-(4-amino-1-(1-isopropylpiperidin-4-yl)-1H-pyrazolo[3,4-d]pyrimidin-3-yl)-1H-indol-5-ol (Compound 11-7) is described in Scheme 11. 4-Hydroxypiperidine is protected at nitrogen as the Boc derivative (compound 11-1), then converted to the tosylate (compound 11-2). The tosylate is reacted with pyrazolopyrimidine iodide (compound 1-3) in the presence of cesium carbonate as base, to produce compound 11-3. The Boc protection is removed under acidic conditions and the free amine (compound 11-4) is reacted with isopropyl bromide to yield compound 11-5.

Scheme 11. Synthesis of 2-(4-amino-1-(1-isopropylpiperidin-4-yl)-1H-pyrazolo[3,4-d]pyrimidin-3-yl)-1H-indol-5-ol (Compound 11-7). Palladium catalyzed coupling of indolyl boronic acid 2-2 provides compound 11-7 after deprotection.

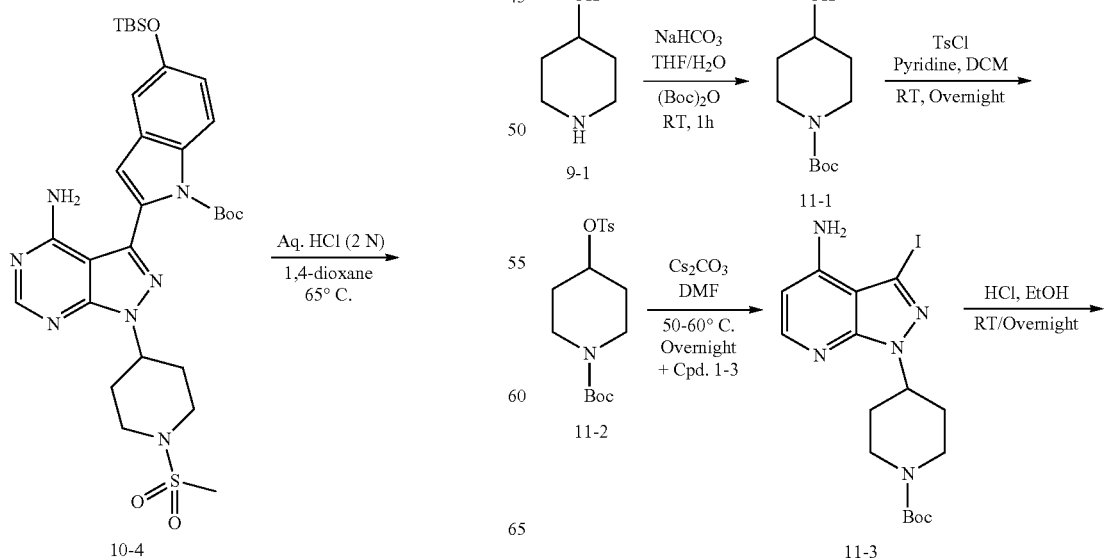

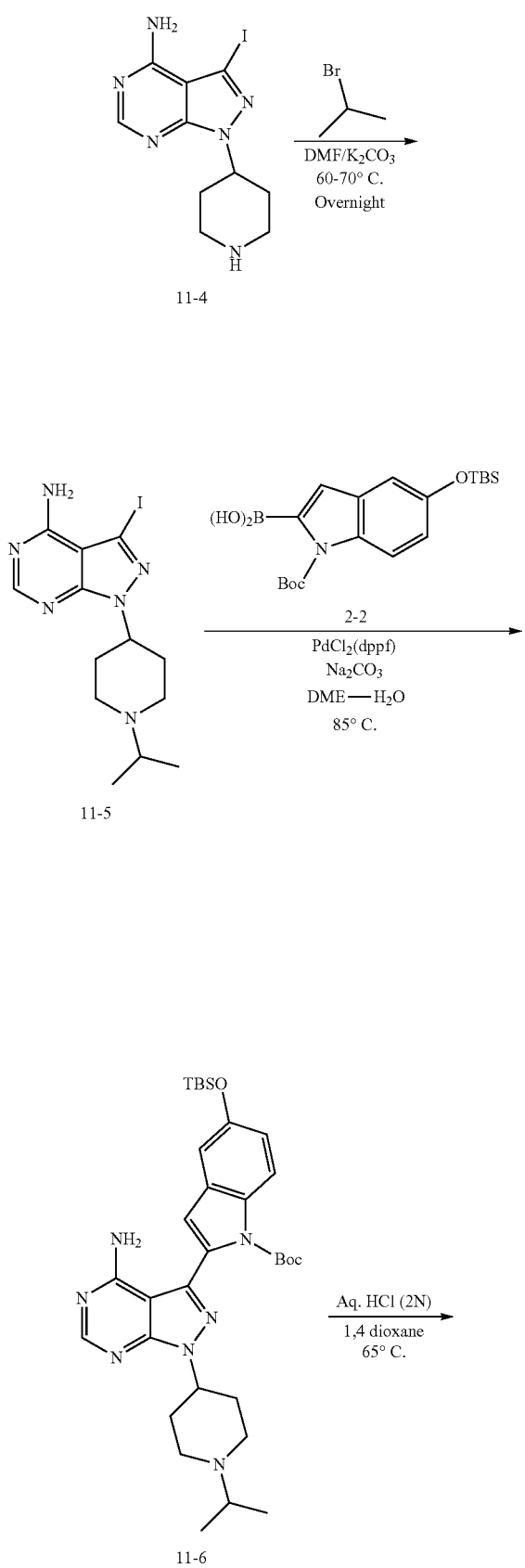

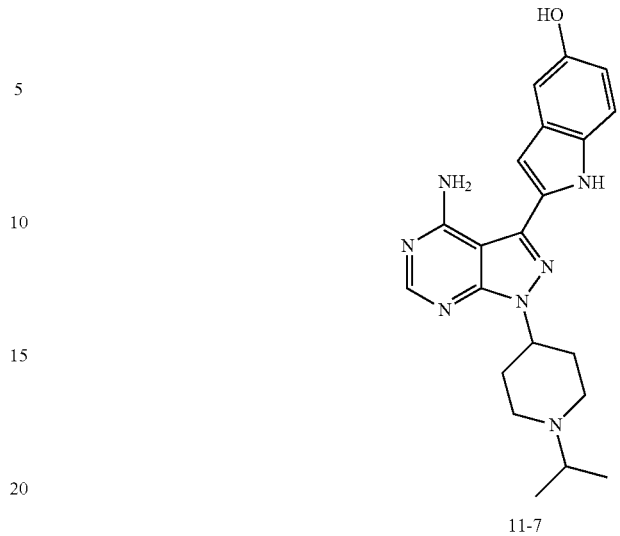

Example 13

The synthesis of 2-(4-amino-1-(3-morpholinocyclobutyl)-1H-pyrazolo[3,4-d]pyrimidin-3-yl)-1H-indol-5-ol (Compound 12-6) is described in Scheme 12. Bromocyclobutanone is produced from compound 12-1 by reaction with mercuric oxide and bromine, which is coupled with pyrazolopyrimidine iodide, compound 2-2, to yield compound 12-3. Reductive amination with morpholine affords compound 12-4. Compound 12-4 is then coupled with a boronic acid derivative to produce compound 12-6.

Scheme 12. Synthesis of 2-(4-amino-1-(3-morpholinocyclobutyl)-1H-pyrazolo [3, 4-d]pyrimidin-3-yl)-1H-indol-5-ol (Compound 12-6).

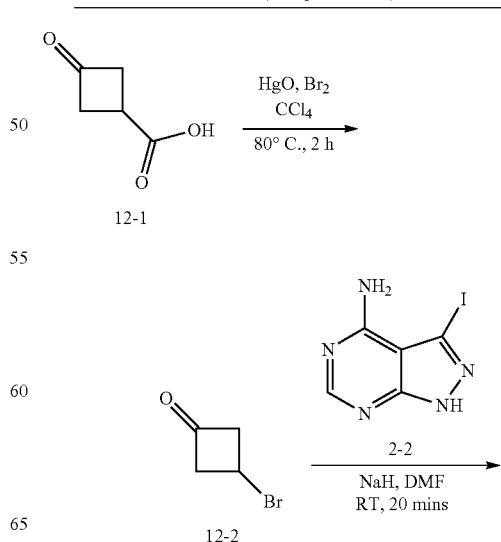

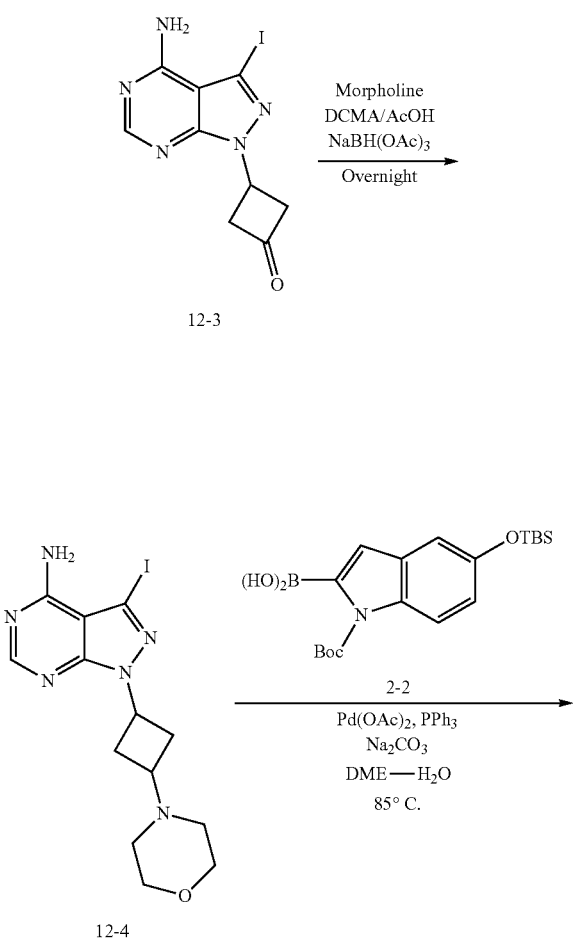

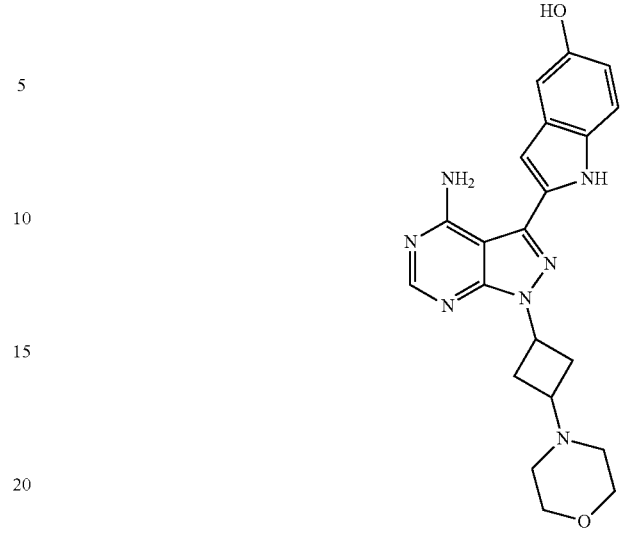

Example 14

The synthesis of 2-(4-amino-1-(3-hydroxycyclobutyl)-1H-pyrazolo[3,4-d]pyrimidin-3-yl)-1H-indol-5-ol (Compound 13-3) is described in Scheme 13. Intermediate 12-3 is reduced to the corresponding alcohol with sodium borohydride, yielding compound 13-1. Compound 13-1 is coupled with indolyl boronic acid 2-2 and produces compound 13-3 after deprotection under standard conditions.

Scheme 13. synthesis of 2-(4-amino-1-(3-hydroxycyclobutyl)-1H-pyrazolo[3,4-d]pyrimidin-3-yl)-1H-indol-5-ol (Compound 13-3)

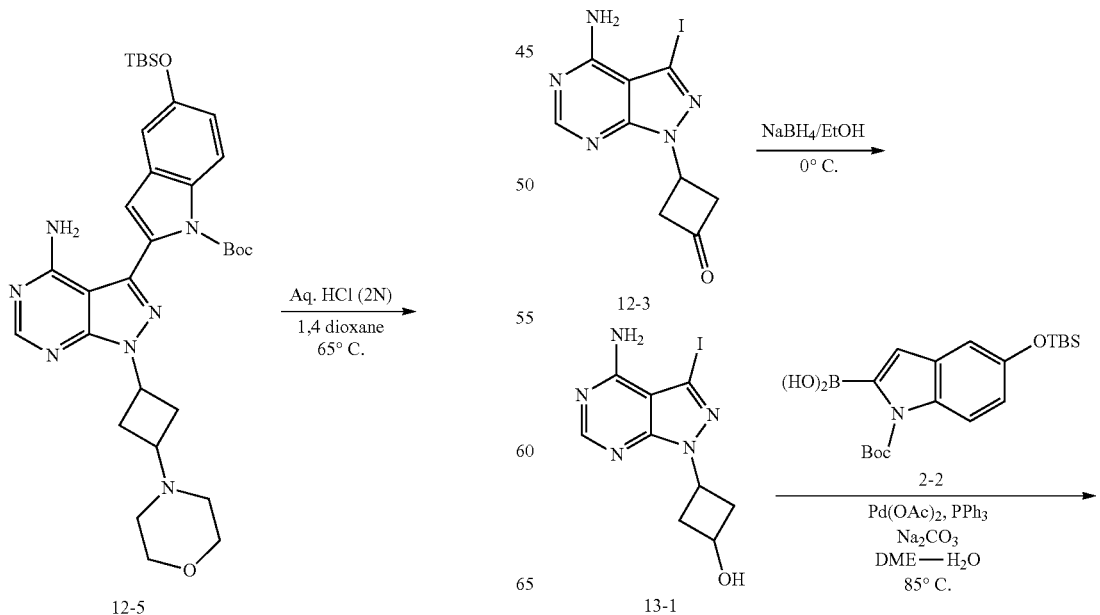

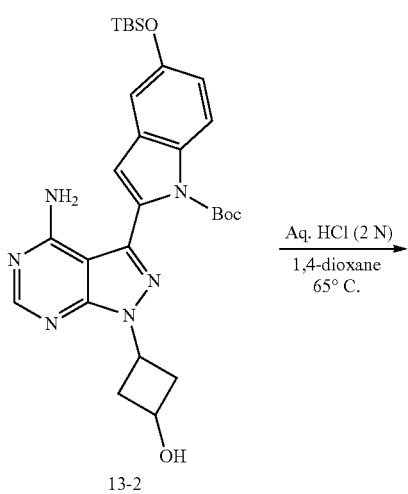

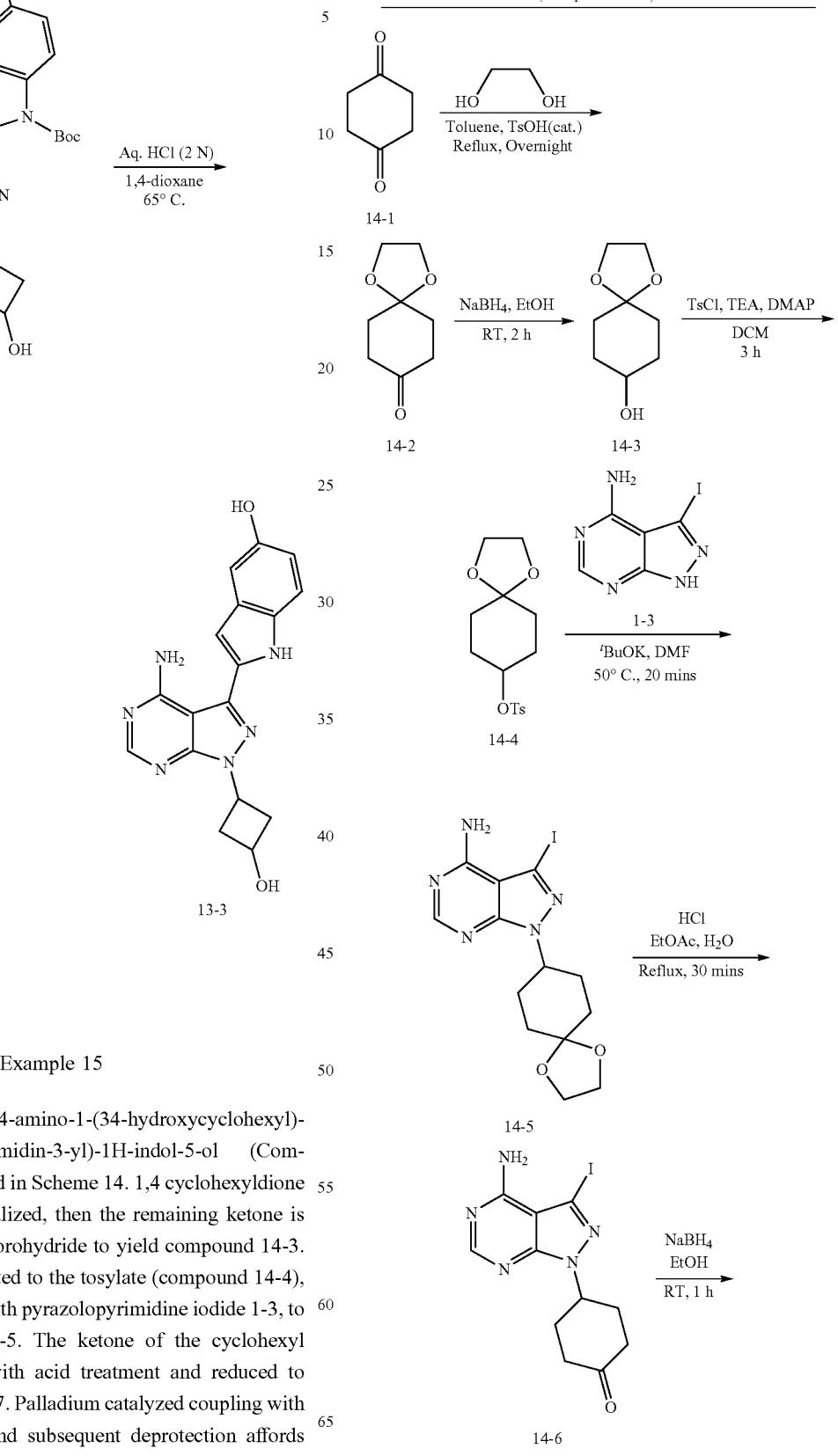

Scheme 14. synthesis of 2-(4-amino-1-(34-hydroxycyclohexyl)-1H-pyrazolo [3, 4-d]pyrimidin-3-yl)-1H-indol-5-ol (Compound 14-9).

Example 15

The synthesis of 2-(4-amino-1-(34-hydroxycyclohexyl)-1H-pyrazolo[3,4-d]pyrimidin-3-yl)-1H-indol-5-ol (Compound 14-9) is described in Scheme 14. 1,4 cyclohexyldione is selectively monoketalized, then the remaining ketone is reduced with sodium borohydride to yield compound 14-3. The hydroxyl is converted to the tosylate (compound 14-4), which is then reacted with pyrazolopyrimidine iodide 1-3, to produce compound 14-5. The ketone of the cyclohexyl moiety is unmasked with acid treatment and reduced to hydroxy compound 14-7. Palladium catalyzed coupling with indolyl boronic acid and subsequent deprotection affords compound 14-9.

185

-continued

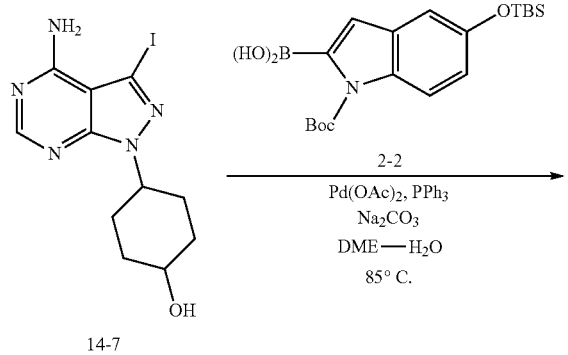

14-7

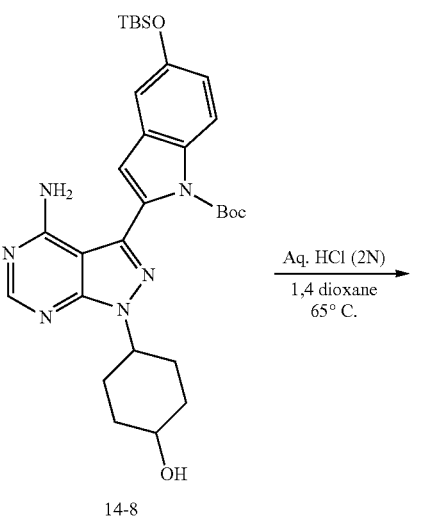

14-8

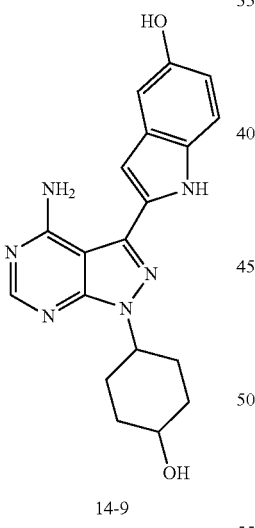

14-9

186

Scheme 15. Synthesis of 2-(4-amino-1-(3-hydroxycyclobutyl)-1H-pyrazolo [3, 4-d]pyrimidin-3-yl)-7 chloro-1H-indol-5-ol (Compound 15-2).

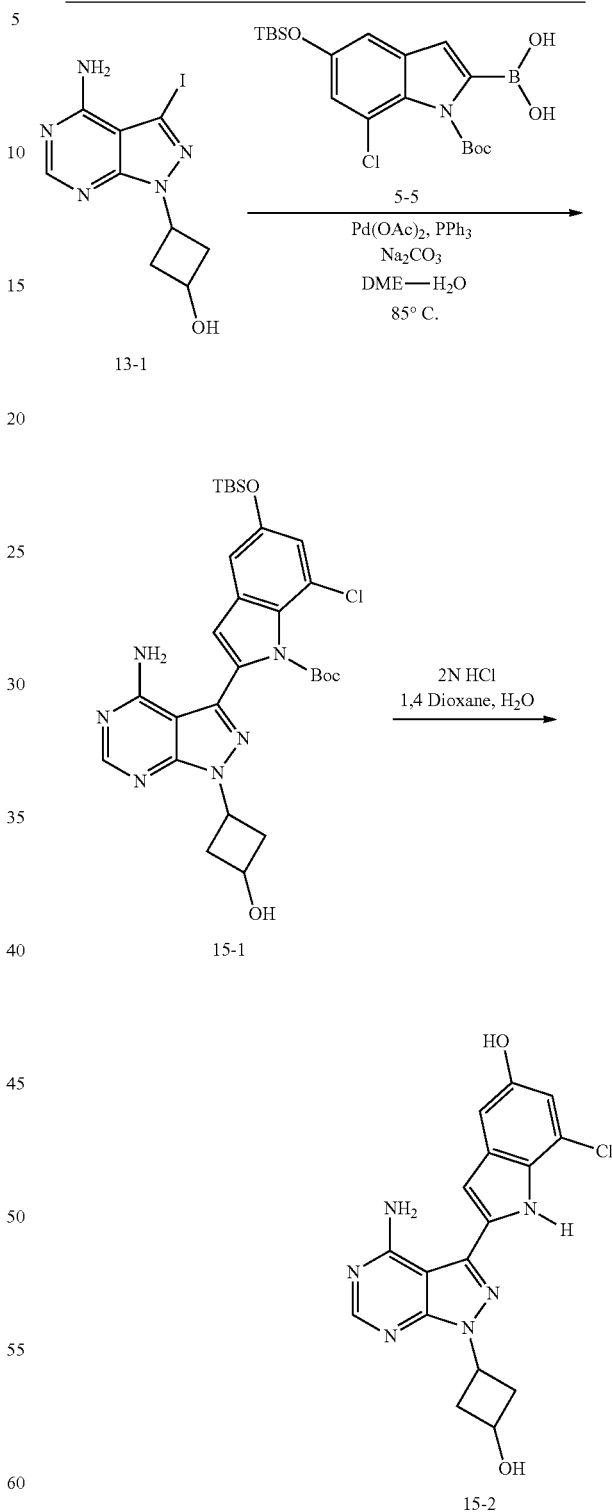

Example 16

The synthesis of 2-(4-amino-1-(3-hydroxycyclobutyl)-1H-pyrazolo[3,4-d]pyrimidin-3-yl)-7 chloro -1H-indol-5-ol (Compound 15-2) is described in Scheme 15. The hydroxycyclobutyl pyrazolopyrimidine 13-1, synthesized as shown in Scheme 13, is reacted with the protected 7-chloro indolyl boronic acid species 5-5 under Suzuki coupling conditions. The product, compound 15-1, is deprotected with acid to remove both the tert-butyldimethylsilyl and Boc protection to produce compound 15-2.

Reaction Schemes 16, 17 and 18 illustrate methods of synthesis of borane reagents useful in preparing intermediates of use in synthesis of the compounds of the invention as described above, to introduce heteroaryl substituents.

Scheme 16. A compound of Formula H-1 is treated with, for example, nitric acid to produce a compound of Formula H-2. The compound of Formula H-2 is treated with a reducing agent such as stannous chloride to produce a compound of Formula H-3. The compound of H-3 is treated with sodium nitrate in acid and cupric bromide to produce a compound of Formula H-4. The compound of H-4 is treated a base such as butyl lithium and boron tris-isopropoxide to produce a compound of Formula H-5.

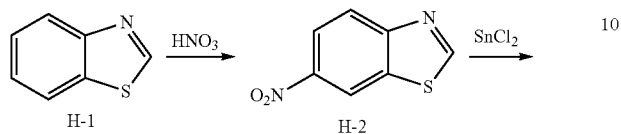

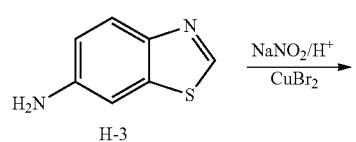

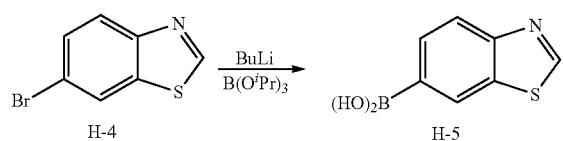

Scheme 17. A compound of Formula I-1 is treated with, for example, potassium thiocyanate and brominein acetic acid to produce a compound of Formula I-2. The compound of Formula I-2 is treated with an acteylating reagent such as acetyl chloride to produce a compound of Formula I-3. The compound of I-3 is reacted with, for example, bis(pinacolato)diboron (compound I-4) in the presence of a catalyst such as palladium chloride to produce a compound of Formula I-5.

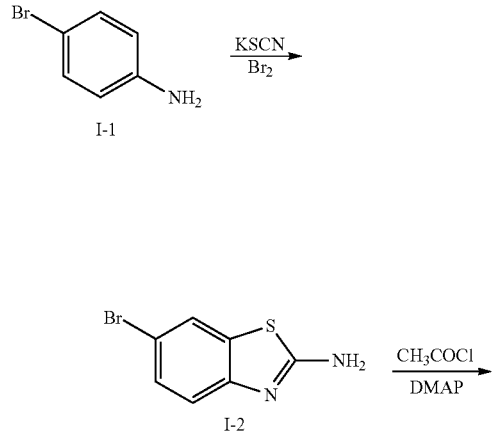

-continued

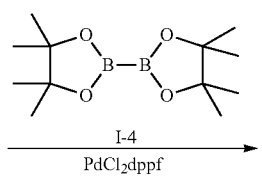

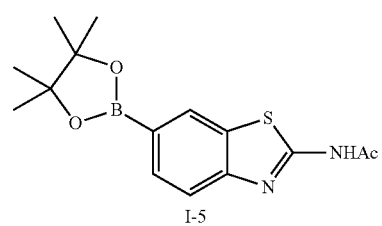

Scheme 18. The compound of Formula I-2 is reacted with, for example, methyl carbamic acid chloride to produce a compound of Formula J-1. The compound of Formula J-1 is reacted with bis(pinacolato)diboron(compound I-4) in the presence of a catalyst such as Pd$_2$(dba)$_3$, 2-chlorohexylphosphino-2,4,6-triisopropylbiphenyl, a base suchy as potassium acetate, to produce the compound of Formula J-2.

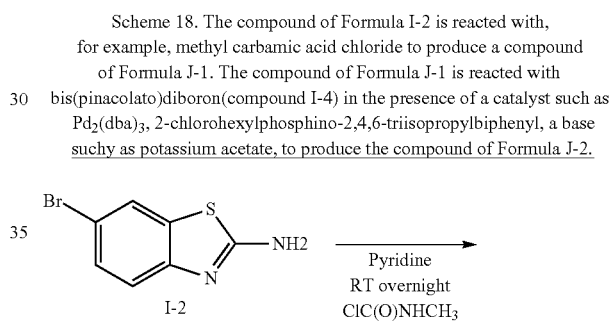

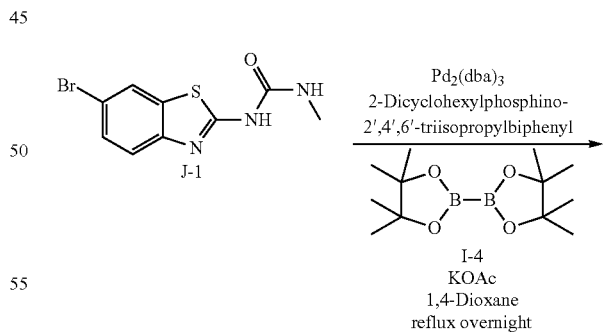

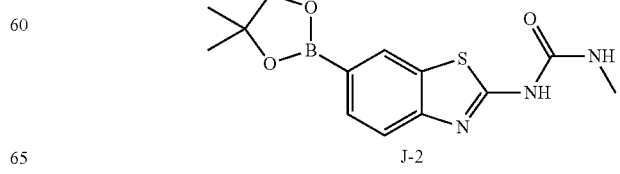

Example 17
TABLE 1
In vitro IC$_{50}$ values for Illustrative Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 1 | 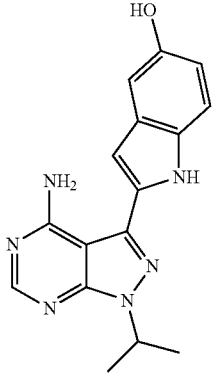 | ++++ | + | + | ++ | ++ | +++ |
| 2 | 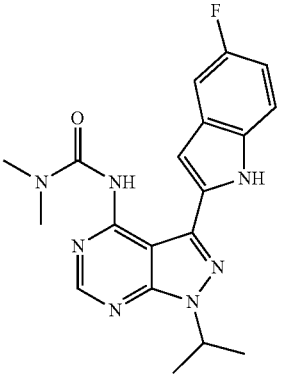 [SMILES: CC(C)n1nc(-c2cc3cc(F)ccc3[nH]2)c2c(NC(=O)N(C)C)ncnc21] | + | — | — | — | — | — |
| 3 | 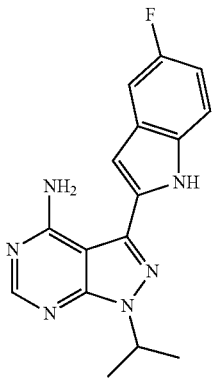 [SMILES: CC(C)n1nc(-c2cc3cc(F)ccc3[nH]2)c2c(N)ncnc21] | ++ | + | — | — | — | — |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 4 | 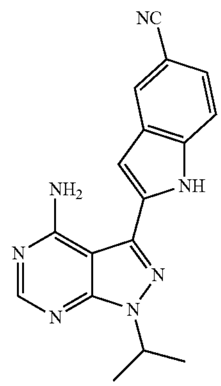 [SMILES: CC(C)n1nc(-c2cc3cc(C#N)ccc3[nH]2)c2c(N)ncnc21] | + | + | | | | — |
| 5 | 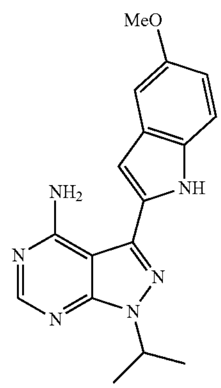 [SMILES: COc1ccc2[nH]c(-c3nn(C(C)C)c4ncnc(N)c34)cc2c1] | + | + | | | | + |
| 6 | 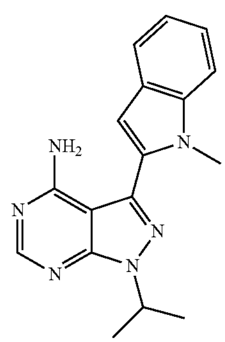 [SMILES: CC(C)n1nc(-c2cc3ccccc3n2C)c2c(N)ncnc21] | + | + | | | | + |
| 7 | 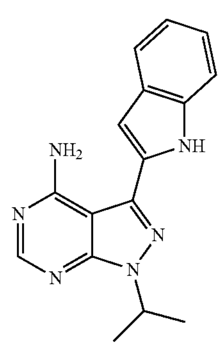 [SMILES: CC(C)n1nc(-c2cc3ccccc3[nH]2)c2c(N)ncnc21] | +++ | + | | | | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 8 | 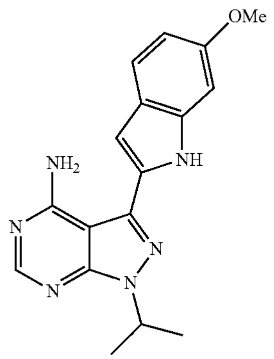 [SMILES: COc1ccc2cc(-c3nn(C(C)C)c4ncnc(N)c34)[nH]c2c1] | + | + | | | | + |
| 9 | 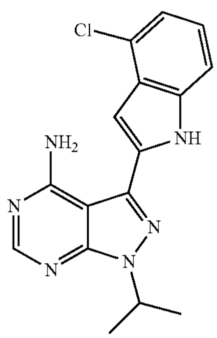 [SMILES: CC(C)n1nc(-c2cc3c(Cl)cccc3[nH]2)c2c(N)ncnc21] | ++++ | + | | | | + |
| 10 | 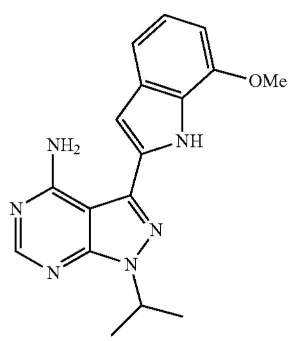 [SMILES: COc1cccc2cc(-c3nn(C(C)C)c4ncnc(N)c34)[nH]c12] | +++++ | + | + | + | + | + |
| 11 | 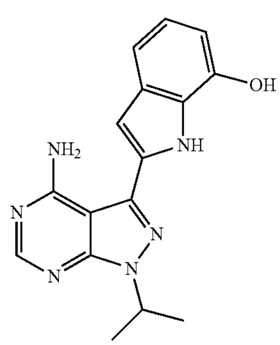 [SMILES: CC(C)n1nc(-c2cc3cccc(O)c3[nH]2)c2c(N)ncnc21] | +++++++ | + | + | ++ | ++ | ++++ |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|-----------|----------------------|------------------------|------------------------|------------------------|------------------------|------------------------|
| 12 | 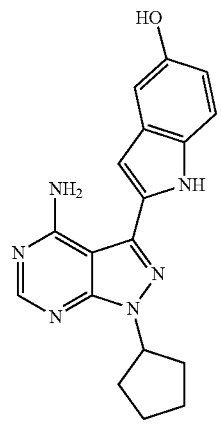 [SMILES: Nc1ncnc2c1c(-c1cc3cc(O)ccc3[nH]1)nn2C1CCCC1] | ++++++ | + | + | ++ | + | ++++ |
| 13 | 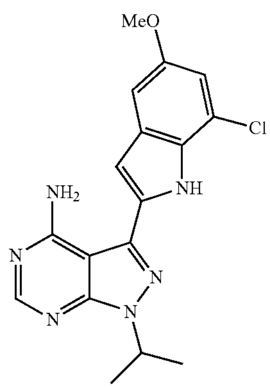 [SMILES: COc1cc(Cl)c2[nH]c(-c3nn(C(C)C)c4ncnc(N)c34)cc2c1] | + | + | | | | + |
| 14 | 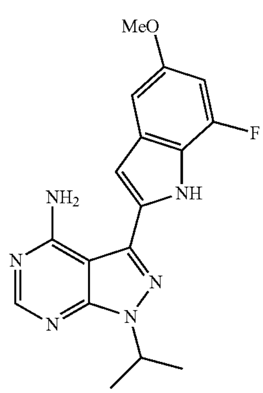 [SMILES: COc1cc(F)c2[nH]c(-c3nn(C(C)C)c4ncnc(N)c34)cc2c1] | + | + | | | | — |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|-----------|----------------------|-----------------------|-----------------------|-----------------------|-----------------------|------------------------|
| 15 | 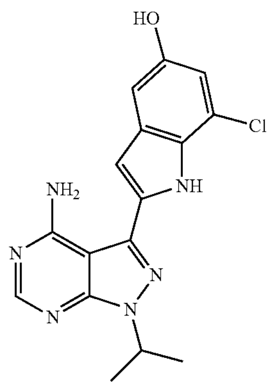 [SMILES: CC(C)n1nc(-c2cc3cc(O)cc(Cl)c3[nH]2)c2c(N)ncnc21] | +++++++ | + | + | ++++ | ++++ | ++++ |
| 16 | 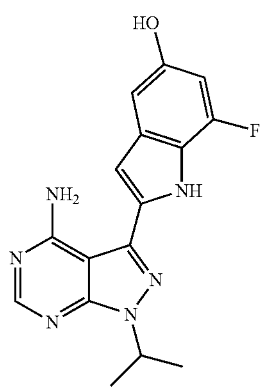 [SMILES: CC(C)n1nc(-c2cc3cc(O)cc(F)c3[nH]2)c2c(N)ncnc21] | +++++++ | + | + | ++ | +++ | ++ |
| 17 | 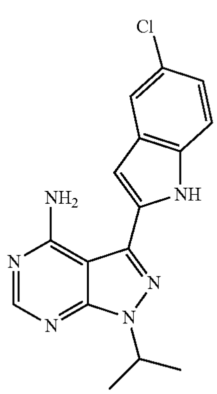 [SMILES: CC(C)n1nc(-c2cc3cc(Cl)ccc3[nH]2)c2c(N)ncnc21] | + | + | | | | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 18 | 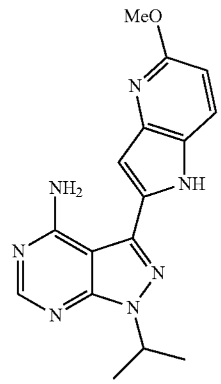 [SMILES: COc1ccc2[nH]c(-c3nn(C(C)C)c4ncnc(N)c34)cc2n1] | + | * | | | | * |
| 19 | 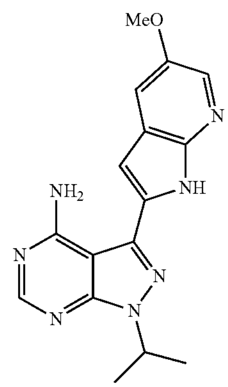 [SMILES: COc1cnc2[nH]c(-c3nn(C(C)C)c4ncnc(N)c34)cc2c1] | + | + | | | | — |
| 20 | 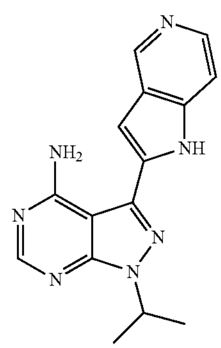 [SMILES: CC(C)n1nc(-c2cc3cnccc3[nH]2)c2c(N)ncnc21] | + | + | | | | — |
| 21 | 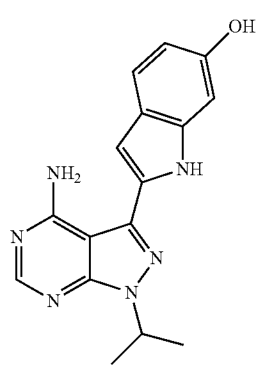 [SMILES: CC(C)n1nc(-c2cc3ccc(C#N)cc3[nH]2)c2c(N)ncnc21] | ++++ | ++ | + | ++ | ++ | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 22 | (structure) | +++++++ | + | + | — | + | ++ |
| 23 | (structure) | + | + | | | | — |
| 24 | (structure) | + | + | | | + | |

TABLE 1-continued
In vitro IC$_{50}$ values for Illustrative Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 25 | 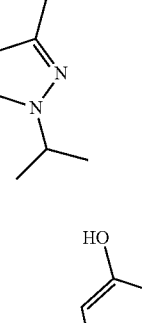 | ++ | + | | | | + |
| 26 | 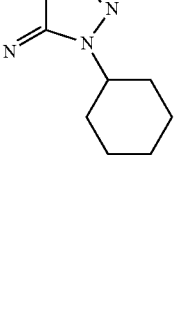 | ++++++ | + | + | ++ | +++ | ++ |
| 27 | 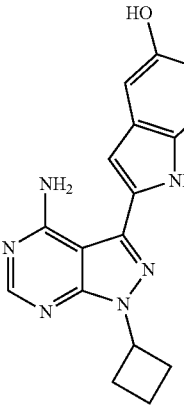 | +++++ | | | | | ++ |

TABLE 1-continued
In vitro IC$_{50}$ values for Illustrative Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 28 | 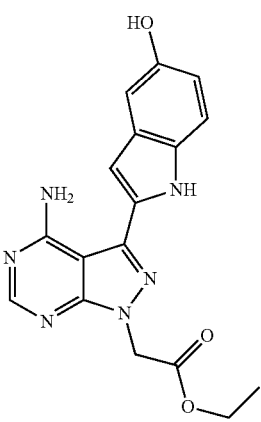 [SMILES: CCOC(=O)Cn1nc(-c2cc3cc(O)ccc3[nH]2)c2c(N)ncnc21] | ++ | + | + | — | + | + |
| 29 | 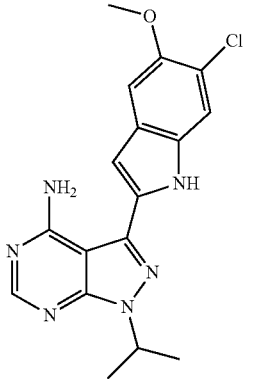 [SMILES: COc1cc2cc(-c3nn(C(C)C)c4ncnc(N)c34)[nH]c2cc1Cl] |  | + |  |  |  | — |
| 30 | 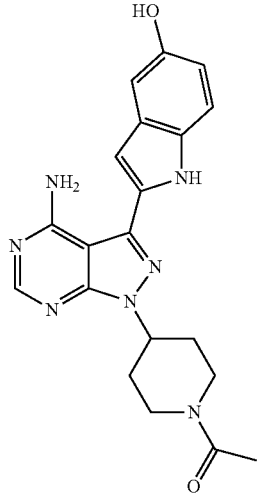 [SMILES: CC(=O)N1CCC(n2nc(-c3cc4cc(O)ccc4[nH]3)c3c(N)ncnc32)CC1] | +++++ | + | + | — | + | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 31 | 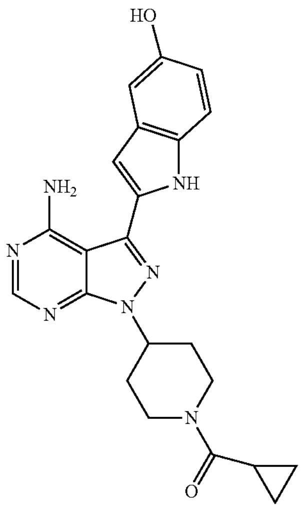 [SMILES: Nc1ncnc2c1c(-c1cc3cc(O)ccc3[nH]1)nn2C1CCN(C(=O)C2CC2)CC1] | +++++ | + | + | — | ++ | + |
| 32 | 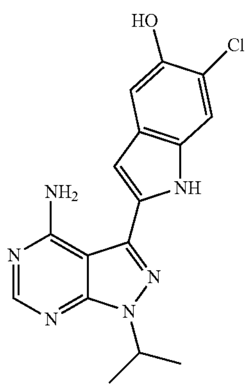 [SMILES: CC(C)n1nc(-c2cc3cc(O)c(Cl)cc3[nH]2)c2c(N)ncnc21] | ++ | + | — | + | + | + |
| 33 | 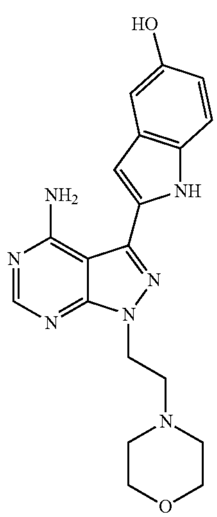 [SMILES: Nc1ncnc2c1c(-c1cc3cc(O)ccc3[nH]1)nn2CCN1CCOCC1] | ++ | + | — | + | + | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 34 | 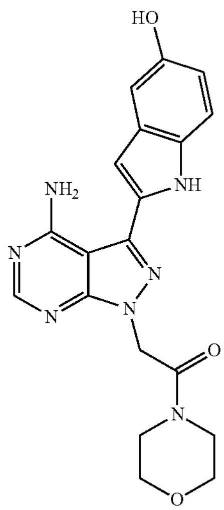 [SMILES: Nc1ncnc2c1c(-c1cc3cc(O)ccc3[nH]1)nn2CC(=O)N1CCOCC1] | + | + | — | + | + | — |
| 35 | 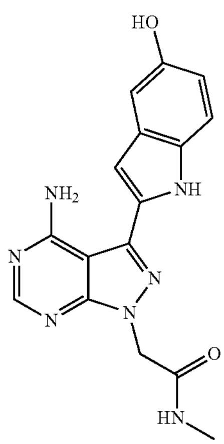 [SMILES: CNC(=O)Cn1nc(-c2cc3cc(O)ccc3[nH]2)c2c(N)ncnc21] | + | + | — | + | + | — |
| 36 | 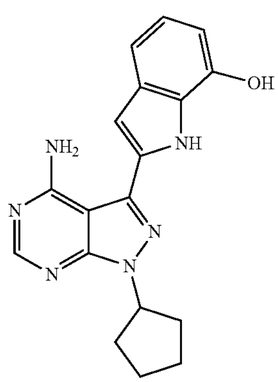 [SMILES: Nc1ncnc2c1c(-c1cc3cccc(O)c3[nH]1)nn2C1CCCC1] | ++++++ | + | — | +++ | ++ | +++ |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 37 | (structure) | + | ++ | — | ++ | ++ | — |
| 38 | (structure) | ++ | + | — | + | + | + |
| 39 | (structure) | +++++ | + | — | + | + | + |
| 40 | (structure) | +++ | + | — | + | + | + |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 41 | 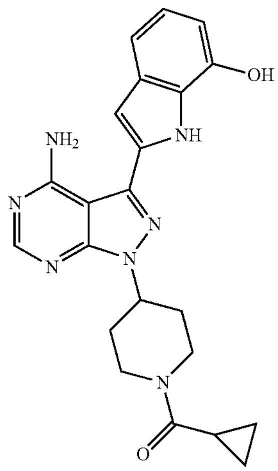 [SMILES: Nc1ncnc2c1c(-c1cc3cccc(O)c3[nH]1)nn2C1CCN(C(=O)C2CC2)CC1] | ++++++ | + | + | ++++ | + | + |
| 42 | 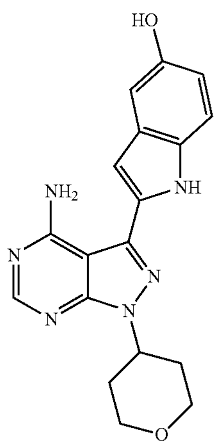 [SMILES: Nc1ncnc2c1c(-c1cc3cc(O)ccc3[nH]1)nn2C1CCOCC1] | +++++++ | + | + | — | +++ | + |
| 43 | 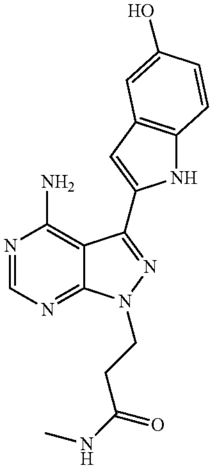 [SMILES: CNC(=O)CCn1nc(-c2cc3cc(O)ccc3[nH]2)c2c(N)ncnc21] | + | + | + | — | + | — |

TABLE 1-continued
In vitro IC$_{50}$ values for Illustrative Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 44 | 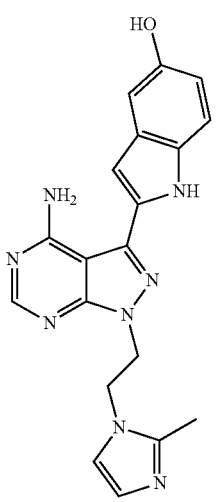 [SMILES: Cc1nccn1CCn1nc(-c2cc3cc(O)ccc3[nH]2)c2c(N)ncnc21] | +++ | + | + | — | + | — |
| 45 | 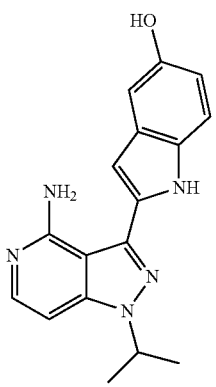 [SMILES: CC(C)n1nc(-c2cc3cc(O)ccc3[nH]2)c2c(N)nccc21] | + | | | | | |
| 46 | 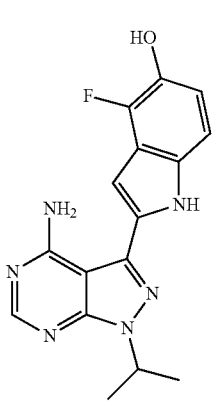 [SMILES: CC(C)n1nc(-c2cc3c(F)c(O)ccc3[nH]2)c2c(N)ncnc21] | — | | | | | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 47 | 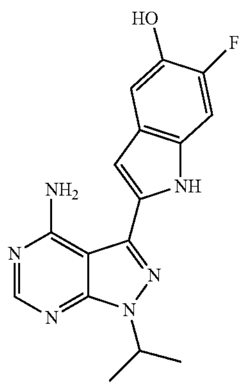 [SMILES: CC(C)n1nc(-c2cc3cc(O)c(F)cc3[nH]2)c2c(N)ncnc21] | | | | | | — |
| 48 | 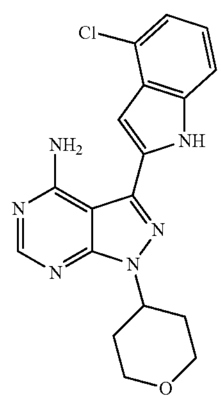 [SMILES: Nc1ncnc2c1c(-c1cc3c(Cl)cccc3[nH]1)nn2C1CCOCC1] | ++++ | + | + | + | + | |
| 49 | 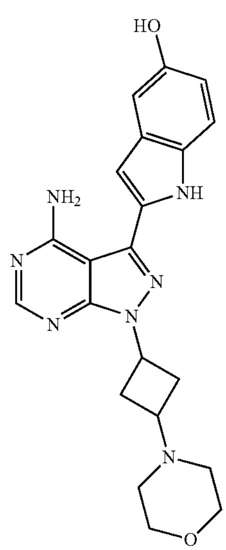 [SMILES: Nc1ncnc2c1c(-c1cc3cc(O)ccc3[nH]1)nn2C1CC(N2CCOCC2)C1] | ++++++ | + | + | ++ | ++ | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 50 | 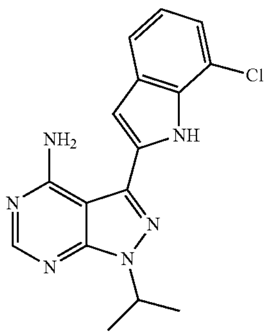 [SMILES: CC(C)n1nc(-c2cc3cccc(Cl)c3[nH]2)c2c(N)ncnc21] | ++++ | + | + | ++ | ++ | |
| 51 | 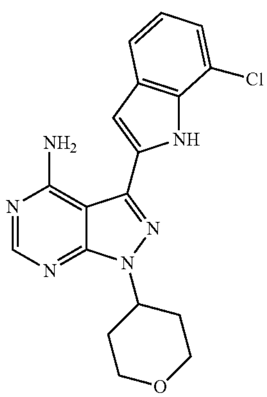 [SMILES: Nc1ncnc2c1c(-c1cc3cccc(Cl)c3[nH]1)nn2C1CCOCC1] | ++++ | + | + | ++ | ++ | |
| 52 | 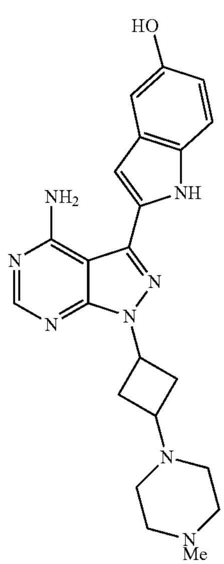 [SMILES: CN1CCN(C2CC(n3nc(-c4cc5cc(O)ccc5[nH]4)c4c(N)ncnc43)C2)CC1] | ++ | + | + | + | ++ | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|-----------|----------------------|-----------------------|-----------------------|-----------------------|-----------------------|------------------------|
| 53 | 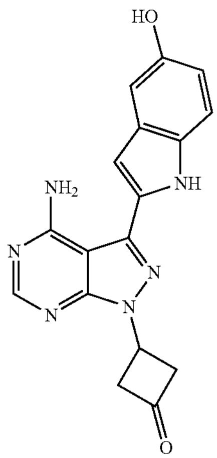 [SMILES: Nc1ncnc2c1c(-c1cc3cc(O)ccc3[nH]1)nn2C1CC(=O)C1] | +++ | + | + | + | — | |
| 54 | 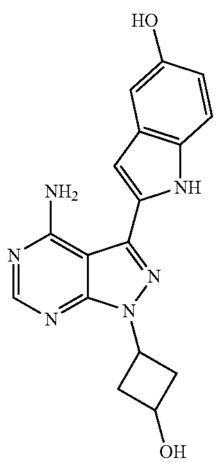 [SMILES: Nc1ncnc2c1c(-c1cc3cc(O)ccc3[nH]1)nn2C1CC(O)C1] | +++++ | + | + | + | — | |
| 55 | 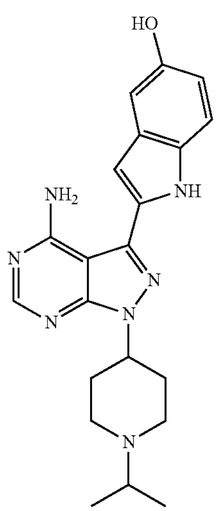 [SMILES: CC(C)N1CCC(n2nc(-c3cc4cc(O)ccc4[nH]3)c3c(N)ncnc32)CC1] | ++ | + | + | + | — | |

TABLE 1-continued
In vitro IC$_{50}$ values for Illustrative Compounds of the Invention.
| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 56 | 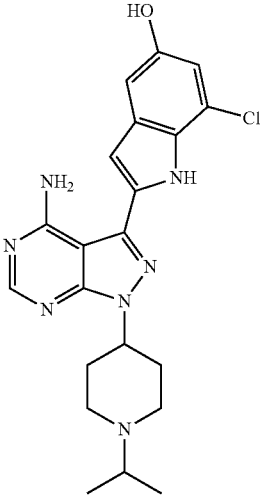 [SMILES: CC(C)N1CCC(n2nc(-c3cc4cc(O)cc(Cl)c4[nH]3)c3c(N)ncnc32)CC1] | + | + | + | + | — | |
| 57 | 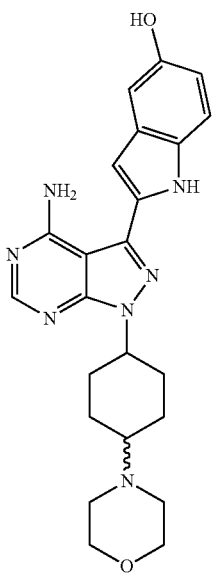 [SMILES: Nc1ncnc2c1c(-c1cc3cc(O)ccc3[nH]1)nn2C1CCC(N2CCOCC2)CC1] | +++++ | + | + | + | — | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 58 | 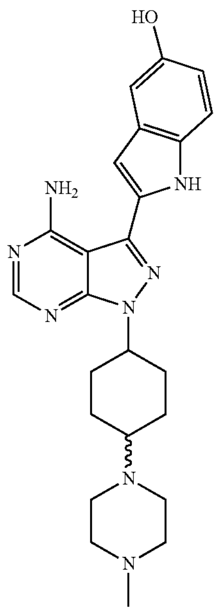 [SMILES: CN1CCN(C2CCC(n3nc(-c4cc5cc(O)ccc5[nH]4)c4c(N)ncnc43)CC2)CC1] | + | + | + | + | — | |
| 59 | 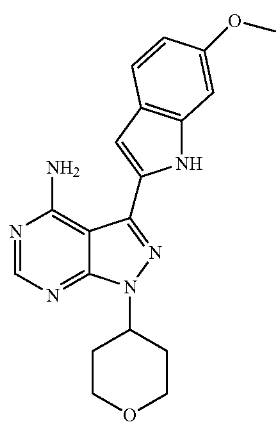 [SMILES: COc1ccc2cc(-c3nn(C4CCOCC4)c4ncnc(N)c34)[nH]c2c1] | + | + | + | + | — | |
| 60 | 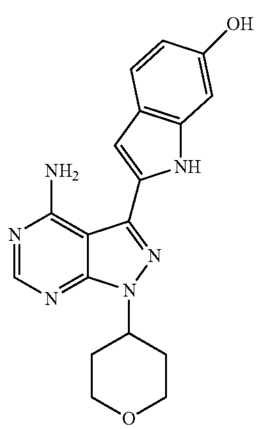 [SMILES: Nc1ncnc2c1c(-c1cc3ccc(O)cc3[nH]1)nn2C1CCOCC1] | +++ | + | + | +++ | — | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 61 | 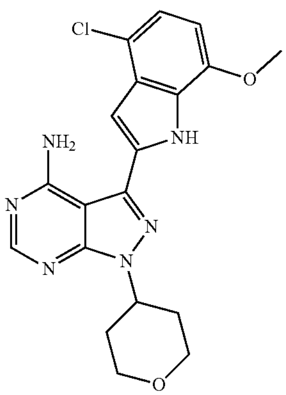 [SMILES: COc1ccc(Cl)c2cc(-c3nn(C4CCOCC4)c4ncnc(N)c34)[nH]c12] | +++++ | + | + | + | + | |
| 62 | 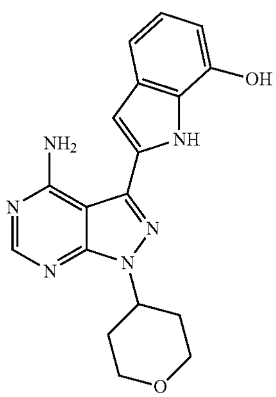 [SMILES: Nc1ncnc2c1c(-c1cc3cccc(O)c3[nH]1)nn2C1CCOCC1] | ++++++ | + | + | + | +++ | |
| 63 | 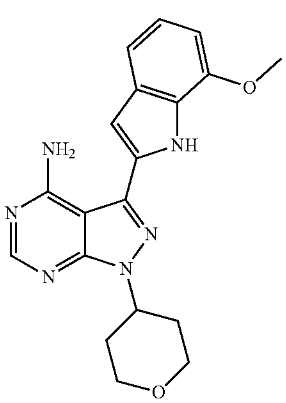 [SMILES: COc1cccc2cc(-c3nn(C4CCOCC4)c4ncnc(N)c34)[nH]c12] | +++++++ | ++ | + | +++++ | +++++ | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 64 | 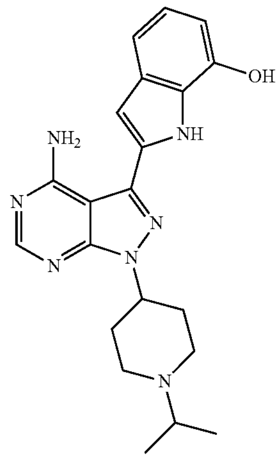 [SMILES: CC(C)N1CCC(n2nc(-c3cc4cccc(O)c4[nH]3)c3c(N)ncnc32)CC1] | +++++ | + | + | ++ | ++ | |
| 65 | 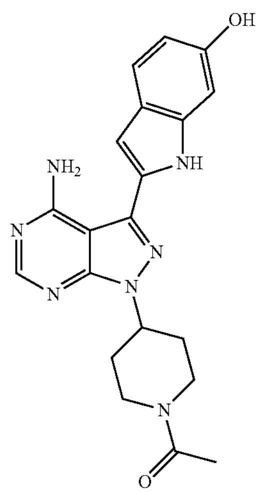 [SMILES: CC(=O)N1CCC(n2nc(-c3cc4ccc(O)cc4[nH]3)c3c(N)ncnc32)CC1] | ++++++ | ++++ | + | +++++ | +++++ | |
| 66 | 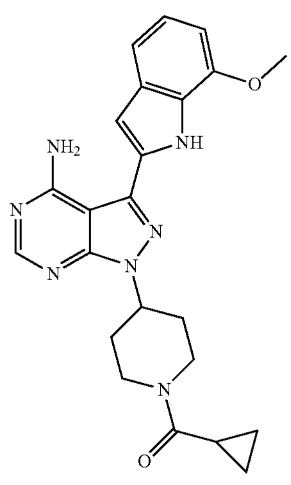 [SMILES: COc1cccc2cc(-c3nn(C4CCN(C(=O)C5CC5)CC4)c4ncnc(N)c34)[nH]c12] | + | + | + | + | + | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 67 | 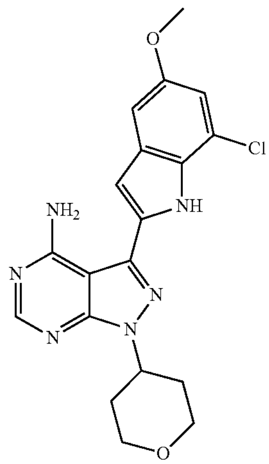 [SMILES: COc1cc(Cl)c2[nH]c(-c3nn(C4CCOCC4)c4ncnc(N)c34)cc2c1] | + | + | + | + | + | |
| 68 | 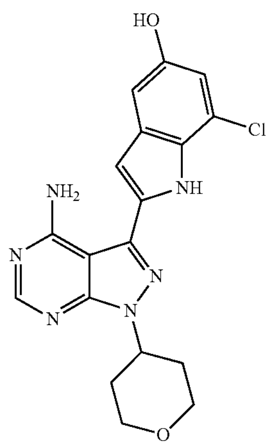 [SMILES: Nc1ncnc2c1c(-c1cc3cc(O)cc(Cl)c3[nH]1)nn2C1CCOCC1] | +++++++ | ++ | + | ++++ | +++++ | |
| 69 | 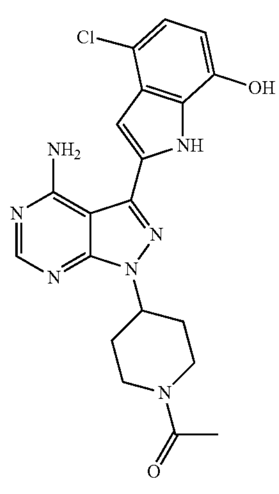 [SMILES: CC(=O)N1CCC(n2nc(-c3cc4c(Cl)ccc(O)c4[nH]3)c3c(N)ncnc32)CC1] | +++++++ | + | + | + | ++ | |

TABLE 1-continued

In vitro IC$_{50}$ values for Illustrative Compounds of the Invention.

| # | Structure | mTORC IC$_{50}$ (nM) | PI3K α IC$_{50}$ (nM) | PI3K β IC$_{50}$ (nM) | PI3K γ IC$_{50}$ (nM) | PI3K δ IC$_{50}$ (nM) | PC3 proliferation (nM) |
|---|---|---|---|---|---|---|---|
| 70 | (structure) | +++++++ | ++ | + | +++ | +++++ | |
| 71 | (structure) | +++ | + | + | + | + | |

In Table 1 above, a +++++++ indicates an IC$_5$ of 5 nM or less; a ++++++ indicates an IC$_5$ of 10 nM or less; a +++++ indicates an IC$_{50}$ of 25 nM or less; an ++++ indicates an IC$_{50}$ of 50 nm or less, a +++ indicates an IC$_{50}$ of 100 nM or less, a ++ indicates an IC$_{50}$ of 500 nM or less, and a + indicates an IC$_{50}$ of more than 500 nM.

TABLE 2

IC50 values for selected assays. The compound numbers correspond to the compounds shown in Table 3.

| IC$_{50}$ results | 50 nM or less (Compound #) | 100 nM or less (Compound #) | 500 nM or less (Compound #) | 1000 nM or less (Compound #) | >1000 nM (Compound #) |
|---|---|---|---|---|---|
| mTORC | 1, 3, 4, 5, 11, 19, 20, 21, 22, 23 | 10 | 8, 9, 12, 15, | 15, 16, 17, | 2, 6, 7, 13, 14, 18 |
| PI3K alpha | 4, 20, 21, 22, 23 | 5, 10, 11, | 1, 3, 9, 12, 19, 30 | 6, 8, 16, | 2, 7, 13, 14, 15, 17, 18 |
| PI3K beta | 21, 22 | 23 | 20 | | 1, 3, 4, 5, 10, 11, 12, 15, 18, 19 |
| PI3K gamma | 1, 3, 4, 5, 10, 11, 19, 20, 21, 22, 23 | | 12 | | 18 |

TABLE 2-continued

IC50 values for selected assays. The compound numbers correspond to the compounds shown in Table 3.

| IC$_{50}$ results | 50 nM or less (Compound #) | 100 nM or less (Compound #) | 500 nM or less (Compound #) | 1000 nM or less (Compound #) | >1000 nM (Compound #) |
|---|---|---|---|---|---|
| PI3K delta | 1, 4, 5, 19, 20, 21, 22, 23 | 3, 10, | 11, | 12, | 18 |
| PC3 proliferation | | 22 | | 21 | 23 |

TABLE 3

Structures corresponding to the compound number listed in Table 4.

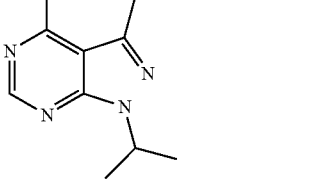

Compound 1

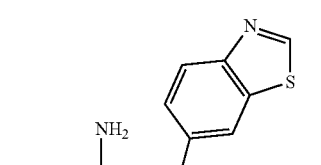

Compound 2

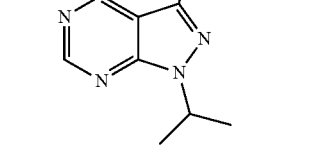

Compound 3

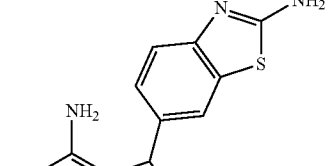

Compound 4

TABLE 3-continued

Structures corresponding to the compound number listed in Table 4.

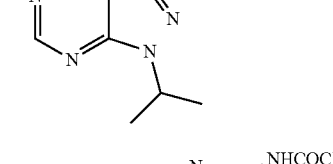

Compound 5

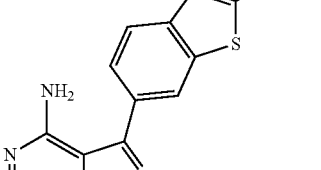

Compound 6

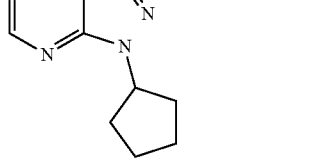

Compound 7

TABLE 3-continued
Structures corresponding to the compound number listed in Table 4.
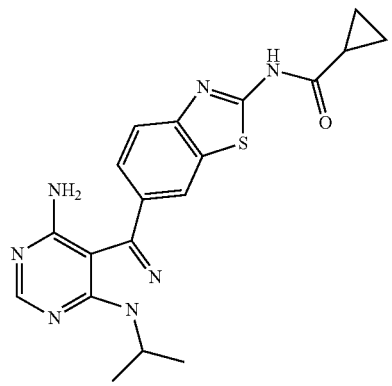 [SMILES: CC(C)Nc1ncnc(N)c1C(=N)c1ccc2nc(NC(=O)C3CC3)sc2c1]
Compound 8
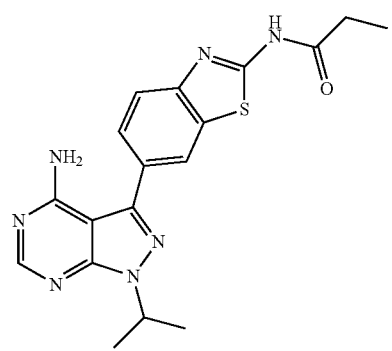 [SMILES: CCC(=O)Nc1nc2ccc(-c3nn(C(C)C)c4ncnc(N)c34)cc2s1]
Compound 9
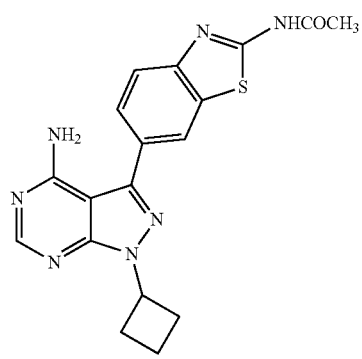
Compound 10
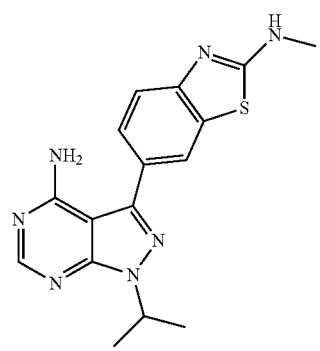 [SMILES: CNc1nc2ccc(-c3nn(C(C)C)c4ncnc(N)c34)cc2s1]
Compound 11
TABLE 3-continued
Structures corresponding to the compound number listed in Table 4.
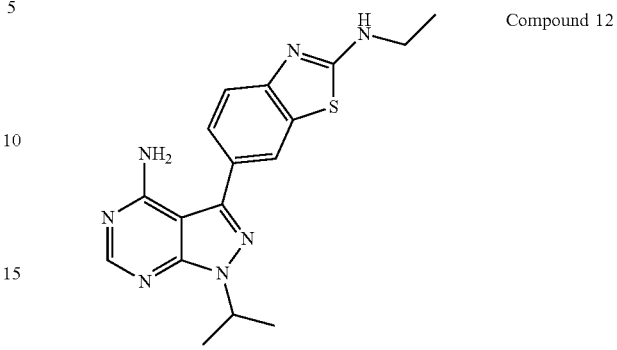
Compound 12
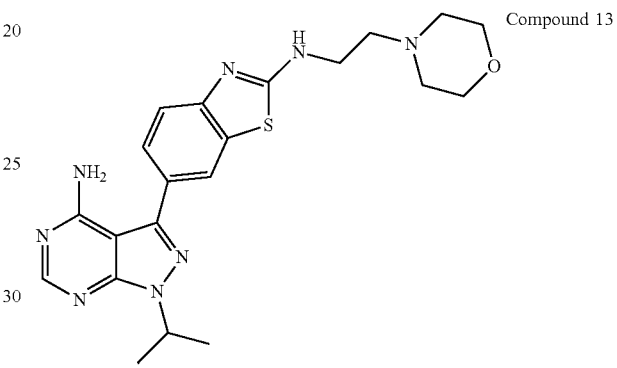
Compound 13
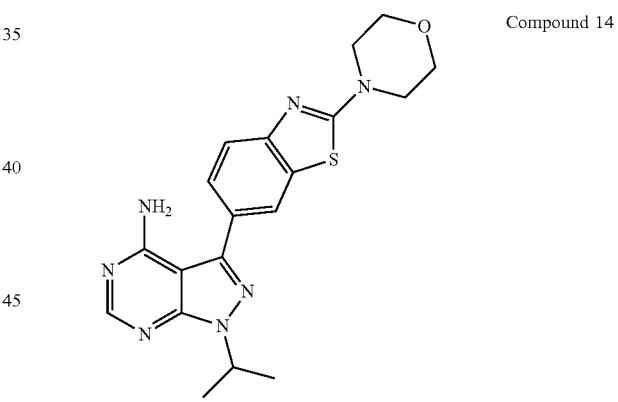
Compound 14
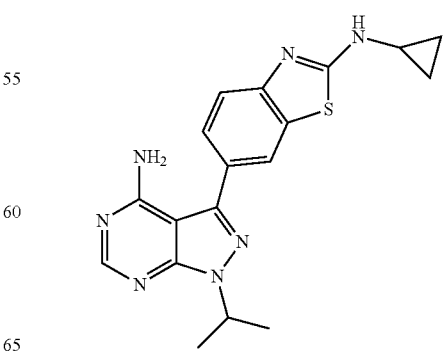
Compound 15

TABLE 3-continued
Structures corresponding to the compound number listed in Table 4.
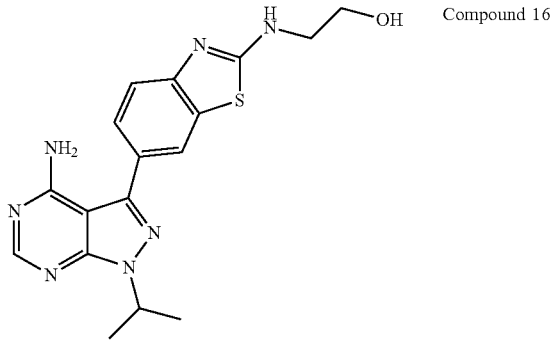
Compound 16
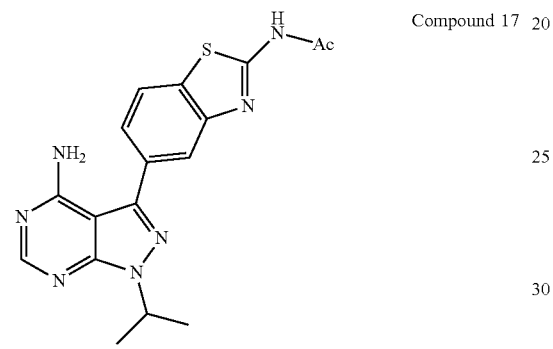
Compound 17
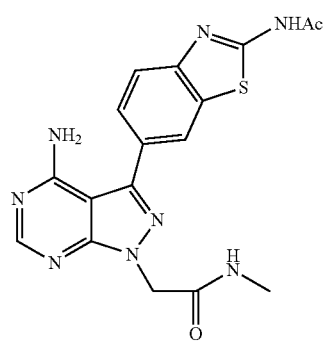 [SMILES: CNC(=O)Cn1nc(-c2ccc3nc(NC(C)=O)sc3c2)c2c(N)ncnc21]
Compound 18
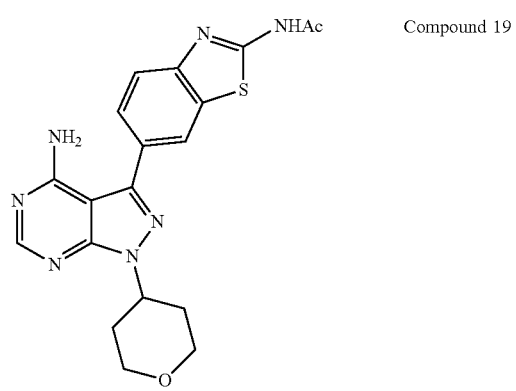
Compound 19
TABLE 3-continued
Structures corresponding to the compound number listed in Table 4.
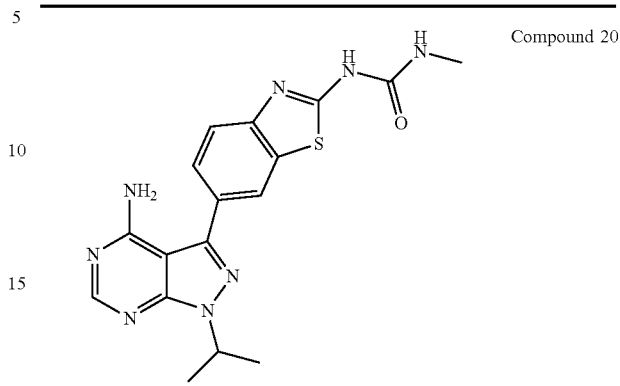
Compound 20
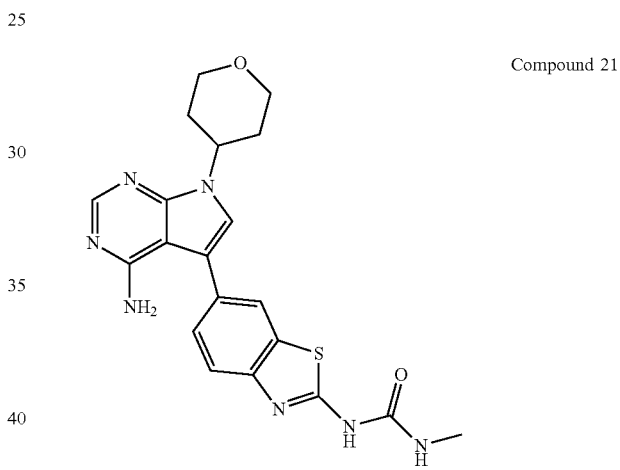
Compound 21
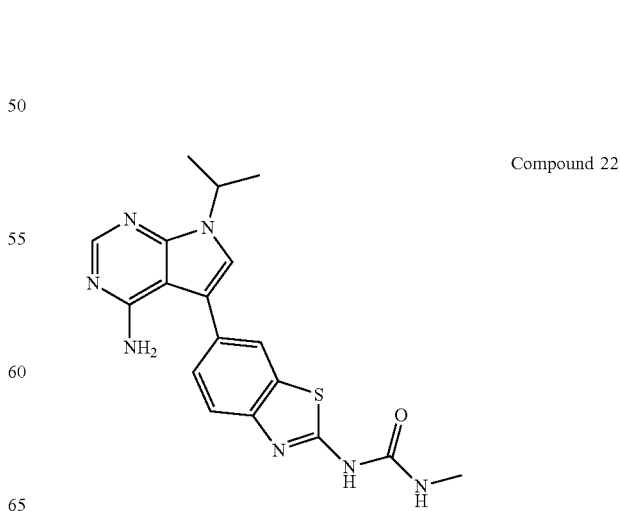
Compound 22

TABLE 3-continued

Structures corresponding to the compound number listed in Table 4.

Compound 23

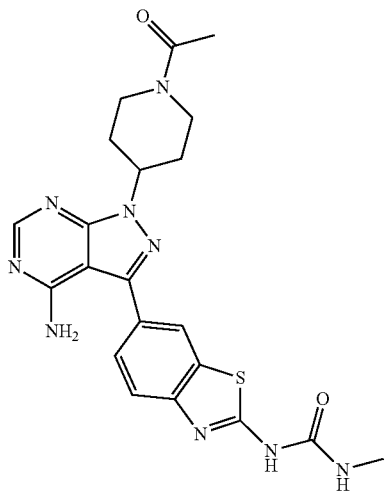 [SMILES: CNC(=O)Nc1nc2ccc(-c3nn(C4CCN(C(C)=O)CC4)c4ncnc(N)c34)cc2s1]

In some embodiments, one or more subject compounds bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor-2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP 004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a subject compound for pi 10a, pi 10p, pi IOy, or pi 108 is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class IPI3 kineasse) as well as a protein kinase (e.g., mTor) with an IC50 value less than about 1 uM, less than about 100 nM, less than about 50 nM, less than about 10 nM, less than 1 nM or even less than about 0.5 nM.

One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, one or more of the subject compounds yield selective inhibition of mTor-mediated signal transduction without affecting upstream PI3K. In some other embodiments, the compounds provided herein can inhibit mTor-mediated activity more effectively than rapamycin, hence providing an alternative treatment for rapamycin-resistant conditions.

In some embodiments, one or more of the subject compounds selectively inhibits mTorC1 relative to one, two, three or all type I phosphatidylinositol 3-kinases (PI3-kinase) consisting of PI3-kinase α, PI3-kinase β, PI3-kinase γ, and PI3-kinase δ. In one embodiment, a compound inhibits mTorC1 relative to PI3-kinase α. In another embodiment, the compound inhibits mTorC1 relative to PI3-kinase 3. In another embodiment, the compound inhibits mTorC1 relative to PI3-kinase γ. In another embodiment, the compound inhibits mTorC1 relative to PI3-kinase δ. In some embodiments, the compound inhibits mTorC1 relative to PI3-kinase α and β, but not γ or δ. In other embodiments, the compound inhibits mTorC1 relative to PI3-kinase α and γ, but not β or δ. In other embodiments, the compound inhibits mTorC1 relative to PI3-kinase α and δ, but not β or γ. In other embodiments, the compound inhibits mTorC1 relative to PI3-kinase β and γ, but not α or δ. In other embodiments, the compound inhibits mTorC1 relative to PI3-kinase β and δ, but not α or γ. In other embodiments, the compound inhibits mTorC1 relative to PI3-kinase γ and δ, but not α or β. In other embodiments, the compound inhibits mTorC1 relative to PI3-kinase α, β, and γ, but not δ. In other embodiments, the compound inhibits mTorC1 relative to PI3-kinase α, β, and δ, but not γ. In other embodiments, the compound inhibits mTorC1 relative to PI3-kinase α, β, and γ, but not γ. In other embodiments, the compound inhibits mTorC1 relative to PI3-kinase γ, β, and δ, but not α. In other embodiments, the compound inhibits mTorC1 relative to PI3-kinase α, β, γ, and δ.

In some embodiments, one or more of the subject compounds selectively inhibits mTorC2 relative to one, two, three or all type I phosphatidylinositol 3-kinases (PI3-kinase) consisting of PI3-kinase α, PI3-kinase β, PI3-kinase γ, and PI3-kinase δ. In one embodiment, a compound inhibits mTorC2 relative to PI3-kinase α. In another embodiment, the compound inhibits mTorC2 relative to PI3-kinase β. In another embodiment, the compound inhibits mTorC2 relative to PI3-kinase γ. In another embodiment, the compound inhibits mTorC2 relative to PI3-kinase δ. In some embodiments, the compound inhibits mTorC2 relative to PI3-kinase α and β, but not γ or δ. In other embodiments, the compound inhibits mTorC2 relative to PI3-kinase α and γ, but not β or δ. In other embodiments, the compound inhibits mTorC2 relative to PI3-kinase α and δ, but not β or γ. In other embodiments, the compound inhibits mTorC2 relative to PI3-kinase β and γ, but not α or δ. In other embodiments, the compound inhibits mTorC2 relative to PI3-kinase β and δ, but not α or γ. In other embodiments, the compound inhibits mTorC2 relative to PI3-kinase γ and δ, but not α or β. In other embodiments, the compound inhibits mTorC2 relative to PI3-kinase α, β, and γ, but not 8. In other embodiments, the compound inhibits mTorC2 relative to PI3-kinase α, β, and 8, but not γ. In other embodiments, the compound inhibits mTorC2 relative to PI3-kinase α, δ, and γ, but not β. In other embodiments, the compound inhibits mTorC2 relative to PI3-kinase γ, β, and δ, but not α. In other embodiments, the compound inhibits mTorC2 relative to PI3-kinase α, β, γ, and δ.

In some embodiments, one or more of the subject compound selectively inhibits both mTorC1 and mTorC2 activity relative to one, two, three or all type I phosphatidylinositol 3-kinases (PI3-kinase) consisting of PI3-kinase α, PI3-kinase β, PI3-kinase γ, and PI3-kinase δ. In one embodiment, a compound inhibits mTorC1 and mTorC2 relative to PI3-kinase α. In another embodiment, the compound inhibits mTorC1 and mTorC2 relative to PI3-kinase β. In another embodiment, the compound inhibits mTorC1 and mTorC2 relative to PI3-kinase γ. In another embodiment, the compound inhibits mTorC1 and mTorC2 relative to PI3-kinase 8. In some embodiments, the compound inhibits mTorC1 and mTorC2 relative to PI3-kinase α and β, but not γ or δ. In other embodiments, the compound inhibits mTorC1 and mTorC2 relative to PI3-kinase α and γ, but not 0 or 8. In other embodiments, the compound inhibits mTorC1 and mTorC2 relative to PI3-kinase α and δ, but not β or γ. In other embodiments, the compound inhibits mTorC1 and mTorC2 relative to PI3-kinase β and γ, but not α or δ. In other embodiments, the compound inhibits mTorC1 and mTorC2 relative to PI3-kinase β and δ, but not α or γ. In other embodiments, the compound inhibits mTorC1 and mTorC2 relative to PI3-kinase γ and δ, but not α or β. In other embodiments, the compound inhibits mTorC1 and mTorC2 relative to PI3-kinase α, β, and γ, but not δ. In other embodiments, the compound inhibits mTorC1 and mTorC2 relative to PI3-kinase α, β, and δ, but not γ. In other embodiments, the compound inhibits mTorC1 and mTorC2 relative to PI3-kinase α, δ, and γ, but not β. In other embodiments, the compound inhibits mTorC1 and mTorC2 relative to PI3-kinase γ, β, and δ, but not α. In other embodiments, the compound inhibits mTorC1 and mTorC2 relative to PI3-kinase α, β, γ, and δ.

In some embodiments, one or more of the subject compound selectively inhibits both mTor activity with an IC50 value of about 100 nM, 50 nM, 10 nM, 5 nM, 100 pM, 10 pM or even 1 pM, or less as ascertained in an in vitro kinase assay.

In some embodiments, the selective inhibition of both mTor activity by one or more of the subject compound respect to a given type I PI3-kinase is evidenced by the fact that such compound exhibits with respect to both mTorC1 and mTorC2 an IC50 value that is at least 10-fold, at least 20-fold, at least 50-fold, at least 100-fold, at least 1000-fold, at least 10,100-fold, or lower, than the compound's IC50 with respect to one, two, three or all type I PI3-kinases including PI3-kinase α, β, γ, and δ.

In some embodiments, one or more of the subject compound is substantially ineffective in inhibiting a type I PI3-kinase at a concentration of 100 nM, 200 nM, 500 nM, or 1 uM, 5 uM or 10 uM, or higher in an in vitro kinase assay.

In some embodiments, one or more of the subject compound inhibits phosphorylation of Akt (S473) and Akt (T308) more effectively than rapamycin when tested at a comparable molar concentration in an in vitro kinase assay.

In some embodiments, one or more of the subject compound competes with ATP for binding to ATP-binding site on mTorC1 and/or mTorC2. In some embodiments, one or more of the subject compound causes apoptosis of said cell or cell cycle arrest.

The invention provides pharmaceutical compositions comprising one or more compounds of the present invention. In some embodiments, the invention provides pharmaceutical compositions for the treatment of disorders such as hyperproliferative disorder including but not limited to cancer such as acute myeloid leukemia, *thymus*, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rheumatoid arthritis, graft versus host disease, and lupus erythematosus.

The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 50/%, 4%, 3%, 20%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25%, 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v, v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g. 0.0003 g. 0.0004 g. 0.0005 g. 0.0006 g. 0.0007 g. 0.0008 g. 0.0009 g. 0.001 g. 0.0015 g. 0.002 g. 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the present invention typically contains an active ingredient (e.g., a compound of the present invention or a pharmaceutically acceptable salt and/or coordination complex thereof, and one or more pharmaceutically acceptable excipients, carriers, including but not limited inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as *acacia*, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofiurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N. Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to diseases associated with malfunctioning of one or more types of PI3 kinase and/or mTOR.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, *thymus*, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit mTorC1 and/or mTorC2 as compared to one or more type I PI3 kinases. Autoimmune diseases or diseases related to an undesirable immune response including but not limited to asthma, emphysema, allergy, dermatitis, rheumatoid arthritis, psoriasis, lupus erythematosus, or graft versus host disease.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, photo-toxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer, ovarian cancer, including epithelial ovarian tumors such as adenocarcinoma in the ovary and an adenocarcinoma that has migrated from the ovary into the abdominal cavity; uterine cancer, cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer, lung cancer such as non-small cell lung cancer (NSCLC), which is divided into squamous cell carcinomas, adenocarcinomas, and large cell undifferentiated carcinomas, and small cell lung cancer, skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer, thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer, central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor, oral cavity and oropharyngeal cancer such as, hypopharyngeal cancer, laryngeal cancer, nasopharyngeal cancer, and oropharyngeal cancer, stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; *thymus* cancer such as to thymomas, thymic carcinomas, Hodgkin disease, non-Hodgkin lymphomas carcinoids or carcinoid tumors; rectal cancer, and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barrb syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

The invention further provides methods of modulating mTor kinase activity by contacting the kinase with an amount of an effective amount of compound of the invention. Modulate can be inhibiting or activating kinase activity. In some embodiments, the invention provides methods of inhibiting kinase activity by contacting the kinase with an amount of an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 50%, 60%, 70%, 80%, or 90%.

In some embodiments, the kinase is selected from the group consisting of PI3 kinase including different isoforms such as PI3 kinase α, PI3 kinase β, PI3 kinase γ, PI3 kinase δ; DNA-PK; mTor, Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR hSmg-1; Hck; Src; Epidermal growth factor receptor (EGFR); KIT; Inulsin Receptor (IR) and IGFR.

The invention further provides methods of modulating mTOR activity by contacting mTOR with an amount of a compound of the invention sufficient to modulate the activity of mTOR. Such modulation can take place in vitro or in vivo. In some embodiments, the invention provides methods of inhibiting mTOR activity in a cell by contacting said cell with an amount of a compound of the invention sufficient to inhibit the activity of mTOR in said cell. In some embodiments, the invention provides methods of inhibiting mTOR activity in a tissue by contacting said tissue with an amount of a compound of the invention sufficient to inhibit the activity of mTOR in said tissue. In some embodiments, the invention provides methods of inhibiting mTOR activity in an organism by contacting said organism with an amount of a compound of the invention sufficient to inhibit the activity of mTOR in said organism. The present invention provides methods of treating a disease mediated by mTOR activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to methods and pharmaceutical compositions for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (-)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, D-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. bydividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention unit dose forms of the agent and the compound of the invention may be adjusted accordingly.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl3:MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 2

Expression and Inhibition Assays of Abl

The compounds described herein can be assayed in triplicate against recombinant full-length Abl or Abl (T315I) (Upstate) in an assay containing 25 mM HEPES, pH 7.4, 10 mM MgCl2, 200 µM ATP (2.5 µCi of γ-32P-ATP), and 0.5 mg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 3

Expression and Inhibition Assays of Hck

The compounds described herein can be assayed in triplicate against recombinant full-length Hck in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 4

Expression and Inhibition Assays of Inulsin Receptor (IR)

The compounds described herein can be assayed in triplicate against recombinant insulin receptor kinase domain (Upstate) in an assay containing 25 mM HEPES, pH 7.4, 10 mM MgCl2, 10 mM MnCl2, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1 M NaCl/1% phosphoric acid (approximately 6 times, 5-10 minutes each). Sheets are dried and the transferred radioactivity quantitated by phosphorimaging.

Example 5

Expression and Inhibition Assays of Src

The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 6

Expression and Inhibition Assays of DNA-PK (DNAK)

DNA-PK can be purchased from Promega and assayed using the DNA-PK Assay System (Promega) according to the manufacturer's instructions.

Example 7

Expression and Inhibition Assays mTOR

The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of p-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 8

Expression and Inhibition Assays of Vascular endothelial growth receptor

The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of p-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Ephrin receptor B4 (EphB4)

The compounds described herein can be tested against recombinant Ephrin receptor B4 kinase domain (Invitrogen) in an assay containing 25 mM HEPES, pH 7.4, 10 mM MgCl2, 0.1% BME, 10 μM ATP (2.5 μCi of p-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Epidermal Growth Factor Receptor (EGFR)

The compounds described herein can be tested against recombinant EGF receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of KIT Assay

The compounds described herein can be tested against recombinant KIT kinase domain (Invitrogen) in an assay containing 25 mM HEPES, pH 7.4, 10 mM MgCl2, 1 mM DTT, 10 mM MnCl2, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 12

Expression and Inhibition Assays of RET

The compounds described herein can be tested against recombinant RET kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 13

Expression and Inhibition Assays of Platelet derived growth factor receptor (PDGFR)

The compounds described herein can be tested against recombinant PDG receptor kinase domain (Invitrogen) in an assay containing 25 mM HEPES, pH 7.4, 10 mM MgCl2, 2.5 mM DTT, 10 μMATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 14

Expression and Inhibition Assays of FMS-Related Tyrosine Kinase 3 (FLT-3)

The compounds described herein can be tested against recombinant FLT-3 kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 15

Expression and Inhibition Assays of TEK receptor tyrosine kinase (TIE2)

The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1 M NaCl/1% phosphoric acid (approximately 6 times, 5-10 minutes each). Sheets are dried and the transferred radioactivity quantitated by phosphorimaging.

Example 16

B Cell Activation and Proliferation Assay

The ability of one or more subject compounds to inhibit B cell activitation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C., and 5% $CO_2$. A volume of 15 uL of Alamar Blue reagent is added to each well and plates are incubated for 5 hours at 37 C and 5% $CO_2$. Alamar Blue fluoresce is read at 560Ex/590Em, and IC50 values are calculated using GraphPad Prism 5.

Example 17

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5.

Example 18

Antitumor Activity In Vivo

The compounds described herein can be evaluated in a panel of human and murine tumor models.
Paclitaxel-refractory Tumor Models
1. Clinically-derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days.times.5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days.times.5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days.times.5 schedule.
4. M5076 Murine Sarcoma Model
M5076 is a mouse fibrosarcoma that is inherently refractory to paclitaxel in vivo.
The compounds described herein can be administered to mice bearing staged tumors on an every 2 days.times.5 schedule.

One or more compounds of the invention can be used in combination other therapeutic agents in vivo in the multi-drug resistant human colon carcinoma xenografts HCT/VM46 or any other model known in the art including those described herein.

Example 19

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/ml NADPH; 75 μL of 20.0 mg/ml mouse, rat or human liver microsome; 0.4 μL of 0.2 M phosphate buffer, and 425 μL of dd$H_2O$. Negative control (without NADPH) tube contains 75 μL of 20.0 mg/ml mouse, rat or human liver microsome; 0.4 μL of 0.2 M phosphate buffer, and 525 μL of dd$H_2O$. The reaction is started by adding 1.0 μL of 10.0 mM tested compound. The reaction tubes are incubated at 37° C. 100 μL sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 20

Plasma Stability Assay

The stability of one or more subject compounds in plasma is determined according to standard procedures known in the art. See, e.g., Rapid Commun. Mass Spectrom., 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μL for half-life determination), containing 5 μM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 μL of the incubation mixture to 200 μL of ice-cold acetonitrile and mixed by shaking for 5 minutes. The samples are centrifuged at 6000×g for 15 minutes at 4° C., and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 21

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37 C; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 22

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, phillaldelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

It is expected that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and may be indicative of mTORC2 inhibitors or inhibitors of upstream kinases such as PI3K or Akt.

Example 23

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of the inhibitors disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt -S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells are then analyzed by flow cytometery. The results are are expected to indicate one or more compounds disclosed herein that inhibit the phosphorylation of kinase substrates such as PI3K substrates, Akt substrates, mTORC1 substrates, mTORC2 substrates, mTOR substrates, MAPK substrates, ERK substrates, MAPKK substrates, and/or MEK substrates.

Example 24

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope. The results show that, compared to rapamycin, compounds of the present disclosure potentiate the effects of a half maximal concentration of known chemotherapeutic agents such as and without limitation imatinib, rapamycin, and dasatinib at the concentrations examined.

Alternatively, human peripheral blood mononuclear cells are obtained from philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later.

Example 25

In Vivo Effect of Kinase Inhibitors on Leukemic Cells

Female recipient mice are lethally irradiated from a γ source in two doses about 4 hr apart, with approximately 5 Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labled anti-hCD4 antibodies and counted by flow cytometry. It is expected that one or more compounds disclosed herein alone or in combination with known chemotherapeutic agents significantly reduce leukemic blood cell counts as compared to treatment with known chemotherapeutic agents (e.g. Gleevac) alone under the conditions tested.

Example 26

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R3KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 10 mg/kg to about 50 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

It is expected that one or more compounds disclosed herein suppresses or delays the onset of lupus symptoms in lupus disease model mice.

Example 35

Murine Bone Marrow Transplant Assay

Female recipient mice are lethally irradiated from a γ ray source. About 1 hr after the radiation dose, mice are injected with about 1×106 leukemic cells from early passage p190 transduced cultures (e.g. as described in *Cancer Genet Cytogenet.* 2005 August; 161(1):51-6). These cells are administered together with a radioprotective dose of approximately 5×106 normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 μl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

It is expected that the results of the analysis demonstrate effective therapeutic doses of the compounds disclosed herein for inhibiting the proliferation of leukemic cells. It is further expected that combination therapy of the inhibitors disclosed herein with other chemotherapeutic agents (e.g. dasatinib) exhibit a greater degree of efficacy or decreased toxicity in comparison to the use of a single chemotherapeutic agent.

The invention claimed is:

1. A compound of Formula:

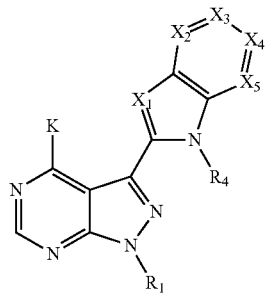

or a pharmaceutically acceptable salt thereof,
wherein K is $NH_2$, $CH_3$, or H;

$X_1$, $X_2$, $X_3$, $X_4$, and $X_5$ are independently N or $CR_2$, wherein no more than two adjacent ring atoms are N and the total number of $X_1$, $X_2$, $X_3$, $X_4$, and $X_5$ which are N is no more than 4;

$R_1$ is H, -L-$C_{1-10}$alkyl, -L-$C_{3-8}$cycloalkyl, -L-aryl, -L-heteroaryl, L-$C_{1-10}$alkylaryl, -L-$C_{1-10}$alkylhetaryl, -L-$C_{1-10}$alkylheterocyclyl, -L-$C_{2-10}$alkenyl, -L-$C_{2-10}$alkynyl, -L-$C_{2-10}$alkenyl-L-$C_{3-8}$cycloalkyl, -L-$C_{2-10}$alkynyl-L-$C_{3-8}$cycloalkyl, -L-heteroalkyl, -L-heteroalkylaryl, -L-heteroalkylheteroaryl, -L-heteroalkylheterocyclyl, -L-heteroalkyl-$C_{3-8}$cycloalkyl, -L-aralkyl, -L-heteroaralkyl, -L-heterocycloalkyl, -L-$C_{3-8}$cycloalkyl-heterocycloalkyl, or -L-$C_{3-8}$cycloalkyl-heteroaryl, each of which is unsubstituted or substituted by one or more independent $R_3$ substituents;

L is absent, C=O, —C(=O)O—, —C(=O)$NR^{31}$—, —S(O)—, —S(O)$_2$—, —S(O)$_2NR^{31}$—, or —$NR^{31}$—;

each instance of $R_2$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=)$OR^{33}$, —OC(=O)$NR^{31}R^{32}$, $C_{1-10}$alkyl, $C_{3-8}$cycloalkyl, —$C_{2-10}$alkenyl, —$C_{2-10}$alkynyl, —$C_{1-10}$alkoxy, -heterocycloalkyl, aryl, hetaryl, or heteroalkyl;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, —$NR^{31}$C(=$NR^{32}$)$OR^{33}$, —OC(=O)$OR^{33}$, —OC(=O)$NR^{31}R^{32}$, —$C_{1-10}$alkyl, —$C_{3-8}$cycloalkyl, —$C_{2-10}$alkenyl, —$C_{2-10}$alkynyl, —$C_{1-10}$alkoxy, -heterocycloalkyl, -aryl, -hetaryl, or -heteroalkyl;

$R_4$ is hydrogen, —C(O)$R^{31}$, —$C_{1-10}$alkyl, —$C_{3-8}$cycloalkyl, —$C_{2-10}$alkenyl, —$C_{2-10}$alkynyl, —$C_{1-10}$alkoxy, -heterocycloalkyl, or -heteroalkyl;

$R^{31}$, $R^{32}$, and $R^{33}$, in each instance, is independently hydrogen, —$C_{1-10}$alkyl, —$C_{3-8}$cycloalkyl, -aryl, -hetaryl, or -heterocycloalkyl; and provided that when $X_1$, $X_2$, $X_4$, and $X_5$ are CH; $X_3$ is C(OH); K is $NH_2$; and $R_4$ is hydrogen; then $R_1$ is not —CH(CH$_3$)$_2$; and when $X_1$, $X_2$, $X_3$, $X_4$, and $X_5$ are CH, K is $NH_2$; then $R_1$ is not -cycloC$_4$H$_7$.

2. The compound or pharmaceutically acceptable salt of claim 1, wherein K is $NH_2$.

3. The compound or pharmaceutically acceptable salt of claim 1, wherein K is hydrogen or methyl.

4. The compound or pharmaceutically acceptable salt of claim 1, wherein $R_4$ is hydrogen or $C_{1-10}$alkyl.

5. The compound or pharmaceutically acceptable salt of claim 1, wherein $X_1$, $X_2$, $X_3$, $X_4$, and $X_5$ are $CR_2$.

6. The compound or pharmaceutically acceptable salt of claim 5, wherein each $R_2$ is independently hydrogen, halo, —OH, —$CF_3$, —$OCF_3$, —$OR^{31}$, —$NR^{31}R^{32}$, —C(O)$R^{31}$, —C(=O)$NR^{31}R^{32}$, —$NO_2$, —CN, —S(O)$_{0-2}R^{31}$, —$SO_2NR^{31}R^{32}$, —$C_{1-10}$alkyl, -heterocycloalkyl, -aryl, or -hetaryl.

7. The compound or pharmaceutically acceptable salt of claim 1, wherein $R_1$ is -L-$C_{1-10}$alkyl, -L-$C_{3-8}$cycloalkyl, -L-heteroaryl, -L-heterocycloalkyl, -L-$C_{1-10}$alkylheterocyclyl, -L-$C_{3-8}$cycloalkyl-heterocycloalkyl, or -L-$C_{1-10}$alkylhetaryl.

8. The compound or pharmaceutically acceptable salt of claim 7, wherein L is absent.

9. The compound or pharmaceutically acceptable salt of claim 1, wherein $R_3$ is independently halo, —OH, —$NR^{31}R^{32}$, —C(O)$R^{31}$, —$CO_2R^{31}$, —C(=O)$NR^{31}R^{32}$, —$NR^{31}$C(=O)$R^{32}$, —$NR^{31}$C(=O)$OR^{32}$, —$NR^{31}$S(O)$_{0-2}R^{32}$, $C_{1-10}$alkyl, $C_{3-8}$ cycloalkyl, —$C_{2-10}$alkynyl, —$C_{1-10}$alkoxy, -heterocycloalkyl, -aryl, -hetaryl, or -heteroalkyl.

10. A pharmaceutical composition comprising the compound or pharmaceutically acceptable salt of claim 1 and a pharmaceutically acceptable carrier.

11. A compound of Formula:

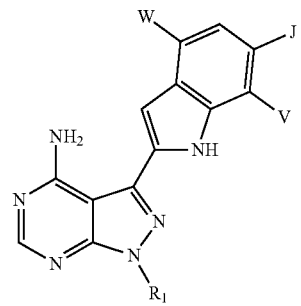

or a pharmaceutically acceptable salt thereof,
wherein $R_1$ is —$C_{1-10}$alkyl, unsubstituted or substituted by one or more independent $R_3$ substituents;

each instance of $R_3$ is independently hydrogen, halo, —OH, —$R^{31}$, —$CF_3$, —$OCF_3$, —$OR^{31}$, —$NR^{31}R^{32}$, —C(O)$R^{31}$, —$CO_2R^{31}$, —C(=O)$NR^{31}R^{32}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —$NR^{31}$C(=$NR^{32}$)$NR^{33}R^{32}$, $NR^{31}$C(=$NR^{32}$)$OR^{33}$, OC(=O)$OR^{33}$, —OC(=O)$NR^{31}R^{32}$, —$C_{1-10}$alkyl, —$C_{3-8}$cycloalkyl, —$C_{2-10}$alkenyl, —C$_{2-10}$alkynyl, —C$_{1-10}$alkoxy, -heterocycloalkyl, -aryl, -hetaryl, or -heteroalkyl;

J, V, and W are independently hydrogen, halo, —OH, —OR$^{31}$, —NR$^{31}$R$^{32}$, —C(O)R$^{31}$, —CO$_2$R$^{31}$, —C(=O)NR$^{31}$R$^{32}$, or —NR$^{31}$C(=O)R$^{32}$;

wherein at least one of J, V, and W is not hydrogen; and R$^{31}$, R$^{32}$, and R$^{33}$, in each instance, is independently hydrogen, —C$_{1-10}$alkyl, —C$_{3-8}$cycloalkyl, -aryl, -hetaryl, or -heterocycloalkyl.

12. The compound or pharmaceutically acceptable salt of claim 11, wherein R$_3$ is independently halo, —OH, —NR$^{31}$R$^{32}$, —C(O)R$^{31}$, —CO$_2$R$^{31}$, —C(=O)NR$^{31}$R$^{32}$, —NR$^{31}$C(=O) R$^{32}$, —NR$^{31}$C(=O)OR$^{32}$, —NR$^{31}$S(O)$_{0-2}$R$^{32}$, C$_{1-10}$alkyl, C$_{3-8}$cycloalkyl, —C$_{2-10}$alkynyl, —C$_{1-10}$alkoxy, -heterocycloalkyl, -aryl, -hetaryl, or -heteroalkyl.

13. A pharmaceutical composition comprising the compound or pharmaceutically acceptable salt of claim 11 and a pharmaceutically acceptable carrier.

14. A compound of Formula:

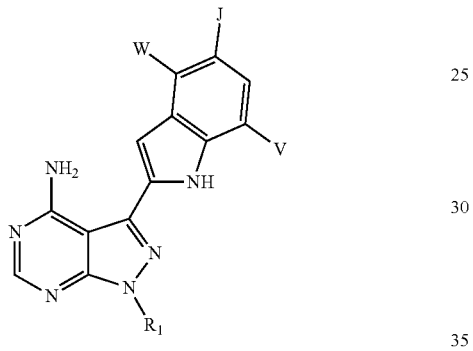

or a pharmaceutically acceptable salt thereof,
wherein R$_1$ is —C$_{1-10}$alkyl, unsubstituted or substituted by one or more independent R$_3$ substituents;

each instance of R$_3$ is independently hydrogen, halo, —OH, —R$^{31}$, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(O)NR$^{32}$R$^{33}$, —NR$^{31}$S(O)$_{0-2}$R$^{32}$, —NR$^{31}$C(=NR$^{32}$)NR$^{33}$R$^{32}$, NR$^{31}$C(=NR$^{32}$)OR$^{33}$, OC(=O)OR$^{33}$, —OC(=O)NR$^{31}$R$^{32}$, —C$_{1-10}$alkyl, —C$_{3-8}$cycloalkyl, —C$_{2-10}$alkenyl, —C$_{2-10}$alkynyl, —C$_{1-10}$alkoxy, -heterocycloalkyl, -aryl, -hetaryl, or -heteroalkyl;

J, V, and W are independently hydrogen, halo, —OH, —OR$^{31}$, —NR$^{31}$R$^{32}$, —C(O)R$^{31}$, —CO$_2$R$^{31}$, —C(=O)NR$^{31}$R$^{32}$, or —NR$^{31}$C(=O)R$^{32}$;

wherein at least one of J, V, and W is not hydrogen;
R$^{31}$, R$^{32}$, and R$^{33}$, in each instance, is independently hydrogen, —C$_{1-10}$alkyl, —C$_{3-8}$cycloalkyl, -aryl, -hetaryl, or -heterocycloalkyl; and wherein when J is —OH, then R$_1$ is not —CH(CH$_3$)$_2$.

15. The compound or pharmaceutically acceptable salt of claim 14, wherein R$_3$ is independently halo, —OH, —NR$^{31}$R$^{32}$, —C(O)R$^{31}$, —CO$_2$R$^{31}$, —C(=O)NR$^{31}$R$^{32}$, —NR$^{31}$C(=O)R$^{32}$, —NR$^{31}$C(=O)OR$^{32}$, —NR$^{31}$S(O)$_{0-2}$R$^{32}$, C$_{1-10}$alkyl, C$_{3-8}$cycloalkyl, —C$_{2-10}$alkynyl, —C$_{1-10}$alkoxy, -heterocycloalkyl, -aryl, -hetaryl, or -heteroalkyl.

16. A pharmaceutical composition comprising the compound or pharmaceutically acceptable salt of claim 14 and a pharmaceutically acceptable carrier.

17. A compound selected from:

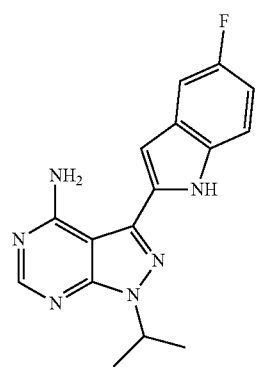

3

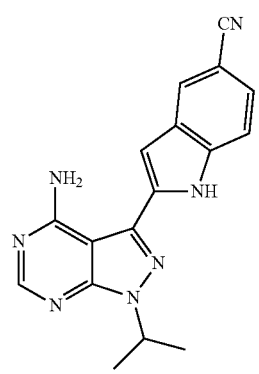

4

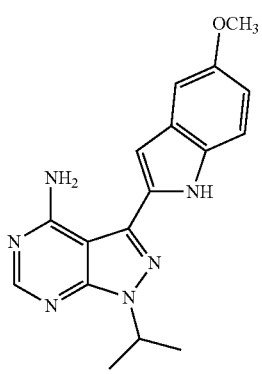

5

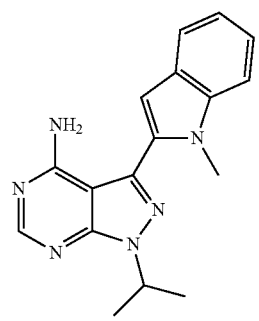

6

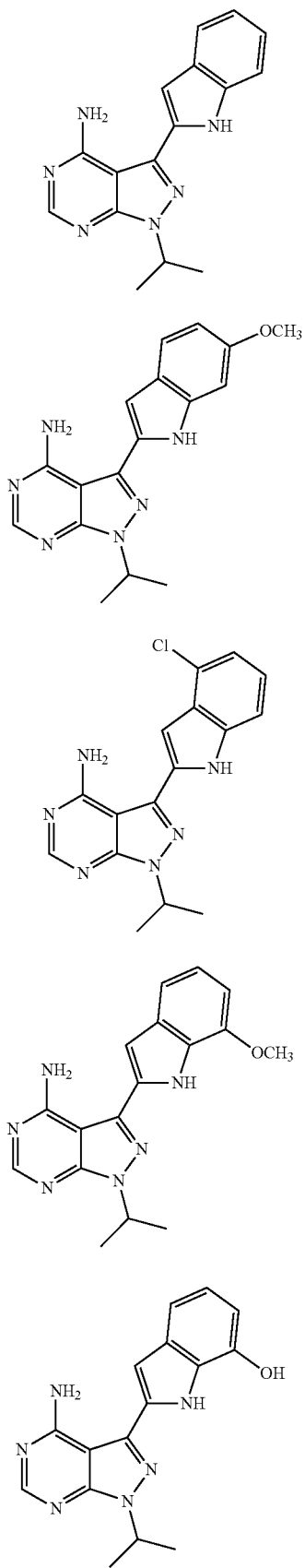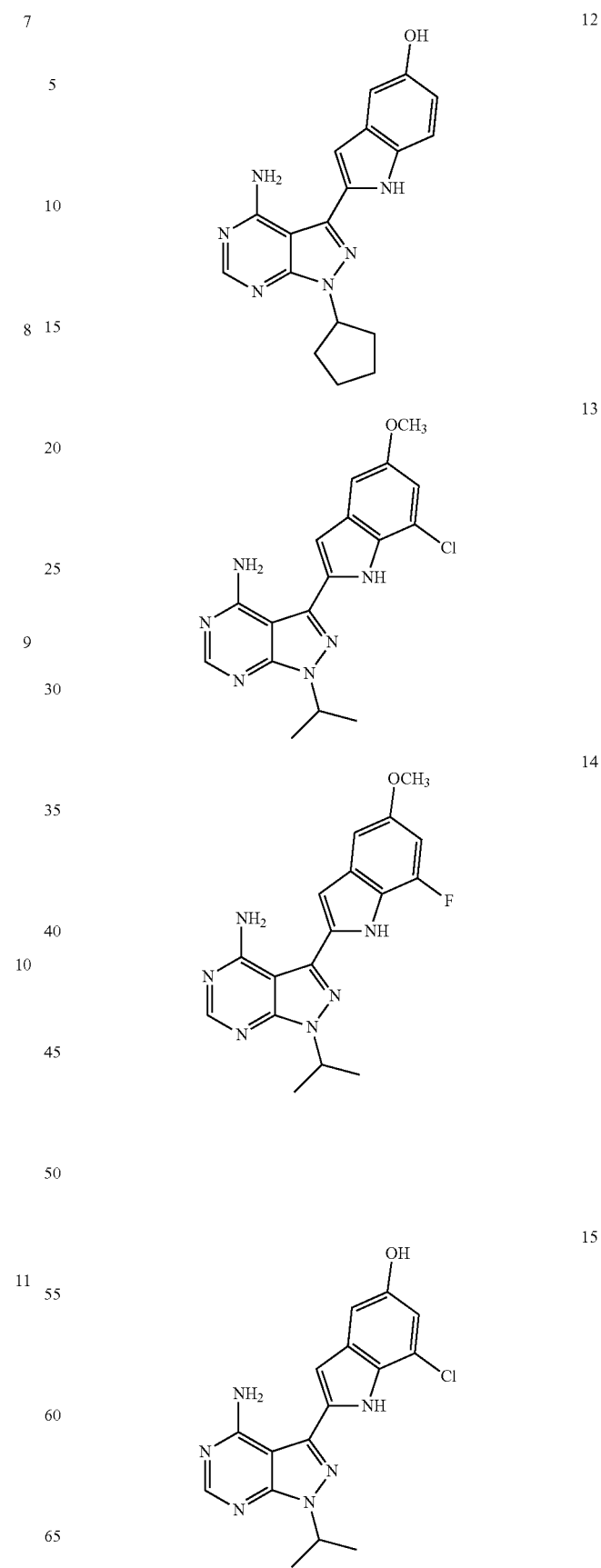

-continued
16
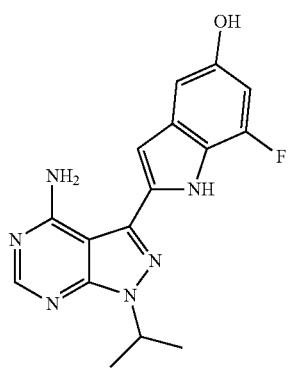
17
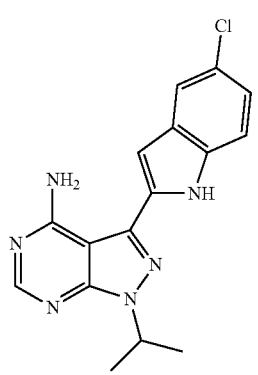
18
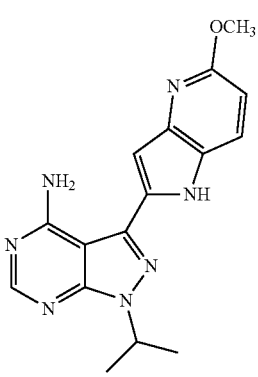
19
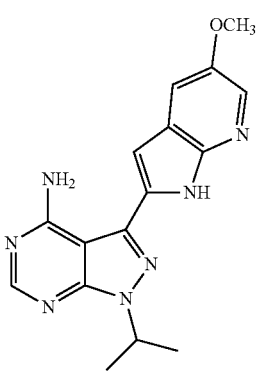
-continued
20
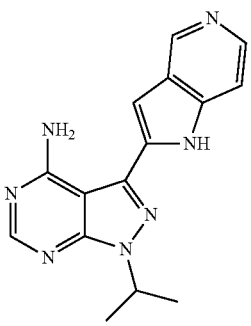
21
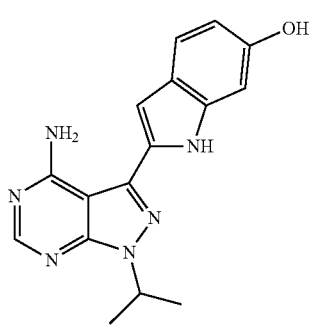
22
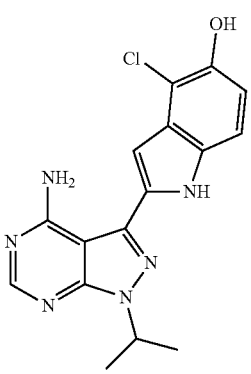
23
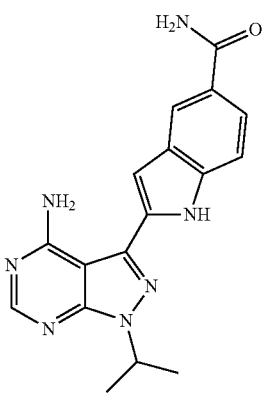

24
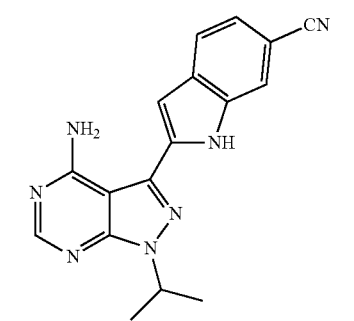
25
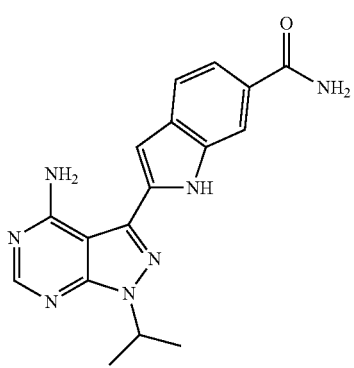
26
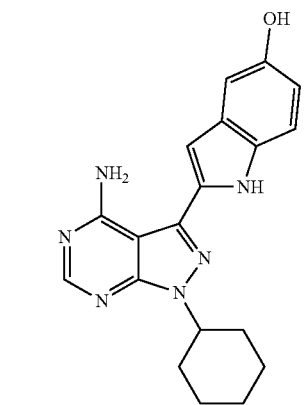
28
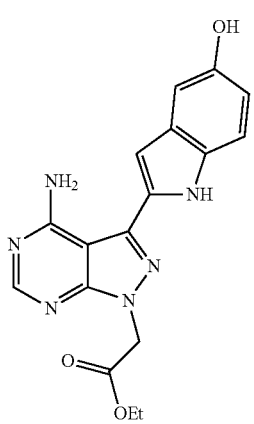
29
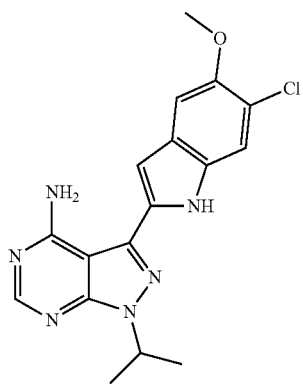
30
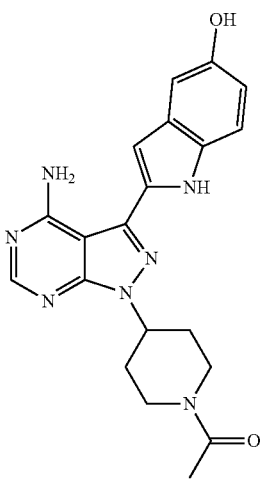

31
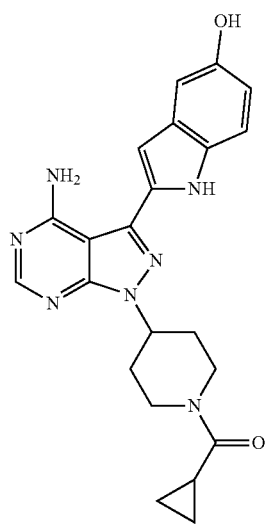
32
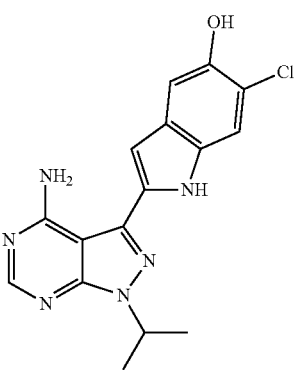
33
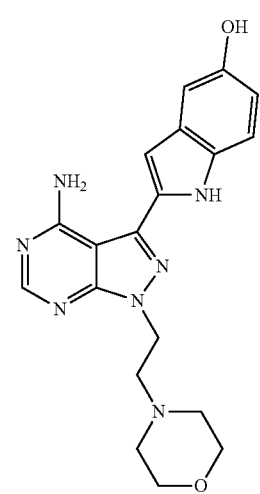
34
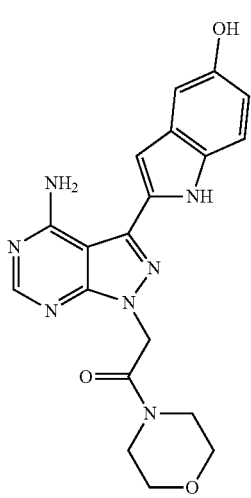
35
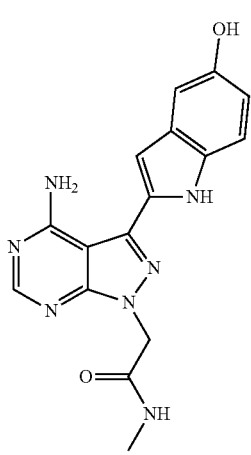
36
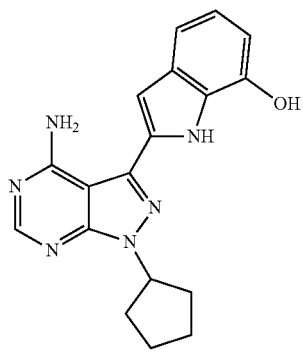
37
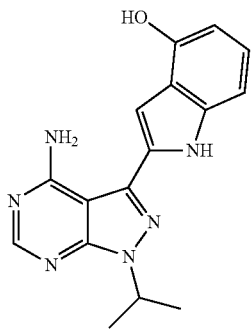

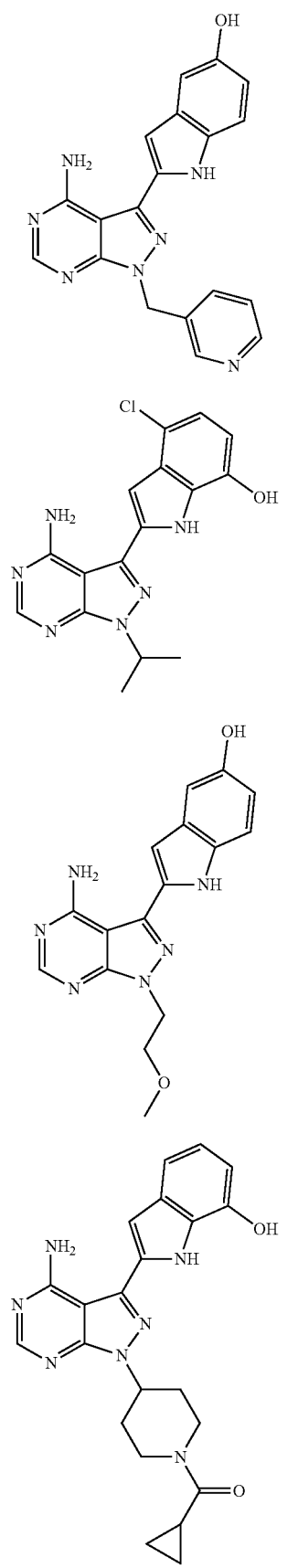
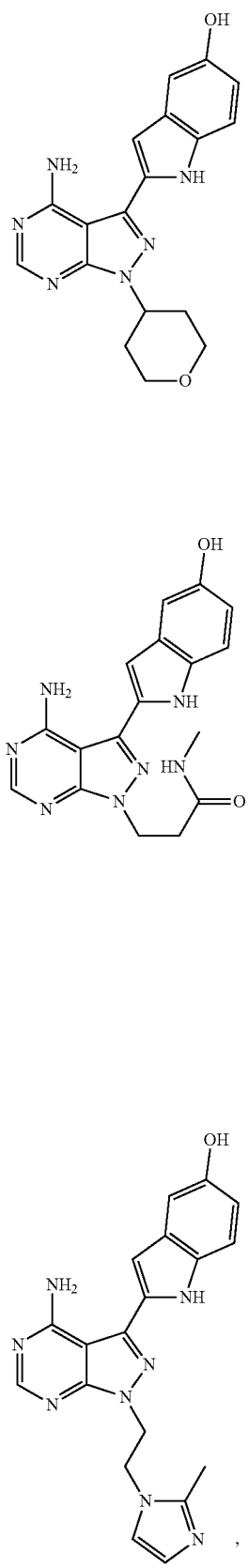
or a pharmaceutically acceptable salt thereof.

18. A compound selected from:
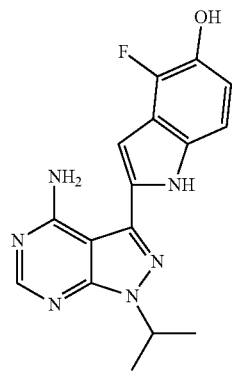
46
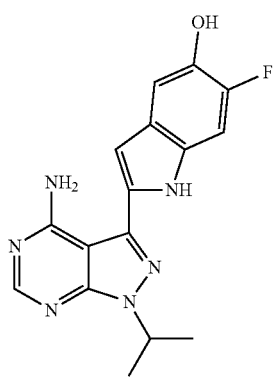
47
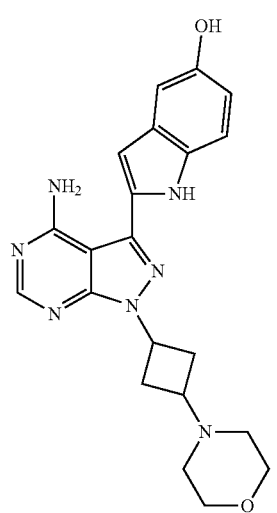
49
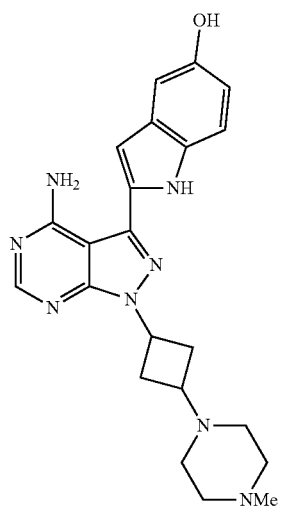
52
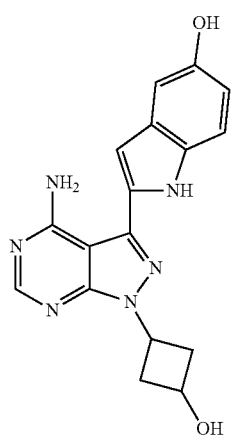
54
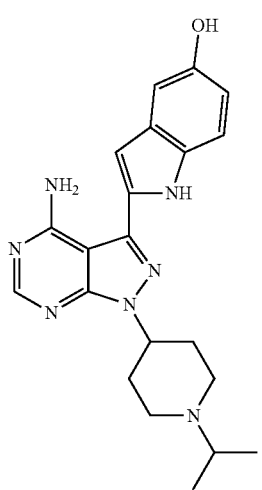
55

56 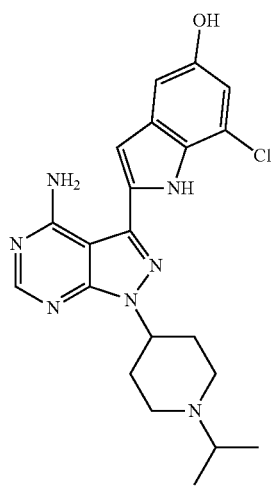
57 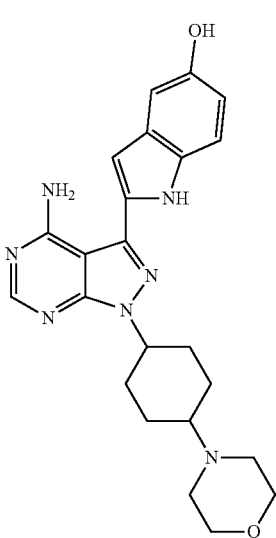
58 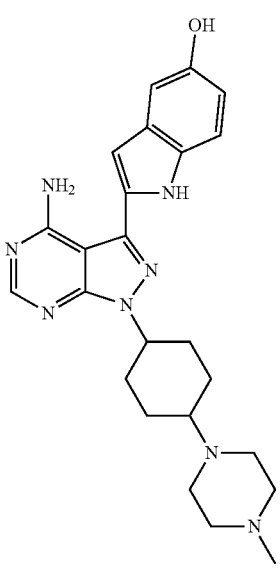
59 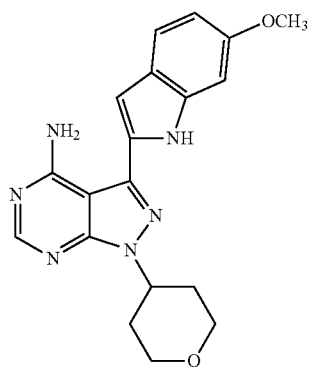
60 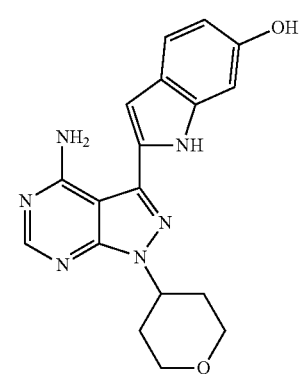
61 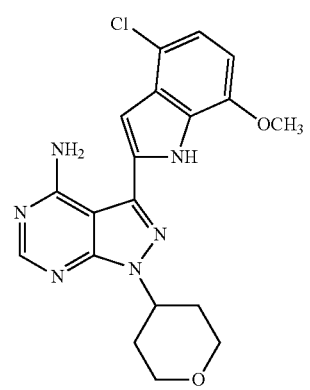
63 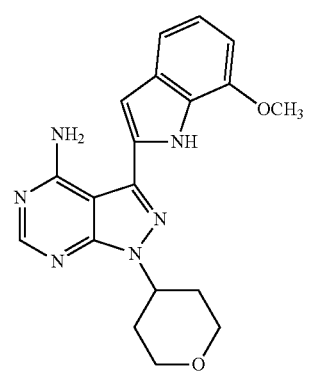

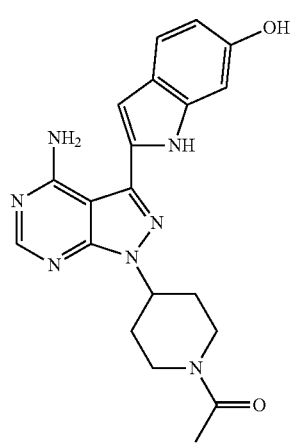
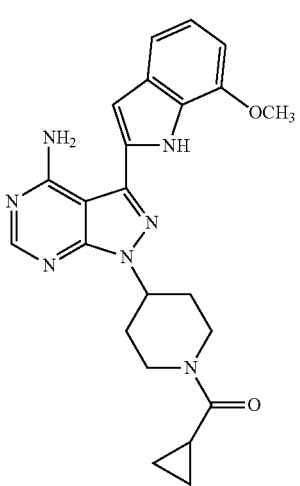
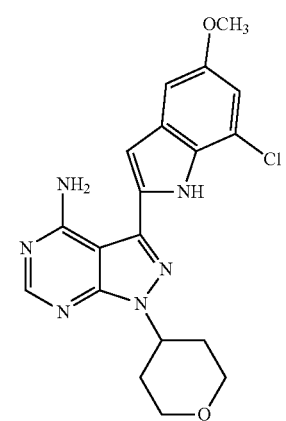
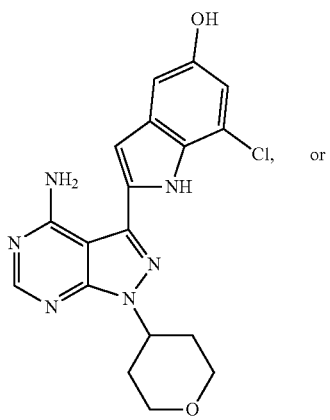
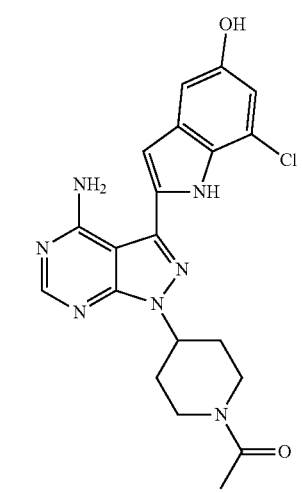
a pharmaceutically acceptable salt thereof.
* * * * *